(12) United States Patent
Roden et al.

(10) Patent No.: US 9,138,470 B2
(45) Date of Patent: Sep. 22, 2015

(54) MULTI-COMPONENT L2 VACCINE FOR PREVENTION OF HUMAN PAPILLOMA VIRUS INFECTION

(75) Inventors: Richard B. S. Roden, Severna Park, MD (US); Ratish Gambhira, Baltimore, MD (US); Hannah H. Alphs, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 846 days.

(21) Appl. No.: 12/740,873

(22) PCT Filed: Nov. 3, 2008

(86) PCT No.: PCT/US2008/082293
§ 371 (c)(1),
(2), (4) Date: Oct. 12, 2010

(87) PCT Pub. No.: WO2009/059328
PCT Pub. Date: May 7, 2009

(65) Prior Publication Data
US 2011/0177112 A1     Jul. 21, 2011

Related U.S. Application Data

(60) Provisional application No. 61/001,631, filed on Nov. 2, 2007.

(51) Int. Cl.
| | | |
|---|---|---|
| A61K 39/12 | (2006.01) | |
| C07K 19/00 | (2006.01) | |
| C07K 16/08 | (2006.01) | |
| A61P 37/04 | (2006.01) | |
| A61P 31/20 | (2006.01) | |
| C07K 14/005 | (2006.01) | |
| C12N 7/00 | (2006.01) | |
| A61K 39/00 | (2006.01) | |

(52) U.S. Cl.
CPC ............... *A61K 39/12* (2013.01); *C07K 14/005* (2013.01); *C12N 7/00* (2013.01); *A61K 2039/543* (2013.01); *A61K 2039/6018* (2013.01); *A61K 2039/645* (2013.01); *C12N 2710/20022* (2013.01); *C12N 2710/20034* (2013.01)

(58) Field of Classification Search
CPC ......... A61K 39/00; A61K 39/12; A61K 7/00; C07K 14/0005; C07K 14/195; C07K 14/32; C07K 16/084; C07K 16/18; C12N 7/00
See application file for complete search history.

(56) References Cited

U.S. PATENT DOCUMENTS

| | | |
|---|---|---|
| 3,791,932 A | 2/1974 | Schuurs et al. |
| 3,949,064 A | 4/1976 | Bornstein et al. |
| 4,174,384 A | 11/1979 | Ullman et al. |
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 5,084,269 A | 1/1992 | Kullenberg |
| 5,700,910 A | 12/1997 | Metzger et al. |
| 6,651,655 B1 | 11/2003 | Licalsi et al. |
| 6,656,462 B2 | 12/2003 | Dondero et al. |
| 6,733,754 B2 | 5/2004 | Roberts et al. |
| 6,793,923 B2 | 9/2004 | Brown et al. |
| 6,803,192 B1 | 10/2004 | Chen |
| 6,814,971 B2 | 11/2004 | Roberts et al. |
| 6,936,704 B1 | 8/2005 | Freeman et al. |
| 2004/0223976 A1* | 11/2004 | Bianchi et al. ............. 424/186.1 |
| 2008/0145375 A1 | 6/2008 | Bembridge et al. |
| 2009/0214598 A1* | 8/2009 | Blaszczak .................. 424/279.1 |
| 2011/0177112 A1* | 7/2011 | Roden et al. ............... 424/192.1 |

FOREIGN PATENT DOCUMENTS

| | | |
|---|---|---|
| WO | WO-2004/014956 A1 | 2/2004 |
| WO | WO-2004/014957 A1 | 2/2004 |
| WO | WO-2004014956 | 2/2004 |

OTHER PUBLICATIONS

Sequence alignment of SEQ ID No. 4 with geneseq accession No. AAR04994. Dillner et al. 1990.*
Roden et al. (Human Pathology. 2004; 35 (8): 971-982).*
Singh et al. (PLOS One. May 2013; 88 (5) e62216: 1-8).*
Pastrana et al. (Virology. 2005; 337: 365-372).*
Gambhira, R. et al. "A Protective and Broadly Cross-Neutralizing Epitope of Human Papillomavirus L2", *Journal of Virology*, Oct. 10, 2007 (published online ahead of print date), doi: 10.1128/JV1.00936-07.p. 4, first full paragraph, Fig. 1A.
International Search Report of International Application No. PCT/US2008/082293, Mar. 20, 2009.
Beutler, Bruce, *Molecular Immunology*, 40 (2004) pp. 845-859.
Blazar et al., *The Journal of Immunology*, 1996, 157: 3250-3259.
Buck et al., *J. Virol*, 78: pp. 751-757, 2004.
Buck et al., *J. Virol.*, 79: pp. 2839-2846, 2005.
Christensen et al., *Virology*, 181:572-579, 1991.
de Villiers et al., *Virology*, 324 (2004) pp. 17-27.
Edwards et al., J. Immunology, 169:3652, 2002.
Embers et al., *J. Virology*, 76:9798-9805, 2002.
Embers et al., *Vaccine*, 22:670-680, 2004.
Fleury et al., *Archives Virol.*, 151:1511-1523, 2006.
Gambhira et al. *J. Virology*, 81:11585-11592, 2007.
Ghosh et al, *Immunology*. 104:58-66, 2001.
Hashimoto et al,*Cell*, 52:269-279, 1988.

(Continued)

*Primary Examiner* — Shanon A Foley
(74) *Attorney, Agent, or Firm* — Venable LLP; Stefan J. Kirchanski; Miguel A. Lopez

(57) ABSTRACT

Embodiments of the invention are directed to methods and compositions for generating an antibody response against HPV epitopes using multi-component vaccines. One such multi-component vaccine requires a T cell helper component and a toll-like receptor (TLR) agonist. In one embodiment, the inventors described a lipopeptide composition comprising an HPV L2 epitope.

23 Claims, 6 Drawing Sheets

(56) References Cited

OTHER PUBLICATIONS

Hayashi et al., *Blood*, 102:2660-2669, 2003.
Huang, *Pharmacology & Therapeutics* 86 (2002), 201-215.
Janeway et al, *Annu. Rev. Immunol.*, 20:197-216, 2002.
Jenkins et al., *Immunity*, 1:443-446, 1994.
Kawana et al., *J. Virol*, 75:2331-2336, 2001.
Kawana et al, *Vaccine*, 19:1496-1502, 2001.
Kawana et al., *Vaccine*, 21:4256-4260, 2003.
Köhler et al., *Natue*, vol. 256 Aug. 7, 1975.
Medzhitov et al., *Mol. Cell*, 2:253-259, 1998.
Medzhitov et al., *Semin. Immunol.*, 10:351-353, 1998.
Medzhitov et al., *Nature*, vol. 388, 394-397, Jul. 24, 1997.
Medzhitov et al., *Trends Microbiol.*, 8:452-456, 2000.
Mondino et al.,: *Proc. National Academy Sci.* USA, vol. 93, pp. 2245-2252, Mar. 1996.
Mosmann and Coffman, *Ann. Rev. Immunol.*, 7:145-173, 1989.
Muhlradt et al., *J. Exp. Med.*, 185:1951-1958, 1997.
Nagase et al., *J. Immunol.*, 171:3977-3982, 2003.
Parkin, *Lancet. Oncol.*, 2:533-543, 2001.
Pastrana et al., *Virology*, 279:361-369, 2001.
Pastrana et al., *Virology*, 321:205-216, 2004.
Poltorok et al., *Science*, 282:2085-2088, 1998.
Pulendran et al., *J. Exp. Med.*, 188:2075-2082, 1998.
Roberts et al., *Nature Medicine*, 13:857-861, 2007.
Roden et al., *Virology*, 270:254-257, 2000.
Skeiky et al, *Infect. Immun.*, 67(8):3998-4007, 1999.
Takeda and Akira, *Semin. Immunol.*, 16:3-9, 2004.
Takeuchi et al, *Int. Immunol.*, 13:933-940, 2001.
Vaughan et al, *Nat. Biotech.*, 16; 535-539, 1998.
Walboomers et al.,*Pathol.*, 189:12-19, 1999.
Zeng et al., *J. Immunol.*, 169:4905-4912, 2002.
Alphs et al., "Protection against heterologous human papillomavirus challenge by a synthetic lipopeptide vaccine containing a broadly cross-neutralizing epitope of L2," PNAS, Apr. 15, 2008, pp. 5850-5855, vol. 105, No. 15.

* cited by examiner

MULTI-COMPONENT L2 VACCINE FOR PREVENTION OF HUMAN PAPILLOMA VIRUS INFECTION

This application is a §371 of PCT Patent Application No.: PCT/US2008/082293, filed Nov. 2, 2008, and claims priority to U.S. Provisional Patent Application Ser. No. 61/001,631 filed Nov. 2, 2007, each of which is incorporated herein by reference in its entirety.

This invention was made with government support under grant number CA098252 awarded by the National Institutes of Health (NIH). The government has certain rights in the invention.

BACKGROUND OF THE INVENTION

I. Field of the Invention

Embodiments of this invention are directed generally to biology and medicine. In certain embodiments the invention is directed to multicomponent HPV vaccines comprising an HPV epitope, a T cell helper (Th) epitope, and a TLR ligand.

II. Background

Genital-tropic human papillomavirus (HPV) infections are considered the most common sexually transmitted infection in the United States (CDC Report to Congress, Prevention of Genital Human Papillomavirus Infection, January 2004). The major manifestations of anogenital HPV include genital warts (condyloma acuminatum) and intraepithelial neoplasia of the vulva, cervix, anus, or penis. A small fraction of persistent high-risk HPV infections, if left untreated, progress to cancer. The presence of HPV DNA has been reported in 99.7% of cervical carcinomas worldwide, suggesting that HPV infection is a cause of this cancer and that this disease can be prevented by prophylactic HPV vaccination (Walboomers et al., 1999).

Approximately 35 of the more than 100 subtypes of HPV are specific for the anogenital epithelium and have varying potentials for malignant transformation (Munoz et al., 2003). Of the 15 currently known oncogenic genital HPV types, HPV16 is the most common, followed by HPV18 and HPV45 (contributing ~50%, ~20% and ~10% of cervical cancer cases, respectively). Despite the successes of public health efforts to reduce the incidence and mortality of cervical cancer with the implementation of cervical cytology screening programs, women who do not undergo regular screening account for most of the patients with invasive cancers (Hoffman and Cavanagh, 1995) and cervical cancer remains the second most common cause of cancer death in women worldwide and the most prevalent cancer in women of sub-Saharan Africa, Central America, south-central Asia and Melanesia (a subregion of Oceania extending from the western side of the West Pacific to the Arafura Sea, north and northeast of Australia—the term was first used to denote an ethnic and geographical grouping of islands distinct from Polynesia and Micronesia) (Parkin, 2001). Approximately 471,000 cases of invasive cervical carcinoma are diagnosed annually (Parkin, 2001). The disease burden resulting from the plethora of HPV types suggest that a broadly protective vaccine is necessary.

The HPV genome is surrounded by a 60-nm, non-enveloped icosahedral capsid (Baker et al., 1991) containing two, genetically-unrelated, major capsid protein L1 and the minor capsid protein L2. Recombinant L1 self-assembles into virus-like particles (VLPs) which are morphologically and immunologically similar to native virions (Kirnbauer et al., 1992). L1 VLP-based vaccines are highly protective against infection corresponding to the papillomavirus type used to derive the immunogen (homologous vaccine), but are ineffective against all but the most closely related HPV types (Roden et al., 2000). Licensed HPV vaccines have circumvented this obstacle by designing multivalent vaccine preparations; CERVARIX™ contains L1 VLP derived from HPV16 and HPV18, while GARDASIL™ also contains HPV6 and HPV11 L1 VLPs for prevention of benign genital warts. Unfortunately, the expense and the need for refrigeration of these L1 VLP vaccines currently renders them impractical for use in low resource and remote areas where they are most needed. Furthermore, because these vaccines are ineffective against a significant fraction of oncogenic HPV types, costly cytologic screening programs remain necessary. To realize the full potential of HPV prevention globally, the vaccine should be safe and effective, stable at ambient temperature to facilitate delivery in remote locations, inexpensive to manufacture, administered without needles, and preferably available in a single dose formulation. Thus, there is a need for additional cross-neutralizing HPV vaccines.

SUMMARY OF THE INVENTION

Immunization with minor capsid protein L2 peptides in animal models protects from experimental papillomavirus infection at both mucosal and cutaneous sites (Roden et al., 2000; Embers et al., 2004). Protection is mediated by neutralizing antibodies and the work of several laboratories has identified cross-neutralizing epitopes (Roden et al., 2000; Gambhira et al., 2007; Kawana et al., 2001a; Christensen et al., 1991; Fleury et al., 2006; Kawana et al., 2001b; Embers et al., 2002). Previously, the inventors generated an HPV16 L2 residues 17-36-specific monoclonal antibody RG-1 that neutralizes both HPV16 and HPV18, and protected naive mice from HPV16 challenge (Gambhira et al., 2007). While there have been attempts to create an L2 peptide vaccine (Kawana et al., 2003), L2 is less immunogenic than L1 VLP, suggesting the need for novel vaccine strategies. Robust, high-affinity antibody responses can be generated against monomeric epitopes using multi-component vaccines (Jackson et al., 2004). One such multi-component vaccine requires a T cell helper component and a toll-like receptor (TLR) recognition component, e.g., a TLR2 ligand corresponding to the lipid component of macrophage-activating lipopeptide 2 (MALP-2) isolated from mycoplasma (Muhlradt et al., 1997)). The TLR component, like T helper (Th) epitopes, functions most effectively when directly (i.e., covalently) linked to the target epitope. The synthesis of target epitopes as fusions with both a TLR ligand and a T helper epitope has emerged as a promising vaccine strategy even for poorly immunogenic self epitopes (Jackson et al., 2004; WO 2004/014956; WO 2004/014957, each of which is incorporated herein by reference in its entirety).

In certain aspects, a multi-component PV L2 composition comprises (a) a peptide component comprising a PV L2 peptide coupled to a T helper cell (Th)) epitope; and (b) one or more Toll Like Receptor agonist coupled to the peptide component of (a). In one embodiment, the inventors described an multi-component papillomavirus (PV) or a human papillomavirus (HPV) L2 composition as a low cost, synthetically-produced vaccine for prevention of infection by several clinically significant HPV types. A multi-component HPV L2 composition is a non-naturally occurring peptide comprising one or more amino acid sequences coupled with one or more immune stimulating moieties, e.g., TLR agonist such as lipids and the like. In certain aspects the immune stimulating moiety is a TLR agonist and in further aspects the TLR agonist is a lipid. Typically, the one or more immune stimulating moieties are directly or indirectly conjugated to the multi-component HPV L2 composition. In certain aspects the multi-component HPV L2 composition is substantially free of non-specific non-conjugated immune stimulator or peptide. In one aspect, a multi-component HPV L2 composition comprises an HPV L2 epitope coupled to a Th epitope (HPV L2-Th), and a TLR agonist conjugated to the HPV L2/Th epitope (HPV L2/Th/TLR). The components can be in a linear or branched configuration with either the HPV L2 peptide sequences at the amino terminus or carboxy terminus of the HPV L2/Th peptide. In certain embodiments a Th epitope can be derived PV or HPV. In other aspects the amino acid sequence of the HPV target epitope may overlap in sequence with the Th epitope (Kawana et al., 2001). In another aspect the HPV L2 peptide, Th peptide, and immune stimulating moiety can be attached individually or as a complex to a bead or other substrate that can be administered to a subject. The immune stimulating moiety can be coupled to the HPV L2/Th peptide at 1, 2, 3, 4, 5, 6, 7, 8, 9, or more selected or random locations along the HPV L2/Th peptide. The multi-component HPV L2 composition can comprise at least, at most, or about 1, 2, 3, 4, 5, 6, 7, 8, 9, 10 or more distinct immune stimulating moieties. In certain aspects, an immune stimulating moiety is located at the amino terminus, in the amino terminal region, at the carboxy terminus, in the carboxy terminal region, between the HPV L2 peptide sequence and Th peptide sequence, in an intermediate region of the HPV L2/Th peptide and/or coupled to an amino acid sequence linking the HPV L2 peptide sequence and the Th peptide sequence, including any combination thereof. In certain aspects, the immune stimulating moiety is coupled to a linker region. The term "amino terminal region" and "carboxy terminal region" refers to a region that spans at most 1, 2, 3, 4, 5, 6, 7, 8, 9, 10, 11, 12, 13, 14, 15, 16, 17, 18, 19, 20 amino acids from the amino terminus or carboxy terminus, respectively. The term "intermediate region" refers to the amino acid sequence located at the junction or connection between the HPV L2 peptide sequence and the Th peptide sequence and includes at most 1, 2, 3, 4, 5, 6, 7, 8, 9, 10, 11, 12, 13, 14, 15, 16, 17, 18, 19, or 20 amino acids amino terminal and/or carboxy terminal from the junction or connection between the HPV L2 peptide sequence and the Th peptide sequence.

The HPV L2 epitope can comprise all or part of the amino acid sequence of a L2 protein of a virus in the family papovavirus; polyomavirus; papillomavirus; and/or a papillomavirus within the α genus, or the genera β, γ, δ, ε, ζ, η, θ, ι, κ, λ, μ, ν, ξ, o, π (See de Villiers et al., Classification of papillomaviruses. Virology. 2004 Jun. 20; 324(1):17-27); and/or human papillomaviruses: HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70, HPV71, HPV72, HPV73, HPV74, HPV75, HPV76, HPV77, HPV78, HPV79, HPV80, HPV81, HPV82, HPV83, HPV84, HPV85, HPV86, HPV87, HPV88, HPV89, HPV90, HPV91, HPV92, HPV93, HPV94, HPV95, HPV96, HPV97, HPV98, HPV99, HPV100; and/or animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPV), Rhesus monkey papillomavirus (RhPV) and rabbit oral papillomavirus (ROPV).

An HPV antigen or epitope or peptide of the invention can comprise 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200, 250, 300, 350, 400, 450, 500 consecutive amino acids, including all values and ranges there between, of an papillomavirus L2 polypeptide SEQ ID NO:1-3 and SEQ ID NO:54-118. In other aspects, an HPV peptide can comprise a consecutive amino acid sequence from amino acid x to amino acid y of HPV L2 protein, wherein in x is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, or 463; and y is amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, or 473. In certain embodiments, the L2 peptide is an HPV16 epitope (SEQ ID NO:1), an HPV18 epitope (SEQ ID NO:2), or an HPV45 epitope (SEQ ID NO:3). In certain aspects the L2 peptide is an HPV16 peptide. In further aspects, the L2 peptide comprises amino acids 17-36 of SEQ ID NO:1 (HPV16 L2 17-36 (SEQ ID NO:4)). While this fragment is designated 17-36 based on HPV16 the actual amino acid position from other HPV types may differ but are easily identified by alignment with the HPV16 sequences disclosed herein. In certain aspects, the L2 peptide is at least or more than 80%, 85%, 90%, 91%, 92%, 93%, 94%, 95%, 96%, 97%, 98%, or 99% identical to SEQ ID NO:1-3 or SEQ ID NO:54-118, or segments thereof. In certain embodiments the L2 peptide comprises the consensus amino acid sequence (D/Q/H)(L/I)Y(KPRQS)(TSA)CK(Q/I/VLA)(A/S/T)(G/N)(T/N)CPPD(I/V)(I/V/Q)(PND)(K R)(V/I) (SEQ ID NO:119) OR abYcdCKefghCPPDijklm (SEQ ID NO:120), where a=(D/Q/H); b=(L/I); c=(KPRQS); d=(TSA); e=(Q/I/VLA); f=(A/S/T); g=(G/N); h=(T/N); i=(I/V); j=(I/V/Q); k=(PND); l=(KR); m=(V/I). In certain aspects, one or more cysteine residues of any L2 peptide described herein can be substituted with serine residues. In a further aspect, the HPV-L2 peptide is at least 70, 80, 90, 95, 99, or 100% identical to of SEQ ID NO:4, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In other aspects, the HPV L2 peptide can comprise an amino acid sequence that is 60, 70, 80, 90, 95, or 100% identical, including all values and ranges there between, to the amino acid sequence of SEQ ID NO:38-53.

In certain aspects, Th epitopes include, but are not limited to T-cell epitopes derived from xenogeneic (non-host) sources (such as bacterial proteins and toxins, like Tetanus and Diphtheria toxins, or viral antigens) or alternatively host antigens (that also include embryonic, testis/tumor-associated antigens or host epitopes containing polymorphic changes or other germline or somatic mutations found within the species), or alternatively peptides not found in nature but recognized as MHC II epitopes. For example, the P2 and P30 epitopes from Tetanus toxin, Hepatitis B core antigen, tuberculosis, *Mycobacterium tuberculosis* RA12 (a sub-sequence (amino acids 192 to 323) of MTB32A (Skeiky et al. 1999)), p25 protein of morbillivirus/canine distemper virus ("P25"): KLIPNASLIENCTKAEL (SEQ ID NO:5) PV (poliovirus) sequence 103-115: KLFAVWKITYKDT (SEQ ID NO:6) M5: NKLIAYPAVEALS (SEQ ID NO:7), TT (tetanus toxin) 830-844: QYIKANSKFIGITEL (SEQ ID NO:8), PADRE: aKXVMWTLKAAa (a=D-Ala, X=L-cyclohexyl-Ala) (SEQ ID NO:9), E7 p20-29 TDLYCYEQLN (SEQ ID NO:10), E7 p45-54: AEPDRAHYNI (SEQ ID NO:11), E7 p60-79: KCDSTLRLCVQSTHVIRTL (SEQ ID NO:12), E7 p85-94: GTLGIVGPIC (SEQ ID NO:13), ras p5-17: KLVVVGARGVGKS (SEQ ID NO:14), neu p42-56: HLDMLRHLYQGGQVV (SEQ ID NO:15), neu p783-797: SRLLGICLTSTVQLV (SEQ ID NO:16), and MAGE-3$_{121-134}$: LLKYRAREPVTKAE (SEQ ID NO:17)). In a further aspect, a Th epitope can be a PV L2 segment.

In certain embodiments, a Th epitope can comprise 10 or more amino acids from an influenza virus hemaglutinin peptide, a canine distemper virus F peptide, a tetanus toxoid peptide, a *Plasmodium falciparum* pfg27 peptide, a lactate dehydrogenase peptide, a PADRE peptide, a measles virus peptide, a mucin peptide, a foot and mouth disease virus VP3 peptide, or HIVgp120 peptide.

TLR agonists include, but are not limited to lipoteichoic acid, mannuronic acids, peptidoglycans, atypical LPS, MALP-2 and MALP-404 (lipoproteins), OspA, Porin, LcrV, lipomannan, lysophosphatidylserine, lipophosphoglycan (LPG), glycophosphatidylinositol (GPI), zymosan, and analogs or derivatives thereof. In a further aspect, TLR2 agonists include bacterial lipopeptide from *M. tuberculosis, B. burgdorferi, T. pallidum*; peptidoglycans from species including *Staphylococcus aureus; Neisseria porins*; bacterial fimbriae; *Yersina virulence* factors; CMV virions; measles haemagglutinin; and zymosan from yeast. In certain aspects, the TLR agonist is a lipid moiety. Lipid moieties include, but are not limited to fatty acids such as palmitoyl, myristoyl, lauroyl, octanoyl, stearoyl and decanoyl groups or, more generally, any C2 to C30 saturated, monounsaturated, or polyunsaturated fatty acyl group. In certain aspects the lipid moiety is a Pam$_2$Cys [S-[2,3-bis(palmitoyloxy)propyl]cysteine] or Pam$_3$Cys [N-palmitoyl-S-[2,3-bis(palmitoyloxy)propyl]cysteine] moiety.

One or more of the mutlicomponent PV compositions are useful as a vaccine composition. In certain aspects a mutlicomponent PV composition can be used for prophylaxis, treatment, or prevention of papovavirus and/or papillomavirus infection. In certain instances a multicomponent PV L2 composition can be combined with a pharmaceutical carrier. In certain aspects, a composition is administered to an individual prior to, after, and/or during virus exposure to minimize or prevent virus infection or to reduce the severity of infection and retard or halt progression of the disease, or to prevent transmission of a virus from the infected host to another individual who does have such a virus infection by vaccination of the infected host.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant" or "epitope" and are synonymous. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant or epitope need not be a contiguous/consecutive sequence or segment of protein and may include various sequences that are not immediately adjacent to one another.

With regard to a particular amino acid sequence, an "epitope" is a set of amino acid residues which is involved in recognition by a particular immunoglobulin, or in the context of T-cells, those residues necessary for recognition by T-cell receptor proteins and/or Major Histocompatibility Complex (MHC) receptors. The amino acid residues of an epitope need not be contiguous/consecutive. In an immune system setting, in vivo or in vitro, an epitope is the collective features of a molecule, such as primary, secondary and tertiary peptide structure, and charge, that together form a site recognized by an immunoglobulin, T-cell receptor or HLA molecule. Throughout this disclosure, "epitope" and "peptide" are often used interchangeably.

As used herein, "B-cell epitope" or "target epitope" (e.g., HPV L2), refers to a feature of a peptide or protein that is recognized by a B-cell receptor in the immunogenic response to the peptide comprising that antigen (e.g., an HPV L2 epitope (immunogen or target epitope)).

As used herein "helper T-cell epitope" or "Th epitope" means a feature of a peptide or protein that is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II Major Histocompatibility Complex (MHC) molecules expressed on antigen-presenting cells (See e.g., Moeller, 1987). In some embodiments of the present invention, the epitopes or epitopic fragments identified as described herein find use in the detection of antigen presenting cells having MHC molecules capable of binding and displaying the epitopes or fragments.

As used herein, "HPV" and "human papillomavirus" refer to the members of the family Papillomavirus that are capable of infecting humans. There are two major groups of HPVs defined by their tropism (genital and cutaneous groups), each of which contains multiple virus "types" or "strains" (e.g., HPV 16, HPV 18, HPV 31, HPV 32, etc.). Of particular interest in the present invention are the HPV types that are associated with genital infection and malignancy, as well as those that produce benign papillomas resulting in morbidity to the patient.

The term "vaccine" refers to a formulation which contains 1, 2, 3, 4, 5, or more multi-component HPV compositions of the present invention. The multi-component HPV compositions will typically be in a form that is capable of being administered to a subject and induces a protective or therapeutic immune response sufficient to induce immunity to prevent and/or ameliorate an infection and/or to reduce at least one symptom of an infection and/or to enhance the efficacy of another anti-HPV therapy or prophylactic. Typically, a vaccine comprises a conventional saline or buffered aqueous solution medium in which the composition of the present invention is suspended or dissolved, although administration of dry powder, for example by inhalation, and even formulation with an additional adjuvant, such as alum, is also contemplated. The composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses. Typically, such a response will be cross reactive between various types of papillomavirus, including, but not limited to 2, 3, 4, 5, 6, 7, 8, 9, 10 or more of the HPV types described herein.

As used herein, "prophylactic" and "preventive" vaccines are vaccines that are designed and administered to prevent infection, disease, and/or any related sequela(e) caused by or associated with a pathogenic organism, particularly HPV.

As used herein, "therapeutic" vaccines are vaccines that are designed and administered to patients already infected with a pathogenic organism such as at least one HPV strain. Therapeutic vaccines (e.g., therapeutic HPV vaccines) are used to prevent and/or treat the development of benign or malignant tumors in these infected individuals.

"TLR" refers to a toll-like receptor of any species origin, e.g., human, rodent et al. Examples include TLR1, TLR2, TLR3, TLR4, TLR5, TLR6, TLR7, TLR8, TLR9, TLR10 and TLR11. "TLR agonist" refers to a compound that upon binding a TLR, activates at least one TLR.

The terms "inhibiting," "reducing," or "prevention," or any variation of these terms, when used in the claims and/or the specification includes any measurable decrease or complete inhibition to achieve a desired result, such as inhibiting, reducing, or preventing viral infection, viral spread, viral growth, or viral transmission.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that one or more members of a list provided herein may be specifically excluded from or included in a claimed invention.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic representation of the three components of the lipopeptide construct, P25-P2C-HPV, used herein. (FIG. 1B) Mice vaccinated with P25-P2C-HPV via either the subcutaneous (s.c.) (FIGS. 1A and 1C) or intranasal (i.n.) routes (FIGS. 1B and 1D) were bled two weeks after the second immunization (wk 6) or two weeks after the third immunization (wk 10). The titer for HPV16 L2-specific antibody was determined by ELISA (FIGS. 1A and 1B). In vitro HPV16 neutralization titers were also determined (FIGS. 1C and 1D). HPV=HPV16 minor capsid protein L2 amino acids 17-36; P25 =Th epitope derived from the fusion protein of the morbillivirus canine distemper virus; Lys=lysine; Ser=serine; $Pam_2Cys$=lipid component of macrophage-activating lipopeptide 2; $OD_{405}$=optical density at 405 nm.

(FIGS. 2A and 2C) or i.n. routes (FIGS. 2B and 2D) were bled two weeks after the second immunization (wk6) or two weeks after the third immunization (wk10). The titer for HPV16 L2-specific antibody was determined by ELISA (FIGS. 2A and 2B). In vitro HPV16 neutralization titers were also determined (FIGS. 2C and 2D).

DETAILED DESCRIPTION OF THE INVENTION

Figure 1:
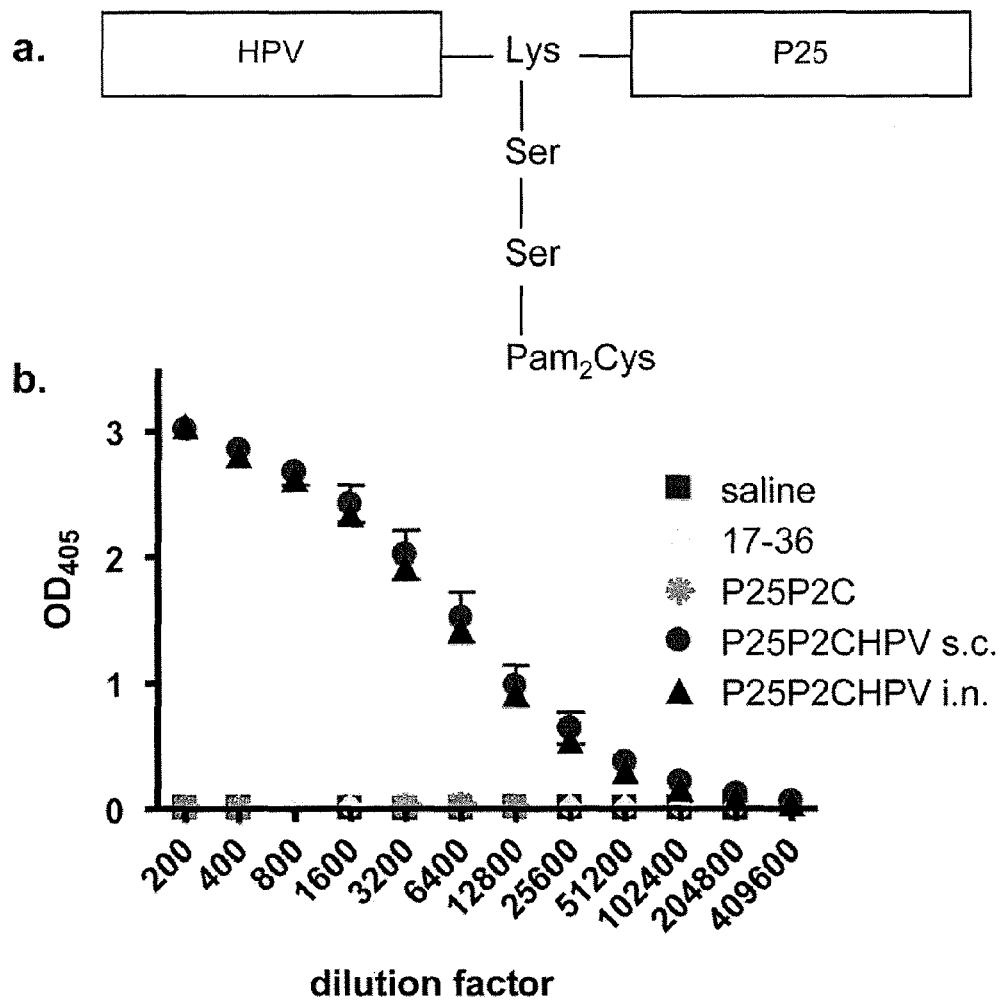
FIG. 1. The combination of the three components of the P25-P2C-HPV vaccine generate potent L2-specific antibody response.

Genital-tropic human papillomavirus (HPV) infections are the most common sexually transmitted infection in the United States and persistent infection with the high-risk subset of genotypes is a necessary cause of cervical cancer. Given the burden of cervical cancer in developing countries, a low-cost, broadly protective vaccine that can be delivered without needles is needed. The HPV capsid is composed of the major and minor antigens, L1 and L2, respectively. RG-1 is a cross-neutralizing and protective monoclonal antibody that recognizes HPV16 L2 residues 17-36. Since this epitope is highly conserved in divergent HPV types, the inventors contemplated broadly protective vaccination with HPV16 L2 17-36 peptide and other HPV L2 epitopes.

HPV epitopes were incorporated into synthetic multi-component constructs (e.g., a P25-P2C-HPV lipopeptide) produced by linkage of the HPV peptide with a broadly recognized T helper epitope (e.g., P25) and a TLR2 ligand (e.g., P2C). In contrast to vaccination with HPV16 L2 17-36 peptide or P25-P2C adjuvant alone, which failed to induce an L2-specific antibody response, a potent L2-specific antibody response was generated to the multi-component HPV composition when delivered either subcutaneously or intranasally. Sera from mice vaccinated with the multi-component HPV composition neutralized not only HPV 16 pseudovirions but also other evolutionarily divergent oncogenic genital (e.g., HPV 18, HPV 45) and cutaneous (HPV 5, BPV 1) types. Vaccination with a multi-component HPV composition protected mice from homologous challenge with HPV 16 pseudovirions at cutaneous and genital sites, and heterologous challenge with HPV 45 pseudovirions. Thus, HPV epitopes, if provided in the appropriate context, can be utilized in a synthetic cross-protective HPV vaccine.

I. Prophylactic and/or Therapeutic Compositions

Embodiments of the invention include HPV vaccines comprising an HPV epitope, a Th epitope, and an immune stimulating moiety, e.g, a TLR agonist. In certain aspects, the HPV epitope is a peptide comprising all or part of an HPV L2 amino acid sequence.

The methods of the present invention include prevention and/or treatment for a disease or condition caused by or related to papillomavirus infection (e.g., HPV infection). An immunogenic HPV peptide and/or antibody that binds the same, can be given to induce or provide a protective and/or therapeutic response in a person infected with or suspected of having been exposed to or at risk of becoming infected with HPV. Methods may be employed with respect to individuals who have tested positive for exposure to HPV or who are deemed to be at risk for infection based on possible exposure. In particular, the invention encompasses methods of treatment for HPV infection.

In some embodiments, the treatment is administered in the presence of adjuvants or carriers or other antigens, either HPV antigens or antigens from other pathogens. Furthermore, in some examples, treatment comprises administration of other agents commonly used against viral infection, such as one or more anti-virals.

A. HPV Vaccines

The present invention includes methods for preventing or ameliorating HPV infections. As such, the invention contemplates vaccines for use in both active and passive immunization embodiments. Immunogenic compositions, proposed to be suitable for use as a vaccine, may be prepared from immunogenic HPV peptide(s), such as the HPV L2 protein or immunogenic fragments thereof (e.g., fragments represented by amino acids 17-36, 1-88, 88-200 of SEQ ID NO:1, plus or minus 1, 2, 3, 4, 5, 6, 7, 8, 9 or 10 amino acids. In other embodiments, HPV L2 peptides can be used in combination with other HPV proteins or segments thereof, such as E1, E2, E3, E4, E5, E6, E7, E8, and/or L1 protein. See for example U.S. Pat. Nos. 7,425,438, 7,416,846, 7,416,732, 7,407,807, 7,374,767, 7,201,908, 7,189,513, and 7,288,258, each of which is incorporated herein by reference in its entirety.

Typically, vaccines are administered in a manner compatible with a vaccine formulation, and in such amount as will be therapeutically effective and/or immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of nanograms through several hundred micrograms of active ingredient per vaccination. Suitable regimes for initial administration and booster shots are also variable, but are typified by an initial administration followed by subsequent inoculations or other administrations.

1. HPV Epitopes

In certain aspects of the invention various segments of HPV polypeptides are used as the HPV epitope component. In certain aspects, the HPV polypeptide is an L2 polypeptide. In a further aspect the L2 polypeptide is a HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70; and animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPV), Rhesus monkey papillomavirus (RhPV) or rabbit oral papillomavirus (ROPV) L2 peptide epitope. The Human Papillomaviruses Compendium On Line compiles and publishes relevant molecular data concerning the human papillomaviruses (HPV) and related animal papillomaviruses. The compendium is accessed on the internet at (hpv-web.lanl.gov/stdgen/viras/hpv/compendium/htdocs/HTML_FILES/HPVcompintro4.html) and is incorporated by reference as of the priority date and filing date of this application.

Examples of L2 polypeptides can be found in publicly available protein databases such as GenBank (gb), SwissPro (sp), EMBL, and the like. Representative database entries, listed by HPV type with accession number in parenthesis, include, but are not limited to: HPV2 (gb/AAY86489, gb/ABN49461, gb/ABN49469, gb/AB014925, gb/NP 077121); HPV3 (sp/P36744); HPV7 (gb/NP_041858.1); HPV10 (gb/NP_041745); HPV16 (gb/AA085414, gb/AA015703, gb/AA015711, gb/AAQ10726, gb/AAV91650); HPV18 (gb/AAF14009, gb/ABP99710, gb/ABP99718, gb/ABP99726, gb/ABP99742, gb/ABP99766, gb/ABP99774, gb/ABP99782, gb/ABP99790, gb/ABP99798, gb/ABP99806, gb/NP 040316); HPV26 (gb/NP_041786.1); HPV27 (dbj/BAE16268, sp/P36755); HPV28 (sp/P50799); HPV29 (sp/P50800); HPV30 (sp/P36756); HPV33 (sp/P06418); HPV39 (gb/AAA47055); HPV40 (sp/P36760); HPV43 (sp/Q705H5); HPV45 (gb/AAY86493); HPV45 (gb/ABP99814, gb/ABP99854, gb/ABP99862, gb/ABP99870, gb/ABP99878, gb/ABP99894, gb/ABP99902, sp/P36761); HPV51 (sp/P26539); HPV52 (sp/P36763); HPV53 (gb/ABU54103, gb/ABU54117, gb/ABU54131, gb/ABU54152, gb/ABU54159, gb/ABU54173, gb/NP_041847); HPV56 (gb/AB076808, gb/AB076815, gb/AB076822, gb/AB076829, sp/P36765); HPV57 (dbj/BAF80485, sp/P22164); HPV58 (sp/P26538); HPV59 (emb/CAA54855); HPV61 (ref/NP_043449); HPV62 (sp/Q676U7); HPV66 (gb/AB076836, gb/AB076843, gb/AB076857, gb/AB076864, gb/AB076885, gb/AB076892, gb/AB076899, sp/Q80960); HPV68a (gb/AAZ39497); HPV69 (sp/Q9JH45); HPV70 (gb/AAC54856); HPV71 (gb/AAQ95182, gb/AAQ95189, gb/AAQ95203, ref/NP_597937); HPV72 (emb/CAA63878); HPV77 (emb/CAA75467); HPV81 (emb/CAF05697); HPV82 (gb/AAK28455, sp/Q91R53); HPV83 (gb/AAD38973); HPV84 (gb/AAK09276); HPV85 (gb/AAD24187); HPV86 (gb/AAL06740); HPV87 (emb/CAC17717); HPV89 (gb/AAM92156); HPV90 (ref/NP_671508); HPV91 (gb/AAM89135); HPV94 (dbj/BAD89178, emb/CAF05714); HPV97 (gb/AAZ39505, gb/AB027082); HPV102 (gb/AAZ39525); or HPV106 (gb/AAZ39518). Each amino acid sequence represented by the accession number is incorporated herein by reference as of the filing date of this application.

Peptides of the invention are typically synthesized using methods of peptide synthesis known to those skilled in the art, but the use of recombinant technologies to generate the peptides/polypeptides is also envisaged. For more detail see below.

2. T Helper Epitopes

Two types of major T lymphocytes have been described, CD8+ cytotoxic lymphocytes (CTLs) and CD4 helper cells (Th cells). CD8+ T cells are effector cells that, via the T cell receptor (TCR), recognize foreign antigens presented by class I MHC molecules on, for instance, virally or bacterially infected cells. Upon recognition of foreign antigens, CD8+ cells undergo an activation, maturation, and proliferation process. This differentiation process results in CTL clones which have the capacity of destroying the target cells displaying foreign antigens. T helper cells on the other hand are involved in both humoral and cell-mediated forms of effector immune responses. With respect to the humoral, or antibody immune response, antibodies are produced by B lymphocytes through interactions with Th cells. Specifically, extracellular antigens, such as circulating microbes, are taken up by specialized antigen presenting cells (APCs), processed, and presented in association with class II major histocompatibility complex (MHC) molecules to CD4+ Th cells. These Th cells in turn activate B lymphocytes, resulting in antibody production. The cell-mediated, or cellular immune response, in contrast, functions to neutralize microbes which inhabit intracellular locations, such as after successful infection of a target cell. Foreign antigens, such as for example, microbial antigens, are synthesized within infected cells and presented on the surfaces of such cells in association with Class I MHC molecules. Presentation of such epitopes leads to the above described stimulation of CD8+ CTLs, a process which in turn is also stimulated by CD4+ Th cells. Th cells are composed of at least two distinct subpopulations, termed Th1 and Th2 cells. The Th1 and Th2 subtypes represent polarized populations of Th cells which differentiate from common precursors after exposure to antigen.

In some aspects, it is preferred that a component of a vaccine be selected to be a preferential inducer of either a Th1 or a Th2 or a Th17 type of response.

The distinction between Th1, Th2 and Th17-type immune response is not absolute. In reality an individual will support an immune response which is described as being predominantly Th1 or predominantly Th2 or predominantly Th17. However, it is often convenient to consider the families of cytokines in terms of that described in murine CD4+ T cell clones by Mosmann and Coffman (Mosmann and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10, whereas Th17-type responses are associated with IL-17 and IL-23.

In certain aspects, Th epitopes include, but are not limited to T-cell epitopes derived from bacterial proteins and toxins, such as Tetanus and Diphtheria toxins. For example, the P2 and P30 epitopes from Tetanus toxin, Hepatitis B core antigen, tuberculosis, *Mycobacterium tuberculosis* RA12 (a subsequence (amino acids 192 to 323) of MTB32A (Skeiky et al. 1999)), p25 protein of morbillivirus/canine distemper virus: KLIPNASLIENCTKAEL (SEQ ID NO:5) PV (poliovirus) sequence 103-115: KLFAVWKITYKDT (SEQ ID NO:6) M5: NKLIAYPAVEALS (SEQ ID NO:7), TT (tetanus toxin) 830-844: QYIKANSKFIGITEL (SEQ ID NO:8), PADRE: aKXVMWTLKAAa (a=D-Ala, X=L-cyclohexyl-Ala) (SEQ ID NO:9), E7 p20-29 TDLYCYEQLN (SEQ ID NO:10), E7 p45-54: AEPDRAHYNI (SEQ ID NO:11), E7 p60-79: KCD-STLRLCVQSTHVIRTL (SEQ ID NO:12), E7 p85-94: GTL-GIVGPIC (SEQ ID NO:13), ras p5-17: KLV-VVGARGVGKS (SEQ ID NO:14), neu p42-56: HLDMLRHLYQGGQVV (SEQ ID NO:15), neu p783-797, SRLLGICLTSTVQLV (SEQ ID NO:16), and MAGE-3$_{121-134}$: LLKYRAREPVTKAE (SEQ ID NO:17)).

3. Immune Stimulatory Moiety and Toll-Like Receptor Agonist

An immune stimulatory moiety is a moiety that stimulates or otherwise enhances an immune response to the target antigen or to a plurality of target antigens (e.g., cytokines or TLR agonist).

It is now widely recognized that the generation of protective immunity depends not only on exposure to antigen, but also the context in which the antigen is encountered. Numerous examples exist in which introduction of a novel antigen into a host in an inflammatory context generates immunological tolerance rather than long-term immunity whereas exposure to antigen in the presence of an inflammatory agent (adjuvant) induces immunity. (Mondino et al., 1996; Pulendran et al., 1998; Jenkins et al., 1994; and Kearney et al., 1994). Since it can mean the difference between tolerance and immunity, much effort has gone into discovering the "adjuvants" present within infectious agents that stimulate the molecular pathways involved in creating the appropriate immunogenic context of antigen presentation. It is now known that a good deal of the adjuvant activity is due to interactions of microbial and viral products with different members of the Toll Like Receptors (TLRs) expressed on immune cells (Beutler et al, 2004; Kaisho, 2002: 1; Akira et al., 2003; and Takeda and Akira, 2004). The TLRs are named for their homology to a molecule in the *Drosophila*, called Toll, which functions in the development thereof and is involved in anti-microbial immunity (Lemaitre et al., 1996; and Hashimoto et al., 1988).

Early work showed the mammalian homologues to Toll and Toll pathway molecules were critical to the ability of cells of the innate immune system to respond to microbial challenges and microbial byproducts (Medzhitov et al., 1997; Medzhitov et al., 1998; Medzhitov et al., 2000; Medzhitov et al., 2000; and Janeway et al., 2002). Since the identification of LPS as a TLR4 agonist (Poltorok et al., 1998) numerous other TLR agonists have been described such as tri-acyl lipopeptides (TLR1), peptidoglycan, lipoteichoic acid and Pam3Cys (TLR2), dsRNA (TLR3), flagellin (TLR5), diacyl lipopeptides such as Malp-2 (TLR6), imidazoquinolines and single stranded RNA (TLR7,8), bacterial DNA, unmethylated CpG DNA sequences, and even human genomic DNA antibody complexes (TLR9). Takeuchi et al., 2001; Edwards et al., 2002; Hayashi et al., 2003; Nagase et al., 2003).

TLR2 agonist (i.e., a compound that, upon association with a TLR2, activates TLR2) include, but are not limited to lipoteichoic acid, mannuronic acids, peptidoglycans, atypical LPS, MALP-2 and MALP-404 (lipoproteins), OspA, Porin, LcrV, lipomannan, lysophosphatidylserine, lipophosphoglycan (LPG), glycophosphatidylinositol (GPI), zymosan, and analogs or derivatives thereof. In a further aspect, TLR2 agonist include bacterial lipopeptide from *M. tuberculosis, B. burgdorferi, T pallidum; peptidoglycans* from species including *Staphylococcus aureus; Neisseria porins*, bacterial fimbriae, *Yersina virulence* factors, CMV virions, measles haemagglutinin, and zymosan from yeast. In certain aspects, the TLR agonist is a lipid moiety. Lipid moieties include, but are not limited to fatty acids such as palmitoyl, myristoyl, stearoyl and decanoyl groups or, more generally, any C2 to C30 saturated, monounsaturated, or polyunsaturated fatty acyl group. In certain aspects the lipid moiety is a Pam$_2$Cys [S-[2,3-bis(palmitoyloxy)propyl]cysteine] or Pam$_3$Cys [N-palmitoyl-S-[2,3-bis(palmitoyloxy)propyl]cysteine] moiety. Pam$_3$Cys or Pam$_3$Cys-OH (Wiesmuller et al., 1983), is a synthetic version of the N-terminal moiety of Braun's lipoprotein that spans the inner and outer membranes of Gram negative bacteria. U.S. Pat. No. 5,700,910 describes several N-acyl-S-(2-hydroxyalkyl)cysteines for use as intermediates in the preparation of lipopeptides that are used as synthetic adjuvants, B lymphocyte stimulants, macrophage stimulants, or synthetic vaccines.

Additional TLR agonists are described in U.S. Patent Publication 20080145375, which is incorporated herein by reference in its entirety.

4. Linker

In certain aspects, one or more component of the invention can be separated by a linker or spacer. Linker or spacer can comprise 1, 2, 3, 4, 5, 6, 7, 8, 9, 10 or more amino acids or molecules. In certain aspects, a TLR agonist (e.g., lipid moiety) is attached to a peptide moiety via the epsilon amino group of a lysine residue or the terminal side-chain group of an internal lysine analog residue positioned between the amino acid sequences of the T helper epitope and the HPV L2 peptide. In other aspects cysteine residues may also be used as a conjugation point. By "internal" means at a location other than the N-terminus or the C-terminus of a polypeptide comprising a T helper epitope and antigenic B cell epitope. In other aspects the TLR agonist can be attached via a terminal or approximately terminal residue. An amino acid spacer can be added at either side of the internal lysine or lysine analog to which the lipid moiety is to be attached, such as, for example, between the T-helper and B-cell epitopes.

A spacer peptide is generally of a flexible nature, although other chemical linkages are not excluded. Currently, it is contemplated that the most useful linker sequences will generally be peptides of between about 2 and about 40 amino acids in length, e.g., from about 2 amino acids to about 10 amino acids, from about 10 amino acids to about 20 amino acids, or from about 6 amino acids to about 25 amino acids in length. The linking peptides may have virtually any amino acid sequence. The use of small amino acids, such as glycine and alanine, can be used in forming a peptide linker. For example, peptide linkers include $(Gly)_{2-40}$, $(Ser)_{2-40}$, and $(Ala)_{2-40}$. The creation of such sequences is routine to those of skill in the art. A variety of different linkers are commercially available and are considered suitable for use according to the present invention. However, any linker generally between about 2 amino acids and about 40 amino acids, e.g., from about 6 amino acids to about 10 amino acids in length may be used.

Linkages for homo- or hetero-polymers or for coupling to carriers can be provided in a variety of ways. For example, cysteine residues can be added at both the amino- and carboxyl-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, Jansen et al. (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particular coupling agent is succinimidyl 4-(N-maleimidomethyl)cyclohexane-1-carboxylate (SMCC). It will be understood that linkage should not substantially interfere with either of the linked groups to function for its intended use, e.g., as an immunogen.

5. Peptide Synthesis and Conjugation

Typically, HPV epitopes and/or Th epitopes are synthesized using conventional methods as modified for the particular amino acid sequences. Such techniques include, but are not limited to methods well known to those skilled in the art of peptide synthesis, e.g., solution phase synthesis [see Finn and Hoffman, 1976], or solid phase synthesis [see Barany and Merrifield, 1979], or stepwise solid phase synthesis as reported by Merrifield et al., 1963], the contents of each of which are incorporated herein by reference. Other references to peptide synthesis techniques include peptides synthesized by the Fmoc-polyamide mode of solid-phase peptide synthesis as disclosed by Lu et al. (1981), peptides synthesized using an Fmoc/tBu procedure (Atherton and Sheppard, 1989). Fmoc amino acids can be obtained from various vendors, e.g., Chem-Impex International (Wood Dale, Ill., USA), Merck Biosciences (Nottingham, UK), and Bachem UK Ltd. (St. Helens, UK).

After or during synthesis a peptide can be conjugated to a spacer, amino acid, or lipid. In certain aspects, the terminal side chain group of a lysine or a lysine analog (e.g., epsilon amino group of the internal lysine) is protected by one of a number of protecting groups. Blocking groups or protecting groups or masking groups are used to protect the amino group of the amino acid having an activated carboxyl group that is involved in the coupling reaction, or to protect the carboxyl group of the amino acid having an acylated amino group that is involved in the coupling reaction. For coupling to occur, a blocking group must be removed without disrupting a peptide bond, or any protecting group attached to another part of the peptide. Peptides can be lipidated by methods well known in the art. Standard condensation, addition, substitution or oxidation (e.g., disulfide bridge formation or amide bond formation between a terminal amino group on the internal lysine or lysine analog with the carboxy terminal group of an incoming amino acid or peptide or lip amino acid) reactions result in the addition of lipid to the peptide.

The present invention also provides recombinant cloning and expression vectors containing DNA, as well as host cell containing the recombinant vectors. Expression vectors comprising DNA may be used to prepare the polypeptides or polypeptide fragments of the invention encoded by a DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell. Polypeptides of the invention can include various leader sequences that direct trafficking or assist in purification.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells.

Appropriate cloning and expression vectors for use with bacterial, fungal, yeast, and mammalian cellular hosts are described, for example, in Pouwels et al. (1985). Cell-free translation systems could also be employed to produce polypeptides using RNAs derived from DNA constructs disclosed herein.

B. Adjuvants

The immunogenicity of polypeptide or peptide or lipopeptide compositions can be enhanced by the use of additional non-specific stimulators of the immune response, known as adjuvants. Suitable adjuvants include all acceptable immunostimulatory compounds, such as cytokines, toxins, or synthetic compositions such as alum.

A number of adjuvants can be used to enhance an antibody response against a lipopeptide or any other composition described herein. Adjuvants can be used to (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GM-CSF, BCG, aluminum salts, such as aluminum hydroxide or other aluminum compound, MDP compounds, such as thur-MDP and nor-MDP, CGP (MTP-PE), lipid A, and monophosphoryl lipid A (MPL), or inactivated microbial agents. RIM, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (FLUOSOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

C. Lipid Components and Moieties

In certain embodiments, the present invention concerns compositions comprising one or more lipids non-covalently associated with a lipopeptide/polypeptide/peptide. A lipid is a substance that is insoluble in water and extractable with an organic solvent. Compounds other than those specifically described herein are understood by one of skill in the art as lipids, and are encompassed by the compositions and methods of the present invention.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A lipopeptide/polypeptide/peptide, associated with a lipid may be dispersed in a solution containing a lipid, dissolved with a lipid, emulsified with a lipid, mixed with a lipid, combined with a lipid, contained as a suspension in a lipid or otherwise associated with a lipid. A lipid-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL) or Superfect (Qiagen) complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% weight percent lipid, or any range or value there between, of a particular lipid, lipid type, or non-lipid component such as an adjuvant, sugar, nucleic acid or other material disclosed herein or as would be known to one of skill in the art. Thus, it is contemplated that compositions of the present invention may comprise any of the lipids, lipid types or other components in any combination or percentage range.

D. Formulation and Administration

The manner of application may be varied widely. Any of the conventional methods for administration of a vaccine are applicable. These are believed to include oral application on a solid physiologically acceptable base or in a physiologically acceptable dispersion, parenterally by injection, inhalation of a powder, via transcutaneous patch, via vaginal instillation and the like. The dosage of the vaccine will depend on the route of administration and will vary according to the size and health of the subject.

The preparation of vaccines that contain polypeptide or peptide sequence(s) as active ingredients is generally well understood in the art, as exemplified by U.S. Pat. Nos. 4,608, 251; 4,601,903; 4,599,231; 4,599,230; 4,596,792; and 4,578, 770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be administered by inhalation. In certain embodiments a vaccine can be administered as an aerosol. As used herein the term "aerosol" or "aerosolized composition" refers to a suspension of solid or liquid particles in a gas. The terms may be used generally to refer to a composition that has been vaporized, nebulized, or otherwise converted from a solid or liquid form to an inhalable form including suspended solid or liquid drug particles. Such aerosols can be used to deliver a vaccine via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a vaccine to the respiratory system indicates that a drug is delivered to one or more of the air passages of the respiratory system, in particular to the lungs.

Additional formulations which are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptide, peptide, and lipopeptide compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In many instances, it will be desirable to have multiple administrations of the vaccine, usually at most, at least, or not exceeding 1, 2, 3, 4, 5, 6, 7, 8, 9, 10, 11, 12, 13, 14, 15, or more vaccinations including all ranges there between. The vaccinations will normally be at 1, 2, 3, 4, 5, 6, to 5, 6, 7, 8, 9, 10, 11, to 12 week/month/year intervals, including all values and ranges there between, more usually from three to five week intervals. Typically, periodic boosters at intervals of 1-15 years, usually ten years, will be desirable to maintain protective levels of the antibodies. The course of the immunization may be followed by assays for antibodies against the antigens, as described supra, U.S. Pat. Nos. 3,791,932; 4,174,384 and 3,949,064, which are illustrative of these types of assays.

E. Combination Therapy

The compositions and related methods of the present invention, particularly administration of an HPV epitope, including a polypeptide or peptide of an HPV L2 protein to a patient/subject, may also be used in combination with the administration of traditional HPV screening and/or other vaccines, including, but not limited to, antibodies or antibody fragments, Pap smears, PCR, Southern blotting, administering CERVARIX™, GARDASIL™, vaccines for HPV or other infectious agents, ablative therapy of HPV lesions, immunomodulatory therapies for HPV lesions (e.g. Aldara™), or the like.

In one aspect, it is contemplated that an HPV peptide composition and/or therapy is used in conjunction with HPV screening and/or other treatment. Alternatively, the therapy may precede or follow the other treatment by intervals ranging from minutes to weeks. In embodiments where the other agents are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several months (1, 2, 3, 4, 5, 6, 7, 8, 9, 10, 11, 12), or years (2, 3, 4, 5, 6, 7, 8, 9, 10, 11, 12) lapse between the respective administrations.

Various combinations may be employed, for example a lipopeptide therapy is "A" and another vaccine or antibody given as an immune therapy, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the immunogenic compositions of the present invention to a patient/subject will follow general protocols for the administration of such compounds, taking into account the toxicity, if any, of the lipopeptide composition, or composition of any other antigen or antigen combination described herein. It is expected that the treatment cycles would be repeated as necessary. It also is contemplated that various standard therapies, such as hydration, may be applied in combination with the described therapy.

II. Therapeutic Methods

In some embodiments, pharmaceutical compositions are administered to a subject. Different aspects of the present invention involve administering an effective amount of a composition to a subject. In some embodiments of the present invention, lipopeptide comprising an HPV epitope are administered to the patient to protect against or treat infection by one or more HPV pathogens. Such compositions will generally be dissolved or dispersed in a pharmaceutically acceptable carrier or aqueous medium.

As used herein, the term "pharmaceutically acceptable" or "pharmacologically acceptable" refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent. Pharmaceutically acceptable carrier includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present invention can be formulated for parenteral administration, e.g., formulated for injection via the intravenous, intramuscular, sub-cutaneous, or even intraperitoneal routes. In addition to the compounds formulated for aerosol or parenteral administration, such as those for intravenous or intramuscular injection, other pharmaceutically acceptable forms include, e.g., tablets or other solids for oral administration; time release capsules.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The lipopeptide compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, respiratory, or intravenous administration. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

A. In Vitro, Ex Vivo, or In Vivo Administration

As used herein, the term in vitro administration refers to manipulations performed on cells removed from or outside of an animal, including, but not limited to cells in culture. The term ex vivo administration refers to cells which have been manipulated in vitro, and are subsequently administered to a living animal. The term in vivo administration includes all manipulations performed within an animal.

In certain aspects of the present invention, the compositions may be administered either in vitro, ex vivo, or in vivo. In certain in vitro embodiments, autologous B-lymphocyte cell lines are incubated with a HPV peptide composition(S). The activated cells can then be used for in vitro analysis, or alternatively for ex vivo administration.

B. Antibodies And Passive Immunization

Another aspect of the invention is a method of preparing an immunoglobulin for use in prevention or treatment of HPV infection comprising the steps of immunizing a recipient with a vaccine of the invention and isolating immunoglobulin or antibodies from the recipient, and/or recombinantly producing such immunoglobulins or fragments thereof. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of HPV infection. A method for treatment or prevention of HPV infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, 1988).

Antibodies can include antiserum preparations from a variety of commonly used animals, e.g., goats, primates, donkeys, swine, horses, guinea pigs, rats, or man. The animals are bled and serum recovered.

An immunoglobulin produced in accordance with the present invention can include whole antibodies, antibody fragments or subfragments. Antibodies can be whole immunoglobulins of any class, e.g., IgG, IgM, IgA, IgD or IgE, chimeric antibodies or hybrid antibodies with dual specificity to two or more antigens of the invention. They may also be fragments, e.g., F(ab')2, Fab', Fab, Fv and the like including hybrid fragments. An immunoglobulin can also include natural, synthetic, or genetically engineered proteins that act like an antibody by binding to specific antigens to form a complex.

An HPV composition or vaccine of the present invention can be administered to a recipient who then acts as a source of immunoglobulin, produced in response to challenge from the HPV composition. A subject thus treated would donate plasma from which hyperimmune globulin would be obtained via conventional plasma fractionation methodology. The hyperimmune globulin would be administered to another subject in order to impart resistance against or treat HPV infection. Hyperimmune globulins of the invention are particularly useful for treatment or prevention of HPV infection in infants, immune compromised individuals or where treatment is required and there is no time for the individual to produce antibodies in response to vaccination.

An additional aspect of the invention is a pharmaceutical composition comprising one or more monoclonal antibodies (or fragments thereof; preferably human or humanized) reactive against constituents of the immunogenic composition of the invention, which could be used to treat or prevent infection by one or more HPV type.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be human, humanized, or partly humanized by known methods.

III. Kits

Another aspect of the invention is a kit for vaccination or treatment according to the present invention. In one embodiment, the kit comprises a vial and optionally a package insert with administration instructions, the vial comprises a lipopeptide composition or vaccine for administration according to the methods of the present invention.

Any of the compositions described herein may be comprised in a kit. In a non-limiting example, reagents for preparing a lipopeptide, formulating a lipopeptide, and/or administering a lipopeptide, or antibodies generated by vaccination with lipopeptide can be included in a kit. The kit may further include reagents for assessing the activity of the lipopetide both in vitro and in vivo. The kits will thus comprise, in suitable container means, a lipopeptide composition. In certain aspects, the kit can include reagents and/or devices for administration, e.g., inhaler or nebulizer. It may also include one or more buffers, compounds, or devices for preparing the composition for administration.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the preparation and/or administration of a lipopeptide vaccine.

IV. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

A. Materials and Methods

Synthesis and assembly of lipidated, epitope-based vaccine. The assembly, purification and characterization of synthetic lipopeptides has been described in detail elsewhere (Zeng et al., 2002, which is incorporated herein by reference). All peptide constructs were synthesized using standard Fmoc chemistry. In brief, the vaccine consisted of the P25 Th epitope synthesized contiguously with and N-terminally to the broadly neutralizing epitope of HPV16 minor capsid protein L2 residues 17-36 (QLYKTCKQAGTCPPDIIPKV (SEQ ID NO:4)). The Th epitope (P25) has the sequence KLIPNASLIENCTKAEL (SEQ ID NO:5) and is derived from the fusion protein of the morbillivirus canine distemper virus (Ghosh et al., 2001). P25 and the HPV16 L2 17-36 epitope were separated in sequence by a single lysine residue. The lipid moiety $Pam_2Cys$, corresponding to the lipid component of macrophage-activating lipopeptide 2 (MALP-2) isolated from mycoplasma (Muhlradt et al., 1997), was attached to the $\epsilon$-amino group of the intervening lysine through two serine residues. A diagrammatic representation of the structure can be found in FIG. 1 (Jackson et al., 2004).

Immunization of mice. All animal experimental work was done in accordance with Johns Hopkins Medical Institutions Animal Care and Use Committee guidelines. BALB/c and C57BL/6 (NCI, Frederick, Md.) wild type or MyD88 (D. Golenbock, UMass Medical Center, Amherst, Mass.), CD40, or MHCII deficient mice (Jackson Laboratories, Bar Harbor, Me.) were used. Mice aged 4-6 wks were immunized with P25-P2C-HPV vaccine or various controls. All vaccine and control peptides were dissolved in phosphate-buffered saline (PBS). Mice received two booster immunizations at 4 wks and 8 wks after priming immunization in the same fashion and dose. (i) subcutaneous (s.c.): Each mouse was administered 20 nmols of vaccine in a total volume of 100 μL or an equivalent amount of several control preparations at the base of the tail. (ii) intranasal (i.n.): Anesthesia induction was accomplished within 3 to 5 mins using a chamber filled with 2.5% isoflurane (Baxter, Deerfield, Ill.). While anesthetized, each mouse was administered 20 nmols of lipopeptide in a total volume of 50 μL of vaccine or an equivalent amount of several control preparations via controlled micropipetting into the nares.

Collection and quantification of HPV specific antibody responses. Blood was collected from mice via the tail artery at 6 and 10 wks after priming immunization. Samples were allowed to clot for 12 hr at 4° C.; and after centrifugation for 10 min at 1000×g, antiserum was subsequently decanted. Presence of serum antibodies against HPV16 was assessed by enzyme-linked immunosorbent assays (ELISA). MAX-ISORP™ flat-bottom 96-well plates (Nunc, Rochester, N.Y.) were coated with 100 ng/well of HPV16 L2 17-36 (Sigma Genosys, St. Louis, Mo.), HPV16 L2 11-200, whole L2 protein or HPV16 VLPs (see below) in 0.05 M carbonate buffer at pH 9.6 for 12 hr in 4° C. The plates were blocked with 200 μl of 1% bovine serum albumin in PBS for 1 hr at room temperature. Two-fold serial dilutions of each serum sample were assayed, starting at a dilution of 1:200, and incubated for 1 hr at room temperature. After being washed with 0.05% Tween 20 in PBS (PBST), the plates were incubated for another 1 hr at 37° C. with sheep anti-mouse immunoglobulin G (IgG) coupled to horseradish peroxidase (Amersham Biosciences, Buckinghamshire, England) in 1% bovine serum albumin in PBS. The plates were washed with PBST and developed with 100 μL of ABTS (2,2'-azino-bis(3-ethylbenzthiazoline-6-sulphonic acid) solution (Roche Biosciences, Indianapolis, Ind.). After 30 min of incubation at room temperature, the absorbance was read at 405 nm with a reference wavelength of 490 nm using a BENCHMARK PLUS™ microplate spectrophotometer (Biorad, Hercules, Calif.). The antibody titers were reported as the reciprocals of the highest dilution showing positive reactivity in each assay. Sera were designated ELISA positive at a given dilution if the absolute optical density was greater than or equal to four standard deviations (SDs) above the mean optical density of control wells in which preparations containing pre-immune mouse serum was used as the primary antibody.

Production and Purification of HPV Pseudovirions. Pseudovirions were produced as previously described (Buck et al., 2004; Buck et al., 2005; Pastrana et al., 2001). Briefly, plasmids encoding L1 and L2 genes were cotransfected into 293TT cells along with a reporter plasmid encoding either secreted alkaline phosphatase (pYSEAP) (Pastrana et al., 2004), luciferase (pYLUC) or RFP (p8RwB or ptwB) (Roberts et al., 2007). After 48 hrs, cells were lysed with 0.2% Brij-58, 9.5 mM $MgCl_2$, 0.1-0.2% Benzonase (Sigma-Aldrich, St. Louis, Mo.) and 0.1% PLASMID-SAFE™ ATP-Dependent DNase (Epicentre Biotechnologies, Madison, Wis.) and incubated at 37° C. for 15 min. The resulting pseudovirions were then matured by overnight incubation of the lysates at 25° C. overnight (Buck et al., 2005). Mature pseudovirions were solubilized by addition of 0.17 volumes of 5 M NaCl, clarified by low speed (1500×g) centrifugation, and finally purified on a preformed 27%, 33%, and 39% Optiprep (Sigma-Aldrich) step gradient. Optiprep fractions containing SEAP-, luciferase- or RFP-transducing activity were finally pooled and stored at −80° C.

In vitro neutralization of HPV pseudovirions. The in vitro neutralization of pseudovirions has been described elsewhere (Buck et al., 2004; Buck et al., 2005; Pastrana et al., 2001). Detailed protocols regarding the in vitro neutralization of HPV pseudovirions can be found on the worldwideweb at: home.ccr.cancer.~ov/lco/assays.asp. Serum from individual mice was collected and serially diluted two-fold, using a 1:50 dilution as the initial concentration tested. Diluted sera were incubated with pYSEAP containing pseudovirions in colorless DMEM (10% FBS, penicillin/streptomycin) at 4° C. for 1 hr. The pseudovirus solution was then used to infect 293TT cells. Supernatants were analyzed for SEAP activity after 54 hr using 2M diethanolamine in water with 1 mM $MgCl_2$ and 0.5 mM $ZnCl_2$ adjusted to a pH 9.8. Neutralization titers were reported as the reciprocals of the highest dilution showing 50% reduction in SEAP activity in each assay.

Cutaneous HPV challenge. A patch of skin on the ventral torso of anesthetized BALB/c mice was shaved with an electric razor, taking care not to traumatize the epithelium. Challenge was performed by application of $3\times10^9$ pYLUC-expressing pseudovirion particles (100 ng) in 10 μl 0.6% carboxymethylcellulose (CMC, Sigma) to the freshly shaved epithelial patches. Three days later, mice were reanesthetized, injected with luciferin (100 µl at 7 mg/ml) and their image acquired for 10 min with an IVIS 200 bioluminescent imaging system (Xenogen, Cranbury, N.J.). Equal areas encompassing the site of virus inoculation were analyzed using Living Image 2.20 software (Xenogen), and background was determined by challenge with non-infectious HPV pseudovirions lacking L2.

Vaginal HPV challenge. Female BALB/c mice aged 6-8 wks were pre-treated 4 days prior to infection by s.c. injection of 3 mg of DEPO-PROVERA™ (Pfizer Inc, Groton, Conn.). The mice were anesthetized by isoflurane inhalation as described above. To mimic the micro-trauma of coitus, a standard plastic cytobrush (Fisher Scientific, Pittsburgh, Pa.) was gently rotated 10 times within the vaginal vault. An aliquot of $4.5 \times 10^7$ HPV16 pseudovirion particles containing L1 and L2 capsid proteins and the encapsidated RFP reporter construct and suspended in 10 µl 0.6% CMC (Sigma) was instilled in the vagina using a 10 µl siliconized pipette tip. Mice were sacrificed at 72 hours post challenge and their genital tracts (uterine horns, cervix and vaginal tract) dissected, isolated, and splayed opened to reveal the mucosal epithelium. Specimens were stored in PBS on ice for no more than 6 hrs prior to imaging. A Maestro (CRi, Woburn, Mass.) imaging device with a green excitation filter and a 580-nm long-pass emission filter was used to obtain images from 550 nm to 900 nm in 10-nm wavelength increments. Using the spectral signature of RFP in infected tissues as signal, and the background autofluorescence in uninfected tissues as noise, a spectral unmixing algorithm was applied to the composite images to determine the intensity and location of infection. The open-source software Image J was used to calculate the mean signal per pixel in a region of interest (ROI) in the grayscale representation of unmixed signal.

B. Results

P25-P2C-HPV generates potent immune responses. To measure immune responses generated by vaccination with P25-P2C-HPV, sera from immunized mice were tested using HPV16 L2 17-36 peptide (FIG. 1B), HPV 16 L2 11-200 polypeptide (data not shown), whole L2 protein (data not shown) and HPV 16 VLP (data not shown) enzyme-linked immunosorbent assays (ELISAs). Subcutaneous and intranasal preparations of P25-P2C-HPV vaccine generate potent immune responses as measured by optical densities from these assays. Multiple analysis of variance (MANOVA) demonstrates that immune response to vaccination with P25-P2C-HPV vaccines were significantly different than the response produced by control immunizations ($P \ll 0.0001$). Within group analysis of HPV16 L2 17-36 ELISAs shows that these differences are significant to titers of 51,200. Further analysis with Bonferoni pairwise comparisons establish that HPV16 L2 17-36 peptide alone or P25-P2C adjuvant alone generate immune responses similar to saline controls ($P > 0.05$). Vaccination was thus found to only be effective when all elements of the lipopeptide are present together.

Figure 3:
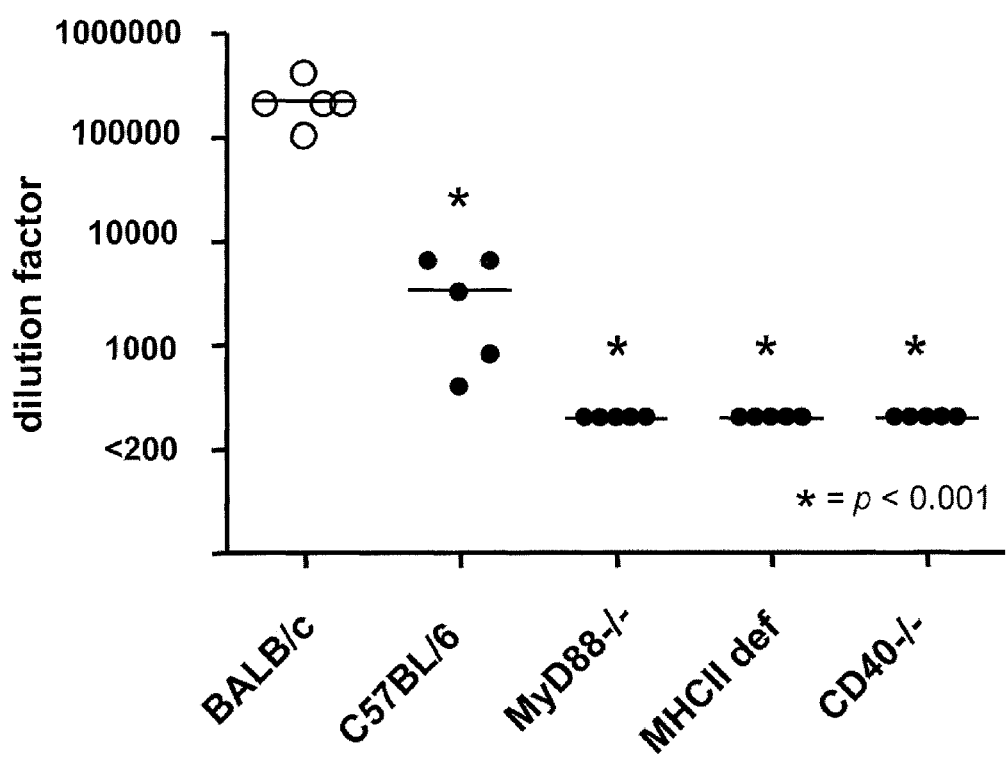
FIG. 3. MHCII and MyD88 signaling are critical for an L2-specific antibody response to P25-P2C-HPV. BALB/c or C57BL/6 wild type mice as well as MyD88 deficient, MHCII deficient or CD40 deficient mice were three times vaccinated s.c. with P25-P2C-HPV and were bled two weeks after the third immunization (week 10). The titer of HPV16 L2-specific antibody was determined by ELISA. L2-specific antibody was not detected in sera diluted at 1:200 derived from MyD88 deficient, MHCII deficient or CD40 deficient mice that were vaccinated with P25-P2C-HPV.

Sera from P25-P2C-HPV vaccinated mice neutralize HPV16 pseudovirions. To test the ability of antibodies generated by immunization with P25-P2C-HPV vaccine to neutralize homologous HPV virions, the antisera from P25-P2C-HPV mice were titrated in an HPV 16 pseudovirion infectivity assay. Vaccination with P25-P2C-HPV induced equivalently high titers of HPV16 neutralizing antibody regardless of the route of administration. ($P > 0.05$; FIG. 3). However, in contrast to the L2 ELISA data reported above, analysis of HPV16 neutralization titers across two different timepoints show that P25-P2C-HPV vaccinated mice generated significantly different immune responses after second and third immunizations in both groups ($P < 0.05$ for s.c, $P < 0.01$ for i.n.; FIGS. 3C and 3D). These findings suggest that the third P25-P2C-HPV immunization confers an increased neutralizing serum antibody titer for both s.c. and i.n. vaccinated mice.

Sera from P25-P2C-HPV vaccinated mice cross-neutralize multiple heterologous HPV pseudovirions. Because L2 17-36 has been previously shown to be a highly conserved epitope across multiple HPV subtypes (Gambhira et al., 2007), the inventors studied the ability of mice antiserum generated by three immunizations with P25-P2C-HPV vaccine to neutralize heterologous HPV5, HPV18, HPV45 and BPV1 pseudovirions. Using serial dilutions of antiserum, mean neutralization titers of 1:5320, 1:2845, 1:360, 1:110 and 1:180 were obtained for HPV16, HPV5, HPV18, HPV45 and BPV1 pseudovirions, respectively.

Figure 2:
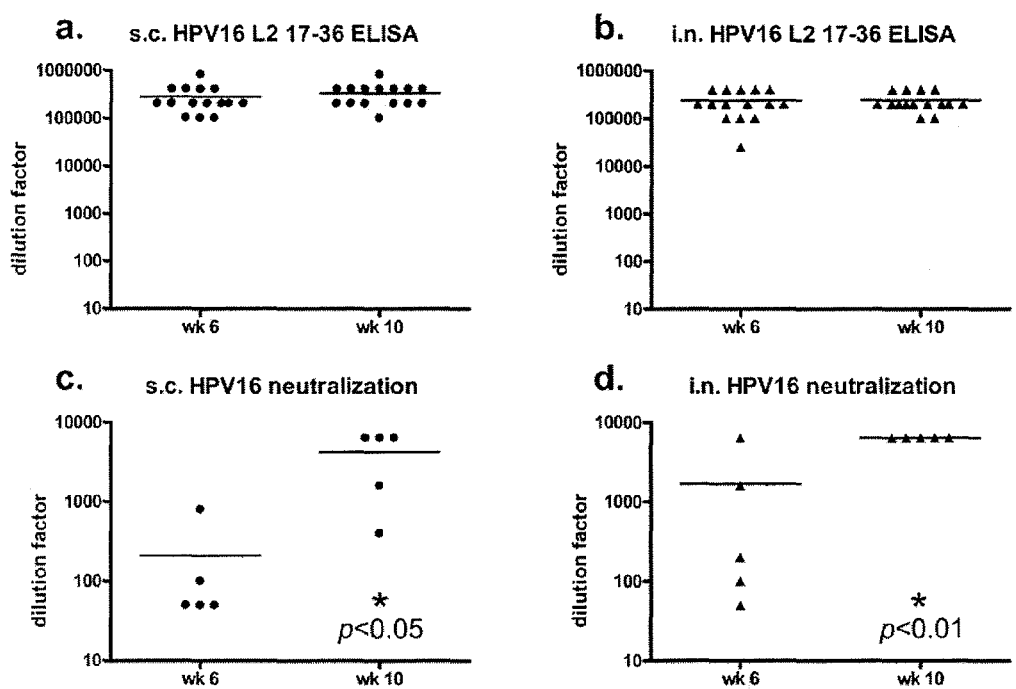
FIG. 2. Vaccination with P25-P2C-HPV via subcutaneous or intranasal routes induces high titers of L2-specific HPV16 neutralizing serum antibodies. BALB/c mice vaccinated with P25-P2C-HPV via either the s.c.

L2 Antibody response to P25-P2C-HPV is dependent upon MyD88, MHCII and CD40. To further understand the mechanism by which P25-P2C-HPV stimulates the production of L2-specific antibodies, mice deficient for the TLR signaling mediator MyD88 were immunized with the P25-P2C-HPV lipopeptide construct. These mice failed to generate detectable antibody (FIG. 2), consistent with the previously identified role of MyD88 in the downstream signaling initiated by TLR-Pam$_2$Cys ligand interactions. Likewise, both MHCII and CD40 deficient mice also failed to generate L2-specific antibodies after vaccination with P25-P2C-HPV (FIG. 2), further supporting the importance of T help in the mechanism of immunogenicity. The P25 epitope is poorly recognized by MHCII $D^b$ in the C57BL/6 background as opposed to the robust interaction with MHCII $H^k$ in the BALB/c strain. Consistent with this observation, a significantly lower L2-specific antibody response to P25-P2C-HPV vaccination was observed in C57BL/6 as compared to BALB/c mice (FIG. 2).

Intranasal vaccination with P25-P2C-HPV. To investigate potential alternative needle-free routes of immunization with the P25-P2C-HPV vaccine, BALB/c mice were immunized with the lipopeptide construct both subcutaneously and intranasally. Titers from sera of s.c. and in immunized mice were measured two weeks after second and third immunizations (FIGS. 3A and 3B). Simple t-tests comparing i.n. and s.c. routes of administration demonstrate generation of equivalent L2-specific serum antibody titers in these groups ($P > 0.05$) at both time points. Further analysis of L2 antibody titers show that both s.c. and i.n. P25-P2C-HPV vaccinated BALB/c mice generated similar titers after two or three immunizations ($P > 0.05$; FIGS. 3A and 3B).

Figure 4:
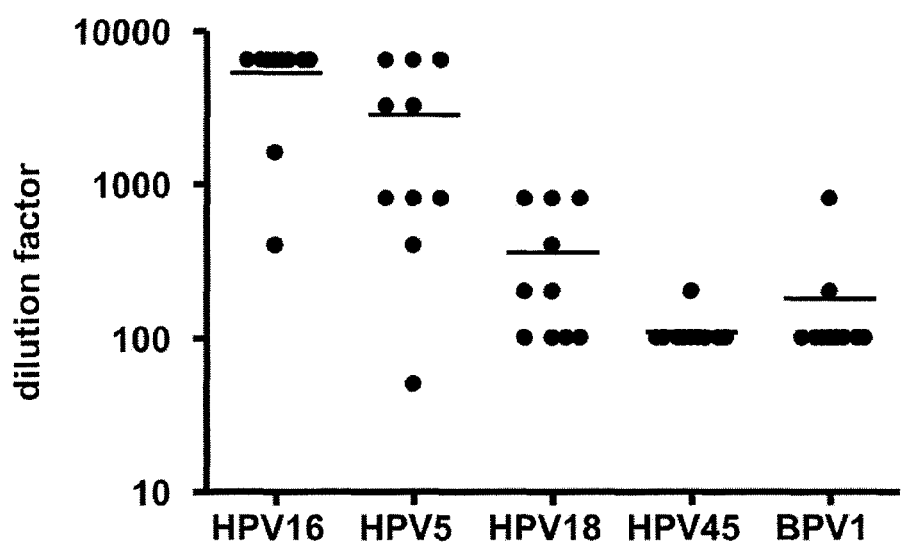
FIG. 4. Antibodies elicited by vaccination with P25-P2C-HPV cross-neutralizes multiple heterologous HPV pseudovirions. The ability of antiserum generated by immunization of mice with P25P2CHPV vaccine to neutralize heterologous HPVS, HPV18, HPV45 and BPV1 pseudovirions was tested. Using serial dilutions of antiserum, mean titers of 5320, 2845, 360, 110 and 180 were generated when reacted with HPV16, -5, -18-45 and BPV1, respectively.

P25-P2C-HPV vaccination protects mice against cutaneous challenge with HPV16 and HPV45 pseudovirions. Since native HPV does not produce visible lesions in nonhuman hosts, a model for monitoring HPV infection in the cutaneous epithelium of mice was used that employs an HPV pseudovirion construct carrying a luciferase reporter gene. Cutaneous infection is detected 3 days post-challenge as a bioluminescent signal after injection of the challenged mice with luciferin. Background bioluminescence is determined using challenge with a noninfectious pseudovirus lacking L2 (not shown). One-way analysis of variance (ANOVA) demonstrates that protection from HPV16 infection with P25-P2C-HPV and control immunizations were significantly different ($P < 0.001$; FIG. 4). Vaccination of mice with HPV16 L1 VLP protected mice from cutaneous challenge with HPV16 pseudovirions, whereas HPV45 L1 VLP vaccination did not (FIG. 4). Vaccination with the 17-36 peptide alone failed to protect the mice, consistent with its failure to induce L2-specific antibody. However, vaccination with the P25-P2C-HPV protected mice as effectively as HPV16 μl VLP vaccination from HPV16 pseudovirus challenge (FIG. 4).

Figure 5:
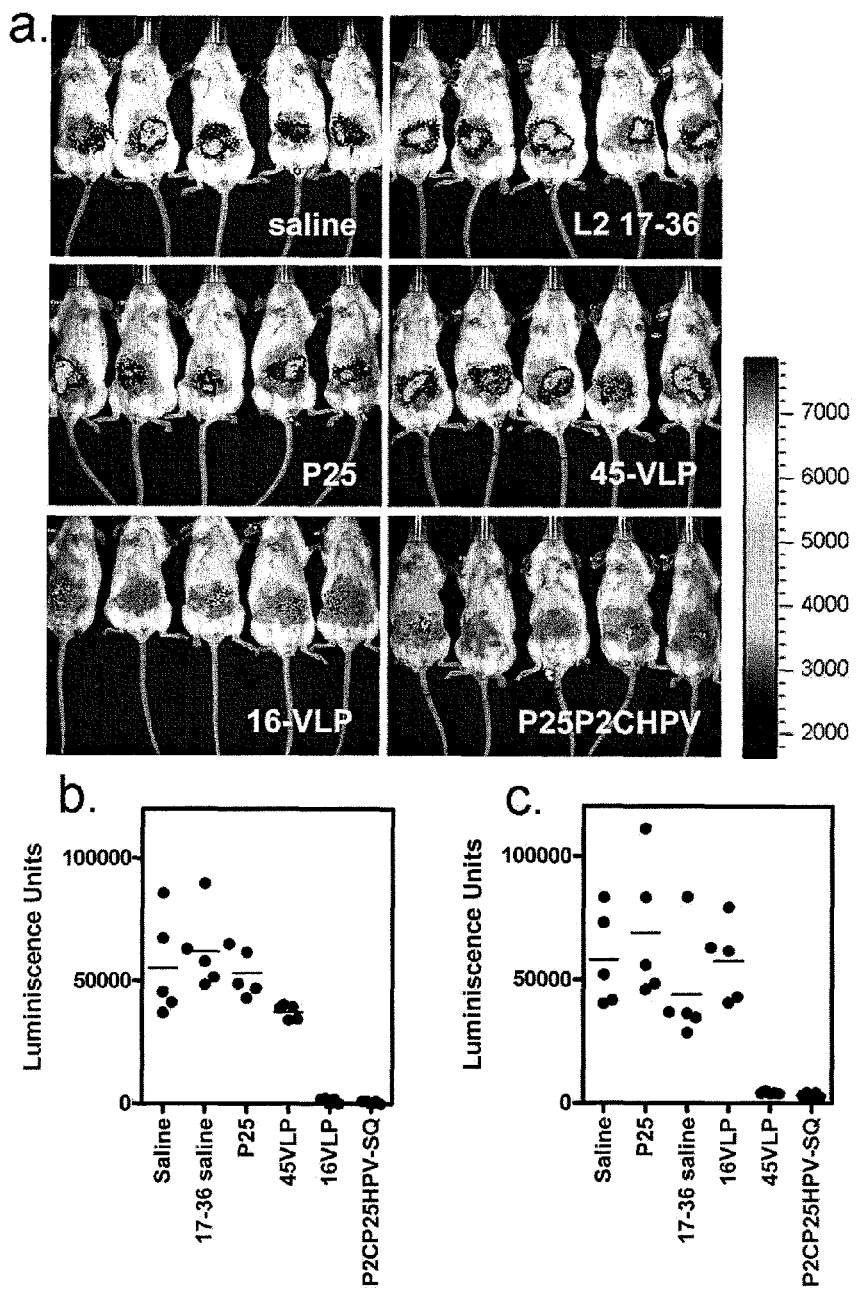
FIG. 5. P25-P2C-HPV vaccination protects mice from cutaneous challenge with heterologous type papillomavirus HPV45. BALB/c mice were vaccinated s.c. three times with saline, HPV16 L2 17-36 peptide, P25 peptide, HPV45 L1 VLP, HPV16 µl VLP or P25-P2CHPV and challenged on their belly with HPV45 pseudovirions carrying a luciferase reporter two weeks after the third immunization (wk 10). To detect pseudo-infection, the mice were injected with luciferin three days after viral challenge and imaged for bioluminescence using an IVIS 200 instrument (FIG. 5A). The bioluminescence was quantified in relative light units using Living Image 2.20 software (FIG. 5B).

HPV45 is phylogenically divergent from HPV16 (species 7 and 9, respectively according to recent papillomavirus classification scheme (de Villiers et al., 2004)), but sera of mice vaccinated with P25-P2C-HPV (which contains HPV16 L2 17-36) neutralized HPV45 pseudovirions with a mean titer of 110. To address the potential for cross-protection against a divergent HPV type and to evaluate the in vivo significance of the titer value, P25-P2C-HPV vaccinated mice were challenged with luminescent HPV45 virions and levels of protection 72 hrs post-challenge were measured (FIG. 5). ANOVA demonstrates that neutralization response to vaccination with P25-P2C-HPV vaccines and controls were significantly different for HPV45 challenge (P<0.001). Post-hoc Bonferoni pairwise comparisons demonstrate that luminescence measured in cutaneously challenged mice vaccinated with homologous HPV45 L1 VLP and P25-P2C-HPV vaccine are significantly similar (P>0.05). Likewise, luminescence in mice immunized with heterologous VLPs and L2 17-36 were statistically equivalent to saline controls. In sum, in an animal model, saline, L2 17-36 peptide, and heterologous VLP did not protect against challenge with luciferase-expressing HPV pseudovirions, while homologous VLP and P25-P2C-HPV effectively prevented cutaneous HPV infection.

Figure 6:
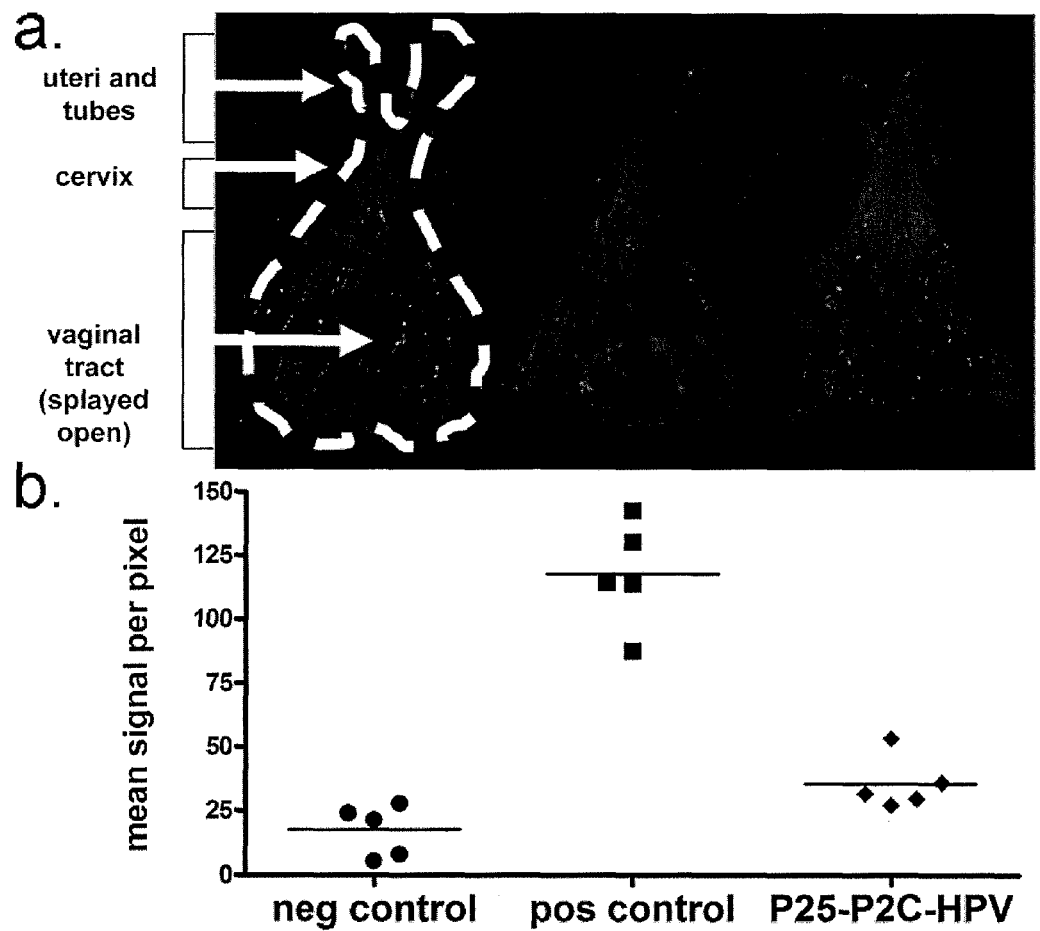
FIG. 6. P25-P2C-HPV vaccination protects mice from vaginal challenge with HPV16. BALB/c mice were vaccinated s.c. three times with P25-P2C-HPV or not (controls) and challenged on their belly with HPV45 pseudovirions carrying a luciferase reporter two weeks after the third immunization (except for negative control). To detect pseudo-infection, the mice were sacrificed three days after viral challenge and their genital tracts dissected. The lumen of each genital tract was imaged for red fluorescence using a Maestro instrument (FIG. 6A). The red fluorescence was quantified in relative light units using Image J software (FIG. 6B).

P25-P2C-HPV vaccination protects mice against vaginal challenge with HPV16. Because the primary site of HPV16-related pathology is in the genital tract, the ability of P25-P2C-HPV vaccination to protect against vaginal challenge was studied with HPV16 pseudovirions carrying the red fluorescent protein (RFP) reporter (FIG. 6). Baseline negative control genital tracts from unchallenged mice emitted signal of 17.4±8.39 fluorescence units (FIG. 6). In the mice challenged with RFP-expressing HPV16 pseudovirions, unvaccinated mice (positive controls) emitted a signal of 118±9.24 units while vaccinated mice emitted 35.4±4.70 units (FIG. 6). P25-P2C-HPV vaccination demonstrated significant protection from vaginal challenge (P<0.001, ANOVA) and this was consistently observed in three independent experiments. In additional experiments, a similar level of protection was observed in mice vaccinated intranasally with P25-P2C-HPV (data not shown). Thus, vaccination with P25-P2C-HPV protects against HPV pseudovirions carrying two different reporters (luciferase, FIG. 5; RFP, FIG. 6) at two different biological sites demonstrating that the protective effect is independent of the reporter and anatomic site of infection.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 5,084,269
U.S. Pat. No. 5,700,910
U.S. Pat. No. 6,651,655
U.S. Pat. No. 6,656,462
U.S. Pat. No. 6,733,754
U.S. Pat. No. 6,793,923
U.S. Pat. No. 6,814,971
U.S. Patent Pubin. 20080145375
PCT Appln. WO 2004/014956
PCT Appln. WO 2004/014957
Akira et al., Scand. *J Infect. Dis.*, 35555, 2003.
Atherton and Sheppard, In: *Solid Phase Peptide Synthesis: A Practical Approach*, IRL Press, Oxford, 1989.
Barany and Merrifield, In: *The Peptides*, Gross and Meienhofer (Eds.), Academic Press, NY, 3-284, 1979.
Beutler et al, *Mol. Immunol.*, 409345, 2004.
Buck et al., *J. Virol*, 78:751-757, 2004.
Buck et al., *J. Virol.*, 79:2839-2846, 2005.
Buck et al., *Methods Mol. Med.*, 119:445-462, 2005.
Christensen et al., *Virology*, 181:572-579, 1991.
de Villiers et al., *Virology*, 324:17-27, 2004.
Edwards et al., *J. Immunol.*, 169:3652, 2002.
Embers et al., *J. Virol.* 76:9798-9805, 2002.
Embers et al., *Vaccine* 22:670-680, 2004.
Finn and Hoffman, In: *Proteins*, 3$^{rd}$ Ed., Neurath and Hill (Eds.), Academic Press, NY, 2:105-253, 1976.
Fleury et al., *Archives Virol.*, 151:1511-1523, 2006.
Gambhira et al. *J. Virol*, 81:11585-11592, 2007.
Ghosh et al., *Immunology.* 104:58-66, 2001.
Harlow and Lane, In: *Antibodies: A Laboratory Manual*, Cold Spring Harbor Laboratory, 1988.
Hashimoto et al., *Cell*, 52:269, 1988.
Hayashi et al., *Blood*, 102:2660, 2003.
Hoffman and Cavanagh, *Cancer Control*, 2:503-509, 1995.
Jackson et al., *Proc. Natl. Acad. Sci. USA*, 101:15440-15445, 2004.
Janeway et al., *Annu. Rev. Immunol.*, 20:197, 2002.
Jansen et al., *Immunol Rev.*, 62:185-216, 1982. Baker et al. Biophys. J., 60:1445-1456, 1991.
Jenkins et al., *Immunity*, 1:443, 1994.
Kaisho, *Biochim. Biophys. Acta*, 1589, 2002.
Kawana et al., *J. Virol*, 75:2331-2336, 2001.
Kawana et al., *Vaccine*, 19:1496-1502, 2001.
Kawana et al., *Vaccine*, 21:4256-4260, 2003.
Keamey et al., *Immunity*, 1:327, 1994.
Kirnbauer et al., *Proc. Natl. Acad. Sci. USA*, 89:12180-12184, 1992.
Kohler and Milstein, *Nature*, 256:495-497, 1975.
Lernaitre et al., *Cell*, 86:973, 1996.
Lu et al., *J. Org. Chem.*, 46:3433, 1981.
Medzhitov et al., *Mol. Cell*, 2:253, 1998.
Medzhitov et al., *Nature*, 388:394, 1997.
Medzhitov et al., *Semin. Immunol.*, 10:351, 2000.
Medzhitov et al., *Trends Microbiol.*, 8:452 (2000.
Merrifield, *J. Am. Chem. Soc.*, 85:2149-2154, 1963.
Moeller, *Immunol. Rev.*, 98:187, 1987.
Mondino et al., *Proc. Natl. Acad. Sci., USA*, 93:2245, 1996.
Mosmann and Coffman, *Ann. Rev. Immunol.*, 7:145-173, 1989.
Muhlradt et al., *J. Exp. Med.*, 185:1951-1958, 1997.
Munoz et al., *J. Exp. Med.*, 348:518-527, 2003.
Nagase et al., *J. Immunol.*, 171:3977, 2003.
Parkin, *Lancet. Oncol.*, 2:533-543, 2001.
Pastrana et al., *Virology*, 279:361-369, 2001.
Pastrana et al., *Virology*, 321:205-216, 2004.
Poltorok et al., *Science*, 282:2085, 1998.
Pouwels et al., In: *Cloning Vectors: A Laboratory Manual*, Elsevier, N.Y., 1985.
Pulendran et al., *J. Exp. Med.*, 188:2075, 1998.
Remington's Pharmaceutical Sciences, 18th Ed. Mack Printing Company, 1289-1329, 1990.
Roberts et al., *Nature Medicine*, 13:857-861, 2007.
Roden et al., *Virology*, 270:254-257, 2000.

Skeiky et al., *Infect. Immun.*, 67(8):3998-4007, 1999.
Takeda and Akira, *Semin. Immunol.*, 16:3, 2004.
Takeuchi et al., *Int. Immunol.*, 13:933, 2001.
Vaughan et al., *Nat. Biotech.*, 16; 535-539, 1998.

Walboomers et al., *J. Pathol.*, 189:12-19, 1999.
Wiesmuller et al., *Hoppe Seylers Z Physiol Chem.*, 364(5): 593-606, 1983.
Zeng et al., *J. Immunol.*, 169:4905-4912, 2002.

The invention claimed is:

1. A multi-component human papillomavirus (PV) L2 composition comprising one or more constructs comprising:
   (a) a peptide component comprising a Human Papillomavirus L2 (HPV-L2) peptide coupled to a T helper cell (Th) epitope; and
   (b) a lipid Toll Like Receptor (TLR) agonist, wherein the multi-component human papillomavirus (PV) L2 composition induces a humoral immune response, and wherein the TLR agonist is simultaneously linked to both the HPV-L2 peptide and the Th epitope forming a junction therebetween.

2. The composition of claim 1, wherein the HPV-L2 peptide comprises at least 15, or 20 consecutive amino acids of an entire HPV-L2 polypeptide.

3. The composition of claim 1, wherein the HPV-L2 peptide is at least 90% identical to SEQ ID NO:4, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37.

4. The composition of claim of claim 3, wherein the HPV-L2 peptide is at least 90% identical to SEQ ID NO:4.

5. The composition of claim 1, wherein the HPV-L2 peptide is SEQ ID NO:4 SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37.

6. The composition of claim 5, wherein the HPV-L2 peptide has an amino acid sequence of SEQ ID NO:4.

7. The composition of claim 5, wherein cysteine residues are replaced by serine residues.

8. The composition of claim 1, wherein the lipid comprises at least 7, 8, 9, 10, 11, 12, 13, or 14 carbon atoms.

9. The composition of claim 1, wherein the TLR agonist is a TLR2 binding moiety.

10. The composition of claim 9, wherein the TLR2 binding moiety comprises at least one of palmitoyl, stearoyl, lauroyl, octanoyl, or decanoyl.

11. The composition of claim 9, wherein the TLR2 binding moiety comprises a Pam2Cys, Pam3Cys, Ste2Cys, Lau2Cys, or Oct2Cys group.

12. The composition of claim 1, wherein the Th epitope is 10, 11, 12, 13, 14, 15, 16, 17, 18, 19, or 20 amino acids in length.

13. The composition of claim 1, wherein the TLR agonist is coupled to a linker positioned between the Human Papillomavirus L2 (HPV-L2) peptide and the Th epitope.

14. The composition of claim 13, wherein the linker is a peptide linker.

15. The composition of claim 14, wherein the peptide linker comprises at least one lysine, serine, arginine, or analog thereof.

16. The composition of claim 1, further comprising an adjuvant.

17. The composition of claim 1, wherein the composition is a pharmaceutical formulation.

18. A vaccine composition comprising multi-component HPV L2 composition of claim 1.

19. The composition of claim 18, wherein the composition is formulated for administration by inhalation.

20. The composition of claim 18, wherein the composition is in a lyophilized or powdered form.

21. A method of vaccinating a subject against PV infection comprising administering to a subject an effective amount of a composition of claim 1.

22. A method of treating PV infection in a subject having an PV infection or at risk of being exposed to PV comprising administering to a subject an effective amount of a composition of claim 1.

23. A kit comprising a multi-component composition comprising a composition of claim 1.

* * * * *

SEQUENCE LISTING

```
<160> NUMBER OF SEQ ID NOS: 121

<210> SEQ ID NO 1
<211> LENGTH: 473
<212> TYPE: PRT
<213> ORGANISM: Human papillomavirus type 16

<400> SEQUENCE: 1

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Pro Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Ala Pro Thr Lys Leu Ile Thr Tyr Asp Asn Pro Ala
                245                 250                 255

Tyr Glu Gly Ile Asp Val Asp Asn Thr Phe Tyr Phe Pro Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asn Pro Ala
                325                 330                 335
```

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Val Thr Thr Pro Val Pro Ala
            370                 375                 380

Ile Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Thr Thr Asp Gln Thr Pro Ser Leu Ile Pro Ile Val Pro
            420                 425                 430

Gly Ser Pro Gln Tyr Thr Ile Ile Ala Asp Gly Gly Asp Phe Tyr Leu
            435                 440                 445

His Pro Ser Tyr Tyr Met Leu Arg Lys Arg Arg Lys Arg Leu Pro Tyr
            450                 455                 460

Phe Phe Ser Asp Val Ser Leu Ala Ala
465                 470

<210> SEQ ID NO 2
<211> LENGTH: 462
<212> TYPE: PRT
<213> ORGANISM: Human papillomavirus type 18

<400> SEQUENCE: 2

Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Ser Asp Val Val
            20                  25                  30

Asn Lys Val Glu Gly Thr Thr Leu Ala Asp Lys Ile Leu Gln Trp Ser
            35                  40                  45

Ser Leu Gly Ile Phe Leu Gly Gly Leu Gly Ile Gly Thr Gly Ser Gly
        50                  55                  60

Thr Gly Gly Arg Thr Gly Tyr Ile Pro Leu Gly Gly Arg Ser Asn Thr
65              70                  75                  80

Val Val Asp Val Gly Pro Thr Arg Pro Pro Val Val Ile Glu Pro Val
                85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
            115                 120                 125

Asp Ile Thr Ser Ala Gly Thr Thr Thr Pro Ala Val Leu Asp Ile Thr
        130                 135                 140

Pro Ser Ser Thr Ser Val Ser Ile Ser Thr Thr Asn Phe Thr Asn Pro
145             150                 155                 160

Ala Phe Ser Asp Pro Ser Ile Ile Glu Val Pro Gln Thr Gly Glu Val
                165                 170                 175

Ser Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
            195                 200                 205

Pro Ile Ser Ser Thr Pro Leu Pro Thr Val Arg Arg Val Thr Gly Pro
        210                 215                 220

Arg Leu Tyr Ser Arg Ala Tyr Gln Gln Val Ser Val Ala Asn Pro Glu

```
                225                 230                 235                 240
        Phe Leu Thr Arg Pro Ser Ser Leu Ile Thr Tyr Asp Asn Pro Ala Phe
                        245                 250                 255

Glu Pro Met Asp Thr Thr Leu Thr Phe Glu Pro Arg Ser Asn Val Pro
                        260                 265                 270

Asp Ser Asp Phe Met Asp Ile Ile Arg Leu His Arg Pro Ala Ser Thr
                        275                 280                 285

Ser Arg Arg Gly Thr Val Arg Phe Ser Arg Leu Gly Gln Arg Ala Thr
                290                 295                 300

Met Phe Thr Arg Ser Gly Thr Gln Ile Gly Ala Arg Val His Phe Tyr
        305                 310                 315                 320

His Asp Ile Ser Pro Ile Ala Pro Ser Pro Glu Tyr Ile Glu Leu Gln
                        325                 330                 335

Pro Leu Val Ser Ala Thr Glu Asp Asn Gly Leu Phe Asp Ile Tyr Ala
                        340                 345                 350

Asp Asp Ile Asp Pro Ala Leu Pro Val Pro Ser Arg Pro Thr Thr Ser
                        355                 360                 365

Ser Ala Val Ser Thr Tyr Ser Pro Thr Ile Ser Ser Ala Ser Ser Tyr
                370                 375                 380

Ser Asn Val Thr Val Pro Leu Thr Ser Ser Trp Asp Val Pro Val Tyr
        385                 390                 395                 400

Thr Gly Pro Asp Ile Thr Leu Pro Ser Thr Thr Ser Val Trp Pro Ile
                        405                 410                 415

Val Ser Pro Thr Asp Pro Ala Ser Thr Gln Tyr Ile Gly Ile His Gly
                        420                 425                 430

Thr His Tyr Tyr Leu Trp Pro Leu Tyr Tyr Phe Ile Pro Lys Lys Arg
                        435                 440                 445

Lys Arg Val Pro Tyr Phe Phe Ala Asp Gly Phe Val Ala Ala
                450                 455                 460

<210> SEQ ID NO 3
<211> LENGTH: 463
<212> TYPE: PRT
<213> ORGANISM: Human papillomavirus type 45

<400> SEQUENCE: 3

Met Val Ser His Arg Ala Ala Arg Arg Lys Arg Ala Ser Ala Thr Asp
        1               5                   10                  15

Leu Tyr Lys Thr Cys Lys Gln Ser Gly Thr Cys Pro Pro Asp Val Ile
                        20                  25                  30

Asn Lys Val Glu Gly Thr Thr Leu Ala Asp Arg Ile Leu Gln Trp Ser
                        35                  40                  45

Ser Leu Gly Ile Phe Leu Gly Gly Leu Gly Ile Gly Thr Gly Ser Gly
                50                  55                  60

Ser Gly Gly Arg Thr Gly Tyr Val Pro Leu Gly Gly Arg Ser Asn Thr
        65                  70                  75                  80

Val Val Asp Val Gly Pro Thr Arg Pro Pro Val Val Ile Asp Pro Val
                        85                  90                  95

Gly Pro Thr Asp Pro Ser Ile Val Thr Leu Val Glu Glu Ser Ser Val
                        100                 105                 110

Val Ser Ser Gly Ala Pro Val Pro Thr Phe Thr Gly Thr Ser Gly Phe
                        115                 120                 125

Glu Ile Thr Ser Ser Gly Thr Thr Thr Pro Ala Val Leu Asp Ile Thr
                130                 135                 140
```

```
Pro Thr Val Asp Ser Val Ser Ile Ser Ser Thr Phe Thr Asn Pro
145                 150                 155                 160

Ala Phe Ser Asp Pro Ser Ile Ile Glu Val Pro Gln Thr Gly Glu Val
                165                 170                 175

Ser Gly Asn Ile Phe Val Gly Thr Pro Thr Ser Gly Ser His Gly Tyr
            180                 185                 190

Glu Glu Ile Pro Leu Gln Thr Phe Ala Ser Ser Gly Ser Gly Thr Glu
        195                 200                 205

Pro Ile Ser Ser Thr Pro Leu Pro Thr Val Arg Val Ala Gly Pro
    210                 215                 220

Arg Leu Tyr Ser Arg Ala Asn Gln Gln Val Arg Val Ser Thr Ser Gln
225                 230                 235                 240

Phe Leu Thr Arg Pro Ser Ser Leu Val Thr Phe Asp Asn Pro Ala Tyr
                245                 250                 255

Glu Pro Leu Asp Thr Thr Leu Ser Phe Glu Pro Thr Ser Asn Val Pro
            260                 265                 270

Asp Ser Asp Phe Met Asp Ile Ile Arg Leu His Arg Pro Ala Leu Ser
        275                 280                 285

Ser Arg Arg Gly Thr Val Arg Phe Ser Arg Leu Gly Gln Arg Ala Thr
    290                 295                 300

Met Phe Thr Arg Ser Gly Lys Gln Ile Gly Gly Arg Val His Phe Tyr
305                 310                 315                 320

His Asp Ile Ser Pro Ile Ala Ala Thr Glu Glu Ile Glu Leu Gln Pro
                325                 330                 335

Leu Leu Ser Ala Thr Asp Asp Ser Asp Leu Phe Asp Val Tyr Ala Asp
            340                 345                 350

Phe Pro Pro Pro Ala Ser Thr Thr Pro Ser Thr Ile Asn Lys Ser Phe
        355                 360                 365

Thr Tyr Pro Lys Tyr Ser Leu Thr Met Pro Ser Thr Ala Ala Ser Ser
    370                 375                 380

Tyr Ser Asn Val Thr Val Pro Leu Thr Ser Ala Trp Asp Val Pro Ile
385                 390                 395                 400

Tyr Thr Gly Pro Asp Ile Ile Leu Pro Ser His Thr Pro Met Trp Pro
                405                 410                 415

Ser Thr Ser Pro Thr Asn Ala Ala Thr Ser Thr Tyr Ile Gly Ile His
            420                 425                 430

Gly Thr Gln Tyr Tyr Leu Trp Pro Trp Tyr Tyr Phe Pro Lys Lys
        435                 440                 445

Arg Lys Arg Ile Pro Tyr Phe Phe Ala Asp Gly Phe Val Ala Ala
    450                 455                 460

<210> SEQ ID NO 4
<211> LENGTH: 20
<212> TYPE: PRT
<213> ORGANISM: Human papillomavirus

<400> SEQUENCE: 4

Gln Leu Tyr Lys Thr Cys Lys Gln Ala Gly Thr Cys Pro Pro Asp Ile
1               5                   10                  15

Ile Pro Lys Val
            20

<210> SEQ ID NO 5
<211> LENGTH: 17
<212> TYPE: PRT
<213> ORGANISM: Human papillomavirus
```

<400> SEQUENCE: 5

Lys Leu Ile Pro Asn Ala Ser Leu Ile Glu Asn Cys Thr Lys Ala Glu
1               5                   10                  15

Leu

<210> SEQ ID NO 6
<211> LENGTH: 13
<212> TYPE: PRT
<213> ORGANISM: Human papillomavirus

<400> SEQUENCE: 6

Lys Leu Phe Ala Val Trp Lys Ile Thr Tyr Lys Asp Thr
1               5                   10

<210> SEQ ID NO 7
<211> LENGTH: 13
<212> TYPE: PRT
<213> ORGANISM: Human papillomavirus

<400> SEQUENCE: 7

Asn Lys Leu Ile Ala Tyr Pro Ala Val Glu Ala Leu Ser
1               5                   10

<210> SEQ ID NO 8
<211> LENGTH: 15
<212> TYPE: PRT
<213> ORGANISM: Human papillomavirus

<400> SEQUENCE: 8

Gln Tyr Ile Lys Ala Asn Ser Lys Phe Ile Gly Ile Thr Glu Leu
1               5                   10                  15

<210> SEQ ID NO 9
<211> LENGTH: 12
<212> TYPE: PRT
<213> ORGANISM: Human papillomavirus
<220> FEATURE:
<221> NAME/KEY: MISC_FEATURE
<222> LOCATION: (1)..(12)
<223> OTHER INFORMATION: a = D-Ala
<220> FEATURE:
<221> NAME/KEY: MISC_FEATURE
<222> LOCATION: (2)..(2)
<223> OTHER INFORMATION: x = L-cyclohexyl-Ala

<400> SEQUENCE: 9

Ala Lys Xaa Val Met Trp Thr Leu Lys Ala Ala Ala
1               5                   10

<210> SEQ ID NO 10
<211> LENGTH: 10
<212> TYPE: PRT
<213> ORGANISM: Human papillomavirus

<400> SEQUENCE: 10

Thr Asp Leu Tyr Cys Tyr Glu Gln Leu Asn
1               5                   10

<210> SEQ ID NO 11
<211> LENGTH: 10
<212> TYPE: PRT
<213> ORGANISM: Human papillomavirus

<400> SEQUENCE: 11

Ala Glu Pro Asp Arg Ala His Tyr Asn Ile
1               5                   10

<210> SEQ ID NO 12
<211> LENGTH: 19
<212> TYPE: PRT
<213> ORGANISM: Human papillomavirus

<400> SEQUENCE: 12

Lys Cys Asp Ser Thr Leu Arg Leu Cys Val Gln Ser Thr His Val Ile
1               5                   10                  15

Arg Thr Leu

<210> SEQ ID NO 13
<211> LENGTH: 10
<212> TYPE: PRT
<213> ORGANISM: Human papillomavirus

<400> SEQUENCE: 13

Gly Thr Leu Gly Ile Val Gly Pro Ile Cys
1               5                   10

<210> SEQ ID NO 14
<211> LENGTH: 13
<212> TYPE: PRT
<213> ORGANISM: Human papillomavirus

<400> SEQUENCE: 14

Lys Leu Val Val Val Gly Ala Arg Gly Val Gly Lys Ser
1               5                   10

<210> SEQ ID NO 15
<211> LENGTH: 15
<212> TYPE: PRT
<213> ORGANISM: Human papillomavirus

<400> SEQUENCE: 15

His Leu Asp Met Leu Arg His Leu Tyr Gln Gly Gly Gln Val Val
1               5                   10                  15

<210> SEQ ID NO 16
<211> LENGTH: 15
<212> TYPE: PRT
<213> ORGANISM: Human papillomavirus

<400> SEQUENCE: 16

Ser Arg Leu Leu Gly Ile Cys Leu Thr Ser Thr Val Gln Leu Val
1               5                   10                  15

<210> SEQ ID NO 17
<211> LENGTH: 14
<212> TYPE: PRT
<213> ORGANISM: Human papillomavirus

<400> SEQUENCE: 17

Leu Leu Lys Tyr Arg Ala Arg Glu Pro Val Thr Lys Ala Glu
1               5                   10

<210> SEQ ID NO 18
<211> LENGTH: 20
<212> TYPE: PRT
<213> ORGANISM: Human papillomavirus

<400> SEQUENCE: 18

```
Asp Ile Tyr Pro Ser Cys Lys Ile Ser Asn Thr Cys Pro Pro Asp Ile
1               5                   10                  15

Gln Asn Lys Ile
            20

<210> SEQ ID NO 19
<211> LENGTH: 20
<212> TYPE: PRT
<213> ORGANISM: Human papillomavirus

<400> SEQUENCE: 19

Asp Leu Tyr Arg Thr Cys Lys Gln Ala Gly Thr Cys Pro Pro Asp Ile
1               5                   10                  15

Ile Pro Arg Val
            20

<210> SEQ ID NO 20
<211> LENGTH: 20
<212> TYPE: PRT
<213> ORGANISM: Human papillomavirus

<400> SEQUENCE: 20

Asp Ile Tyr Pro Ala Cys Lys Val Ala Asn Asn Cys Pro Pro Asp Ile
1               5                   10                  15

Gln Asn Lys Ile
            20

<210> SEQ ID NO 21
<211> LENGTH: 20
<212> TYPE: PRT
<213> ORGANISM: Human papillomavirus

<400> SEQUENCE: 21

His Ile Tyr Gln Thr Cys Lys Gln Ala Gly Thr Cys Pro Pro Asp Val
1               5                   10                  15

Ile Asn Lys Val
            20

<210> SEQ ID NO 22
<211> LENGTH: 20
<212> TYPE: PRT
<213> ORGANISM: Human papillomavirus

<400> SEQUENCE: 22

His Ile Tyr Gln Thr Cys Lys Gln Ala Gly Thr Cys Pro Pro Asp Val
1               5                   10                  15

Ile Asn Lys Val
            20

<210> SEQ ID NO 23
<211> LENGTH: 20
<212> TYPE: PRT
<213> ORGANISM: Human papillomavirus

<400> SEQUENCE: 23

Gln Leu Tyr Gln Thr Cys Lys Leu Thr Gly Thr Cys Pro Pro Asp Val
1               5                   10                  15

Ile Pro Lys Val
            20

<210> SEQ ID NO 24
<211> LENGTH: 20
```

```
<212> TYPE: PRT
<213> ORGANISM: Human papillomavirus

<400> SEQUENCE: 24

Gln Leu Tyr Gln Thr Cys Lys Ala Thr Gly Thr Cys Pro Pro Asp Val
1               5                   10                  15

Ile Pro Lys Val
            20

<210> SEQ ID NO 25
<211> LENGTH: 20
<212> TYPE: PRT
<213> ORGANISM: Human papillomavirus

<400> SEQUENCE: 25

Asp Leu Tyr Lys Thr Cys Lys Gln Ser Gly Thr Cys Pro Pro Asp Val
1               5                   10                  15

Val Pro Lys Val
            20

<210> SEQ ID NO 26
<211> LENGTH: 20
<212> TYPE: PRT
<213> ORGANISM: Human papillomavirus

<400> SEQUENCE: 26

Gln Leu Tyr Gln Thr Cys Lys Ala Ala Gly Thr Cys Pro Ser Asp Val
1               5                   10                  15

Ile Pro Lys Ile
            20

<210> SEQ ID NO 27
<211> LENGTH: 20
<212> TYPE: PRT
<213> ORGANISM: Human papillomavirus

<400> SEQUENCE: 27

Gln Leu Tyr Gln Thr Cys Lys Ala Thr Gly Thr Cys Pro Pro Asp Val
1               5                   10                  15

Ile Pro Lys Val
            20

<210> SEQ ID NO 28
<211> LENGTH: 20
<212> TYPE: PRT
<213> ORGANISM: Human papillomavirus

<400> SEQUENCE: 28

Gln Leu Tyr Arg Thr Cys Lys Ala Ala Gly Thr Cys Pro Pro Asp Val
1               5                   10                  15

Ile Pro Lys Val
            20

<210> SEQ ID NO 29
<211> LENGTH: 20
<212> TYPE: PRT
<213> ORGANISM: Human papillomavirus

<400> SEQUENCE: 29

Asp Leu Tyr Arg Thr Cys Lys Gln Ser Gly Thr Cys Pro Pro Asp Val
1               5                   10                  15

Val Asp Lys Val
```

-continued

20

<210> SEQ ID NO 30
<211> LENGTH: 20
<212> TYPE: PRT
<213> ORGANISM: Human papillomavirus

<400> SEQUENCE: 30

Asp Leu Tyr Arg Thr Cys Lys Gln Ser Gly Thr Cys Pro Pro Asp Val
1               5                   10                  15

Ile Asn Lys Val
        20

<210> SEQ ID NO 31
<211> LENGTH: 20
<212> TYPE: PRT
<213> ORGANISM: Human papillomavirus

<400> SEQUENCE: 31

Gln Leu Tyr Ser Thr Cys Lys Ala Ala Gly Thr Cys Pro Pro Asp Val
1               5                   10                  15

Val Asn Lys Val
        20

<210> SEQ ID NO 32
<211> LENGTH: 20
<212> TYPE: PRT
<213> ORGANISM: Human papillomavirus

<400> SEQUENCE: 32

Gln Leu Tyr Gln Thr Cys Lys Ala Ser Gly Thr Cys Pro Pro Asp Val
1               5                   10                  15

Ile Pro Lys Val
        20

<210> SEQ ID NO 33
<211> LENGTH: 20
<212> TYPE: PRT
<213> ORGANISM: Human papillomavirus

<400> SEQUENCE: 33

Gln Leu Tyr Lys Thr Cys Lys Leu Ser Gly Thr Cys Pro Glu Asp Val
1               5                   10                  15

Val Asn Lys Ile
        20

<210> SEQ ID NO 34
<211> LENGTH: 20
<212> TYPE: PRT
<213> ORGANISM: Human papillomavirus

<400> SEQUENCE: 34

Gln Leu Tyr Gln Thr Cys Lys Ala Ser Gly Thr Cys Pro Pro Asp Val
1               5                   10                  15

Ile Pro Lys Val
        20

<210> SEQ ID NO 35
<211> LENGTH: 20
<212> TYPE: PRT
<213> ORGANISM: Human papillomavirus

<400> SEQUENCE: 35

```
Asp Leu Tyr Lys Thr Cys Lys Gln Ala Gly Thr Cys Pro Ser Asp Val
1               5                   10                  15

Ile Asn Lys Val
            20

<210> SEQ ID NO 36
<211> LENGTH: 20
<212> TYPE: PRT
<213> ORGANISM: Human papillomavirus

<400> SEQUENCE: 36

Asp Leu Tyr Lys Thr Cys Lys Gln Ser Gly Thr Cys Pro Ser Asp Val
1               5                   10                  15

Ile Asn Lys Val
            20

<210> SEQ ID NO 37
<211> LENGTH: 20
<212> TYPE: PRT
<213> ORGANISM: Human papillomavirus

<400> SEQUENCE: 37

Gln Leu Tyr Lys Thr Cys Lys Gln Ala Gly Thr Cys Pro Pro Asp Val
1               5                   10                  15

Ile Pro Lys Val
            20

<210> SEQ ID NO 38
<211> LENGTH: 78
<212> TYPE: PRT
<213> ORGANISM: Human papillomavirus

<400> SEQUENCE: 38

Lys Arg Ala Ser Ala Thr Gln Leu Tyr Lys Thr Cys Lys Gln Ala Gly
1               5                   10                  15

Thr Cys Pro Pro Asp Ile Ile Pro Lys Val Glu Gly Lys Thr Ile Ala
            20                  25                  30

Asp Gln Ile Leu Gln Tyr Gly Ser Met Gly Val Phe Phe Gly Gly Leu
        35                  40                  45

Gly Ile Gly Thr Gly Ser Gly Thr Gly Gly Arg Thr Gly Tyr Ile Pro
    50                  55                  60

Leu Gly Thr Arg Pro Pro Thr Ala Thr Asp Thr Leu Ala Pro
65                  70                  75

<210> SEQ ID NO 39
<211> LENGTH: 76
<212> TYPE: PRT
<213> ORGANISM: Human papillomavirus

<400> SEQUENCE: 39

Lys Arg Ala Ser Val Thr Asp Leu Tyr Lys Thr Cys Lys Gln Ser Gly
1               5                   10                  15

Thr Cys Pro Pro Asp Trp Pro Lys Val Glu Gly Thr Thr Leu Ala Asp
            20                  25                  30

Lys Ile Leu Gln Trp Ser Ser Leu Gly Phe Leu Gly Leu Gly Ile
        35                  40                  45

Gly Thr Gly Ser Gly Thr Gly Gly Arg Thr Gly Tyr Ile Pro Leu Gly
    50                  55                  60

Gly Arg Ser Asn Thr Val Val Asp Val Gly Pro Thr
```

<210> SEQ ID NO 40
<211> LENGTH: 77
<212> TYPE: PRT
<213> ORGANISM: Human papillomavirus

<400> SEQUENCE: 40

Lys Arg Ala Ala Pro Lys Asp Leu Tyr Pro Ser Cys Lys Leu Ser Asn
1               5                   10                  15

Thr Cys Pro Pro Asp Leu Gln Asn Lys Leu Glu His Thr Thr Leu Ala
            20                  25                  30

Asp Lys Leu Leu Gln Tyr Gly Ser Leu Gly Val Phe Leu Gly Gly Leu
        35                  40                  45

Gly Leu Gly Thr Ala Arg Gly Ser Gly Gly Arg Leu Gly Met Pro Leu
    50                  55                  60

Gly Glu Gly Gly Gly Val Arg Val Ala Thr Arg Pro Thr
65                  70                  75

<210> SEQ ID NO 41
<211> LENGTH: 77
<212> TYPE: PRT
<213> ORGANISM: Human papillomavirus

<400> SEQUENCE: 41

Lys Arg Asp Ser Val Thr His Ile Tyr Gln Thr Cys Lys Gln Ala Gly
1               5                   10                  15

Thr Cys Pro Pro Asp Val Ile Asn Lys Val Glu Gln Thr Thr Val Ala
            20                  25                  30

Asp Asn Ile Leu Lys Tyr Gly Ser Ala Gly Val Phe Phe Gly Gly Leu
        35                  40                  45

Gly Ile Ser Thr Gly Arg Gly Thr Gly Gly Ala Thr Gly Trp Pro Leu
    50                  55                  60

Gly Glu Gly Pro Gly Val Arg Val Gly Gly Thr Pro Thr
65                  70                  75

<210> SEQ ID NO 42
<211> LENGTH: 77
<212> TYPE: PRT
<213> ORGANISM: Human papillomavirus

<400> SEQUENCE: 42

Lys Arg Ala Ser Ala Thr Gln Leu Tyr Gln Thr Cys Lys Leu Thr Gly
1               5                   10                  15

Thr Cys Pro Pro Asp Val Ile Pro Lys Val Glu His Asn Thr Ile Ala
            20                  25                  30

Asp Gln Ile Leu Lys Trp Gly Ser Leu Gly Val Phe Phe Gly Gly Leu
        35                  40                  45

Gly Ile Gly Thr Gly Ser Gly Thr Gly Gly Arg Thr Gly Trp Pro Leu
    50                  55                  60

Gly Thr Ser Ala Lys Pro Ser Ile Thr Ser Gly Pro Met
65                  70                  75

<210> SEQ ID NO 43
<211> LENGTH: 79
<212> TYPE: PRT
<213> ORGANISM: Human papillomavirus

<400> SEQUENCE: 43

```
Ser Ala Thr Gln Leu Tyr Gln Thr Cys Lys Leu Thr Gly Thr Cys Pro
1               5                   10                  15

Pro Asp Val Ile Pro Lys Val Glu His Asn Thr Ile Ala Asp Gln Ile
                20                  25                  30

Leu Lys Trp Gly Ser Leu Gly Val Phe Phe Gly Gly Leu Gly Ile Gly
            35                  40                  45

Thr Gly Ser Gly Thr Gly Arg Thr Gly Tyr Val Pro Leu Gln Thr
        50                  55                  60

Ser Ala Lys Pro Ser Ile Thr Ser Gly Pro Met Ala Lys Arg Ala
65                  70                  75
```

<210> SEQ ID NO 44
<211> LENGTH: 77
<212> TYPE: PRT
<213> ORGANISM: Human papillomavirus

<400> SEQUENCE: 44

```
Ser Ala Thr Gln Leu Tyr Lys Thr Cys Lys Gln Ala Gly Thr Cys Pro
1               5                   10                  15

Pro Asp Ile Ile Pro Lys Val Glu Gly Lys Thr Ile Ala Asp Gln Ile
                20                  25                  30

Leu Gln Tyr Gly Ser Met Gly Val Phe Phe Gly Gly Leu Gly Ile Gly
            35                  40                  45

Thr Gly Ser Gly Thr Gly Arg Thr Gly Tyr Ile Pro Leu Gly Thr
        50                  55                  60

Arg Pro Pro Thr Ala Thr Asp Thr Leu Ala Pro Arg Ala
65                  70                  75
```

<210> SEQ ID NO 45
<211> LENGTH: 78
<212> TYPE: PRT
<213> ORGANISM: Human papillomavirus

<400> SEQUENCE: 45

```
Ser Val Thr Asp Leu Tyr Lys Thr Cys Lys Gln Ser Gly Thr Cys Pro
1               5                   10                  15

Pro Asp Val Val Pro Lys Val Glu Gly Thr Thr Leu Ala Asp Lys Ile
                20                  25                  30

Leu Gln Trp Ser Ser Leu Gly Ile Phe Leu Gly Gly Leu Gly Ile Gly
            35                  40                  45

Thr Gly Ser Gly Thr Gly Gly Arg Thr Gly Tyr Ile Pro Leu Gly Gly
        50                  55                  60

Arg Ser Asn Thr Trp Asp Val Gly Pro Thr Arg Lys Arg Ala
65                  70                  75
```

<210> SEQ ID NO 46
<211> LENGTH: 77
<212> TYPE: PRT
<213> ORGANISM: Human papillomavirus

<400> SEQUENCE: 46

```
Ser Ala Thr Gln Leu Tyr Gln Thr Cys Lys Ala Ala Gly Thr Cys Pro
1               5                   10                  15

Ser Asp Val Ile Pro Lys Ile Glu His Thr Thr Ile Ala Asp Gln Ile
                20                  25                  30

Leu Arg Tyr Gly Ser Met Gly Val Phe Phe Gly Gly Leu Gly Ile Gly
            35                  40                  45

Ser Gly Ser Gly Thr Gly Gly Arg Thr Gly Tyr Val Pro Leu Ser Thr
```

```
         50                  55                  60
Arg Pro Ser Thr Val Ser Glu Ala Ser Ile Pro Arg Ala
 65                  70                  75

<210> SEQ ID NO 47
<211> LENGTH: 77
<212> TYPE: PRT
<213> ORGANISM: Human papillomavirus

<400> SEQUENCE: 47

Ser Ala Thr Asp Leu Tyr Arg Thr Cys Lys Gln Ser Gly Thr Cys Pro
 1               5                  10                  15

Pro Asp Trp Asp Lys Val Glu Gly Thr Thr Leu Ala Asp Lys Ile Leu
             20                  25                  30

Gln Trp Thr Ser Leu Gly Ile Phe Leu Gly Gly Leu Gly Ile Gly Thr
         35                  40                  45

Gly Thr Gly Thr Gly Gly Arg Thr Gly Tyr Ile Pro Leu Gly Gly Arg
     50                  55                  60

Pro Asn Thr Val Val Asp Val Ser Pro Ala Arg Arg Ala
 65                  70                  75

<210> SEQ ID NO 48
<211> LENGTH: 77
<212> TYPE: PRT
<213> ORGANISM: Human papillomavirus

<400> SEQUENCE: 48

Ser Val Thr Gln Leu Tyr Ser Thr Cys Lys Ala Ala Gly Thr Cys Pro
 1               5                  10                  15

Pro Asp Val Val Asn Lys Val Glu Gly Thr Thr Leu Ala Asp Lys Ile
             20                  25                  30

Leu Gln Trp Ser Gly Leu Gly Ile Phe Leu Gly Gly Leu Gly Ile Gly
         35                  40                  45

Thr Gly Ser Gly Ser Gly Gly Arg Thr Gly Tyr Ile Pro Leu Gly Gly
     50                  55                  60

Gly Gly Arg Pro Gly Trp Asp Ile Ala Pro Ala Arg Ala
 65                  70                  75

<210> SEQ ID NO 49
<211> LENGTH: 80
<212> TYPE: PRT
<213> ORGANISM: Human papillomavirus

<400> SEQUENCE: 49

Ser Ala Thr Gln Leu Tyr Lys Thr Cys Lys Leu Ser Gly Thr Cys Pro
 1               5                  10                  15

Glu Asp Val Val Asn Lys Ile Glu Gln Lys Thr Trp Ala Asp Lys Ile
             20                  25                  30

Leu Gln Trp Gly Ser Leu Phe Thr Tyr Phe Gly Gly Leu Gly Ile Gly
         35                  40                  45

Thr Gly Thr Gly Ser Gly Gly Arg Ala Gly Tyr Val Pro Leu Gly Ser
     50                  55                  60

Arg Pro Ser Thr Ile Val Asp Val Thr Pro Ala Arg Lys Lys Arg Ala
 65                  70                  75                  80

<210> SEQ ID NO 50
<211> LENGTH: 74
<212> TYPE: PRT
<213> ORGANISM: Human papillomavirus
```

<400> SEQUENCE: 50

Ser Ala Thr Gln Leu Tyr Lys Thr Cys Lys Gln Ala Gly Thr Cys Pro
1               5                   10                  15

Pro Asp Val Ile Pro Lys Val Glu Gly Ser Thr Ile Ala Asp Asn Ile
            20                  25                  30

Leu Lys Tyr Gly Ser Ile Gly Val Phe Phe Gly Gly Leu Gly Ile Gly
        35                  40                  45

Ser Gly Ser Gly Ser Gly Gly Arg Thr Gly Tyr Val Pro Leu Ser Thr
    50                  55                  60

Gly Thr Pro Ser Lys Pro Val Glu Ile Pro
65                  70

<210> SEQ ID NO 51
<211> LENGTH: 192
<212> TYPE: PRT
<213> ORGANISM: Human papillomavirus

<400> SEQUENCE: 51

Lys Arg Ala Ser Ala Thr Gln Leu Tyr Gln Thr Cys Lys Ala Ser Gly
1               5                   10                  15

Thr Cys Pro Pro Asp Ile Ile Ala Lys Val Glu Gln Asn Thr Leu Ala
            20                  25                  30

Asp Lys Ile Leu Lys Trp Gly Ser Leu Gly Val Phe Phe Gly Gly Leu
        35                  40                  45

Gly Ile Gly Thr Gly Ser Gly Thr Gly Gly Arg Thr Gly Tyr Val Pro
    50                  55                  60

Val Gln Thr Ala Pro Arg Pro Ala Ile Pro Phe Gly Pro Thr Ala Arg
65                  70                  75                  80

Pro Pro Ile Ile Val Asp Thr Val Gly Pro Ser Asp Ser Ser Ile Val
                85                  90                  95

Ser Leu Val Glu Asp Ser Thr Ile Ile Asn Ser Ala Ala Ser Asp Phe
            100                 105                 110

Val Pro Pro Ile Arg Glu Gly Phe Glu Ile Ser Thr Ser Glu Thr Thr
        115                 120                 125

Thr Pro Ala Ile Leu Asp Val Ser Val Thr Thr His Asn Thr Thr Ser
    130                 135                 140

Thr Ser Ile Phe Lys Asn Pro Ala Phe Ala Glu Pro Ser Ile Val Gln
145                 150                 155                 160

Ser Gln Pro Ser Val Glu Ala Ser Gly His Val Leu Thr Ser Thr Tyr
                165                 170                 175

Thr Ser Thr Ile Ser Ser His Ser Val Glu Asp Ile Pro Leu Asp Thr
            180                 185                 190

<210> SEQ ID NO 52
<211> LENGTH: 191
<212> TYPE: PRT
<213> ORGANISM: Human papillomavirus

<400> SEQUENCE: 52

Lys Arg Ala Ser Ala Thr Gln Leu Tyr Lys Thr Cys Lys Gln Ala Gly
1               5                   10                  15

Thr Cys Pro Pro Asp Ile Ile Pro Lys Val Glu Gly Lys Thr Ile Ala
            20                  25                  30

Asp Gln Ile Leu Gln Tyr Gly Ser Met Gly Val Phe Phe Gly Gly Leu
        35                  40                  45

```
Gly Ile Gly Thr Gly Ser Gly Thr Gly Gly Arg Thr Gly Tyr Ile Pro
            50                  55                  60

Leu Gly Thr Arg Pro Pro Thr Ala Thr Asp Thr Leu Ala Pro Val Arg
 65                  70                  75                  80

Pro Pro Leu Thr Val Asp Pro Val Gly Pro Ser Asp Pro Ser Ile Val
                85                  90                  95

Ser Leu Val Glu Glu Thr Ser Phe Ile Asp Ala Gly Ala Pro Thr Pro
               100                 105                 110

Val Pro Ser Ile Pro Pro Asp Val Ser Gly Phe Ser Ile Thr Thr Ser
               115                 120                 125

Thr Asp Thr Thr Pro Ala Ile Leu Asp Ile Asn Asn Thr Val Phe Thr
130                 135                 140

Thr Val Thr Thr His Asn Asn Pro Thr Phe Thr Asp Pro Ser Val Leu
145                 150                 155                 160

Gln Pro Pro Thr Pro Ala Glu Thr Gly Gly His Phe Thr Leu Ser Ser
                165                 170                 175

Ser Thr Ile Ser Thr His Asn Tyr Glu Glu Ile Pro Met Asp Thr
                180                 185                 190

<210> SEQ ID NO 53
<211> LENGTH: 191
<212> TYPE: PRT
<213> ORGANISM: Human papillomavirus

<400> SEQUENCE: 53

Lys Arg Ala Ser Val Thr Asp Leu Tyr Lys Thr Cys Lys Gln Ser Gly
 1               5                  10                  15

Thr Cys Pro Pro Asp Val Val Pro Lys Val Glu Gly Thr Thr Leu Ala
                20                  25                  30

Asp Lys Ile Leu Gln Trp Ser Ser Leu Gly Ile Phe Leu Gly Gly Leu
            35                  40                  45

Gly Ile Gly Thr Gly Ser Gly Thr Gly Gly Arg Thr Gly Tyr Ile Pro
         50                     55                  60

Leu Gly Gly Arg Ser Asn Thr Val Val Asp Val Gly Pro Thr Arg Pro
 65                 70                  75                  80

Pro Val Val Ile Glu Pro Val Gly Pro Thr Asp Pro Ser Ile Val Thr
                85                  90                  95

Leu Ile Glu Asp Ser Ser Val Val Thr Ser Gly Ala Pro Arg Pro Thr
               100                 105                 110

Phe Thr Gly Thr Ser Gly Phe Ile Asp Ile Thr Ser Ala Gly Thr Thr
               115                 120                 125

Thr Pro Ala Val Leu Asp Ile Thr Pro Ser Ser Thr Ser Val Ser Ile
130                 135                 140

Ser Thr Thr Asn Phe Thr Asn Pro Ala Phe Ser Asp Pro Ser Ile Ile
145                 150                 155                 160

Glu Val Pro Gln Thr Gly Glu Val Ala Gly Asn Val Phe Val Gly Thr
                165                 170                 175

Pro Thr Ser Gly Thr His Gly Tyr Glu Glu Ile Pro Leu Gln Thr
                180                 185                 190

<210> SEQ ID NO 54
<211> LENGTH: 507
<212> TYPE: PRT
<213> ORGANISM: Human papillomavirus type 1a

<400> SEQUENCE: 54
```

```
Met Tyr Arg Leu Arg Arg Lys Arg Ala Ala Pro Lys Asp Ile Tyr Pro
1               5                   10                  15

Ser Cys Lys Ile Ser Asn Thr Cys Pro Pro Asp Ile Gln Asn Lys Ile
            20                  25                  30

Glu His Thr Thr Ile Ala Asp Lys Ile Leu Gln Tyr Gly Ser Leu Gly
        35                  40                  45

Val Phe Leu Gly Gly Leu Gly Ile Gly Thr Ala Arg Gly Ser Gly Gly
    50                  55                  60

Arg Ile Gly Tyr Thr Pro Leu Gly Glu Gly Gly Val Arg Val Ala
65                  70                  75                  80

Thr Arg Pro Thr Pro Val Arg Pro Thr Ile Pro Val Glu Thr Val Gly
                85                  90                  95

Pro Ser Glu Ile Phe Pro Ile Asp Val Val Asp Pro Thr Gly Pro Ala
                100                 105                 110

Val Ile Pro Leu Gln Asp Leu Gly Arg Asp Phe Pro Ile Pro Thr Val
            115                 120                 125

Gln Val Ile Ala Glu Ile His Pro Ile Ser Asp Ile Pro Asn Ile Val
            130                 135                 140

Ala Ser Ser Thr Asn Glu Gly Glu Ser Ala Ile Leu Asp Val Leu Arg
145                 150                 155                 160

Gly Asn Ala Thr Ile Arg Thr Val Ser Arg Thr Gln Tyr Asn Asn Pro
                165                 170                 175

Ser Phe Thr Val Ala Ser Thr Ser Asn Ile Ser Ala Gly Glu Ala Ser
                180                 185                 190

Thr Ser Asp Ile Val Phe Val Ser Asn Gly Ser Gly Asp Arg Val Val
                195                 200                 205

Gly Glu Asp Ile Pro Leu Val Glu Leu Asn Leu Gly Leu Glu Thr Asp
210                 215                 220

Thr Ser Ser Val Val Gln Glu Thr Ala Phe Ser Ser Thr Pro Ile
225                 230                 235                 240

Ala Glu Arg Pro Ser Phe Arg Pro Ser Arg Phe Tyr Asn Arg Arg Leu
                245                 250                 255

Tyr Glu Gln Val Gln Val Gln Asp Pro Arg Phe Val Glu Gln Pro Gln
                260                 265                 270

Ser Met Val Thr Phe Asp Asn Pro Ala Phe Glu Pro Glu Leu Asp Glu
                275                 280                 285

Val Ser Ile Ile Phe Gln Arg Asp Leu Asp Ala Leu Ala Gln Thr Pro
            290                 295                 300

Val Pro Glu Phe Arg Asp Val Val Tyr Leu Ser Lys Pro Thr Phe Ser
305                 310                 315                 320

Arg Glu Pro Gly Gly Arg Leu Arg Val Ser Arg Leu Gly Lys Ser Ser
                325                 330                 335

Thr Ile Arg Thr Arg Leu Gly Thr Ala Ile Gly Ala Arg Thr His Phe
                340                 345                 350

Phe Tyr Asp Leu Ser Ser Ile Ala Pro Glu Asp Ser Ile Glu Leu Leu
                355                 360                 365

Pro Leu Gly Glu His Ser Gln Thr Thr Val Ile Ser Ser Asn Leu Gly
                370                 375                 380

Asp Thr Ala Phe Ile Gln Gly Glu Thr Ala Asp Asp Leu Glu Val
385                 390                 395                 400

Ile Ser Leu Glu Thr Pro Gln Leu Tyr Ser Glu Glu Leu Leu Asp
                405                 410                 415

Thr Asn Glu Ser Val Gly Glu Asn Leu Gln Leu Thr Ile Thr Asn Ser
```

```
                    420                 425                 430
Glu Gly Glu Val Ser Ile Leu Asp Leu Thr Gln Ser Arg Val Arg Pro
                435                 440                 445

Pro Phe Gly Thr Glu Asp Thr Ser Leu His Val Tyr Tyr Pro Asn Ser
            450                 455                 460

Ser Lys Gly Thr Pro Ile Ile Asn Pro Glu Ser Phe Thr Pro Leu
465                 470                 475                 480

Val Ile Ile Ala Leu Asn Asn Ser Thr Gly Asp Phe Glu Leu His Pro
                485                 490                 495

Ser Leu Arg Lys Arg Lys Arg Ala Tyr Val
                500                 505

<210> SEQ ID NO 55
<211> LENGTH: 468
<212> TYPE: PRT
<213> ORGANISM: Human papillomavirus type 2

<400> SEQUENCE: 55

Met Ser Ile Arg Ala Lys Arg Lys Arg Ala Ser Pro Thr Asp Leu
1               5                   10                  15

Tyr Arg Thr Cys Lys Gln Ala Gly Thr Cys Pro Pro Asp Ile Ile Pro
                20                  25                  30

Arg Val Glu Gln Asn Thr Leu Ala Asp Lys Leu Leu Lys Trp Gly Ser
            35                  40                  45

Leu Gly Val Phe Phe Gly Gly Leu Gly Ile Gly Thr Gly Ser Gly Thr
        50                  55                  60

Gly Gly Arg Thr Gly Tyr Ile Pro Val Gly Ser Arg Pro Thr Thr Val
65                  70                  75                  80

Val Asp Ile Gly Pro Thr Pro Arg Pro Pro Val Ile Ile Glu Pro Val
                85                  90                  95

Gly Ala Ser Glu Pro Ser Ile Val Thr Leu Val Glu Asp Ser Ser Ile
            100                 105                 110

Ile Asn Ala Gly Ala Ser His Pro Thr Phe Thr Gly Thr Gly Gly Phe
        115                 120                 125

Glu Val Thr Thr Ser Thr Val Thr Asp Pro Ala Val Leu Asp Ile Thr
130                 135                 140

Pro Ser Gly Thr Ser Val Gln Val Ser Ser Ser Phe Leu Asn Pro
145                 150                 155                 160

Leu Tyr Thr Glu Pro Ala Ile Val Glu Ala Pro Gln Thr Gly Glu Val
                165                 170                 175

Ser Gly His Val Leu Val Ser Thr Ala Thr Ser Gly Ser His Gly Tyr
            180                 185                 190

Glu Glu Ile Pro Met Gln Thr Phe Ala Thr Ser Gly Gly Ser Gly Thr
        195                 200                 205

Glu Pro Ile Ser Ser Thr Pro Leu Pro Gly Val Arg Arg Val Ala Gly
210                 215                 220

Pro Arg Leu Tyr Ser Arg Ala Asn Gln Gln Val Gln Val Arg Asp Pro
225                 230                 235                 240

Ala Phe Leu Ala Arg Pro Ala Asp Leu Val Thr Phe Asp Asn Pro Val
                245                 250                 255

Tyr Asp Pro Glu Glu Thr Ile Ile Phe Gln His Pro Asp Leu His Glu
            260                 265                 270

Pro Pro Asp Pro Asp Phe Leu Asp Ile Val Ala Leu His Arg Pro Ala
        275                 280                 285
```

-continued

```
Leu Thr Ser Arg Arg Gly Thr Val Arg Phe Ser Leu Gly Arg Arg
290                 295                 300

Ala Thr Leu Arg Thr Arg Ser Gly Lys Gln Ile Gly Ala Arg Val His
305                 310                 315                 320

Phe Tyr His Asp Ile Ser Pro Ile Gly Thr Glu Glu Leu Glu Met Glu
                325                 330                 335

Pro Leu Leu Pro Pro Ala Ser Thr Asp Asn Thr Asp Met Leu Tyr Asp
                340                 345                 350

Val Tyr Ala Asp Ser Asp Val Leu Gln Pro Leu Leu Asp Glu Leu Pro
                355                 360                 365

Ala Ala Pro Arg Gly Ser Leu Ser Leu Ala Asp Thr Ala Val Ser Ala
370                 375                 380

Thr Ser Ala Ser Thr Leu Arg Gly Ser Thr Thr Val Pro Leu Ser Ser
385                 390                 395                 400

Gly Ile Asp Val Pro Val Tyr Thr Gly Pro Asp Ile Glu Pro Pro Asn
                405                 410                 415

Val Pro Gly Met Gly Pro Leu Ile Pro Val Ala Pro Ser Leu Pro Ser
                420                 425                 430

Ser Val Tyr Ile Phe Gly Gly Asp Tyr Tyr Leu Met Pro Ser Tyr Val
                435                 440                 445

Leu Trp Pro Lys Arg Arg Lys Arg Val His Tyr Phe Phe Ala Asp Gly
450                 455                 460

Phe Val Ala Ala
465

<210> SEQ ID NO 56
<211> LENGTH: 473
<212> TYPE: PRT
<213> ORGANISM: Human papillomavirus type 3

<400> SEQUENCE: 56

Met Val Ala His Arg Ala Arg Arg Arg Lys Arg Ala Ser Ala Thr Gln
1               5                   10                  15

Leu Tyr Arg Thr Cys Lys Ala Ala Gly Thr Cys Pro Pro Asp Val Ile
                20                  25                  30

Pro Lys Val Glu Gly Thr Thr Leu Ala Asp Arg Ile Leu Gln Trp Gly
                35                  40                  45

Ser Leu Gly Val Tyr Leu Gly Gly Leu Gly Ile Gly Thr Gly Ser Gly
                50                  55                  60

Thr Gly Gly Arg Thr Gly Tyr Ala Pro Ile Ser Thr Arg Pro Gly Thr
65                  70                  75                  80

Val Val Asp Val Ser Val Pro Ala Lys Pro Pro Val Val Ile Glu Pro
                85                  90                  95

Val Gly Pro Ser Asp Pro Ser Ile Val Asn Leu Leu Glu Asp Ser Ser
                100                 105                 110

Ile Ile Asn Ser Gly Ser Thr Ile Pro Thr Phe Thr Gly Thr Asp Gly
                115                 120                 125

Phe Glu Val Ile Ser Ser Ala Thr Thr Thr Pro Ala Val Leu Asp Ile
                130                 135                 140

Thr Pro Ala Ser Asp Asn Val Val Val Ser Ser Thr Asn Phe Ser Asn
145                 150                 155                 160

Pro Ala Phe Thr Glu Pro Ser Leu Leu Glu Val Pro Gln Asn Gly Glu
                165                 170                 175

Val Ser Gly His Ile Leu Ile Ser Thr Pro Thr Ser Gly Thr His Gly
                180                 185                 190
```

-continued

Tyr Glu Glu Ile Pro Met Glu Thr Phe Ala Ser Pro Gly Thr Gly Thr
            195                 200                 205

Glu Pro Ile Ser Ser Thr Pro Val Pro Gly Val Ser Arg Ile Ala Gly
210                 215                 220

Pro Arg Leu Tyr Ser Lys Ala Val Thr Gln Val Lys Val Thr Asp Pro
225                 230                 235                 240

Ala Phe Leu Thr Arg Pro Arg Ser Leu Met Thr Phe Asp Asn Pro Val
            245                 250                 255

Phe Glu Pro Glu Asp Glu Thr Ile Ile Phe Glu Arg Pro Tyr Ser Pro
            260                 265                 270

Ser Gln Val Pro Asp Ser Asp Phe Leu Asp Ile Leu Arg Leu His Arg
            275                 280                 285

Pro Ala Leu Thr Ser Arg Arg Gly Thr Val Arg Tyr Ser Arg Val Gly
290                 295                 300

Gln Lys Leu Ser Met Arg Thr Arg Ser Gly Lys Gly Leu Gly Ala Arg
305                 310                 315                 320

Val His Tyr Tyr Gln Asp Leu Ser Pro Ile Gly Pro Thr Glu Asp Ile
            325                 330                 335

Glu Met Glu Pro Leu Ile Ala Pro Ala Ser Ala Ser Ala Tyr Asp Ser
            340                 345                 350

Leu Tyr Asp Val Tyr Ala Asp Val Asp Ala Asp Ile Gly Phe Thr
            355                 360                 365

Ser Gly Gly Arg Ser Asp Thr Leu Ser Arg Gly Arg Ala Thr Val Ser
370                 375                 380

Pro Leu Ser Ser Thr Leu Ser Thr Lys Tyr Gly Asn Val Thr Ile Pro
385                 390                 395                 400

Phe Val Ser Pro Val Asp Val Pro Leu Gln Pro Gly Pro Asp Ile Leu
            405                 410                 415

Leu Pro Ala Ser Ala Gln Trp Pro Phe Val Pro Leu Ser Pro Val Asp
            420                 425                 430

Thr Thr His Tyr Val Tyr Ile Asp Gly Gly Asp Phe Tyr Leu Trp Pro
            435                 440                 445

Val Thr Phe Phe Leu Pro Arg Arg Arg Arg Lys Arg Val Ser Tyr
            450                 455                 460

Phe Leu Ala Asp Gly Thr Val Ala Leu
465                 470

<210> SEQ ID NO 57
<211> LENGTH: 521
<212> TYPE: PRT
<213> ORGANISM: Human papillomavirus type 4

<400> SEQUENCE: 57

Met Gln Ser Leu Ser Arg Arg Lys Arg Asp Ser Val Pro Asn Leu Tyr
1               5                   10                  15

Ala Lys Cys Gln Leu Ser Gly Asn Cys Leu Pro Asp Val Lys Asn Lys
            20                  25                  30

Val Glu Ala Asp Thr Leu Ala Asp Arg Leu Leu Arg Trp Leu Gly Ser
        35                  40                  45

Val Ile Tyr Leu Gly Gly Leu Gly Ile Gly Thr Gly Arg Gly Ser Gly
    50                  55                  60

Gly Ser Thr Gly Tyr Asn Pro Ile Gly Ala Pro Ser Arg Val Thr Pro
65                  70                  75                  80

Ser Gly Thr Leu Val Arg Pro Thr Val Pro Val Glu Ser Leu Gly Pro

```
            85                  90                  95
Ser Glu Ile Ile Pro Ile Asp Ala Ile Asp Pro Thr Thr Ser Ser Val
            100                 105                 110

Val Pro Leu Glu Asp Leu Thr Ile Pro Asp Val Thr Val Asp Ser Gly
            115                 120                 125

Asp Thr Arg Gly Ile Gly Glu Thr Thr Leu Gln Pro Ala Gln Val Asp
            130                 135                 140

Ile Ser Thr Ser His Asp Pro Ile Ser Asp Val Thr Gly Ala Ser Ser
145                 150                 155                 160

His Pro Thr Ile Ile Ser Gly Glu Asp Asn Ala Ile Ala Val Leu Asp
                165                 170                 175

Val Ser Pro Ile Glu Pro Pro Thr Lys Arg Ile Ala Leu Ala Thr Arg
            180                 185                 190

Gly Ala Ser Ala Thr Pro His Val Ser Val Ile Ser Gly Thr Thr Glu
            195                 200                 205

Phe Gly Gln Ser Ser Asp Leu Asn Val Phe Val Asn Ala Thr Phe Ser
            210                 215                 220

Gly Asp Ser Ile Gly Tyr Thr Glu Glu Ile Pro Leu Glu Pro Leu Asn
225                 230                 235                 240

Pro Phe Gln Glu Phe Glu Ile Glu Ser Pro Pro Lys Thr Ser Thr Pro
                245                 250                 255

Arg Asp Val Leu Asn Arg Ala Ile Gly Arg Ala Arg Asp Leu Tyr Asn
            260                 265                 270

Arg Arg Val Gln Gln Ile Pro Thr Arg Asn Pro Ala Leu Leu Thr Gln
            275                 280                 285

Pro Ser Arg Ala Ile Val Phe Gly Phe Glu Asn Pro Ala Phe Asp Ala
            290                 295                 300

Asp Ile Thr Gln Thr Phe Glu Arg Asp Leu Glu Gln Val Ala Ala Ala
305                 310                 315                 320

Pro Asp Ala Asp Phe Ala Asp Ile Val Thr Ile Gly Arg Pro Arg Phe
                325                 330                 335

Ser Glu Thr Asp Ala Gly Gln Ile Arg Val Ser Arg Leu Gly Arg Arg
            340                 345                 350

Gly Thr Ile Lys Thr Arg Ser Gly Val Gln Ile Gly Gln Ala Val His
            355                 360                 365

Phe Tyr Tyr Asp Leu Ser Thr Ile Asp Thr Ala Asp Ala Ile Glu Leu
            370                 375                 380

Ser Thr Leu Gly Gln His Ser Gly Glu Gln Ser Ile Val Asp Ala Met
385                 390                 395                 400

Ile Glu Ser Ser Leu Ile Asp Pro Phe Glu Met Pro Asp Pro Thr Phe
                405                 410                 415

Thr Glu Glu Gln Gln Leu Leu Asp Pro Leu Thr Glu Asp Phe Ser Gln
            420                 425                 430

Ser His Leu Val Leu Thr Ser Ser Arg Arg Gly Thr Ser Phe Thr Ile
            435                 440                 445

Pro Thr Ile Pro Pro Gly Leu Gly Leu Arg Ile Tyr Val Asp Asp Val
            450                 455                 460

Gly Ser Asp Leu Phe Val Ser Tyr Pro Glu Ser Arg Val Ile Pro Ala
465                 470                 475                 480

Gly Gly Leu Pro Thr Glu Pro Phe Val Pro Leu Glu Pro Ala Leu Leu
                485                 490                 495

Ser Asp Ile Phe Ser Thr Asp Phe Val Tyr Arg Pro Ser Leu Tyr Arg
            500                 505                 510
```

Lys Lys Arg Lys Arg Leu Glu Met Phe
         515                 520

<210> SEQ ID NO 58
<211> LENGTH: 518
<212> TYPE: PRT
<213> ORGANISM: Human papillomavirus type 5

<400> SEQUENCE: 58

Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Ile Asn Lys
            20                  25                  30

Val Glu Gln Thr Thr Val Ala Asp Asn Ile Leu Lys Tyr Gly Ser Ala
        35                  40                  45

Gly Val Phe Phe Gly Gly Leu Gly Ile Ser Thr Gly Arg Gly Thr Gly
    50                  55                  60

Gly Ala Thr Gly Tyr Val Pro Leu Gly Glu Gly Pro Gly Val Arg Val
65                  70                  75                  80

Gly Gly Thr Pro Thr Val Val Arg Pro Ser Leu Val Pro Glu Thr Ile
                85                  90                  95

Gly Pro Val Asp Ile Leu Pro Ile Asp Thr Val Asn Pro Val Glu Pro
            100                 105                 110

Thr Ala Ser Ser Val Val Pro Leu Thr Glu Ser Thr Gly Ala Asp Leu
        115                 120                 125

Leu Pro Gly Glu Val Glu Thr Ile Ala Glu Ile His Pro Val Pro Glu
    130                 135                 140

Gly Pro Ser Val Asp Thr Pro Val Val Thr Thr Ser Thr Gly Ser Ser
145                 150                 155                 160

Ala Val Leu Glu Val Ala Pro Glu Pro Ile Pro Pro Thr Arg Val Arg
                165                 170                 175

Val Ser Arg Thr Gln Tyr His Asn Pro Ser Phe Gln Ile Ile Thr Glu
            180                 185                 190

Ser Thr Pro Ala Gln Gly Glu Ser Ser Leu Ala Asp His Val Leu Val
        195                 200                 205

Thr Ser Gly Ser Gly Gly Gln Arg Ile Gly Gly Asp Ile Thr Asp Ile
    210                 215                 220

Ile Glu Leu Glu Glu Ile Pro Ser Arg Tyr Thr Phe Glu Ile Glu Glu
225                 230                 235                 240

Pro Thr Pro Pro Arg Arg Ser Ser Thr Pro Leu Pro Arg Asn Gln Ser
                245                 250                 255

Val Gly Arg Arg Arg Gly Phe Ser Leu Thr Asn Arg Arg Leu Val Gln
            260                 265                 270

Gln Val Gln Val Asp Asn Pro Leu Phe Leu Thr Gln Pro Ser Lys Leu
        275                 280                 285

Val Arg Phe Ala Phe Asp Asn Pro Val Phe Glu Glu Val Thr Asn
    290                 295                 300

Ile Phe Glu Asn Asp Leu Asp Val Phe Glu Glu Pro Pro Asp Arg Asp
305                 310                 315                 320

Phe Leu Asp Val Arg Glu Leu Gly Arg Pro Gln Tyr Ser Thr Thr Pro
                325                 330                 335

Ala Gly Tyr Val Arg Val Ser Arg Leu Gly Thr Arg Ala Thr Ile Arg
            340                 345                 350

Thr Arg Ser Gly Ala Gln Ile Gly Ser Gln Val His Phe Tyr Arg Asp

```
                355                 360                 365
Leu Ser Ser Ile Asn Thr Glu Asp Pro Ile Glu Leu Gln Leu Leu Gly
    370                 375                 380

Gln His Ser Gly Asp Ala Thr Ile Val Gln Gly Pro Val Glu Ser Thr
385                 390                 395                 400

Phe Ile Asp Met Asp Ile Ser Glu Asn Pro Leu Ser Glu Ser Ile Glu
                405                 410                 415

Ala Tyr Ser His Asp Leu Leu Leu Asp Glu Thr Val Glu Asp Phe Ser
                420                 425                 430

Gly Ser Gln Leu Val Ile Gly Asn Arg Arg Ser Thr Asn Ser Tyr Thr
                435                 440                 445

Val Pro Arg Phe Glu Thr Thr Arg Asn Gly Ser Tyr Tyr Thr Gln Asp
                450                 455                 460

Thr Lys Gly Tyr Tyr Val Ala Tyr Pro Glu Ser Arg Asn Asn Ala Glu
465                 470                 475                 480

Ile Ile Tyr Pro Thr Pro Asp Ile Pro Val Val Ile Ile His Pro His
                485                 490                 495

Asp Ser Thr Gly Asp Phe Tyr Leu His Pro Ser Leu Arg Arg Arg Lys
                500                 505                 510

Arg Lys Arg Lys Tyr Leu
                515

<210> SEQ ID NO 59
<211> LENGTH: 459
<212> TYPE: PRT
<213> ORGANISM: Human papillomavirus type 6

<400> SEQUENCE: 59

Met Ala His Ser Arg Ala Arg Arg Lys Arg Ala Ser Ala Thr Gln
1               5                   10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
        50                  55                  60

Thr Gly Gly Arg Thr Gly Tyr Val Pro Leu Gly Thr Ser Ala Lys Pro
65                  70                  75                  80

Ser Ile Thr Ser Gly Pro Met Ala Arg Pro Pro Val Val Glu Pro
                85                  90                  95

Val Ala Pro Ser Asp Pro Ser Ile Val Ser Leu Ile Glu Glu Ser Ala
                100                 105                 110

Ile Ile Asn Ala Gly Ala Pro Glu Ile Val Pro Pro Ala His Gly Gly
            115                 120                 125

Phe Thr Ile Thr Ser Ser Glu Thr Thr Thr Pro Ala Ile Leu Asp Val
    130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Ile Thr Ser His Pro Ile Glu Glu
            180                 185                 190

Ile Pro Leu Asp Thr Phe Val Ile Ser Ser Ser Asp Ser Gly Pro Thr
        195                 200                 205
```

Ser Ser Thr Pro Val Pro Gly Thr Ala Pro Arg Pro Arg Val Gly Leu
    210                 215                 220

Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
                245                 250                 255

Glu Asp Val Ser Val Gln Phe Ser His Asp Ser Ile His Asn Ala Pro
            260                 265                 270

Asp Glu Ala Phe Met Asp Ile Ile Arg Leu His Arg Pro Ala Ile Ala
        275                 280                 285

Ser Arg Arg Gly Leu Val Arg Tyr Ser Arg Ile Gly Gln Arg Gly Ser
    290                 295                 300

Met His Thr Arg Ser Gly Lys His Ile Gly Ala Arg Ile His Tyr Phe
305                 310                 315                 320

Tyr Asp Ile Ser Pro Ile Ala Gln Ala Ala Glu Ile Glu Met His
                325                 330                 335

Pro Leu Val Ala Ala Gln Glu Asp Thr Phe Asp Ile Tyr Ala Glu Ser
            340                 345                 350

Phe Glu Pro Asp Ile Asn Pro Thr Gln His Pro Val Thr Asn Ile Ser
        355                 360                 365

Asp Thr Tyr Leu Thr Ser Thr Pro Asn Thr Val Thr Gln Pro Trp Gly
    370                 375                 380

Asn Thr Thr Val Pro Leu Ser Ile Pro Asn Asp Leu Phe Leu Gln Ser
385                 390                 395                 400

Gly Pro Asp Ile Thr Phe Pro Thr Ala Pro Met Gly Thr Pro Phe Ser
                405                 410                 415

Pro Val Thr Pro Ala Leu Pro Thr Gly Pro Val Phe Ile Thr Gly Ser
            420                 425                 430

Gly Phe Tyr Leu His Pro Ala Trp Tyr Phe Ala Arg Lys Arg Arg Lys
        435                 440                 445

Arg Ile Pro Leu Phe Phe Ser Asp Val Ala Ala
    450                 455

<210> SEQ ID NO 60
<211> LENGTH: 456
<212> TYPE: PRT
<213> ORGANISM: Human papillomavirus type 7

<400> SEQUENCE: 60

Met Val Ser Ser Arg Pro Arg Arg Arg Lys Arg Ala Ser Ala Thr Gln
1               5                   10                  15

Leu Tyr Gln Thr Cys Lys Ala Ala Gly Thr Cys Pro Pro Asp Val Val
                20                  25                  30

Asn Lys Val Glu Gln Thr Thr Val Ala Asp Gln Ile Leu Lys Trp Gly
            35                  40                  45

Ser Met Gly Val Phe Phe Gly Gly Leu Gly Ile Gly Ser Gly Ser Gly
        50                  55                  60

Ser Gly Gly Arg Ala Gly Tyr Val Pro Leu Ser Thr Gly Ser Arg Ala
65                  70                  75                  80

Ile Pro Pro Lys Ser Leu Ala Pro Asp Val Ile Ala Arg Pro Pro Val
                85                  90                  95

Val Val Asp Thr Val Ala Pro Thr Asp Pro Ser Ile Val Ser Leu Ile
            100                 105                 110

Glu Glu Ser Ser Ile Ile Gln Ser Gly Ala Pro Ser Pro Val Ile Pro
        115                 120                 125

Thr Glu Gly Gly Phe Ser Ile Thr Ser Ser Gly Thr Asp Val Pro Ala
                130                 135                 140

Ile Leu Asp Ile Ser Ser Thr Asn Thr Val His Val Thr Ser Thr Thr
145                 150                 155                 160

His His Asn Pro Ile Phe Thr Asp Pro Ser Val Val Gln Pro Ile Pro
                165                 170                 175

Pro Val Glu Ala Ser Gly Arg Ile Ile Val Ser His Ser Ser Ile Thr
                180                 185                 190

Thr Gly Ala Ala Glu Glu Ile Pro Met Asp Thr Phe Val Val His Ser
                195                 200                 205

Asp Pro Leu Ser Ser Thr Pro Val Pro Gly Val Ser Ala Arg Pro Lys
210                 215                 220

Val Gly Leu Tyr Ser Lys Ala Leu Gln Gln Val Glu Ile Val Asp Pro
225                 230                 235                 240

Thr Phe Met Ser Thr Pro Gln Arg Leu Ile Thr Tyr Asp Asn Pro Val
                245                 250                 255

Phe Asp Asn Ile Glu Asp Thr Leu His Phe Glu Gln Pro Ser Ile His
                260                 265                 270

Asn Ala Pro Asp Pro Ala Phe Met Asp Ile Ile Thr Leu His Arg Pro
                275                 280                 285

Ala Leu Thr Ser Arg Arg Gly Val Val Arg Phe Ser Arg Val Gly Gln
290                 295                 300

Arg Gly Thr Met Tyr Thr Arg Arg Gly Thr Arg Ile Gly Gly Arg Val
305                 310                 315                 320

His Phe Phe Lys Asp Ile Ser Pro Ile Ala Ser Glu Glu Ile Glu
                325                 330                 335

Leu His Pro Leu Val Ala Ser Pro Asn Asn Ser Asp Leu Phe Asp Val
                340                 345                 350

Tyr Ala Asp Ile Asp Asp Ile Asp Glu Asn Ile Leu Tyr Ser Thr Ile
                355                 360                 365

Asp Asn Asn Thr Pro Thr Ser Thr Tyr Ser Leu Tyr Pro Gly Asn Ser
370                 375                 380

Thr Arg Ile Ala Asn Thr Ser Ile Pro Leu Ala Thr Ile Pro Asp Thr
385                 390                 395                 400

Phe Leu Thr Ser Gly Pro Asp Ile Val Phe Pro Ser Val Pro Ala Gly
                405                 410                 415

Thr Pro Tyr Leu Pro Val Ser Pro Ser Ile Pro Ala Ile Ser Val Leu
                420                 425                 430

Ile Arg Gly Thr Asp Tyr Tyr Leu Asn Pro Ala Tyr Tyr Phe Arg Lys
                435                 440                 445

Arg Arg Lys Arg Ile Leu Ala Tyr
450                 455

<210> SEQ ID NO 61
<211> LENGTH: 518
<212> TYPE: PRT
<213> ORGANISM: Human papillomavirus type 8

<400> SEQUENCE: 61

Met Ala Arg Ala Arg Arg Val Lys Arg Asp Ser Val Thr His Ile Tyr
1               5                   10                  15

Gln Thr Cys Lys Gln Ala Gly Thr Cys Pro Pro Asp Val Ile Asn Lys
                20                  25                  30

Val Glu Gln Thr Thr Val Ala Asp Asn Ile Leu Lys Tyr Gly Ser Ala

-continued

```
                35                  40                  45
Gly Val Phe Phe Gly Gly Leu Gly Ile Gly Thr Gly Arg Gly Thr Gly
 50                  55                  60
Gly Val Thr Gly Tyr Thr Pro Leu Ser Glu Gly Pro Gly Ile Arg Val
 65                  70                  75                  80
Gly Asn Thr Pro Thr Val Arg Pro Ser Leu Val Pro Glu Ala Val
                 85                  90                  95
Gly Pro Met Asp Ile Leu Pro Ile Asp Thr Ile Asp Pro Val Glu Pro
                100                 105                 110
Ser Val Ser Ser Val Val Pro Leu Thr Glu Ser Ser Gly Ala Asp Leu
            115                 120                 125
Leu Pro Gly Glu Val Glu Thr Ile Ala Glu Ile His Pro Val Pro Glu
130                 135                 140
Gly Pro Thr Ile Asp Ser Pro Val Val Thr Thr Ser Lys Gly Ser Ser
145                 150                 155                 160
Ala Ile Leu Glu Val Ala Pro Glu Pro Thr Pro Thr Arg Val Arg
                165                 170                 175
Val Ser Arg Thr Gln Tyr His Asn Pro Ser Phe Gln Ile Ile Thr Asp
            180                 185                 190
Ser Thr Pro Thr Gln Gly Glu Ser Ser Leu Ala Asp His Ile Leu Val
        195                 200                 205
Thr Ser Gly Ser Gly Gly Gln Thr Ile Gly Ser Asp Ile Thr Asp Val
    210                 215                 220
Ile Glu Leu Gln Glu Phe Pro Ser Arg Tyr Ser Phe Glu Ile Asp Glu
225                 230                 235                 240
Pro Thr Pro Pro Arg Gln Ser Ser Thr Pro Ile Glu Arg Pro Gln Val
                245                 250                 255
Val Gly Arg Arg Arg Gly Ile Ser Leu Thr Asn Arg Arg Leu Ile Gln
            260                 265                 270
Gln Val Ala Val Glu Asp Pro Leu Phe Leu Ser Lys Pro Ser Lys Leu
        275                 280                 285
Val Arg Phe Ser Phe Asp Asn Pro Val Phe Glu Glu Glu Val Thr Asn
    290                 295                 300
Ile Phe Glu Gln Asp Val Asp Met Val Glu Glu Pro Pro Asp Arg Asp
305                 310                 315                 320
Phe Leu Asp Val Arg Gln Leu Gly Arg Pro Gln Tyr Ser Thr Thr Pro
                325                 330                 335
Ala Gly Tyr Val Arg Val Ser Arg Leu Gly Thr Arg Gly Thr Ile Arg
            340                 345                 350
Thr Arg Ser Gly Ala Gln Ile Gly Ser Gln Val His Phe Tyr Arg Asp
        355                 360                 365
Leu Ser Ser Ile Asn Thr Glu Asp Pro Ile Glu Leu Gln Leu Leu Gly
    370                 375                 380
Gln His Ser Gly Asp Ser Thr Ile Val Gln Gly Pro Val Glu Ser Thr
385                 390                 395                 400
Phe Val Asn Val Asp Ile Ser Glu Asn Pro Leu Ser Glu Ser Ile Gln
                405                 410                 415
Ala Phe Ser Asp Asp Leu Leu Asp Glu Thr Val Glu Asp Phe Ser
            420                 425                 430
Gly Ser Gln Leu Val Ile Gly Asn Arg Arg Ser Thr Thr Ser Tyr Thr
        435                 440                 445
Val Pro Arg Phe Glu Thr Thr Arg Ser Gly Ser Tyr Tyr Val Gln Asp
    450                 455                 460
```

```
Thr Lys Gly Tyr Tyr Val Ala Tyr Pro Glu Ser Arg Asn Asn Glu Glu
465                 470                 475                 480

Ile Ile Tyr Pro Thr Pro Asp Leu Pro Val Ile Ile His Thr His
                485                 490                 495

Asp Asn Ser Gly Asp Phe Phe Leu His Pro Ser Leu Arg Arg Lys
            500                 505                 510

Arg Lys Arg Lys Tyr Leu
        515

<210> SEQ ID NO 62
<211> LENGTH: 533
<212> TYPE: PRT
<213> ORGANISM: Human papillomavirus type 9

<400> SEQUENCE: 62

Met Val Arg Ala Lys Arg Thr Lys Arg Ala Ser Val Thr Asp Ile Tyr
1               5                   10                  15

Arg Gly Cys Lys Ala Ala Gly Thr Cys Pro Pro Asp Val Ile Asn Lys
                20                  25                  30

Val Glu His Thr Thr Ile Ala Asp Lys Ile Leu Gln Tyr Gly Ser Ala
            35                  40                  45

Gly Val Phe Phe Gly Gly Leu Gly Ile Ser Thr Gly Arg Gly Thr Gly
        50                  55                  60

Gly Ala Thr Gly Tyr Val Pro Leu Gly Glu Gly Pro Gly Val Arg Val
65                  70                  75                  80

Gly Gly Thr Pro Thr Ile Val Arg Pro Gly Val Ile Pro Glu Ile Ile
                85                  90                  95

Gly Pro Thr Asp Leu Ile Pro Leu Asp Thr Val Arg Pro Ile Asp Pro
                100                 105                 110

Thr Ala Pro Ser Ile Val Thr Gly Thr Asp Ser Thr Val Asp Leu Leu
            115                 120                 125

Pro Gly Glu Ile Glu Ser Ile Ala Glu Ile His Pro Val Pro Val Asp
        130                 135                 140

Asn Ala Val Val Asp Thr Pro Val Val Thr Glu Gly Arg Arg Gly Ser
145                 150                 155                 160

Ser Ala Ile Leu Glu Val Ala Asp Pro Ser Pro Pro Met Arg Thr Arg
                165                 170                 175

Val Ala Arg Thr Gln Tyr His Asn Pro Ala Phe Gln Ile Ile Ser Glu
            180                 185                 190

Ser Thr Pro Met Ser Gly Glu Ser Leu Ala Asp His Ile Ile Val
        195                 200                 205

Phe Glu Gly Ser Gly Gly Gln Leu Val Gly Gly Pro Arg Glu Ser Tyr
        210                 215                 220

Thr Ala Ser Ser Glu Asn Ile Glu Leu Gln Glu Phe Pro Ser Arg Tyr
225                 230                 235                 240

Ser Phe Glu Ile Asp Glu Gly Thr Pro Arg Thr Ser Thr Pro Val
                245                 250                 255

Gln Arg Ala Val Gln Ser Leu Ser Ser Leu Arg Arg Ala Leu Tyr Asn
            260                 265                 270

Arg Arg Leu Thr Glu Gln Val Ala Val Thr Asp Pro Leu Phe Leu Ser
        275                 280                 285

Arg Pro Ser Arg Leu Val Gln Phe Gln Phe Asp Asn Pro Ala Phe Glu
        290                 295                 300

Asp Glu Val Thr Gln Ile Phe Glu Arg Asp Leu Ser Thr Val Glu Glu
```

```
                305                 310                 315                 320
Pro Pro Asp Arg Gln Phe Leu Asp Val Gln Arg Leu Ser Arg Pro Leu
                325                 330                 335
Tyr Thr Glu Thr Pro Gln Gly Tyr Val Arg Val Ser Arg Leu Gly Arg
                340                 345                 350
Arg Ala Thr Ile Arg Thr Arg Ser Gly Ala Gln Val Gly Ala Gln Val
                355                 360                 365
His Phe Tyr Arg Asp Leu Ser Thr Ile Asn Thr Glu Glu Pro Ile Glu
                370                 375                 380
Met Gln Leu Leu Gly Glu His Ser Gly Asp Ser Thr Ile Val Gln Gly
385                 390                 395                 400
Pro Val Glu Ser Ser Ile Val Asp Val Asn Ile Asp Glu Pro Asp Gly
                405                 410                 415
Leu Glu Val Gly Arg Gln Glu Thr Pro Ser Val Glu Asp Val Asp Phe
                420                 425                 430
Asn Ser Glu Asp Leu Leu Leu Asp Glu Gly Val Glu Asp Phe Ser Gly
                435                 440                 445
Ser Gln Leu Val Val Gly Thr Arg Arg Ser Thr Asn Thr Leu Thr Val
                450                 455                 460
Pro Arg Phe Glu Thr Pro Arg Asp Thr Ser Phe Tyr Ile Gln Asp Ile
465                 470                 475                 480
Gln Gly Tyr Thr Val Ser Tyr Pro Glu Ser Arg Gln Thr Thr Asp Ile
                485                 490                 495
Ile Phe Pro His Pro Asp Thr Pro Thr Val Val Ile His Ile Asn Asp
                500                 505                 510
Thr Ser Gly Asp Tyr Tyr Leu His Pro Ser Leu Gln Arg Lys Lys Arg
                515                 520                 525
Lys Arg Lys Tyr Leu
                530

<210> SEQ ID NO 63
<211> LENGTH: 470
<212> TYPE: PRT
<213> ORGANISM: Human papillomavirus type 10

<400> SEQUENCE: 63

Met Val Ala Gln Arg Ala Arg Arg Lys Arg Ala Ser Ala Thr Gln
1                 5                  10                  15
Leu Tyr Arg Thr Cys Lys Ala Ser Gly Thr Cys Pro Pro Asp Val Ile
                20                  25                  30
Pro Lys Val Glu Gly Thr Thr Leu Ala Asp Arg Ile Leu Gln Trp Gly
                35                  40                  45
Ser Leu Gly Val Tyr Leu Gly Gly Leu Gly Ile Gly Thr Gly Ser Gly
                50                  55                  60
Thr Gly Gly Arg Thr Gly Tyr Val Pro Ile Ser Thr Arg Pro Gly Thr
65                  70                  75                  80
Val Val Asp Val Ser Val Pro Ala Arg Pro Pro Val Val Ile Glu Pro
                85                  90                  95
Val Gly Pro Ser Asp Pro Ser Ile Val Asn Leu Leu Glu Asp Ser Ser
                100                 105                 110
Ile Ile Asn Ser Gly Ser Thr Ile Pro Thr Phe Ser Gly Thr Ser Gly
                115                 120                 125
Phe Glu Val Thr Ser Ser Ala Thr Thr Pro Ala Val Leu Asp Ile
                130                 135                 140
```

Thr Pro Ala Ser Glu Asn Val Val Ile Ser Ser Thr Asn Phe Thr Asn
145                 150                 155                 160

Pro Ala Phe Thr Glu Pro Ser Leu Val Glu Val Pro Gln Ser Gly Glu
            165                 170                 175

Val Ser Gly His Ile Leu Ile Ser Thr Pro Thr Ala Gly Thr His Gly
            180                 185                 190

Tyr Glu Glu Ile Pro Met Asp Thr Phe Ala Ser Ser Gly Thr Gly Thr
            195                 200                 205

Glu Pro Ile Ser Ser Thr Pro Val Pro Gly Val Ser Arg Ile Ala Gly
210                 215                 220

Pro Arg Leu Tyr Ser Arg Ala Asn Thr Gln Val Lys Val Ser Asp Pro
225                 230                 235                 240

Ala Phe Leu Ser Arg Pro Ser Ser Leu Leu Thr Phe Asp Asn Pro Val
            245                 250                 255

Phe Glu Pro Glu Asp Glu Thr Ile Ile Phe Glu Arg Pro Tyr Ser Pro
            260                 265                 270

Ser Arg Val Pro Asp Pro Asp Phe Leu Asp Ile Val Arg Leu His Arg
            275                 280                 285

Pro Ala Leu Thr Ser Arg Arg Gly Thr Val Arg Phe Ser Arg Leu Gly
            290                 295                 300

Gln Lys Phe Ser Met Arg Thr Arg Ser Gly Lys Gly Ile Gly Ala Arg
305                 310                 315                 320

Val His Tyr Tyr Gln Asp Leu Ser Pro Ile Ala Pro Ile Glu Asp Ile
            325                 330                 335

Glu Met Glu Pro Leu Leu Ala Pro Ala Ala Ser Asp Thr Ile Tyr Asp
            340                 345                 350

Ile Phe Ala Asp Val Asp Asp Gly Asp Val Ala Phe Thr Glu Gly Tyr
            355                 360                 365

Arg Ser Thr Thr Gln Ser Arg Gly Tyr Asn Thr Thr Ser Pro Leu Ser
370                 375                 380

Ser Thr Leu Ser Thr Lys Tyr Gly Asn Val Thr Ile Pro Phe Val Ser
385                 390                 395                 400

Pro Val Asp Val Thr Leu His Thr Gly Pro Asp Ile Val Leu Pro Thr
            405                 410                 415

Ser Ala Gln Trp Pro Tyr Val Pro Leu Ser Pro Ala Asp Thr Thr His
            420                 425                 430

Tyr Val Tyr Ile Asp Gly Gly Asp Phe Tyr Leu Trp Pro Val Thr Phe
            435                 440                 445

His Phe Ser Arg His Arg Arg Arg Lys Arg Val Ser Tyr Phe Phe Ala
450                 455                 460

Asp Gly Thr Leu Ala Leu
465                 470

<210> SEQ ID NO 64
<211> LENGTH: 455
<212> TYPE: PRT
<213> ORGANISM: Human papillomavirus type 11

<400> SEQUENCE: 64

Met Lys Pro Arg Ala Arg Arg Arg Lys Arg Ala Ser Ala Thr Gln Leu
1               5                   10                  15

Tyr Gln Thr Cys Lys Ala Thr Gly Thr Cys Pro Pro Asp Val Ile Pro
            20                  25                  30

Lys Val Glu His Thr Thr Ile Ala Asp Gln Ile Leu Lys Trp Gly Ser
        35                  40                  45

```
Leu Gly Val Phe Phe Gly Gly Leu Gly Ile Gly Thr Gly Ala Gly Ser
    50                  55                  60

Gly Gly Arg Ala Gly Tyr Ile Pro Leu Gly Ser Ser Pro Lys Pro Ala
65                  70                  75                  80

Ile Thr Gly Gly Pro Ala Ala Arg Pro Pro Val Leu Val Glu Pro Val
                85                  90                  95

Ala Pro Ser Asp Pro Ser Ile Val Ser Leu Ile Glu Glu Ser Ala Ile
                100                 105                 110

Ile Asn Ala Gly Ala Pro Glu Val Val Pro Pro Thr Gln Gly Gly Phe
                115                 120                 125

Thr Ile Thr Ser Ser Glu Ser Thr Thr Pro Ala Ile Leu Asp Val Ser
    130                 135                 140

Val Thr Asn His Thr Thr Thr Ser Val Phe Gln Asn Pro Leu Phe Thr
145                 150                 155                 160

Glu Pro Ser Val Ile Gln Pro Gln Pro Pro Val Glu Ala Asn Gly His
                165                 170                 175

Ile Leu Ile Ser Ala Pro Thr Ile Thr Ser Gln His Val Glu Asp Ile
                180                 185                 190

Pro Leu Asp Thr Phe Val Val Ser Ser Ser Asp Ser Gly Pro Thr Ser
                195                 200                 205

Ser Thr Pro Leu Pro Arg Ala Phe Pro Arg Pro Arg Val Gly Leu Tyr
225                 215                 220

Ser Arg Ala Leu Gln Gln Val Gln Val Arg Asp Pro Ala Phe Leu Ser
225                 230                 235                 240

Thr Pro Gln Arg Leu Val Thr Tyr Asp Asn Pro Val Tyr Glu Gly Glu
                245                 250                 255

Asp Val Ser Leu Gln Phe Thr His Glu Ser Ile His Asn Ala Pro Asp
                260                 265                 270

Glu Ala Phe Met Asp Ile Ile Arg Leu His Arg Pro Ala Ile Thr Ser
                275                 280                 285

Arg Arg Gly Leu Val Arg Phe Ser Arg Ile Gly Gln Arg Gly Ser Met
                290                 295                 300

Tyr Thr Arg Ser Gly Gln His Ile Gly Ala Arg Ile His Tyr Phe Gln
305                 310                 315                 320

Asp Ile Ser Pro Val Thr Gln Ala Ala Glu Glu Ile Glu Leu His Pro
                325                 330                 335

Leu Val Ala Ala Glu Asn Asp Thr Phe Asp Ile Tyr Ala Glu Pro Phe
                340                 345                 350

Asp Pro Ile Pro Asp Pro Val Gln His Ser Val Thr Gln Ser Tyr Leu
                355                 360                 365

Thr Ser Thr Pro Asn Thr Leu Ser Gln Ser Trp Gly Asn Thr Thr Val
    370                 375                 380

Pro Leu Ser Ile Pro Ser Asp Trp Phe Val Gln Ser Gly Pro Asp Ile
385                 390                 395                 400

Thr Phe Pro Thr Ala Ser Met Gly Thr Pro Phe Ser Pro Val Thr Pro
                405                 410                 415

Ala Leu Pro Thr Gly Pro Val Phe Ile Thr Gly Ser Asp Phe Tyr Leu
                420                 425                 430

His Pro Thr Trp Tyr Phe Ala Arg Arg Arg Lys Arg Ile Pro Leu
                435                 440                 445

Phe Phe Thr Asp Val Ala Ala
    450                 455
```

<210> SEQ ID NO 65
<211> LENGTH: 518
<212> TYPE: PRT
<213> ORGANISM: Human papillomavirus type 12

<400> SEQUENCE: 65

```
Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Leu Asn Lys
            20                  25                  30

Val Glu Gln Thr Thr Val Ala Asp Asn Ile Leu Lys Tyr Gly Ser Gly
        35                  40                  45

Gly Val Phe Phe Gly Gly Leu Gly Ile Gly Thr Gly Arg Gly Thr Gly
    50                  55                  60

Gly Val Thr Gly Tyr Arg Pro Leu Pro Glu Gly Pro Gly Ile Arg Val
65                  70                  75                  80

Gly Gly Thr Pro Thr Val Arg Pro Ser Leu Val Pro Glu Ser Val
            85                  90                  95

Gly Pro Ala Asp Ile Leu Pro Ile Asp Thr Ile Asp Pro Val Glu Pro
            100                 105                 110

Thr Ala Ser Ser Val Val Pro Leu Thr Glu Ser Ser Ala Thr Asp Leu
        115                 120                 125

Leu Pro Gly Glu Val Glu Thr Ile Ala Glu Ile Asn Pro Val Ser Glu
    130                 135                 140

Gly Pro Thr Ile Asp Ser Pro Val Val Thr Thr Ser Arg Gly Ser Ser
145                 150                 155                 160

Ala Ile Leu Glu Val Ala Pro Asp Pro Ile Pro Pro Thr Arg Val Arg
                165                 170                 175

Val Ala Arg Thr Gln Tyr His Asn Pro Ala Phe Gln Ile Ile Thr Glu
            180                 185                 190

Ser Thr Pro Ala Gln Gly Glu Thr Ser Leu Ala Asp His Ile Leu Val
        195                 200                 205

Thr Ser Gly Ser Gly Gly Gln Thr Ile Gly Ser Asp Ile Thr Asp Ile
    210                 215                 220

Ile Glu Leu Gln Glu Ile Pro Ser Arg Tyr Ser Phe Glu Ile Glu Glu
225                 230                 235                 240

Pro Thr Pro Pro Arg Gln Ser Ser Thr Pro Leu Gln Arg Thr Gln Thr
                245                 250                 255

Thr Gly Arg Arg Arg Gly Val Ser Leu Thr Asn Arg Arg Leu Val Gln
            260                 265                 270

Gln Val Gln Val Asp Asn Pro Leu Phe Ile Asp Lys Pro Ser Lys Leu
        275                 280                 285

Val Arg Phe Ser Phe Asp Asn Pro Val Phe Glu Glu Asp Ile Thr Asn
    290                 295                 300

Ile Phe Glu Gln Asp Leu Glu Thr Phe Glu Glu Pro Pro Asp Arg Asp
305                 310                 315                 320

Phe Leu Asp Ile Lys Lys Leu Ser Arg Pro Gln Tyr Ser Thr Thr Pro
                325                 330                 335

Ala Gly Tyr Val Arg Val Ser Arg Leu Gly Thr Arg Gly Thr Ile Arg
            340                 345                 350

Thr Arg Ser Gly Ala Gln Ile Gly Ser Gln Val His Phe Tyr Arg Asp
        355                 360                 365

Leu Ser Ser Ile Asp Ser Glu Asp Pro Ile Glu Leu Gln Leu Leu Gly
    370                 375                 380
```

```
Gln His Ser Gly Asp Ala Thr Ile Val Gln Gly Thr Val Glu Ser Thr
385                 390                 395                 400

Phe Val Asp Met Asp Ile Ala Glu Asp Pro Leu Ser Glu Ser Ile Glu
            405                 410                 415

Ala His Ser Asp Asp Leu Leu Leu Asp Glu Ala Val Gly Asp Phe Ser
            420                 425                 430

Gly Ser Gln Leu Val Ile Gly Asn Arg Arg Ser Thr Thr Ser Tyr Thr
            435                 440                 445

Val Pro Arg Phe Glu Thr Thr Arg Ser Ser Tyr Tyr Val Gln Asp
450                 455                 460

Thr Gln Gly Tyr Tyr Val Ala Tyr Pro Glu His Arg Asn Thr Ala Glu
465                 470                 475                 480

Ile Ile Tyr Pro Thr Pro Asp Ile Pro Val Val Ile His Thr His
            485                 490                 495

Asp Asn Ser Gly Asp Phe Tyr Leu His Pro Ser Leu Arg Arg Lys
            500                 505                 510

Arg Lys Arg Lys Tyr Leu
            515
```

<210> SEQ ID NO 66
<211> LENGTH: 463
<212> TYPE: PRT
<213> ORGANISM: Human papillomavirus type 13

<400> SEQUENCE: 66

```
Met Ala His Ser Arg Ala Arg Arg Lys Arg Ala Ser Ala Thr Gln
1               5                   10                  15

Leu Tyr Gln Thr Cys Lys Ala Ser Gly Thr Cys Pro Pro Asp Val Ile
                20                  25                  30

Pro Lys Val Glu Gln Asn Thr Leu Ala Asp Lys Ile Leu Lys Trp Gly
            35                  40                  45

Ser Leu Gly Val Phe Phe Gly Gly Leu Gly Ile Gly Thr Gly Ser Gly
50                  55                  60

Thr Gly Gly Arg Thr Gly Tyr Val Pro Val Gly Ser Thr Pro Arg Pro
65                  70                  75                  80

Ala Ile Ser Thr Gly Pro Thr Ala Arg Pro Pro Ile Val Val Asp Thr
                85                  90                  95

Val Gly Pro Thr Asp Pro Ser Ile Val Ser Leu Val Glu Glu Ser Ala
            100                 105                 110

Ile Ile Asn Ser Gly Val Pro Asp Pro Leu Pro Pro Val His Gly Gly
            115                 120                 125

Phe Glu Ile Thr Thr Ser Gln Ser Ala Thr Pro Ala Ile Leu Asp Val
130                 135                 140

Ser Val Thr Thr Gln Asn Thr Thr Ser Thr Ile Phe Arg Asn Pro
145                 150                 155                 160

Val Phe Ser Glu Pro Ser Ile Thr Gln Ser Gln Pro Ser Ile Glu Ser
                165                 170                 175

Gly Ala His Val Phe Ile Ser Pro Ser Thr Ile Ser Pro His Ser Thr
            180                 185                 190

Glu Asp Ile Pro Leu Asp Thr Phe Ile Val Ser Ser Ser Asp Ser Asn
            195                 200                 205

Pro Ala Ser Ser Thr Pro Val Pro Ala Thr Val Ala Arg Pro Arg Leu
210                 215                 220

Gly Leu Tyr Ser Arg Ala Leu His Gln Val Gln Val Thr Asp Pro Ala
```

```
                225                 230                 235                 240
        Phe Leu Ser Ser Pro Gln Arg Leu Ile Thr Phe Asp Asn Pro Thr Tyr
                        245                 250                 255

Glu Gly Glu Asp Ile Ser Leu Gln Phe Ala His Asn Thr Ile His Glu
                260                 265                 270

Pro Pro Asp Glu Ala Phe Met Asp Ile Ile Arg Leu His Arg Pro Ala
                    275                 280                 285

Ile Thr Ser Arg Arg Gly Leu Val Arg Phe Ser Arg Ile Gly Gln Arg
                290                 295                 300

Gly Ser Met Tyr Thr Arg Ser Gly Lys His Ile Gly Arg Val His
        305                 310                 315                 320

Phe Phe Lys Asp Ile Ser Pro Ile Ser Ala Ala Glu Glu Ile Glu
                        325                 330                 335

Leu His Pro Leu Val Ala Ala Gln Asp His Ser Gly Leu Phe Asp
                        340                 345                 350

Ile Tyr Ala Glu Pro Asp Pro Asp Pro Val Ala Val Asn Thr Ser Gly
                        355                 360                 365

Ser Leu Ser Ser Ala Ser Thr Pro Phe Ala Gln Ser Ser Leu Ser Ser
                370                 375                 380

Ala Pro Trp Gly Asn Thr Thr Val Pro Leu Ser Leu Pro Gly Asp Ile
        385                 390                 395                 400

Phe Ile Gln Pro Gly Pro Asp Ile Thr Phe Pro Thr Ala Pro Thr Val
                            405                 410                 415

Thr Pro Tyr Asn Pro Val Thr Pro Ala Leu Pro Thr Gly Pro Val Phe
                        420                 425                 430

Ile Thr Ala Ser Gly Phe Tyr Leu Tyr Pro Thr Trp Tyr Phe Thr Arg
                        435                 440                 445

Lys Arg Arg Lys Arg Val Ser Leu Phe Phe Thr Asp Val Ala Ala
                450                 455                 460

<210> SEQ ID NO 67
<211> LENGTH: 519
<212> TYPE: PRT
<213> ORGANISM: Human papillomavirus type 14

<400> SEQUENCE: 67

Met Ala Arg Ala Arg Arg Val Lys Arg Asp Ser Ala Thr Asn Ile Tyr
        1               5                   10                  15

Arg Thr Cys Lys Gln Ala Gly Thr Cys Pro Pro Asp Val Ile Asn Lys
                        20                  25                  30

Val Glu Ser Thr Thr Ile Ala Asp Lys Ile Leu Gln Tyr Gly Ser Ala
                    35                  40                  45

Gly Val Phe Phe Gly Gly Leu Gly Ile Ser Thr Gly Lys Gly Thr Gly
                50                  55                  60

Gly Thr Thr Gly Tyr Val Pro Leu Gly Glu Gly Pro Ala Val Arg Val
        65                  70                  75                  80

Gly Gly Ala Pro Thr Ile Ile Arg Pro Ala Leu Val Pro Asp Thr Ile
                        85                  90                  95

Gly Pro Ser Asp Ile Ile Pro Val Asp Thr Leu Asp Pro Val Glu Pro
                    100                 105                 110

Thr Thr Ser Ser Ile Val Pro Leu Thr Asp Ser Thr Gly Pro Asp Leu
                115                 120                 125

Leu Pro Gly Glu Val Glu Thr Ile Ala Glu Val His Pro Gly Pro Ser
            130                 135                 140
```

Arg Pro Pro Thr Asp Thr Pro Val Thr Thr Ser Thr Gly Gly Ser Ser
145                 150                 155                 160

Ala Ile Leu Glu Val Ala Pro Glu Pro Thr Pro Pro Ser Arg Val Arg
                165                 170                 175

Val Thr Arg Thr Gln Tyr His Asn Pro Ser Phe Gln Val Ile Thr Glu
            180                 185                 190

Ser Thr Pro Thr Thr Gly Glu Ser Ser Leu Ala Asp Asn Ile Leu Val
        195                 200                 205

Thr Ser Gly Ser Gly Gly Gln Thr Ile Gly Gly Ala Thr Pro Glu Leu
    210                 215                 220

Ile Glu Leu Gln Glu Leu Pro Ser Arg Tyr Ser Phe Glu Ile Glu Glu
225                 230                 235                 240

Pro Thr Pro Pro Arg Arg Thr Ser Thr Pro Leu Gln Arg Ile Gln Thr
                245                 250                 255

Ala Ile Arg Arg Arg Gly Gly Leu Thr Asn Arg Arg Leu Val Gln Gln
            260                 265                 270

Val Ser Val Glu Asn Pro Leu Phe Leu Thr Arg Pro Ser Arg Leu Val
        275                 280                 285

Gln Phe Gln Phe Asp Asn Pro Ala Phe Glu Glu Val Thr Gln Ile
290                 295                 300

Phe Glu Gln Asp Ile Glu Asp Phe Asn Glu Pro Pro Asp Arg Asp Phe
305                 310                 315                 320

Leu Asp Val Gln Arg Leu Gly Arg Pro Gln Tyr Ser Glu Thr Pro Ala
                325                 330                 335

Gly Tyr Leu Arg Val Ser Arg Leu Gly Gln Arg Arg Thr Ile Arg Thr
            340                 345                 350

Arg Ser Gly Ala Gln Ile Gly Ser Gln Val His Phe Tyr Arg Asp Leu
        355                 360                 365

Ser Ser Ile Asn Thr Glu Asp Pro Ile Glu Leu Gln Leu Leu Gly Gln
    370                 375                 380

His Ser Gly Asp Ala Thr Ile Val Gln Gly Pro Val Glu Ser Thr Phe
385                 390                 395                 400

Val Asp Ile Asn Val Asp Glu Asn Pro Leu Ser Glu Asp Phe Ser Ala
                405                 410                 415

His Ser Asp Asp Leu Leu Leu Asp Glu Ala Asn Glu Asp Phe Ser Gly
            420                 425                 430

Ser Gln Leu Val Val Gly Asn Arg Arg Ser Thr Ser Ser Tyr Thr Val
        435                 440                 445

Pro Arg Phe Glu Thr Thr Arg Ser Gly Ser Tyr Tyr Ala Gln Asp Thr
    450                 455                 460

Lys Gly Tyr Tyr Val Ala Tyr Pro Glu Asp Arg Asp Ile Ser Met Asp
465                 470                 475                 480

Ile Ile Tyr Pro Thr Pro Glu Leu Pro Val Val Ile Ile His Thr Tyr
                485                 490                 495

Asp Thr Ser Gly Asp Phe Tyr Leu His Pro Ser Leu His Lys Arg Leu
            500                 505                 510

Lys Arg Lys Arg Lys Tyr Leu
        515

<210> SEQ ID NO 68
<211> LENGTH: 533
<212> TYPE: PRT
<213> ORGANISM: Human papillomavirus type 15

<400> SEQUENCE: 68

```
Met Ala Arg Ala Arg Val Lys Arg Ala Ser Val Thr Asp Ile Tyr
 1               5                  10                  15

Arg Gly Cys Lys Gln Ala Gly Thr Cys Pro Pro Asp Val Leu Asn Lys
                 20                  25                  30

Val Glu Gln Thr Thr Ile Ala Asp Lys Ile Leu Lys Tyr Gly Ser Ala
             35                  40                  45

Ala Val Phe Phe Gly Gly Leu Gly Ile Gly Thr Gly Arg Gly Ser Gly
 50                  55                  60

Gly Ala Thr Gly Tyr Val Pro Leu Gly Glu Gly Pro Gly Val Arg Val
 65              70                  75                  80

Gly Gly Thr Pro Thr Ile Val Arg Pro Gly Val Thr Pro Glu Leu Ile
                 85                  90                  95

Gly Pro Ala Asp Val Ile Pro Ile Asp Thr Val Thr Pro Ile Asp Pro
                100                 105                 110

Ala Ala Pro Ser Ile Val Thr Ile Thr Asp Ser Ser Ala Val Asp Leu
             115                 120                 125

Leu Pro Glu Leu Glu Thr Ile Ala Glu Ile His Pro Val Pro Thr Asp
 130                 135                 140

Asn Val Asp Ile Asp Thr Pro Val Val Thr Gly Gly Arg Asp Ser Ser
145                 150                 155                 160

Ala Ile Leu Glu Val Ala Asp Pro Ser Pro Pro Val Arg Thr Arg Val
                 165                 170                 175

Ser Arg Thr Gln Tyr His Asn Pro Ser Phe Gln Ile Ile Thr Glu Ser
             180                 185                 190

Thr Pro Leu Ser Gly Glu Ser Ala Leu Ala Asp His Val Ile Val Phe
                 195                 200                 205

Glu Gly Ser Gly Gly Gln Asn Ile Gly Gly Ser Arg Ser Ala Ala Leu
210                 215                 220

Asp Ala Ala Gln Glu Ser Phe Glu Met Gln Thr Trp Pro Ser Arg Tyr
225                 230                 235                 240

Ser Phe Glu Ile Gln Glu Gly Thr Pro Pro Arg Ser Ser Thr Pro Val
                 245                 250                 255

Gln Arg Ala Val Gln Ser Leu Ser Leu Arg Arg Ala Leu Tyr Asn
                 260                 265                 270

Arg Arg Leu Thr Glu Gln Val Ala Val Thr Asp Pro Leu Phe Leu Gly
                 275                 280                 285

Arg Pro Ser Arg Leu Val Gln Phe Gln Phe Asp Asn Pro Thr Phe Glu
                 290                 295                 300

Glu Glu Val Thr Gln Thr Phe Glu Arg Asp Val Glu Ala Phe Glu Glu
305                 310                 315                 320

Pro Pro Asp Arg Gln Phe Leu Asp Val Val Arg Leu Gly Arg Pro Thr
                 325                 330                 335

Tyr Ser Glu Thr Pro Gln Gly Tyr Val Arg Val Ser Arg Leu Gly Arg
                 340                 345                 350

Arg Ala Thr Ile Arg Thr Arg Ser Gly Ala Gln Val Gly Ala Gln Val
                 355                 360                 365

His Phe Tyr Arg Asp Leu Ser Thr Ile Asp Ser Glu Ala Leu Glu Met
                 370                 375                 380

Gln Leu Leu Gly Glu His Ser Gly Asp Ser Thr Ile Val Gln Ala Pro
385                 390                 395                 400

Met Glu Ser Ser Phe Ile Asp Ile Asn Ile Asp Glu Pro Asp Ser Leu
                 405                 410                 415
```

-continued

His Val Gly Leu Gln Asp Ser Thr Glu Ala Asp Ile Asp Tyr Asn
            420                 425                 430

Ser Ala Asp Leu Leu Leu Glu Asp Asn Ile Glu Asp Phe Ser Gly Ser
435                 440                 445

His Leu Val Phe Gly Asn Thr Arg Arg Ser Thr Thr Thr Tyr Thr Val
            450                 455                 460

Pro Arg Phe Glu Ser Pro Arg Asn Thr Gly Phe Tyr Ile Gln Asp Val
465                 470                 475                 480

His Gly Tyr Asn Val Ala Tyr Pro Glu Ser Arg Asp Thr Thr Glu Ile
                485                 490                 495

Ile Leu Pro Gln Ser Asp Thr Pro Thr Val Val Ile Asn Phe Glu Glu
            500                 505                 510

Ala Gly Gly Asp Tyr Tyr Leu His Pro Ser Leu Lys Thr Arg Lys Arg
            515                 520                 525

Lys Arg Lys Tyr Leu
    530

<210> SEQ ID NO 69
<211> LENGTH: 524
<212> TYPE: PRT
<213> ORGANISM: Human papillomavirus type 17

<400> SEQUENCE: 69

Met Ala Arg Ser Arg Arg Ile Lys Arg Ala Ser Val Thr Asp Ile Tyr
1               5                   10                  15

Arg Gly Cys Lys Gln Ala Gly Thr Cys Pro Pro Asp Val Ile Asn Lys
            20                  25                  30

Val Glu Gln Thr Thr Ile Ala Asp Lys Ile Leu Lys Tyr Gly Ser Ser
        35                  40                  45

Gly Val Phe Phe Gly Gly Leu Gly Ile Ser Thr Gly Arg Gly Thr Gly
    50                  55                  60

Gly Ala Thr Gly Tyr Phe Pro Leu Gly Glu Gly Pro Gly Val Arg Val
65                  70                  75                  80

Gly Gly Ala Pro Thr Ile Val Arg Pro Gly Val Ile Pro Glu Leu Ile
                85                  90                  95

Gly Pro Ala Asp Val Ile Pro Ile Asp Thr Val Thr Pro Ile Asp Pro
            100                 105                 110

Ala Ala Pro Ser Ile Val Thr Ile Thr Asp Ser Ser Ala Val Asp Leu
        115                 120                 125

Leu Pro Thr Glu Leu Glu Thr Ile Ala Glu Ile His Pro Val Pro Thr
    130                 135                 140

Asp Asn Leu Asp Ile Asp Thr Pro Val Val Ser Gly Gly Arg Asp Ser
145                 150                 155                 160

Ser Ala Val Leu Glu Val Ala Asp Pro Ser Pro Val Arg Thr Arg
                165                 170                 175

Val Ser Arg Thr Gln Tyr His Asn Pro Ser Phe Gln Val Ile Thr Glu
            180                 185                 190

Ser Thr Pro Leu Ser Gly Glu Ser Ala Met Ala Asp His Val Leu Val
        195                 200                 205

Phe Glu Gly Phe Gly Gly Gln Asn Ile Gly Gly Ser Arg Asn Ala Ala
    210                 215                 220

Ile Asp Thr Ala Gln Glu Ser Phe Glu Met Gln Ser Trp Pro Ser Arg
225                 230                 235                 240

Tyr Ser Phe Glu Leu Glu Glu Gly Thr Pro Pro Arg Thr Ser Thr Pro
                245                 250                 255

Val Gln Arg Ala Val Glu Ser Leu Ser Ser Leu Arg Arg Ala Leu Tyr
         260                 265                 270

Asn Arg Arg Leu Thr Glu Gln Val Ala Val Thr Asp Pro Leu Phe Leu
     275                 280                 285

Ser Arg Pro Ser Arg Leu Val Gln Phe Gln Asp Asn Pro Ala Phe
    290                 295                 300

Glu Glu Glu Val Thr Gln Leu Phe Glu Arg Asp Ile Glu Ala Val Glu
305                 310                 315                 320

Glu Pro Pro Asp Arg Gln Phe Leu Asp Val Val Arg Leu Gly Arg Pro
                325                 330                 335

Thr Tyr Ser Glu Thr Pro Gln Gly Tyr Leu Arg Val Ser Arg Leu Gly
            340                 345                 350

Arg Arg Ala Ser Ile Arg Thr Arg Ser Gly Ala Gln Val Gly Ala Gln
                355                 360                 365

Val His Phe Tyr Arg Asp Val Ser Thr Ile Asp Ser Asp Ala Leu Glu
    370                 375                 380

Met Gln Leu Leu Gly Glu His Ser Gly Asp Thr Thr Ile Val Gln Gly
385                 390                 395                 400

Pro Val Glu Ser Ser Phe Val Asp Ile Asn Ile Asp Glu Pro Gly Pro
                405                 410                 415

Leu Asn Val Gly Ile Gln Glu Ser Pro Leu Ala Asp Thr Ile Glu Glu
            420                 425                 430

Asp Phe Asn Ser Ala Asp Leu Leu Leu Glu Asp Ala Val Asp Asp Phe
            435                 440                 445

Ser Gly Ser Gln Leu Val Phe Gly Asn Pro Arg Arg Ser Thr Thr Ser
    450                 455                 460

Val Thr Val Pro Arg Phe Glu Thr Pro Arg Asp Thr Gly Phe Tyr Ile
465                 470                 475                 480

His Asp Thr Gln Gly Tyr Thr Val Ala Tyr Pro Glu Ser Arg Asp Thr
                485                 490                 495

Thr Glu Ile Ile Leu Pro His Pro Asp Thr Pro Thr Val Val Ile Lys
            500                 505                 510

Phe Ala Glu Ala Gly Gly Arg Phe Leu Phe Thr Pro
    515                 520

<210> SEQ ID NO 70
<211> LENGTH: 520
<212> TYPE: PRT
<213> ORGANISM: Human papillomavirus type 19

<400> SEQUENCE: 70

Met Ala Arg Ala Arg Arg Thr Lys Arg Asp Ser Ala Thr Asn Ile Tyr
1               5                   10                  15

Arg Thr Cys Lys Gln Ala Gly Thr Cys Pro Pro Asp Val Ile Asn Lys
            20                  25                  30

Val Glu Gln Thr Thr Ile Ala Asp Lys Ile Leu Gln Tyr Gly Ser Ala
        35                  40                  45

Gly Val Phe Phe Gly Gly Leu Gly Ile Ser Thr Gly Lys Gly Thr Gly
    50                  55                  60

Gly Ala Thr Gly Tyr Val Pro Leu Gly Glu Gly Pro Val Arg Val Gly
65                  70                  75                  80

Gly Thr Ala Thr Val Ile Arg Pro Ser Leu Val Pro Asp Thr Ile Gly
                85                  90                  95

Pro Ser Asp Ile Ile Pro Val Asp Thr Leu Asn Pro Val Glu Pro Thr

-continued

```
                100                 105                 110
Thr Ser Ser Ile Val Pro Leu Thr Glu Ala Ser Gly Ser Asp Leu Leu
            115                 120                 125
Pro Gly Glu Val Glu Thr Ile Ala Glu Val His Pro Thr Pro Ser Ile
        130                 135                 140
Pro Ser Thr Asp Thr Pro Val Thr Thr Thr Ser Ser Gly Ala Ser Ala
145                 150                 155                 160
Val Leu Glu Val Ala Pro Glu Pro Val Pro Pro Ser Arg Val Arg Val
                165                 170                 175
Thr Arg Thr Gln Tyr His Asn Pro Ser Phe Gln Ile Leu Thr Glu Ser
            180                 185                 190
Thr Pro Thr Gln Gly Glu Ser Ser Leu Ala Asp His Ile Leu Val Thr
        195                 200                 205
Ser Gly Ser Gly Gly Gln Thr Ile Gly Ser Ser Gly Ser Asp Leu Ile
    210                 215                 220
Glu Leu Gln Glu Phe Pro Thr Arg Tyr Ser Phe Glu Ile Glu Glu Pro
225                 230                 235                 240
Thr Pro Pro Arg Gln Ser Ser Thr Pro Ile Gln Arg Leu Arg Thr Ala
                245                 250                 255
Phe Arg Arg Arg Gly Gly Leu Thr Asn Arg Arg Leu Val Gln Gln Val
            260                 265                 270
Ala Val Asp Asp Pro Ile Phe Leu Thr Gln Pro Ser Arg Leu Val Ser
        275                 280                 285
Phe Gln Phe Asp Asn Pro Ala Phe Glu Glu Glu Val Thr Gln Ile Phe
    290                 295                 300
Glu Gln Asp Leu Asp Asn Phe Arg Glu Pro Pro Asn Arg Asp Phe Leu
305                 310                 315                 320
Asp Val Gln Thr Leu Gly Arg Pro Gln Tyr Ser Glu Thr Pro Ser Gly
                325                 330                 335
Tyr Ile Arg Val Ser Arg Leu Gly Gln Arg Arg Thr Ile Arg Thr Arg
            340                 345                 350
Ser Gly Ala Gln Ile Gly Ser Gln Val His Phe Tyr Arg Asp Leu Ser
        355                 360                 365
Thr Ile Asp Ser Glu Asp Pro Ile Glu Leu Gln Leu Leu Gly Gln His
    370                 375                 380
Ser Gly Asp Ala Ser Ile Val Gln Gly Asn Thr Glu Ser Thr Phe Ile
385                 390                 395                 400
Asn Ile Asn Ile Asp Glu Asn Pro Leu Ala Glu Asp Tyr Ser Ile Thr
                405                 410                 415
Ala Asn Ser Glu Asp Leu Leu Leu Asp Glu Ala Gln Glu Asp Phe Ser
            420                 425                 430
Gly Ser Gln Leu Val Val Gly Arg Arg Ser Thr Ser Thr Tyr Thr
        435                 440                 445
Val Pro Gln Phe Glu Thr Thr Arg Ser Gly Ser Tyr Tyr Thr Gln Asp
    450                 455                 460
Thr Lys Gly Tyr Tyr Val Ala Tyr Pro Glu Asp Arg Ser Thr Ser Lys
465                 470                 475                 480
Asp Ile Ile Tyr Pro Met Pro Asp Leu Pro Val Val Ile Ile His Thr
                485                 490                 495
Tyr Asp Thr Ser Gly Asp Phe Tyr Leu His Pro Ser Leu Arg Lys Arg
            500                 505                 510
Phe Lys Arg Lys Arg Lys Tyr Leu
        515                 520
```

<210> SEQ ID NO 71
<211> LENGTH: 518
<212> TYPE: PRT
<213> ORGANISM: Human papillomavirus type 20

<400> SEQUENCE: 71

Met Ala Arg Ala Lys Arg Val Lys Arg Asp Ser Ala Thr Asn Ile Tyr
1               5                   10                  15

Arg Thr Cys Lys Gln Ala Gly Thr Cys Pro Pro Asp Val Ile Asn Lys
            20                  25                  30

Val Glu Ser Thr Thr Ile Ala Asp Lys Ile Leu Gln Tyr Gly Ser Ala
        35                  40                  45

Gly Val Phe Phe Gly Gly Leu Gly Ile Ser Thr Gly Lys Gly Thr Gly
    50                  55                  60

Gly Thr Thr Gly Tyr Val Pro Leu Gly Glu Gly Pro Ser Val Arg Val
65                  70                  75                  80

Gly Gly Thr Pro Thr Val Ile Arg Pro Ala Leu Val Pro Asp Thr Ile
                85                  90                  95

Gly Pro Ser Asp Ile Ile Pro Val Asp Thr Leu Asn Pro Val Glu Pro
            100                 105                 110

Ser Thr Ser Ser Ile Val Pro Leu Thr Glu Ser Thr Gly Pro Asp Leu
        115                 120                 125

Leu Pro Gly Glu Val Glu Thr Ile Ala Glu Ile His Pro Gly Pro Ser
    130                 135                 140

Arg Pro Pro Thr Asp Thr Pro Val Thr Ser Thr Ser Gly Ser Ser
145                 150                 155                 160

Ala Val Leu Glu Val Ala Pro Glu Pro Thr Pro Pro Ala Arg Val Arg
                165                 170                 175

Val Ser Arg Thr Gln Tyr His Asn Pro Ser Phe Gln Ile Ile Thr Glu
            180                 185                 190

Ser Thr Pro Thr Leu Gly Glu Ser Ser Leu Ala Asp His Ile Val Val
        195                 200                 205

Thr Ser Gly Ser Gly Gly Gln Ala Ile Gly Gly Met Thr Pro Glu Leu
    210                 215                 220

Ile Glu Leu Gln Asp Phe Pro Ser Arg Tyr Ser Phe Glu Ile Glu Glu
225                 230                 235                 240

Pro Thr Pro Pro Arg Arg Thr Ser Thr Pro Met Gln Arg Leu Gln Asn
                245                 250                 255

Val Phe Arg Arg Arg Gly Gly Leu Thr Asn Arg Arg Leu Val Gln Gln
            260                 265                 270

Val Pro Val Asp Asn Pro Leu Phe Leu Thr Gln Pro Ser Arg Leu Val
        275                 280                 285

Arg Phe Gln Phe Asp Asn Pro Val Phe Glu Glu Val Thr Gln Ile
    290                 295                 300

Phe Glu Gln Asp Leu Asp Thr Phe Asn Glu Pro Pro Asp Arg Asp Phe
305                 310                 315                 320

Leu Asp Val Gln Ser Leu Gly Arg Pro Gln Tyr Ser Glu Thr Pro Ala
                325                 330                 335

Gly Tyr Val Arg Val Ser Arg Ala Gly Gln Arg Thr Ile Arg Thr
            340                 345                 350

Arg Ser Gly Ala Gln Ile Gly Ser Gln Val His Phe Tyr Arg Asp Leu
        355                 360                 365

Ser Ser Ile Asp Thr Glu Asp Pro Ile Glu Leu Gln Leu Leu Gly Gln

```
                370                 375                 380
His Ser Gly Asp Ala Thr Ile Val Gln Gly Pro Val Glu Ser Thr Phe
385                 390                 395                 400

Val Asp Ile Asn Val Asp Glu Asn Pro Leu Ser Glu Ile Ser Ala Tyr
                405                 410                 415

Ser Asp Asp Leu Leu Leu Asp Glu Ala Asn Glu Asp Phe Ser Gly Ser
                420                 425                 430

Gln Leu Val Val Gly Gly Arg Arg Ser Thr Ser Thr Tyr Thr Val Pro
                435                 440                 445

His Phe Glu Thr Thr Arg Ser Ser Ser Tyr Tyr Val Gln Asp Thr Lys
                450                 455                 460

Gly Tyr Tyr Val Ala Tyr Pro Glu Asp Arg Asp Val Ser Lys Asp Ile
465                 470                 475                 480

Ile Tyr Pro Asn Pro Asp Leu Pro Val Val Ile Ile His Thr Tyr Asp
                485                 490                 495

Thr Ser Gly Asp Phe Tyr Leu His Pro Ser Leu Thr Lys Arg Leu Lys
                500                 505                 510

Arg Lys Arg Lys Tyr Leu
                515

<210> SEQ ID NO 72
<211> LENGTH: 520
<212> TYPE: PRT
<213> ORGANISM: Human papillomavirus type 21

<400> SEQUENCE: 72

Met Ala Arg Ala Lys Arg Val Lys Arg Asp Ser Ala Thr Asn Ile Tyr
1               5                   10                  15

Arg Thr Cys Lys Gln Ala Gly Thr Cys Pro Pro Asp Val Ile Asn Lys
                20                  25                  30

Val Glu Ser Thr Thr Ile Ala Asp Lys Ile Leu Gln Tyr Gly Ser Ala
                35                  40                  45

Gly Val Phe Phe Gly Gly Leu Gly Ile Ser Thr Gly Lys Gly Thr Gly
            50                  55                  60

Gly Thr Thr Gly Tyr Val Pro Leu Gly Glu Gly Pro Ala Val Arg Val
65                  70                  75                  80

Gly Asn Ala Pro Thr Val Ile Arg Pro Ala Leu Val Pro Asp Thr Ile
                85                  90                  95

Gly Pro Ser Asp Ile Ile Pro Val Asp Thr Leu Asn Pro Val Glu Pro
                100                 105                 110

Thr Thr Ser Ser Ile Val Pro Leu Thr Asp Ser Thr Gly Pro Asp Leu
                115                 120                 125

Leu Pro Gly Glu Val Glu Thr Ile Ala Glu Ile His Pro Gly Pro Thr
130                 135                 140

Arg Pro Pro Asp Thr Ala Val Thr Thr Ser Thr Asn Gly Ser Ser
145                 150                 155                 160

Ala Val Leu Glu Val Ala Pro Glu Pro Thr Pro Ser Arg Val Arg
                165                 170                 175

Val Thr Arg Thr Gln Tyr His Asn Pro Ser Phe Gln Val Ile Thr Glu
                180                 185                 190

Ser Thr Pro Thr Thr Gly Glu Ser Ser Leu Ala Asp His Ile Leu Val
                195                 200                 205

Thr Ser Gly Thr Gly Gly Gln Thr Ile Gly Gly Ser Thr Pro Glu Leu
            210                 215                 220
```

-continued

```
Ile Glu Leu Gln Asp Phe Pro Ser Arg Tyr Ser Phe Glu Ile Glu Glu
225                 230                 235                 240

Pro Thr Pro Pro Arg Arg Thr Ser Thr Pro Ile Gln Arg Ile Gln Asn
            245                 250                 255

Ile Ile Arg Arg Arg Gly Gly Gly Leu Thr Asn Arg Arg Leu Val Gln
            260                 265                 270

Gln Val Asn Val Glu Asn Pro Leu Phe Val Ser Arg Pro Ser Arg Leu
        275                 280                 285

Val Gln Phe Gln Phe Asp Asn Pro Ala Phe Glu Glu Val Thr Gln
    290                 295                 300

Ile Phe Glu Gln Asp Ile Asp Thr Phe Asn Glu Pro Pro Asp Arg Asp
305                 310                 315                 320

Phe Leu Asp Ile Lys Thr Leu Gly Arg Pro Gln Tyr Ser Glu Thr Pro
                325                 330                 335

Ala Gly Tyr Val Arg Val Ser Arg Leu Gly Lys Arg Gly Thr Ile Arg
            340                 345                 350

Thr Arg Ser Gly Thr Gln Ile Gly Ser Gln Val His Phe Tyr Arg Asp
        355                 360                 365

Leu Ser Thr Ile Asn Thr Glu Asp Pro Ile Glu Leu Gln Leu Leu Gly
370                 375                 380

Glu His Ser Gly Asp Ala Thr Ile Val Gln Gly Pro Val Glu Ser Thr
385                 390                 395                 400

Phe Ile Asp Ile Asn Val Asp Glu Asn Pro Leu Ser Glu Asp Phe Ser
                405                 410                 415

Ala His Ser Asp Asp Leu Leu Leu Asp Glu Ala Asn Glu Asp Phe Ser
            420                 425                 430

Gly Ser Gln Leu Val Val Gly Gly Arg Arg Ser Thr Ser Ser Tyr Thr
        435                 440                 445

Val Pro Arg Phe Glu Thr Thr Arg Ser Gly Ser Tyr Tyr Val Gln Asp
    450                 455                 460

Thr Lys Gly Tyr Tyr Val Ala Tyr Pro Glu Asp Arg Asp Thr Ser Thr
465                 470                 475                 480

Asp Ile Ile Tyr Pro Thr Pro Asp Leu Pro Val Val Ile Ile His Thr
                485                 490                 495

Phe Asp Thr Ser Gly Asp Phe Tyr Leu His Pro Ser Leu Ser Arg Lys
            500                 505                 510

Phe Lys Arg Arg Arg Lys Tyr Leu
        515                 520

<210> SEQ ID NO 73
<211> LENGTH: 524
<212> TYPE: PRT
<213> ORGANISM: Human papillomavirus type 22

<400> SEQUENCE: 73

Met Ala Arg Ala Arg Arg Thr Lys Arg Ala Ser Val Thr Asp Ile Tyr
1               5                   10                  15

Lys Gly Cys Lys Ala Ser Gly Thr Cys Pro Pro Asp Val Ile Asn Lys
            20                  25                  30

Val Glu Gln Asn Thr Leu Ala Asp Lys Ile Leu Lys Tyr Gly Ser Val
        35                  40                  45

Gly Val Phe Phe Gly Gly Leu Gly Ile Ser Thr Gly Lys Gly Thr Gly
    50                  55                  60

Gly Pro Thr Gly Tyr Ile Pro Leu Gly Gln Gly Pro Gly Val Arg Val
65                  70                  75                  80
```

-continued

```
Gly Ala Thr Pro Thr Val Val Arg Pro Gly Val Ile Pro Glu Ile Ile
                85                  90                  95
Gly Pro Thr Glu Leu Ile Pro Val Asp Ser Val Thr Pro Ile Asp Pro
            100                 105                 110
Ala Ala Pro Ser Ile Val Thr Leu Thr Asp Ser Ser Ala Gly Ala Asp
        115                 120                 125
Leu Leu Pro Gly Glu Val Glu Thr Ile Ala Glu Val His Pro Val Pro
130                 135                 140
Ile Asp Asn Val Glu Leu Asp Thr Pro Leu Val Ser Gly Asp Arg His
145                 150                 155                 160
Ala Ile Leu Glu Val Thr Asp Ala Asn Pro Pro Phe Arg Arg Thr Val
                165                 170                 175
Thr Arg Thr Gln Tyr His Asn Pro Ala Phe Glu Ile Ile Ser Glu Ser
            180                 185                 190
Thr Pro Leu Ile Gly Glu Ser Thr Pro Ser Asp His Val Phe Val Phe
        195                 200                 205
Glu Gly Ser Gly Gly Val Gln Val Gly Asp Ala Asn Glu Ser Ile Glu
    210                 215                 220
Leu Asp Thr Phe Pro Ser Arg Tyr Ser Phe Asp Ile Glu Glu Pro Thr
225                 230                 235                 240
Pro Pro Arg Arg Val Ser Thr Pro Ile Glu Arg Ile Ser Gln Glu Phe
                245                 250                 255
Arg Thr Leu Arg Arg Ala Leu Tyr Asn Arg Arg Leu Thr Glu Gln Val
            260                 265                 270
Gln Val Arg Asp Pro Leu Phe Ile Arg Ser Pro Ser Arg Leu Val Arg
        275                 280                 285
Phe Gln Phe Asp Asn Pro Val Phe Asp Glu Glu Val Thr Gln Ile Phe
    290                 295                 300
Glu Arg Asp Val Ala Ala Val Glu Glu Pro Pro Asp Arg Asp Phe Leu
305                 310                 315                 320
Asp Ile Glu Arg Leu Gly Arg Pro Ile Leu Thr Glu Thr Ala Glu Gly
                325                 330                 335
Arg Val Arg Val Ser Arg Leu Gly Gln Arg Ala Ser Leu Ser Thr Arg
            340                 345                 350
Ser Gly Ala Arg Val Gly Ala Arg Val His Phe Phe Thr Asp Ile Ser
        355                 360                 365
Thr Ile Asn Ala Glu Glu Pro Ile Glu Leu Glu Leu Leu Gly Glu His
    370                 375                 380
Ser Gly Asp Ser Ser Val Val Gln Glu Pro Phe Glu Ser Thr Ile Leu
385                 390                 395                 400
Asp Val Asn Ile Asp Asn Ile Pro Glu Ser Leu Asp Thr Asn Ile Ala
                405                 410                 415
Glu Thr Ser Val Asp Tyr Asp Ser Ala Asp Leu Leu Leu Asp Asn Gly
            420                 425                 430
Val Glu Asp Phe Ser Arg Ser Gln Leu Val Ile Gly Pro Ser Asp Arg
        435                 440                 445
Ser Leu Pro Ser Ile Thr Val Pro Gln Phe Glu Ser Pro Arg Glu Thr
    450                 455                 460
Ile Val Tyr Ile Gln Asp Ile Glu Gly Asn Thr Val Val Tyr Pro Lys
465                 470                 475                 480
Tyr Glu Glu Arg Pro Thr Ile Ile Leu Pro Thr Pro Ser Gly Pro Ala
                485                 490                 495
```

Ile Ile Gln Ser Pro Thr His Ser Ser Phe Asp Tyr Tyr Leu His Pro
                500                 505                 510

Ser Leu Arg Arg Lys Lys Arg Lys Tyr Leu
            515                 520

<210> SEQ ID NO 74
<211> LENGTH: 519
<212> TYPE: PRT
<213> ORGANISM: Human papillomavirus type 23

<400> SEQUENCE: 74

Met Val Arg Ala Gln Arg Thr Lys Arg Ala Ser Val Thr Asp Ile Tyr
1               5                   10                  15

Lys Gly Cys Lys Ala Ser Gly Thr Cys Pro Pro Asp Val Leu Asn Lys
            20                  25                  30

Val Glu Gln Asn Thr Leu Ala Asp Lys Ile Leu Lys Tyr Gly Ser Val
        35                  40                  45

Gly Val Phe Phe Gly Gly Leu Gly Ile Gly Thr Gly Lys Gly Thr Gly
    50                  55                  60

Gly Ala Thr Gly Tyr Val Pro Leu Arg Pro Gly Val Arg Val Gly Gly
65                  70                  75                  80

Thr Pro Thr Val Val Arg Pro Ala Val Ile Pro Glu Ile Ile Gly Pro
                85                  90                  95

Thr Glu Leu Ile Pro Val Asp Ser Ile Ala Pro Ile Asp Pro Glu Ala
            100                 105                 110

Pro Ser Ile Val Ser Leu Thr Asp Ser Gly Ala Ala Ala Asp Leu Phe
        115                 120                 125

Pro Ser Glu Ala Glu Thr Ile Ala Glu Val His Pro Thr Pro Val Asp
    130                 135                 140

Ile Gly Ile Asp Thr Pro Ile Val Ala Gly Gly Arg Asp Ala Ile Leu
145                 150                 155                 160

Glu Val Val Asp Thr Asn Pro Pro Thr Arg Phe Ser Val Thr Arg Thr
                165                 170                 175

Gln Tyr Asp Asn Pro Ser Phe Gln Ile Ile Ser Glu Ser Thr Pro Ile
            180                 185                 190

Thr Gly Glu Ala Ser Leu Ala Asp His Val Phe Val Phe Glu Gly Ser
        195                 200                 205

Gly Gly Gln His Val Gly Ala Val Thr Glu Glu Ile Glu Leu Asp Thr
    210                 215                 220

Tyr Pro Ser Arg Tyr Ser Phe Glu Ile Glu Glu Ala Thr Pro Pro Arg
225                 230                 235                 240

Arg Thr Ser Thr Pro Ile Glu Arg Ile Ser Gln Glu Phe Arg Asn Leu
                245                 250                 255

Arg Arg Ala Leu Tyr Asn Arg Arg Leu Thr Glu Gln Val Gln Val Lys
            260                 265                 270

Asn Pro Leu Phe Leu Thr Thr Pro Ser Lys Leu Val Arg Phe Gln Phe
        275                 280                 285

Asp Asn Pro Val Phe Asp Glu Val Thr Gln Ile Phe Glu Arg Asp
    290                 295                 300

Val Ala Glu Val Glu Glu Pro Pro Asp Arg Asp Phe Leu Asp Ile Asp
305                 310                 315                 320

Arg Leu Gly Arg Pro Leu Leu Thr Glu Ser Thr Glu Gly Arg Ile Arg
                325                 330                 335

Leu Ser Arg Leu Gly Gln Arg Ala Ser Ile Gln Thr Arg Ser Gly Thr
            340                 345                 350

```
Arg Val Gly Ser Arg Val His Phe Tyr Thr Asp Leu Ser Thr Ile Asn
            355                 360                 365

Thr Glu Glu Pro Ile Glu Leu Glu Leu Leu Gly Glu His Ser Gly Asp
370                 375                 380

Ala Ser Val Ile Glu Glu Pro Leu Gln Ser Thr Val Ile Asp Met Asn
385                 390                 395                 400

Leu Asp Asp Val Glu Ala Ile Gln Asp Thr Ile Asp Thr Ala Asp Asp
                405                 410                 415

Tyr Asn Ser Ala Asp Leu Leu Leu Asp Asn Ala Ile Glu Glu Phe Asn
            420                 425                 430

Asn Ser Gln Leu Val Phe Gly Thr Ser Asp Arg Ser Ser Ser Ala Tyr
            435                 440                 445

Ser Ile Pro Arg Phe Glu Ser Pro Arg Glu Thr Ile Val Tyr Val Gln
            450                 455                 460

Asp Ile Glu Gly Asn Gln Val Ile Tyr Pro Gly Pro Thr Glu Arg Pro
465                 470                 475                 480

Thr Ile Ile Phe Pro Leu Pro Ser Ala Pro Ala Val Val Ile His Thr
                485                 490                 495

Leu Asp Lys Ser Phe Asp Tyr Tyr Leu His Pro Ser Leu Arg Lys Lys
            500                 505                 510

Arg Arg Lys Arg Lys Tyr Leu
            515

<210> SEQ ID NO 75
<211> LENGTH: 523
<212> TYPE: PRT
<213> ORGANISM: Human papillomavirus type 24

<400> SEQUENCE: 75

Met Val Arg Ala Lys Arg Thr Lys Arg Asp Ser Ala Thr Asn Ile Tyr
1               5                   10                  15

Arg Thr Cys Lys Gln Ala Gly Thr Cys Pro Pro Asp Val Ile Asn Lys
            20                  25                  30

Val Glu Gln Ser Thr Ile Ala Asp Asn Ile Leu Lys Tyr Gly Ser Ala
            35                  40                  45

Gly Val Phe Phe Gly Gly Leu Gly Ile Ser Thr Gly Arg Gly Thr Gly
        50                  55                  60

Gly Thr Thr Gly Tyr Val Pro Leu Gly Glu Gly Thr Gly Val Arg Val
65                  70                  75                  80

Gly Ser Thr Pro Thr Val Arg Pro Ala Leu Val Pro Glu Val Ile
                85                  90                  95

Gly Pro Ala Asp Leu Leu Pro Val Asp Thr Ile Ala Pro Val Asp Pro
                100                 105                 110

Ala Ser Ser Ser Ile Val Pro Leu Thr Glu Ser Ser Gly Val Asp Leu
            115                 120                 125

Leu Pro Gly Glu Ile Glu Thr Ile Ala Glu Val His Pro Ile Pro Asp
            130                 135                 140

Val Pro Thr Phe Asp Thr Pro Val Val Thr Thr Ser Lys Gly Ser Ser
145                 150                 155                 160

Ala Ile Leu Glu Val Ala Pro Glu Pro Thr Pro Thr Arg Val Arg
                165                 170                 175

Val Ser Arg Thr Gln Tyr His Asn Pro Ala Phe His Ile Ile Thr Glu
            180                 185                 190

Ser Thr Pro Ser Gln Gly Glu Ser Ser Leu Ser Asp Glu Ile Ile Val
```

```
                195                 200                 205
Ala Ser Gly Ala Gly Gln Ser Val Gly Val Ser Glu Asn Ile Glu
    210                 215                 220

Leu Gln Asp Leu Ser Asn Arg Tyr Ser Phe Glu Ile Glu Thr Pro Thr
225                 230                 235                 240

Pro Pro Arg Arg Ser Ser Thr Pro Leu Gln Arg Ala Thr Gln Ala Phe
                245                 250                 255

Arg Gln Arg Ser Leu Thr Asn Arg Arg Leu Leu Gln Gln Val Pro Val
            260                 265                 270

Glu Asp Pro Leu Phe Leu Thr Gln Pro Ser Lys Leu Val Arg Phe Ala
        275                 280                 285

Phe Glu Asn Pro Ala Phe Glu Glu Val Thr Gln Val Phe Glu Gln
    290                 295                 300

Asp Leu Ala Gly Phe Val Glu Pro Pro Asn Arg Asp Phe Leu Asp Ile
305                 310                 315                 320

Ala Glu Leu Gly Arg Pro Arg Phe Ser Glu Thr Arg Glu Gly Tyr Val
                325                 330                 335

Arg Leu Ser Arg Leu Gly Arg Arg Ala Thr Ile Arg Thr Arg Ala Gly
            340                 345                 350

Thr Gln Ile Gly Ala Gln Val His Phe Tyr Lys Asp Leu Ser Ser Ile
        355                 360                 365

Asn Thr Glu Ala Pro Ile Glu Leu Asp Leu Leu Gly Gln His Ser Gly
    370                 375                 380

Asp Ala Thr Ile Val His Gly Thr Val Glu Ser Thr Phe Ile Asp Thr
385                 390                 395                 400

Asn Ile Glu Glu Asn Pro Leu Ala Glu Gln Met Glu Leu Glu Ile Asp
                405                 410                 415

Thr Tyr Pro Glu Ala His Ser Phe Asp Ala Leu Leu Asp Glu Ala Thr
            420                 425                 430

Asp Asp Phe Ser Gly Ser Gln Leu Val Ile Gly Asn Arg Arg Ser Thr
        435                 440                 445

Thr Ser Tyr Thr Val Pro Arg Phe Glu Ser Pro Arg Asn Ser Ser Tyr
    450                 455                 460

Tyr Val Gln Asp Leu Gln Gly Tyr Tyr Val Ala Tyr Pro Glu Ser Arg
465                 470                 475                 480

Asp Lys Ile Glu Leu Ile Tyr Pro Ser Pro Thr Leu Pro Ala Val Val
                485                 490                 495

Ile His Thr Glu Asp Ser Ser Gly Asp Phe Tyr Leu His Pro Ser Leu
            500                 505                 510

Leu Gln Arg Arg Arg Arg Lys Arg Lys Tyr Leu
        515                 520

<210> SEQ ID NO 76
<211> LENGTH: 520
<212> TYPE: PRT
<213> ORGANISM: Human papillomavirus type 25

<400> SEQUENCE: 76

Met Ala Arg Ala Arg Arg Val Lys Arg Asp Ser Ala Thr Asn Ile Tyr
1               5                   10                  15

Arg Thr Cys Lys Gln Ala Gly Thr Cys Pro Pro Asp Val Leu Asn Lys
                20                  25                  30

Val Glu Asn Thr Thr Ile Ala Asp Lys Ile Leu Gln Tyr Gly Ser Ala
            35                  40                  45
```

```
Gly Val Phe Phe Gly Gly Leu Gly Ile Ser Thr Gly Lys Gly Thr Gly
    50                  55                  60
Gly Thr Thr Gly Tyr Val Pro Leu Gly Glu Gly Pro Ile Arg Val Gly
65                  70                  75                  80
Gly Thr Pro Thr Val Ile Arg Pro Ser Leu Val Pro Asp Thr Ile Gly
                85                  90                  95
Pro Ser Asp Ile Ile Pro Val Asp Thr Leu Asn Pro Val Glu Pro Thr
            100                 105                 110
Ser Ser Ser Ile Val Pro Leu Thr Glu Ser Ser Gly Pro Asp Leu Leu
        115                 120                 125
Pro Gly Glu Val Glu Thr Ile Ala Glu Ile His Pro Gly Pro Val Val
    130                 135                 140
Pro Ser Thr Asp Thr Pro Val Thr Thr Ser Arg Gly Ala Ser Ala
145                 150                 155                 160
Val Leu Glu Val Ala Pro Glu Pro Thr Pro Ser Arg Val Arg Val
                165                 170                 175
Ser Gly Thr Gln Tyr His Asn Pro Ser Phe Gln Val Ile Thr Glu Ser
            180                 185                 190
Thr Pro Ala Gln Gly Glu Ser Ser Leu Ala Asp His Ile Leu Val Thr
        195                 200                 205
Ser Gly Ser Gly Gly Gln Thr Ile Gly Gly Thr Ala Ser Asp Leu Ile
    210                 215                 220
Glu Leu Gln Glu Phe Pro Thr Arg Tyr Ser Phe Glu Ile Asp Glu Pro
225                 230                 235                 240
Thr Pro Pro Arg Gln Ser Ser Thr Pro Leu Gln Arg Ile Arg Thr Ala
                245                 250                 255
Leu Arg Arg Arg Gly Gly Leu Thr Asn Arg Arg Leu Val Gln Gln Val
            260                 265                 270
Pro Val Glu Asp Pro Leu Phe Leu Ser Gln Pro Ser Arg Leu Val Arg
        275                 280                 285
Phe Gln Phe Asp Asn Pro Val Phe Glu Asp Glu Val Thr Gln Ile Phe
    290                 295                 300
Glu Gln Asp Leu Asn Asp Phe Gln Glu Pro Pro Asp Arg Asp Phe Leu
305                 310                 315                 320
Asp Ile Arg Ser Leu Gly Arg Pro Gln Tyr Ser Glu Thr Pro Ala Gly
                325                 330                 335
Tyr Val Arg Val Ser Arg Leu Gly Gln Arg Arg Thr Ile Arg Thr Arg
            340                 345                 350
Ser Gly Ala Gln Ile Gly Ser Gln Val His Phe Tyr Arg Asp Leu Ser
        355                 360                 365
Ser Ile Asn Thr Glu Asp Pro Ile Glu Leu Gln Leu Leu Gly Gln His
    370                 375                 380
Ser Gly Asp Ala Thr Ile Val Gln Gly Leu Thr Glu Ser Thr Phe Val
385                 390                 395                 400
Asp Val Asn Val Asp Glu Asn Pro Leu Ala Glu Asp Phe Ser Ile Ser
                405                 410                 415
Ala His Ser Asp Asp Leu Leu Leu Asp Glu Ala Asn Glu Asp Phe Ser
            420                 425                 430
Gly Ser Gln Leu Val Val Gly Arg Arg Ser Thr Ser Thr Tyr Thr
        435                 440                 445
Val Pro Arg Val Glu Thr Thr Arg Ser Ala Ser Tyr Tyr Thr Gln Asp
    450                 455                 460
Ile Gln Gly Tyr Tyr Val Ser Tyr Pro Glu Asp Arg Asp Thr Ser Lys
```

```
            465                 470                 475                 480
Asp Ile Ile Tyr Pro Met Pro Asp Leu Pro Val Val Ile Ile His Thr
                    485                 490                 495

Tyr Asp Thr Ser Gly Asp Phe Tyr Leu His Pro Ser Leu Thr Thr Arg
                500                 505                 510

Arg Arg Arg Lys Arg Lys Tyr Leu
                515                 520

<210> SEQ ID NO 77
<211> LENGTH: 472
<212> TYPE: PRT
<213> ORGANISM: Human papillomavirus type 26

<400> SEQUENCE: 77

Met Val Ala Val Arg Ala Pro Arg Arg Lys Arg Ala Ser Ala Thr Asp
1               5                   10                  15

Leu Tyr Lys Thr Cys Lys Ala Ala Gly Thr Cys Pro Pro Asp Val Ile
                20                  25                  30

Pro Lys Ile Glu Gly Ser Thr Leu Ala Asp Lys Ile Leu Gln Trp Ser
                35                  40                  45

Gly Leu Gly Ile Phe Leu Gly Gly Leu Gly Ile Gly Thr Gly Thr Gly
                50                  55                  60

Ser Gly Gly Arg Thr Gly Tyr Ile Pro Leu Gly Gly Gly Arg Pro
65                  70                  75                  80

Ser Val Val Asp Ile Gly Pro Thr Arg Pro Pro Ile Ile Glu Pro
                85                  90                  95

Val Gly Pro Thr Glu Pro Ser Ile Val Thr Leu Val Glu Glu Ser Ser
                100                 105                 110

Ile Ile Gln Ser Gly Ala Pro Ile Pro Thr Phe Ser Gly Gly Asn Gly
                115                 120                 125

Phe Glu Leu Thr Thr Ser Ser Ala Thr Thr Pro Ala Val Leu Asp Ile
                130                 135                 140

Thr Pro Ser Ala Gly Thr Val His Val Thr Ser Thr Asn Ile Gln Asn
145                 150                 155                 160

Pro Leu Tyr Ile Glu Pro Pro Ile Asp Ile Pro Gln Ala Gly Glu Ala
                165                 170                 175

Ser Gly His Ile Phe Thr Thr Thr Ser Thr Ala Gly Thr His Ser Tyr
                180                 185                 190

Glu Glu Ile Pro Met Glu Val Phe Ala Ser Thr Asn Gly Thr Gly Leu
                195                 200                 205

Glu Pro Ile Ser Ser Thr Pro Ile Pro Gly Ile Gln Arg Val Ser Ala
                210                 215                 220

Pro Arg Leu Tyr Ser Lys Ala Tyr Gln Gln Val Lys Val Thr Asp Pro
225                 230                 235                 240

Asn Phe Ile Gly Asn Pro Ser Thr Phe Val Thr Phe Asp Asn Pro Ala
                245                 250                 255

Tyr Glu Pro Ile Asp Glu Thr Leu Thr Tyr Ala Ser Ser Ser Thr Val
                260                 265                 270

Ala Pro Asp Pro Asp Phe Leu Asp Ile Ile Ala Leu His Arg Pro Ala
                275                 280                 285

Leu Thr Ser Arg Lys Gly Thr Val Arg Tyr Ser Arg Leu Gly Gln Lys
                290                 295                 300

Ala Thr Met Lys Thr Arg Ser Gly Lys Gln Ile Gly Ala Thr Val His
305                 310                 315                 320
```

```
Tyr Tyr His Asp Ile Ser Pro Ile Gln Ser Phe Ala Glu His Glu Glu
                325                 330                 335

Ile Glu Leu Gln Pro Leu His Thr Ser Thr His Ser Ser Ala Pro Leu
            340                 345                 350

Phe Asp Ile Tyr Ala Asp Pro Asp Thr Val Pro Ser Ile His Thr Pro
        355                 360                 365

Arg Met Ser Tyr Ser Pro Thr Thr Leu Pro Val Pro Arg Tyr Ala Ser
    370                 375                 380

Asn Val Phe Ser Ser Ile Asn Thr Ser Thr Asn Val Thr Val Pro
385                 390                 395                 400

Leu Ser Thr Ser Phe Glu Leu Pro Val Tyr Ser Gly Ser Asp Ile Tyr
                405                 410                 415

Thr Pro Thr Ser Ser Pro Thr Trp Pro Ser Leu Pro Pro Pro Thr
            420                 425                 430

Thr Asn Leu Pro Ala Ile Val Val His Gly Asp Asn Tyr Tyr Leu Trp
        435                 440                 445

Pro Tyr Ile Tyr Leu Ile His Lys Arg Arg Lys Arg Met Pro Tyr Phe
    450                 455                 460

Phe Ser Asp Gly Phe Val Ala Tyr
465                 470

<210> SEQ ID NO 78
<211> LENGTH: 464
<212> TYPE: PRT
<213> ORGANISM: Human papillomavirus type 27

<400> SEQUENCE: 78

Met Pro Arg Ala Lys Arg Arg Lys Arg Ala Ser Pro Thr Asp Leu Tyr
1               5                   10                  15

Arg Thr Cys Lys Gln Ala Gly Thr Cys Pro Pro Asp Ile Ile Pro Arg
            20                  25                  30

Leu Glu Gln Asn Thr Leu Ala Asp Lys Ile Leu Lys Trp Gly Ser Leu
        35                  40                  45

Gly Val Phe Phe Gly Gly Leu Gly Ile Gly Thr Gly Ser Gly Thr Gly
    50                  55                  60

Gly Arg Thr Gly Tyr Ile Pro Val Gly Thr Arg Pro Thr Thr Val Val
65                  70                  75                  80

Asp Ile Gly Val Ala Pro Lys Pro Pro Val Val Ile Glu Pro Val Gly
                85                  90                  95

Ala Ser Glu Pro Ser Ile Val Thr Leu Val Glu Asp Ser Ser Ile Ile
            100                 105                 110

Asn Ala Gly Ala Ser His Pro Thr Phe Thr Gly Thr Gly Gly Phe Glu
        115                 120                 125

Val Thr Thr Ser Thr Val Thr Asp Pro Ala Val Leu Asp Ile Thr Pro
    130                 135                 140

Ser Gly Thr Ser Val Gln Val Ser Ser Ser Phe Leu Asn Pro Leu
145                 150                 155                 160

Tyr Thr Glu Pro Ala Ile Val Glu Ala Pro Gln Thr Gly Glu Val Ser
                165                 170                 175

Gly His Val Leu Val Ser Thr Ala Thr Ser Gly Ser His Gly Tyr Glu
            180                 185                 190

Glu Ile Pro Met Gln Thr Phe Ala Thr Ser Gly Gly Ser Gly Gln Glu
        195                 200                 205

Pro Ile Ser Ser Thr Pro Leu Pro Gly Val Arg Arg Val Ala Gly Pro
    210                 215                 220
```

```
Arg Leu Tyr Ser Arg Ala Asn Gln Gln Val Gln Val Arg Asp Pro Ala
225                 230                 235                 240

Phe Leu Glu Arg Pro Ala Asp Leu Val Thr Phe Asp Asn Pro Val Tyr
            245                 250                 255

Asp Pro Glu Thr Ile Ile Phe Gln His Pro Asp Phe His Glu Pro
        260                 265                 270

Pro Asp Pro Asp Phe Leu Asp Ile Val Ala Leu His Arg Pro Ala Leu
        275                 280                 285

Thr Ser Arg Gln Gly Thr Val Arg Phe Ser Arg Leu Gly Arg Arg Ala
290                 295                 300

Thr Leu Arg Thr Arg Ser Gly Lys Gln Ile Gly Ala Arg Val His Phe
305                 310                 315                 320

Tyr His Asp Ile Ser Pro Val Val Pro Asp Glu Leu Glu Met Glu Pro
                325                 330                 335

Leu Leu Pro Pro Ala Ser Thr Val Gly Ser Asp Val Leu Tyr Asp Val
            340                 345                 350

Tyr Ala Asp Pro Asp Val Leu Gln Pro Leu Asp Asp Tyr Tyr Pro Ala
        355                 360                 365

Pro Arg Gly Ser Leu Ala Asn Thr Thr Val Ser Ala Ser Ser Ala Ser
370                 375                 380

Thr Leu Arg Gly Ser Thr Thr Ala Pro Leu Ser Gly Gly Val Asp Val
385                 390                 395                 400

Pro Val Tyr Thr Gly Pro Asp Ile Glu Pro Pro Val Val Pro Gly Leu
                405                 410                 415

Gly Pro Leu Ile Pro Val Ala Pro Ser Leu Pro Ser Ser Val Tyr Ile
            420                 425                 430

Phe Gly Gly Asp Tyr Tyr Leu Leu Pro Ser Tyr Ile Leu Trp Pro Lys
            435                 440                 445

Arg Arg Lys Arg Val Asn Tyr Phe Phe Ala Asp Gly Phe Val Ala Ala
            450                 455                 460

<210> SEQ ID NO 79
<211> LENGTH: 473
<212> TYPE: PRT
<213> ORGANISM: Human papillomavirus type 28

<400> SEQUENCE: 79

Met Val Ala His Arg Ala Arg Arg Lys Arg Ala Ser Ala Thr Gln
1               5                   10                  15

Leu Tyr Arg Thr Cys Lys Ala Ala Gly Thr Cys Pro Pro Asp Val Ile
            20                  25                  30

Pro Lys Val Glu Gly Thr Thr Leu Ala Asp Arg Ile Leu Gln Trp Gly
        35                  40                  45

Gly Leu Gly Ile Tyr Leu Gly Gly Leu Gly Ile Gly Thr Gly Ser Gly
    50                  55                  60

Thr Gly Gly Arg Thr Gly Tyr Val Pro Leu Ser Thr Arg Pro Gly Thr
65                  70                  75                  80

Val Val Asp Val Ser Val Pro Ala Arg Pro Pro Val Val Ile Glu Pro
                85                  90                  95

Val Gly Pro Ser Asp Pro Ser Ile Val Asn Leu Leu Glu Asp Ser Ser
            100                 105                 110

Ile Ile Asn Ser Gly Ser Thr Val Pro Thr Phe Ser Gly Thr Gly Gly
        115                 120                 125

Phe Glu Val Thr Ser Ser Ala Thr Thr Thr Pro Ala Val Leu Asp Ile
```

```
                130                 135                 140
Thr Pro Ala Thr Asp Asn Val Val Ile Ser Ser Asn Phe Thr Asn
145                 150                 155                 160

Pro Ala Phe Thr Glu Pro Ser Leu Leu Glu Val Pro Gln Asn Gly Glu
                165                 170                 175

Val Ser Gly His Ile Leu Val Ser Thr Pro Ala Gly Thr His Ser
                180                 185                 190

Tyr Glu Glu Ile Pro Met Glu Thr Phe Ala Ser Pro Gly Thr Gly Asn
                195                 200                 205

Glu Pro Ile Ser Ser Thr Pro Val Pro Gly Val Ser Arg Ile Ala Gly
                210                 215                 220

Pro Arg Leu Tyr Ala Lys Ala Val Thr Gln Val Lys Val Thr Asp Pro
225                 230                 235                 240

Ala Phe Leu Ser Arg Pro Thr Ser Leu Val Thr Phe Asp Asn Pro Ala
                245                 250                 255

Phe Glu Pro Gly Asp Glu Thr Ile Ile Phe Glu Arg Pro Tyr Pro Pro
                260                 265                 270

Ser Gln Val Pro Asp Pro Asp Phe Met Asp Ile Ile Arg Leu His Arg
                275                 280                 285

Pro Ala Leu Thr Ser Arg Arg Gly Thr Val Arg Phe Ser Arg Leu Gly
                290                 295                 300

Thr Lys Leu Ser Met His Thr Arg Ser Gly Lys Gly Ile Gly Ala Arg
305                 310                 315                 320

Val His Tyr Tyr Gln Asp Leu Ser Pro Ile Gly Pro Thr Glu Asp Ile
                325                 330                 335

Glu Met Glu Pro Leu Leu Ala Pro Ala Glu Asn Ala Ala Gly Asp Ser
                340                 345                 350

Ile Tyr Asp Val Phe Ala Asp Val Glu Asp Ala Asp Ile Ala Phe Thr
                355                 360                 365

Gly Arg Ser Arg Ser Ala Thr Ser Ser Arg Gly Tyr Thr Thr Val Ser
                370                 375                 380

Pro Leu Ser Ser Thr Leu Thr Thr Lys Tyr Gly Asn Val Thr Ile Pro
385                 390                 395                 400

Phe Val Ser Pro Val Asp Val His Leu His Pro Gly Pro Asp Ile Ile
                405                 410                 415

Thr Pro Ala Ser Thr Gln Trp Pro Phe Val Pro Leu Val Pro Ala Asp
                420                 425                 430

Thr Thr His Tyr Val Tyr Ile Asp Gly Gly Asp Phe Tyr Leu Trp Pro
                435                 440                 445

Val Thr Leu Phe Val Pro Arg Arg Arg Arg Lys Arg Leu Ser Tyr
450                 455                 460

Phe Leu Ala Asp Gly Thr Val Ala Leu
465                 470

<210> SEQ ID NO 80
<211> LENGTH: 473
<212> TYPE: PRT
<213> ORGANISM: Human papillomavirus type 29

<400> SEQUENCE: 80

Met Val Ala His Arg Ala Arg Arg Arg Lys Arg Ala Ser Ala Thr Glu
1               5                   10                  15

Leu Tyr Lys Thr Cys Lys Val Ala Gly Thr Cys Pro Pro Asp Val Ile
                20                  25                  30
```

```
Pro Lys Val Glu Gly Thr Thr Leu Ala Asp Arg Ile Leu Gln Trp Gly
         35                  40                  45

Ser Leu Gly Val Tyr Leu Gly Leu Gly Ile Gly Thr Gly Ser Gly
 50                  55                  60

Thr Gly Gly Arg Thr Gly Tyr Val Pro Val Gly Thr Arg Pro Gly Thr
 65                  70                  75                  80

Val Val Asp Val Ser Ile Pro Thr Arg Pro Pro Val Val Ile Glu Pro
                 85                  90                  95

Val Gly Pro Ser Asp Pro Ser Ile Val Thr Leu Leu Glu Glu Ser Ser
            100                 105                 110

Val Ile Asn Ser Gly Ala Thr Ile Pro Thr Phe Thr Gly Thr Ser Gly
            115                 120                 125

Phe Glu Ile Thr Ser Ser Ala Thr Thr Thr Pro Ala Val Leu Asp Ile
        130                 135                 140

Thr Pro Ala Gly Asp Asn Val Val Ile Thr Ser Thr Asn Phe Asn Asn
145                 150                 155                 160

Pro Leu Phe Thr Glu Pro Ser Leu Leu Glu Ile Pro Gln Thr Gly Glu
                165                 170                 175

Thr Ser Gly Arg Val Leu Val Gly Thr Pro Thr Ser Gly Val His Gly
                180                 185                 190

Tyr Glu Glu Ile Pro Met Asp Thr Phe Ala Thr Ser Gly Thr Gly Leu
            195                 200                 205

Glu Pro Ile Ser Ser Thr Pro Val Pro Gly Val Ser Arg Val Ala Gly
210                 215                 220

Pro Arg Leu Tyr Gly Lys Ala Leu Thr Gln Val Arg Val Ser Asp Pro
225                 230                 235                 240

Ala Phe Leu Thr Gln Pro Ser Ser Phe Val Thr Phe Asp Asn Pro Val
                245                 250                 255

Tyr Asp Pro Glu Asp Glu Thr Ile Ile Phe Glu Arg Pro Ser Pro Gly
                260                 265                 270

Thr Arg Val Pro Asp Pro Asp Phe Met Asp Ile Val Lys Leu His Arg
            275                 280                 285

Pro Ala Leu Thr Ser Arg Arg Gly Thr Val Arg Phe Ser Arg Val Gly
290                 295                 300

Gln Lys Phe Ser Met Arg Thr Arg Ser Gly Thr Asn Ile Gly Ala Arg
305                 310                 315                 320

Val His Tyr Tyr His Asp Leu Ser Pro Ile Leu Pro Thr Glu Asp Ile
                325                 330                 335

Glu Leu Glu Pro Leu Leu Pro Ala Asp Pro Thr Ala Glu Glu Ser
            340                 345                 350

Leu Tyr Asp Ile Tyr Ala Asp Val Asp Glu Ala Asp Met Ala Phe Thr
            355                 360                 365

Gly Gly Gly Arg Gly Ala Thr Thr Tyr Gly Gly Arg Ile Thr Pro Ser
370                 375                 380

Val Phe Ser Ser Thr Leu Ser Arg Tyr Gly Asn Val Thr Ile Pro
385                 390                 395                 400

Phe Val Ser Pro Val Asp Val Pro Leu His Thr Gly Pro Asp Ile Ile
                405                 410                 415

Leu Pro Ser Ser Ala Gln Trp Pro Phe Val Pro Val Ala Pro Ala Asp
            420                 425                 430

Thr Thr His Tyr Val Tyr Ile Asp Gly Gly Asp Tyr Phe Leu Trp Pro
            435                 440                 445

Val Thr Phe Pro Val Ser Arg Lys Arg Arg Arg Lys Arg Leu Ser Tyr
```

```
                450                 455                 460
Phe Leu Ala Asp Gly Phe Val Ala Leu
465                 470

<210> SEQ ID NO 81
<211> LENGTH: 463
<212> TYPE: PRT
<213> ORGANISM: Human papillomavirus type 30

<400> SEQUENCE: 81

Met Val Ala His Arg Ala Arg Arg Lys Arg Ala Ser Ala Thr Gln
1               5                   10                  15

Leu Tyr Gln Thr Cys Lys Gln Ala Gly Thr Cys Pro Ser Asp Val Ile
                20                  25                  30

Asn Lys Ile Glu His Thr Thr Leu Ala Asp Lys Ile Leu Gln Trp Gly
                35                  40                  45

Ser Leu Phe Thr Phe Phe Gly Asn Leu Gly Ile Gly Thr Gly Ala Gly
            50                  55                  60

Ser Gly Gly Arg Ala Gly Tyr Val Pro Leu Gly Thr Arg Pro Thr Thr
65                  70                  75                  80

Val Val Asp Ala Ser Pro Ala Arg Pro Pro Ile Val Val Glu Ser Val
                85                  90                  95

Gly Pro Thr Asp Pro Ser Ile Val Thr Leu Val Glu Glu Ser Ser Val
                100                 105                 110

Val Asn Ala Gly Ala Ser Phe Pro Asn Phe Thr Gly Thr Ala Gly Phe
                115                 120                 125

Glu Val Thr Ser Ser Thr Thr Pro Ala Val Leu Asp Ile Thr
                130                 135                 140

Pro Thr Thr Gly Ser Val His Val Ser Ser Thr His Phe Thr Asn Pro
145                 150                 155                 160

Ser Phe Val Glu Pro Pro Val Ile Glu Val Pro Gln Thr Gly Glu Val
                165                 170                 175

Ser Gly His Ile Leu Val Ser Thr Pro Thr Ser Gly Val His Ser Tyr
                180                 185                 190

Glu Glu Ile Pro Met Gln Thr Phe Ala Val His Gly Thr Gly Thr Glu
                195                 200                 205

Pro Ile Ser Ser Thr Pro Ile Pro Gly Leu Arg Arg Ile Ala Ala Pro
210                 215                 220

Arg Leu Tyr Gln Arg Ala Phe Gln Gln Val Lys Val Thr Asp Pro Thr
225                 230                 235                 240

Phe Leu Thr Lys Pro Glu Thr Leu Ile Thr Val Asp Asn Pro Val Phe
                245                 250                 255

Glu Asp Ala Asp Thr Thr Leu Thr Phe Ser Pro Ser Gly Val Ala Pro
                260                 265                 270

Asp Pro Asp Phe Leu Asp Ile Val Ala Leu His Arg Pro Ala Phe Thr
                275                 280                 285

Thr Arg Arg Gly Gly Val Arg Phe Ser Arg Leu Gly Thr Lys Ala Thr
                290                 295                 300

Met Arg Thr Arg Ser Gly Lys Gln Ile Gly Ala Arg Val His Tyr Tyr
305                 310                 315                 320

Tyr Asp Val Ser Pro Ile Ala His Thr Glu Glu Ile Glu Met Gln Pro
                325                 330                 335

Leu Leu Ser Ala Asn Asn Ser Phe Asp Gly Leu Tyr Asp Ile Tyr Ala
                340                 345                 350
```

```
Asn Leu Asp Asp Glu Ala Pro Val Ser Ser His Leu Ser Ile Ala Thr
            355                 360                 365
Pro Ser Arg Leu Pro Thr Asn Thr Val Pro Leu Ser Phe Ser Ser Gln
    370                 375                 380
Thr Thr Asn Val Thr Ile Pro Leu Gly Lys Tyr Trp Asp Val Pro Ile
385                 390                 395                 400
Tyr Ser Gly Pro Asp Ile Val Leu Pro Thr Gly Pro Thr Thr Trp Pro
                405                 410                 415
Tyr Ala Pro Gln Ala Pro Phe Asp Thr Thr His Asp Val Val Ile His
            420                 425                 430
Gly Ser Thr Phe Ala Leu Trp Pro Val Tyr Phe Leu Arg Arg Arg Arg
        435                 440                 445
Arg Lys His Val Pro Tyr Phe Leu Ala Asp Gly Val Ala Ala
    450                 455                 460
```

<210> SEQ ID NO 82
<211> LENGTH: 466
<212> TYPE: PRT
<213> ORGANISM: Human papillomavirus type 31

<400> SEQUENCE: 82

```
Met Arg Ser Lys Arg Ser Thr Lys Arg Thr Lys Arg Ala Ser Ala Thr
1               5                   10                  15
Gln Leu Tyr Gln Thr Cys Lys Ala Ala Gly Thr Cys Pro Ser Asp Val
            20                  25                  30
Ile Pro Lys Ile Glu His Thr Thr Ile Ala Asp Gln Ile Leu Arg Tyr
        35                  40                  45
Gly Ser Met Gly Val Phe Phe Gly Gly Leu Gly Ile Gly Ser Gly Ser
    50                  55                  60
Gly Thr Gly Gly Arg Thr Gly Tyr Val Pro Leu Ser Thr Arg Pro Ser
65              70                  75                  80
Thr Val Ser Glu Ala Ser Ile Pro Ile Arg Pro Pro Val Ser Ile Asp
            85                  90                  95
Pro Val Gly Pro Leu Asp Pro Ser Ile Val Ser Leu Val Glu Glu Ser
        100                 105                 110
Gly Ile Val Asp Val Gly Ala Pro Ala Pro Ile Pro His Pro Pro Thr
    115                 120                 125
Thr Ser Gly Phe Asp Ile Ala Thr Thr Ala Asp Thr Thr Pro Ala Ile
    130                 135                 140
Leu Asp Val Thr Ser Val Ser Thr His Glu Asn Pro Thr Phe Thr Asp
145                 150                 155                 160
Pro Ser Val Leu Gln Pro Pro Thr Pro Ala Glu Thr Ser Gly His Leu
            165                 170                 175
Leu Leu Ser Ser Ser Ile Ser Thr His Asn Tyr Glu Glu Ile Pro
        180                 185                 190
Met Asp Thr Phe Ile Val Ser Thr Asn Asn Glu Asn Ile Thr Ser Ser
    195                 200                 205
Thr Pro Ile Pro Gly Val Arg Arg Pro Ala Arg Leu Gly Leu Tyr Ser
    210                 215                 220
Lys Ala Thr Gln Gln Val Lys Val Ile Asp Pro Thr Phe Leu Ser Ala
225                 230                 235                 240
Pro Lys Gln Leu Ile Thr Tyr Glu Asn Pro Ala Tyr Glu Thr Val Asn
            245                 250                 255
Ala Glu Glu Ser Leu Tyr Phe Ser Asn Thr Ser His Asn Ile Ala Pro
        260                 265                 270
```

```
Asp Pro Asp Phe Leu Asp Ile Ile Ala Leu His Arg Pro Ala Leu Thr
            275                 280                 285

Ser Arg Arg Asn Thr Val Arg Tyr Ser Arg Leu Gly Asn Lys Gln Thr
290                 295                 300

Leu Arg Thr Arg Ser Gly Ala Thr Ile Gly Ala Arg Val His Tyr Tyr
305                 310                 315                 320

Tyr Asp Ile Ser Ser Ile Asn Pro Ala Gly Glu Ser Ile Glu Met Gln
                325                 330                 335

Pro Leu Gly Ala Ser Ala Thr Thr Ser Thr Leu Asn Asp Gly Leu
            340                 345                 350

Tyr Asp Ile Tyr Ala Asp Thr Asp Phe Thr Val Asp Thr Pro Ala Thr
                355                 360                 365

His Asn Val Ser Pro Ser Thr Ala Val Gln Ser Thr Ser Ala Val Ser
            370                 375                 380

Ala Tyr Val Pro Thr Asn Thr Thr Val Pro Leu Ser Thr Gly Phe Asp
385                 390                 395                 400

Ile Pro Ile Phe Ser Gly Pro Asp Val Pro Ile Glu His Ala Pro Thr
                405                 410                 415

Gln Val Phe Pro Phe Pro Leu Ala Pro Thr Thr Pro Gln Val Ser Ile
            420                 425                 430

Phe Val Asp Gly Gly Asp Phe Tyr Leu His Pro Ser Tyr Tyr Met Leu
            435                 440                 445

Lys Arg Arg Arg Lys Arg Val Ser Tyr Phe Phe Thr Asp Val Ser Val
450                 455                 460

Ala Ala
465

<210> SEQ ID NO 83
<211> LENGTH: 476
<212> TYPE: PRT
<213> ORGANISM: Human papillomavirus type 32

<400> SEQUENCE: 83

Met Pro Pro His Arg Ser Arg Arg Lys Arg Ala Ser Ala Thr Gln
1               5                   10                  15

Leu Tyr Gln Thr Cys Lys Ala Ser Gly Thr Cys Pro Pro Asp Val Ile
                20                  25                  30

Pro Lys Ile Glu Gly Arg Thr Trp Ala Asp Gln Ile Leu Lys Trp Gly
            35                  40                  45

Ser Thr Gly Val Phe Phe Gly Gly Leu Gly Ile Gly Thr Gly Ala Gly
        50                  55                  60

Ser Gly Gly Arg Thr Gly Tyr Val Pro Ile Gly Thr Arg Pro Pro Val
65                  70                  75                  80

Val Ala Glu Pro Gly Pro Ala Ile Arg Pro Pro Val Val Val Asp Thr
                85                  90                  95

Ile Gly Pro Thr Asp Pro Ser Val Ile Ser Leu Leu Glu Glu Ser Ala
            100                 105                 110

Val Ile Asp Ser Ser Ile Pro Val Pro Thr Asp Thr Ser His Gly Gly
        115                 120                 125

Phe Asn Ile Thr Ser Ser Ala Ser Gly Pro Ser Ser Thr Pro Ala Val
    130                 135                 140

Leu Asp Ile Ser Pro Pro Thr Asn Thr Ile Arg Val Ala Ser Thr Thr
145                 150                 155                 160

Ser His Asn Pro Val Tyr Ser Asp Pro Phe Thr Leu Arg Pro Ser Leu
```

```
                165                 170                 175
Pro Val Glu Gly Asn Gly Arg Leu Leu Thr Ser His Pro Thr Ile Ala
            180                 185                 190

Pro His Ser Tyr Glu Glu Ile Pro Met Asp Thr Phe Val Val Ser Thr
        195                 200                 205

Asp Thr Ser Asn Thr Val Thr Ser Thr Pro Ile Pro Gly Pro Arg Pro
210                 215                 220

Thr Met Arg Leu Gly Leu Tyr Thr Arg Val Thr Gln Gln Arg Pro Val
225                 230                 235                 240

Ala Thr Thr Thr Phe Leu Thr Ser Pro Glu Arg Leu Val Thr Tyr Asp
                245                 250                 255

Asn Pro Ala Tyr Glu Gly Pro Ala Glu Gly Thr Leu Glu Phe Glu His
            260                 265                 270

Pro Thr Ile His Glu Ala Pro Asp Ser Asp Phe Met Asp Ile Ile Ala
        275                 280                 285

Leu His Arg Pro Val Leu Ser Ala Arg Gln Gly Thr Val Arg Val Ser
290                 295                 300

Arg Ile Gly Gln Arg Ala Ser Leu Gln Thr Arg Ser Gly Ala Arg Ile
305                 310                 315                 320

Gly Ser Arg Val His Phe Phe His Asp Ile Ser Pro Ile Thr Arg Pro
                325                 330                 335

Ser Glu Ala Ile Glu Leu Gln Pro Leu Gly Ser Ser Thr Ala Val
            340                 345                 350

Ser Thr Thr Ala Ser Ser Ala Ile Asn Asp Gly Leu Phe Asp Val Tyr
        355                 360                 365

Val Asp Pro Asp Ile Pro Pro Ser His Ala Leu Pro Pro Leu Arg Ser
370                 375                 380

Pro Thr His Val Ser Thr Val Ser Leu Thr Ser Leu Gly Ser Val Pro
385                 390                 395                 400

Ala Gln Thr Ala Asn Thr Thr Val Pro Leu Ser Leu Pro Thr Asn Ile
                405                 410                 415

Asn Val Gly Pro Asp Leu Ser Pro Pro Glu Ser Pro Pro Phe Ile Ser
            420                 425                 430

Thr Arg Pro Val Ser Pro Ser Phe Asp Ser Val Met Val Leu Gly Trp
        435                 440                 445

Asp Phe Ile Leu His Pro Ser Tyr Met Trp Arg Lys Arg Arg Lys Pro
450                 455                 460

Val Pro Tyr Phe Phe Ala Asp Val Arg Val Ala Ala
465                 470                 475

<210> SEQ ID NO 84
<211> LENGTH: 467
<212> TYPE: PRT
<213> ORGANISM: Human papillomavirus type 33

<400> SEQUENCE: 84

Met Arg His Lys Arg Ser Thr Arg Arg Lys Arg Ala Ser Ala Thr Gln
1               5                   10                  15

Leu Tyr Gln Thr Cys Lys Ala Thr Gly Thr Cys Pro Pro Asp Val Ile
            20                  25                  30

Pro Lys Val Glu Gly Ser Thr Ile Ala Asp Gln Ile Leu Lys Tyr Gly
        35                  40                  45

Ser Leu Gly Val Phe Phe Gly Gly Leu Gly Ile Gly Thr Gly Ser Gly
    50                  55                  60
```

```
Ser Gly Gly Arg Thr Gly Tyr Val Pro Ile Gly Thr Asp Pro Pro Thr
 65                  70                  75                  80

Ala Ala Ile Pro Leu Gln Pro Ile Arg Pro Val Thr Val Asp Thr
                 85                  90                  95

Val Gly Pro Leu Asp Ser Ser Ile Val Ser Leu Ile Glu Glu Thr Ser
                100                 105                 110

Phe Ile Glu Ala Gly Ala Pro Ala Pro Ser Ile Pro Thr Pro Ser Gly
            115                 120                 125

Phe Asp Val Thr Thr Ser Ala Asp Thr Thr Pro Ala Ile Ile Asn Val
        130                 135                 140

Ser Ser Val Gly Glu Ser Ser Ile Gln Thr Ile Ser Thr His Leu Asn
145                 150                 155                 160

Pro Thr Phe Thr Glu Pro Ser Val Leu His Pro Pro Ala Pro Ala Glu
                165                 170                 175

Ala Ser Gly His Phe Ile Phe Ser Ser Pro Thr Val Ser Thr Gln Ser
            180                 185                 190

Tyr Glu Asn Ile Pro Met Asp Thr Phe Val Ser Thr Asp Ser Ser
        195                 200                 205

Asn Val Thr Ser Ser Thr Pro Ile Pro Gly Ser Arg Pro Val Ala Arg
210                 215                 220

Leu Gly Leu Tyr Ser Arg Asn Thr Gln Gln Val Lys Val Asp Pro
225                 230                 235                 240

Ala Phe Leu Thr Ser Pro His Lys Leu Ile Thr Tyr Asp Asn Pro Ala
                245                 250                 255

Phe Glu Ser Phe Asp Pro Glu Asp Thr Leu Gln Phe Gln His Ser Asp
            260                 265                 270

Ile Ser Pro Ala Pro Asp Pro Asp Phe Leu Asp Ile Ile Ala Leu His
        275                 280                 285

Arg Pro Ala Ile Thr Ser Arg Arg His Thr Val Arg Phe Ser Arg Val
290                 295                 300

Gly Gln Lys Ala Thr Leu Lys Thr Arg Ser Gly Lys Gln Ile Gly Ala
305                 310                 315                 320

Arg Ile His Tyr Tyr Gln Asp Leu Ser Pro Ile Val Pro Leu Asp His
                325                 330                 335

Thr Val Pro Asn Glu Gln Tyr Glu Leu Gln Pro Leu His Asp Thr Ser
            340                 345                 350

Thr Ser Ser Tyr Ser Ile Asn Asp Gly Leu Tyr Asp Val Tyr Ala Asp
        355                 360                 365

Asp Val Asp Asn Val His Thr Pro Met Gln His Ser Tyr Ser Thr Phe
370                 375                 380

Ala Thr Thr Arg Thr Ser Asn Val Ser Ile Pro Leu Asn Thr Gly Phe
385                 390                 395                 400

Asp Thr Pro Val Met Ser Gly Pro Asp Ile Pro Ser Pro Leu Phe Pro
                405                 410                 415

Thr Ser Ser Pro Phe Val Pro Ile Ser Pro Phe Phe Pro Phe Asp Thr
            420                 425                 430

Ile Val Val Asp Gly Ala Asp Phe Val Leu His Pro Ser Tyr Phe Ile
        435                 440                 445

Leu Arg Arg Arg Lys Arg Phe Pro Tyr Phe Phe Thr Asp Val Arg
450                 455                 460

Val Ala Ala
465
```

```
<210> SEQ ID NO 85
<211> LENGTH: 472
<212> TYPE: PRT
<213> ORGANISM: Human papillomavirus type 34

<400> SEQUENCE: 85
```

Met Arg Arg Lys Arg Asp Thr His Ile Arg Lys Arg Ala Ser Ala
1               5                   10                  15

Thr Gln Leu Tyr Lys Thr Cys Lys Gln Ser Gly Thr Cys Pro Pro Asp
            20                  25                  30

Ile Ile Pro Lys Val Glu Gly Asn Thr Leu Ala Asp Gln Ile Leu Lys
        35                  40                  45

Tyr Gly Ser Ile Gly Val Phe Phe Gly Gly Leu Gly Ile Gly Ser Gly
50                  55                  60

Ser Gly Thr Gly Gly Arg Thr Gly Tyr Val Pro Leu Pro Thr Thr Thr
65                  70                  75                  80

Pro Ser Arg Pro Val Glu Ile Pro Leu Gln Pro Thr Arg Pro Pro Val
                85                  90                  95

Ile Thr Ser Val Gly Ala Ser Asp Ser Ser Ile Val Ser Leu Val Glu
            100                 105                 110

Glu Ser Ser Phe Ile Glu Ala Gly Val Pro Gly Pro Thr Ser Ile Val
        115                 120                 125

Pro Ser Ser Ser Gly Phe Asn Val Thr Thr Ser Val Asp Ser Thr Pro
130                 135                 140

Ala Ile Ile Asp Val Ala Thr Ile Ser Asp Thr Thr Gln Val Ser Val
145                 150                 155                 160

Ser Thr Phe Asn Asn Pro Thr Phe Thr Asp Pro Ser Val Leu Gln Pro
                165                 170                 175

Pro Pro Pro Leu Glu Ala Ser Gly Arg Leu Leu Phe Ser Asn Asp Thr
            180                 185                 190

Val Thr Thr His Ser Tyr Glu Asn Ile Pro Leu Asp Thr Phe Val Val
        195                 200                 205

Thr Thr Asp Asn Asn Ser Ile Val Ser Ser Thr Pro Ile Pro Gly Arg
210                 215                 220

His Pro Pro Ala Arg Leu Gly Leu Tyr Gly Arg Ala Ile Gln Gln Val
225                 230                 235                 240

Lys Val Val Asp Pro Ala Phe Val Thr Thr Pro Thr Arg Leu Val Thr
                245                 250                 255

Tyr Asp Asn Pro Ala Phe Glu Gly Leu Gln Asp Thr Thr Leu Glu Phe
            260                 265                 270

Gln His Ser Asp Leu His Asn Ala Pro Asp Ser Asp Phe Leu Asp Ile
        275                 280                 285

Val Lys Leu His Arg Pro Ala Leu Thr Ala Arg Lys Thr Gly Ile Arg
290                 295                 300

Val Ser Arg Leu Gly Gln Arg Ala Thr Met Phe Thr Arg Ser Gly Lys
305                 310                 315                 320

Arg Ile Gly Gly Arg Val His Phe Tyr His Asp Leu Ser Pro Ile Pro
                325                 330                 335

Thr Glu Asn Ile Glu Leu Gln Pro Leu Leu Pro Ser Ala Ser Ala Thr
            340                 345                 350

Val Thr Asp Ala Asn Gly Ile Asn Asp Gly Leu Tyr Asp Val Leu Leu
        355                 360                 365

Asp Asn Asn Val Asp Ile Thr Glu Val Glu Thr Pro Thr Gly Thr Asn
370                 375                 380

```
Thr Gln Ser Val Phe Ala Ser Glu Ile Ser Thr Thr Thr Ala Asn Thr
385                 390                 395                 400

Thr Ile Pro Leu Asn Ala Gly Leu Asp Thr His Pro Gly Pro Asp Ile
            405                 410                 415

Ala Leu Pro Val Pro Thr Ala Glu Thr Ile Phe Thr Pro Thr Val Pro
            420                 425                 430

Val Gln Pro Ser Gly Pro Ile Tyr Ile Tyr Gly Ser Asp Phe Ile Leu
            435                 440                 445

His Pro Ser Leu Tyr Val Ile Pro Arg Lys Arg Lys Arg Leu Ser Tyr
            450                 455                 460

Phe Phe Ala Asp Val Ala Thr Tyr
465                 470
```

<210> SEQ ID NO 86
<211> LENGTH: 469
<212> TYPE: PRT
<213> ORGANISM: Human papillomavirus type 35

<400> SEQUENCE: 86

```
Met Arg His Lys Arg Ser Thr Lys Arg Val Lys Arg Ala Ser Ala Thr
1               5                   10                  15

Gln Leu Tyr Arg Thr Cys Lys Ala Ala Gly Thr Cys Pro Pro Asp Val
            20                  25                  30

Ile Pro Lys Val Glu Gly Asn Thr Val Ala Asp Gln Ile Leu Lys Tyr
            35                  40                  45

Gly Ser Met Ala Val Phe Phe Gly Gly Leu Gly Ile Gly Ser Gly Ser
        50                  55                  60

Gly Thr Gly Gly Arg Ser Gly Tyr Val Pro Leu Gly Thr Thr Pro Pro
65                  70                  75                  80

Thr Ala Ala Thr Asn Ile Pro Ile Arg Pro Pro Val Thr Val Glu Ser
                85                  90                  95

Ile Pro Leu Asp Thr Ile Gly Pro Leu Asp Ser Ser Ile Val Ser Leu
            100                 105                 110

Val Glu Glu Thr Ser Phe Ile Glu Ser Gly Ala Pro Val Val Thr Pro
        115                 120                 125

Arg Val Pro Pro Thr Thr Gly Phe Thr Ile Thr Ser Thr Asp Thr
130                 135                 140

Thr Pro Ala Ile Leu Asp Val Thr Ser Ile Ser Thr His Asp Asn Pro
145                 150                 155                 160

Thr Phe Thr Asp Pro Ser Val Leu His Pro Pro Thr Pro Ala Glu Thr
                165                 170                 175

Ser Gly His Phe Val Leu Ser Ser Ser Ile Ser Thr His Asn Tyr
            180                 185                 190

Glu Glu Ile Pro Met Asp Thr Phe Ile Val Ser Thr Asp Ser Asn Asn
        195                 200                 205

Ile Thr Asn Ser Thr Pro Ile Pro Gly Ser Arg Pro Thr Thr Arg Leu
210                 215                 220

Gly Leu Tyr Ser Lys Gly Thr Gln Gln Val Lys Val Val Asp Pro Ala
225                 230                 235                 240

Phe Met Thr Ser Pro Ala Lys Leu Ile Thr Tyr Asp Asn Pro Ala Tyr
                245                 250                 255

Glu Gly Leu Asn Pro Asp Thr Thr Leu Gln Phe Glu His Glu Asp Ile
            260                 265                 270

Ser Leu Ala Pro Asp Pro Asp Phe Met Asp Ile Ile Ala Leu His Arg
        275                 280                 285
```

-continued

```
Pro Ala Leu Thr Ser Arg Lys Gly Thr Ile Arg Tyr Ser Arg Val Gly
        290                 295                 300

Asn Lys Arg Thr Met His Thr Arg Ser Gly Lys Ala Ile Gly Ala Arg
305                 310                 315                 320

Val His Tyr Tyr Gln Asp Leu Ser Ser Ile Thr Glu Asp Ile Glu Leu
                325                 330                 335

Gln Pro Leu Gln His Val Pro Ser Ser Leu Pro His Thr Thr Val Ser
            340                 345                 350

Thr Ser Leu Asn Asp Gly Met Phe Asp Ile Tyr Ala Pro Ile Asp Thr
        355                 360                 365

Glu Glu Asp Ile Ile Phe Ser Ala Ser Ser Asn Thr Leu Tyr Thr
    370                 375                 380

Thr Ser Asn Thr Ala Tyr Val Pro Ser Asn Thr Thr Ile Pro Leu Ser
385                 390                 395                 400

Ser Gly Tyr Asp Ile Pro Ile Thr Ala Gly Pro Asp Ile Val Phe Asn
                405                 410                 415

Ser Asn Thr Ile Thr Asn Ser Val Leu Pro Val Pro Thr Gly Pro Ile
            420                 425                 430

Tyr Ser Ile Ile Ala Asp Gly Gly Asp Phe Tyr Leu His Pro Ser Tyr
        435                 440                 445

Tyr Leu Leu Lys Arg Arg Arg Lys Ala Ile Pro Tyr Phe Phe Ala Asp
    450                 455                 460

Val Ser Val Ala Val
465
```

<210> SEQ ID NO 87
<211> LENGTH: 518
<212> TYPE: PRT
<213> ORGANISM: Human papillomavirus type 36

<400> SEQUENCE: 87

```
Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Val Asn Lys
            20                  25                  30

Val Glu Gln Thr Thr Val Ala Asp Asn Ile Leu Lys Tyr Gly Ser Ala
        35                  40                  45

Gly Val Phe Phe Gly Gly Leu Gly Ile Gly Ser Gly Arg Gly Thr Gly
    50                  55                  60

Gly Ala Thr Gly Tyr Val Pro Leu Ser Glu Gly Pro Gly Ile Arg Val
65                  70                  75                  80

Gly Gly Thr Pro Thr Val Val Arg Pro Ser Leu Val Pro Glu Ala Ile
                85                  90                  95

Gly Pro Val Asp Ile Leu Pro Ile Asp Thr Ile Asp Pro Val Glu Pro
            100                 105                 110

Thr Ala Ser Ser Val Val Pro Leu Thr Glu Ser Thr Gly Pro Asp Leu
        115                 120                 125

Leu Pro Gly Glu Val Glu Thr Ile Ala Glu Ile His Pro Val Ala Glu
    130                 135                 140

Gly Pro Ser Val Asp Thr Pro Val Val Thr Thr Ser Thr Gly Ser Ser
145                 150                 155                 160

Ala Val Leu Glu Val Ala Pro Glu Pro Ile Pro Pro Thr Arg Val Arg
                165                 170                 175

Ile Ser Arg Thr Gln Tyr His Asn Pro Ser Phe Gln Ile Ile Thr Glu
```

```
            180                 185                 190
Ser Thr Pro Ala Gln Gly Glu Ser Ser Leu Ala Asp His Ile Leu Val
        195                 200                 205

Thr Ser Gly Ser Gly Gly Gln Arg Ile Gly Ala Asp Ile Thr Asp Glu
        210                 215                 220

Ile Glu Leu Gln Glu Leu Pro Ser Arg Tyr Thr Phe Glu Asn Glu Glu
225                 230                 235                 240

Pro Thr Pro Pro Arg Arg Ser Ser Thr Pro Leu Gln Ala Thr Arg Ala
                245                 250                 255

Ala Gly Arg Arg Arg Gly Val Ser Leu Thr Asn Arg Arg Leu Val Gln
            260                 265                 270

Gln Val Pro Val Glu Asn Pro Leu Phe Leu Thr Gln Pro Ser Arg Leu
        275                 280                 285

Val Arg Phe Ala Phe Glu Asn Pro Ala Phe Glu Glu Val Thr Asn
        290                 295                 300

Ile Phe Glu His Asp Val Asp Ala Phe Glu Glu Pro Pro Asp Arg Asp
305                 310                 315                 320

Phe Leu Asp Val Gln Arg Leu Gly Arg Pro Gln Tyr Ser Thr Thr Pro
                325                 330                 335

Ala Gly Tyr Val Arg Val Ser Arg Leu Gly Thr Arg Ala Thr Ile Arg
            340                 345                 350

Thr Arg Ser Gly Ala Gln Ile Gly Ser Gln Val His Phe Tyr Arg Asp
        355                 360                 365

Leu Ser Ser Ile Asn Thr Glu Asp Pro Ile Glu Leu Gln Leu Leu Gly
        370                 375                 380

Gln His Ser Gly Asp Ala Ser Ile Val Gln Gly Pro Val Glu Ser Thr
385                 390                 395                 400

Phe Ile Asp Val Asn Val Ser Glu Asn Pro Leu Ser Glu Ser Val Glu
                405                 410                 415

Ala Phe Ser Asp Asp Leu Leu Leu Asp Glu Ala Val Glu Asp Phe Ser
            420                 425                 430

Gly Ser Gln Leu Val Ile Gly Asn Arg Arg Ser Thr Thr Ser Tyr Thr
        435                 440                 445

Val Pro Arg Phe Glu Thr Thr Arg Ser Gly Ser Tyr Tyr Val Gln Asp
        450                 455                 460

Ser Lys Gly Tyr Tyr Val Ala Tyr Pro Glu Ser Arg Asn Asn Ala Glu
465                 470                 475                 480

Ile Ile Tyr Pro Thr Pro Asp Ile Pro Val Val Ile His Thr His
            485                 490                 495

Asp Asn Thr Gly Asp Phe Tyr Leu His Pro Ser Leu Arg Trp Arg Lys
        500                 505                 510

Arg Lys Arg Lys Tyr Leu
        515

<210> SEQ ID NO 88
<211> LENGTH: 534
<212> TYPE: PRT
<213> ORGANISM: Human papillomavirus type 37

<400> SEQUENCE: 88

Met Ala Arg Ala Arg Arg Thr Lys Arg Ala Ser Val Thr Asp Ile Tyr
1               5                   10                  15

Arg Gly Cys Lys Gln Ala Gly Thr Cys Pro Pro Asp Val Ile Asn Lys
            20                  25                  30
```

```
Val Glu Gln Thr Thr Ile Ala Asp Lys Ile Leu Lys Tyr Gly Gly Ala
             35                  40                  45

Gly Val Phe Phe Gly Gly Leu Gly Ile Ser Thr Gly Arg Gly Thr Gly
 50                  55                  60

Gly Ala Thr Gly Tyr Val Pro Leu Gly Glu Gly Pro Gly Val Arg Val
 65                  70                  75                  80

Gly Gly Ala Pro Thr Ile Val Arg Pro Gly Val Ile Pro Glu Leu Ile
                 85                  90                  95

Gly Pro Ala Asp Val Ile Pro Ile Asp Thr Val Thr Pro Ile Asp Pro
                100                 105                 110

Ala Ala Pro Ser Ile Val Thr Ile Thr Asp Ser Ser Ala Val Asp Leu
            115                 120                 125

Leu Pro Asn Glu Ile Glu Thr Ile Ala Glu Val His Pro Val Pro Thr
130                 135                 140

Asp Asn Leu Asp Ile Asp Thr Pro Val Val Thr Gly Gly Arg Asp Ser
145                 150                 155                 160

Ser Ala Val Leu Glu Val Ala Asp Pro Ser Pro Val Arg Thr Arg
                165                 170                 175

Val Ser Arg Thr Gln Tyr His Asn Pro Ser Phe Gln Ile Ile Thr Glu
            180                 185                 190

Ser Thr Pro Leu Ala Gly Glu Ser Ala Leu Ala Asp His Val Ile Val
            195                 200                 205

Phe Glu Gly Thr Gly Gly Gln Asn Ile Gly Gly Ser Arg Asn Ala Thr
            210                 215                 220

Ile Glu Thr Ala Gln Glu Ser Phe Glu Met Gln Ser Trp Pro Ser Arg
225                 230                 235                 240

Tyr Ser Phe Glu Ile Glu Glu Gly Thr Pro Pro Arg Ser Ser Thr Pro
                245                 250                 255

Val Gln Arg Ala Val Gln Ser Leu Ser Ser Leu Arg Arg Ala Leu Tyr
            260                 265                 270

Asn Arg Arg Leu Thr Glu Gln Val Ala Val Thr Asp Pro Leu Phe Leu
            275                 280                 285

Ser Arg Pro Ser Gln Leu Val Gln Phe Gln Phe Asp Asn Pro Ala Phe
290                 295                 300

Glu Glu Glu Val Thr Gln Ile Phe Glu Arg Asp Leu Glu Ala Val Glu
305                 310                 315                 320

Glu Pro Pro Asp Arg Gln Phe Leu Asp Val Ile Arg Leu Gly Arg Pro
                325                 330                 335

Thr Val Ala Glu Thr Pro Gln Ala Tyr Leu Arg Val Ser Arg Leu Gly
            340                 345                 350

Arg Arg Ala Thr Ile Arg Thr Arg Ser Gly Ala Gln Val Gly Ala Gln
            355                 360                 365

Val His Phe Tyr Arg Asp Leu Ser Thr Ile Asp Ser Asp Ala Leu Glu
370                 375                 380

Met Gln Leu Leu Gly His Ser Gly Asp Thr Thr Ile Val Gln Gly
385                 390                 395                 400

Pro Val Glu Ser Ser Phe Val Asp Ile Asn Ile Asp Glu Pro Gly Pro
                405                 410                 415

Leu Asn Ile Gly Gln Gln Glu Ser Met Ala Asp Thr Asp Phe
            420                 425                 430

Asn Ser Ala Asp Leu Leu Leu Glu Asp Ala Val Glu Asp Phe Ser Gly
            435                 440                 445

Ser Gln Leu Val Phe Gly Thr Ser Arg Arg Ser Thr Asn Ser Ile Thr
```

```
            450                 455                 460
Ile Pro Arg Phe Glu Thr Pro Arg Asp Thr Gly Phe Tyr Ile Gln Asp
465                 470                 475                 480

Ile Gln Gly Tyr Asn Val Ala Tyr Pro Glu Ser Arg Asp Thr Thr Gln
                485                 490                 495

Val Ile Leu Pro Gln Pro Glu Thr Pro Thr Val Val Ile Arg Phe Gly
                500                 505                 510

Glu Ala Gly Thr Asp Tyr Tyr Leu His Pro Ser Leu Lys Lys Lys Lys
                515                 520                 525

Arg Lys Arg Lys Tyr Leu
            530

<210> SEQ ID NO 89
<211> LENGTH: 527
<212> TYPE: PRT
<213> ORGANISM: Human papillomavirus type 38

<400> SEQUENCE: 89

Met Val Arg Ala Arg Arg Thr Lys Arg Ala Ser Val Thr Asp Ile Tyr
1               5                   10                  15

Arg Gly Cys Lys Ala Ser Asn Thr Cys Pro Pro Asp Val Ile Asn Lys
                20                  25                  30

Val Glu Gln Ser Thr Ile Ala Asp Lys Ile Leu Lys Tyr Gly Ser Ala
            35                  40                  45

Ala Val Phe Phe Gly Gly Leu Gly Ile Ser Thr Gly Arg Gly Thr Gly
        50                  55                  60

Gly Ala Thr Gly Tyr Val Pro Leu Gly Gln Gly Pro Gly Val Arg Val
65                  70                  75                  80

Gly Gly Ala Pro Thr Val Val Arg Pro Gly Val Ile Pro Glu Val Ile
                85                  90                  95

Gly Pro Thr Glu Leu Ile Pro Ile Asp Ser Val Thr Pro Ile Asp Pro
                100                 105                 110

Thr Ala Pro Ser Ile Val Ser Leu Thr Asp Ser Ser Ala Val Asp Leu
            115                 120                 125

Leu Pro Gly Glu Val Glu Thr Ile Ala Glu Val His Pro Gly Pro Ile
        130                 135                 140

Asp Pro Ile Glu Ile Asp Thr Pro Val Val Ser Gly Gly Arg Asn Thr
145                 150                 155                 160

Asn Ala Ile Leu Glu Val Ala Asp Pro His Pro Pro Thr Arg Ala Thr
                165                 170                 175

Val Ser Arg Thr Gln Tyr Asn Asn Pro Ala Phe Gln Ile Ile Ser Glu
            180                 185                 190

Val Ile Pro Thr Ser Gly Glu Ser Ser Leu Ala Asp His Val Leu Val
        195                 200                 205

Ser Glu Gly Ser Gly Gly Gln Gln Ile Gly Gly Thr Arg Thr Ala Glu
210                 215                 220

Glu Ile Glu Leu Gln Pro Leu Leu Ser Arg Tyr Ser Phe Glu Ile Glu
225                 230                 235                 240

Glu Pro Thr Pro Pro Arg Arg Thr Ser Thr Pro Leu Gln Arg Ala Arg
                245                 250                 255

Gln Gln Phe Ser Ser Leu Arg Arg Ala Leu Tyr Asn Arg Arg Leu Thr
            260                 265                 270

Glu Gln Val Gly Val Thr Asp Pro Leu Phe Phe Thr Ser Pro Ser Lys
        275                 280                 285
```

Leu Val Arg Phe Gln Phe Asp Asn Pro Val Phe Asp Glu Gln Val Thr
    290                 295                 300

Gln Ile Phe Glu Gln Asp Ile Ala Asp Phe Glu Glu Pro Pro Asp Arg
305                 310                 315                 320

Gln Phe Leu Asp Val Val Lys Leu Gly Arg Pro Thr Leu Thr Glu Ser
                325                 330                 335

Ala Glu Gly Tyr Val Arg Val Ser Arg Leu Gly Arg Arg Gly Thr Ile
            340                 345                 350

Arg Thr Arg Ser Gly Thr Gln Ile Gly Ser Gln Val His Phe Tyr Arg
        355                 360                 365

Asp Leu Ser Thr Ile Asn Thr Glu Glu Pro Leu Glu Met Gln Leu Leu
    370                 375                 380

Gly Glu His Ser Gly Asp Ala Ser Ile Val Gln Gly Pro Val Glu Ser
385                 390                 395                 400

Thr Leu Val Asp Val Asn Val Thr Glu Val Pro Glu Gly Val Leu Thr
                405                 410                 415

Glu Thr Ser Met Asp Pro Asp Thr Phe Asn Ser Glu Asp Leu Leu Leu
            420                 425                 430

Asp Asp Ala Ile Glu Asp Phe Ser Gly Ser Gln Leu Val Val Gly Thr
        435                 440                 445

Pro Arg Arg Ser Thr Thr Ser Ile Thr Val Pro Arg Phe Gln Thr Pro
    450                 455                 460

Gln Asn Pro Thr Ile Tyr Tyr Gln Asp Ile Gln Gly Tyr His Val Ser
465                 470                 475                 480

Tyr Pro Glu Ser Arg Glu Arg Pro Ala Ile Ile Tyr Pro Thr Pro Asp
                485                 490                 495

Ile Pro Thr Val Val Ile His Val Ala Asp Ser Ser Gly Asp Phe Tyr
            500                 505                 510

Leu His Pro Ser Leu Arg Trp Arg Arg Lys Arg Lys Tyr Leu
        515                 520                 525

<210> SEQ ID NO 90
<211> LENGTH: 470
<212> TYPE: PRT
<213> ORGANISM: Human papillomavirus type 39

<400> SEQUENCE: 90

Met Val Ser His Arg Ala Ala Arg Arg Lys Arg Ala Ser Ala Thr Asp
1               5                   10                  15

Leu Tyr Arg Thr Cys Lys Gln Ser Gly Thr Cys Pro Pro Asp Val Val
            20                  25                  30

Asp Lys Val Glu Gly Thr Thr Leu Ala Asp Lys Ile Leu Gln Trp Thr
        35                  40                  45

Ser Leu Gly Ile Phe Leu Gly Gly Leu Gly Ile Gly Thr Gly Thr Gly
    50                  55                  60

Thr Gly Gly Arg Thr Gly Tyr Ile Pro Leu Gly Gly Arg Pro Asn Thr
65                  70                  75                  80

Val Val Asp Val Ser Pro Ala Arg Pro Pro Val Val Ile Glu Pro Val
                85                  90                  95

Gly Pro Ser Glu Pro Ser Ile Val Gln Leu Val Glu Asp Ser Ser Val
            100                 105                 110

Ile Thr Ser Gly Thr Pro Val Pro Thr Phe Thr Gly Thr Ser Gly Phe
        115                 120                 125

Glu Ile Thr Ser Ser Ser Thr Thr Thr Pro Ala Val Leu Asp Ile Thr
    130                 135                 140

Pro Ser Ser Gly Ser Val Gln Ile Thr Ser Thr Ser Tyr Thr Asn Pro
145                 150                 155                 160

Ala Phe Thr Asp Pro Ser Leu Ile Glu Val Pro Gln Thr Gly Glu Thr
                165                 170                 175

Ser Gly Asn Ile Phe Val Ser Thr Pro Thr Ser Gly Thr His Gly Tyr
            180                 185                 190

Glu Glu Ile Pro Met Glu Val Phe Ala Thr His Gly Thr Gly Thr Glu
        195                 200                 205

Pro Ile Ser Ser Thr Pro Thr Pro Gly Ile Ser Arg Val Ala Gly Pro
    210                 215                 220

Arg Leu Tyr Ser Arg Ala His Gln Gln Val Arg Val Ser Asn Phe Asp
225                 230                 235                 240

Phe Val Thr His Pro Ser Ser Phe Val Thr Phe Asp Asn Pro Ala Phe
                245                 250                 255

Glu Pro Val Asp Thr Thr Leu Thr Tyr Glu Ala Ala Asp Ile Ala Pro
            260                 265                 270

Asp Pro Asp Phe Leu Asp Ile Val Arg Leu His Arg Pro Ala Leu Thr
        275                 280                 285

Ser Arg Lys Gly Thr Val Arg Phe Ser Arg Leu Gly Lys Lys Ala Thr
    290                 295                 300

Met Val Thr Arg Arg Gly Thr Gln Ile Gly Ala Gln Val His Tyr Tyr
305                 310                 315                 320

His Asp Ile Ser Ser Ile Ala Pro Ala Glu Ser Ile Glu Leu Gln Pro
                325                 330                 335

Leu Val His Ala Glu Pro Ser Asp Ala Ser Asp Ala Leu Phe Asp Ile
            340                 345                 350

Tyr Ala Asp Val Asp Asn Asn Thr Tyr Leu Asp Thr Ala Phe Asn Asn
        355                 360                 365

Thr Arg Asp Ser Gly Thr Thr Tyr Asn Thr Gly Ser Leu Pro Ser Val
    370                 375                 380

Ala Ser Ser Ala Ser Thr Lys Tyr Ala Asn Thr Thr Ile Pro Phe Ser
385                 390                 395                 400

Thr Ser Trp Asn Met Pro Val Asn Thr Gly Pro Asp Ile Ala Leu Pro
                405                 410                 415

Ser Thr Thr Pro Gln Leu Pro Leu Val Pro Ser Gly Pro Ile Asp Thr
            420                 425                 430

Thr Tyr Ala Ile Thr Ile Gln Gly Ser Asn Tyr Tyr Leu Leu Pro Leu
        435                 440                 445

Leu Tyr Phe Phe Leu Lys Lys Arg Lys Arg Ile Pro Tyr Phe Phe Ser
    450                 455                 460

Asp Gly Tyr Val Ala Val
465                 470

<210> SEQ ID NO 91
<211> LENGTH: 467
<212> TYPE: PRT
<213> ORGANISM: Human papillomavirus type 40

<400> SEQUENCE: 91

Met Val Ser Ser Arg Pro Arg Arg Lys Arg Ala Ser Ala Thr Gln
1               5                   10                  15

Leu Tyr Gln Thr Cys Lys Ala Ala Gly Thr Cys Pro Pro Asp Val Val
            20                  25                  30

His Lys Val Glu Gln Thr Thr Val Ala Asp Gln Ile Leu Lys Trp Gly

-continued

```
            35                  40                  45
Ser Met Gly Val Phe Phe Gly Gly Leu Gly Ile Gly Ser Gly Ser Gly
 50                  55                  60

Thr Gly Gly Arg Ala Gly Tyr Val Pro Leu Ser Thr Gly Ser Arg Ala
 65                  70                  75                  80

Val Pro Pro Lys Ser Leu Val Pro Asp Val Ala Arg Pro Pro Val
                     85                  90                  95

Val Val Asp Thr Val Ala Pro Ser Asp Pro Ser Ile Val Ser Leu Ile
                100                 105                 110

Glu Glu Ser Ser Ile Ile Gln Ser Gly Ala Pro Ser Leu Thr Ile Pro
                115                 120                 125

Thr Glu Gly Gly Phe Ser Val Thr Ser Ser Gly Thr Asp Val Pro Ala
130                 135                 140

Ile Leu Asp Val Ser Ser Thr Asn Thr Val His Val Thr Ala Thr Thr
145                 150                 155                 160

His His Asn Pro Val Phe Thr Asp Pro Ser Val Val Gln Pro Ile Pro
                165                 170                 175

Pro Val Glu Ala Gly Gly Arg Leu Ile Val Ser His Ser Thr Ile Thr
                180                 185                 190

Thr Ser Ala Ala Glu Glu Ile Pro Leu Asp Thr Phe Val Val His Ser
                195                 200                 205

Asp Pro Leu Ser Ser Thr Pro Val Pro Gly Thr Ser Gly Arg Pro Arg
210                 215                 220

Leu Gly Leu Tyr Ser Lys Ala Leu Gln Gln Val Glu Ile Val Asp Pro
225                 230                 235                 240

Ala Phe Leu Ser Thr Pro Gln Arg Leu Ile Thr Tyr Asp Asn Pro Val
                245                 250                 255

Phe Glu Asn Val Asp Asp Thr Leu Gln Phe Glu Gln Pro Ser Ile His
                260                 265                 270

Asp Ala Pro Asp Pro Ala Phe Met Asp Ile Ile Thr Leu His Arg Pro
                275                 280                 285

Ala Leu Thr Ser Arg Arg Gly Val Ile Arg Phe Ser Arg Val Gly Gln
290                 295                 300

Arg Gly Thr Met Tyr Thr Arg Arg Gly Thr Arg Ile Gly Gly Arg Val
305                 310                 315                 320

His Phe Phe Arg Asp Ile Ser Pro Ile Gly Ala Ala Asp Asp Ile Glu
                325                 330                 335

Leu His Pro Leu Val Ala Ser Ala Pro His Thr Leu Glu Thr Pro His
                340                 345                 350

Thr Leu Glu Thr Pro Leu Asp Thr Thr Asp Ala Leu Phe Asp Val Tyr
                355                 360                 365

Ala Asp Met Asp Thr Ile Asp Asp Ala Ala Tyr Ala Thr Phe Ser
                370                 375                 380

Leu His Pro Ala Asp Ser Thr Arg Ile Ser Asn Thr Ser Ile Pro Leu
385                 390                 395                 400

Ala Thr Val Ser Asp Thr Leu Leu Thr Ser Gly Pro Asp Ile Val Phe
                405                 410                 415

Pro Ser Ile Pro Ala Gly Thr Pro Tyr Leu Pro Val Ser Pro Ser Ile
                420                 425                 430

Pro Ala Ile Ser Val Leu Ile His Gly Thr Asp Tyr Tyr Leu His Pro
                435                 440                 445

Ala Tyr Tyr Leu Arg Lys Arg Arg Lys Arg Ile Leu Ala His Gln Tyr
450                 455                 460
```

```
Val Ala Thr
465

<210> SEQ ID NO 92
<211> LENGTH: 554
<212> TYPE: PRT
<213> ORGANISM: Human papillomavirus type 41

<400> SEQUENCE: 92

Met Leu Ala Arg Gln Arg Val Lys Arg Ala Asn Pro Glu Gln Leu Tyr
1               5                   10                  15

Lys Thr Cys Lys Ala Thr Gly Gly Asp Cys Pro Pro Asp Val Ile Lys
            20                  25                  30

Arg Tyr Glu Gln Thr Thr Pro Ala Asp Ser Ile Leu Lys Tyr Gly Ser
        35                  40                  45

Val Gly Val Phe Phe Gly Leu Gly Ile Gly Thr Gly Arg Gly Gly
    50                  55                  60

Gly Gly Thr Val Leu Gly Ala Gly Ala Val Gly Gly Arg Pro Ser Ile
65                  70                  75                  80

Ser Ser Gly Ala Ile Gly Pro Arg Asp Ile Leu Pro Ile Glu Ser Gly
                85                  90                  95

Gly Pro Ser Leu Ala Glu Glu Ile Pro Leu Leu Pro Met Ala Pro Arg
            100                 105                 110

Val Pro Arg Pro Thr Asp Pro Phe Arg Pro Ser Val Leu Glu Glu Pro
        115                 120                 125

Phe Ile Ile Arg Pro Pro Glu Arg Pro Asn Ile Leu His Glu Gln Arg
130                 135                 140

Phe Pro Thr Asp Ala Ala Pro Phe Asp Asn Gly Asn Thr Glu Ile Thr
145                 150                 155                 160

Thr Ile Pro Ser Gln Tyr Asp Val Ser Gly Gly Val Asp Ile Gln
                165                 170                 175

Ile Ile Glu Leu Pro Ser Val Asn Asp Pro Gly Pro Ser Val Val Thr
            180                 185                 190

Arg Thr Gln Tyr Asn Asn Pro Thr Phe Glu Val Glu Val Ser Thr Asp
        195                 200                 205

Ile Ser Gly Glu Thr Ser Ser Thr Asp Asn Ile Ile Val Gly Ala Glu
    210                 215                 220

Ser Gly Gly Thr Ser Val Gly Asp Asn Ala Glu Leu Ile Pro Leu Leu
225                 230                 235                 240

Asp Ile Ser Arg Gly Asp Thr Ile Asp Thr Thr Ile Leu Ala Pro Gly
                245                 250                 255

Glu Glu Glu Thr Ala Phe Val Thr Ser Thr Pro Glu Arg Val Pro Ile
            260                 265                 270

Gln Glu Arg Leu Pro Ile Arg Pro Tyr Gly Arg Gln Tyr Gln Gln Val
        275                 280                 285

Arg Val Thr Asp Pro Glu Phe Leu Asp Ser Ala Ala Val Leu Val Ser
    290                 295                 300

Leu Glu Asn Pro Val Phe Asp Ala Asp Ile Thr Leu Thr Phe Glu Asp
305                 310                 315                 320

Asp Leu Gln Gln Ala Leu Arg Ser Asp Thr Leu Arg Asp Val Arg
                325                 330                 335

Arg Leu Ser Arg Pro Tyr Tyr Gln Arg Arg Thr Thr Gly Leu Arg Val
            340                 345                 350

Ser Arg Leu Gly Gln Arg Arg Gly Thr Ile Ser Thr Arg Ser Gly Val
```

```
                    355                 360                 365
Gln Val Gly Ser Ala Ala His Phe Phe Gln Asp Ile Ser Pro Ile Gly
            370                 375                 380

Gln Ala Ile Glu Pro Ile Asp Ala Ile Glu Leu Asp Val Leu Gly Glu
385                 390                 395                 400

Gln Ser Gly Glu Gly Thr Ile Val Arg Gly Asp Pro Thr Pro Ser Ile
                405                 410                 415

Glu Gln Asp Ile Gly Leu Thr Ala Leu Gly Asp Asn Ile Glu Asn Glu
            420                 425                 430

Leu Gln Glu Ile Asp Leu Leu Thr Ala Asp Gly Glu Glu Asp Gln Glu
        435                 440                 445

Gly Arg Asp Leu Gln Leu Val Phe Ser Thr Gly Asn Asp Glu Val Val
    450                 455                 460

Asp Ile Met Thr Ile Pro Ile Arg Ala Gly Gly Asp Asp Arg Pro Ser
465                 470                 475                 480

Val Phe Ile Phe Ser Asp Asp Gly Thr His Ile Val Tyr Pro Thr Ser
                485                 490                 495

Thr Thr Ala Thr Thr Pro Leu Val Pro Ala Gln Pro Ser Asp Val Pro
            500                 505                 510

Tyr Ile Val Val Asp Leu Tyr Ser Gly Ser Met Asp Tyr Asp Ile His
        515                 520                 525

Pro Ser Leu Leu Arg Arg Lys Arg Lys Arg Lys Arg Val Tyr Phe
    530                 535                 540

Ser Asp Gly Arg Val Ala Ser Arg Pro Lys
545                 550

<210> SEQ ID NO 93
<211> LENGTH: 477
<212> TYPE: PRT
<213> ORGANISM: Human papillomavirus type 42

<400> SEQUENCE: 93

Met Pro Pro Gln Arg Ser Arg Arg Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Leu Ala Asp Lys Ile Leu Gln Trp Gly
        35                  40                  45

Ser Leu Gly Val Phe Phe Gly Gly Leu Gly Ile Gly Thr Gly Ala Gly
    50                  55                  60

Thr Gly Gly Arg Thr Gly Tyr Val Pro Leu Gly Thr Arg Pro Pro Val
65                  70                  75                  80

Ile Ala Glu Pro Gly Pro Ala Val Arg Pro Pro Ile Ala Val Asp Thr
                85                  90                  95

Val Gly Pro Ser Asp Pro Ser Ile Val Ser Leu Leu Glu Glu Ser Ser
            100                 105                 110

Val Ile Asp Ala Gly Ile Thr Val Pro Asp Ile Thr Ser His Gly Gly
        115                 120                 125

Phe Asn Ile Thr Thr Ser Thr Gly Gly Pro Ala Ser Thr Pro Ala Ile
    130                 135                 140

Leu Asp Ile Ser Pro Pro Thr Asn Thr Ile Arg Val Thr Thr Thr Thr
145                 150                 155                 160

Ser Thr Asn Pro Leu Tyr Ile Asp Pro Phe Thr Leu Gln Pro Pro Leu
                165                 170                 175
```

Pro Ala Glu Val Asn Gly Arg Leu Leu Ile Ser Thr Pro Thr Ile Thr
            180                 185                 190

Pro His Ser Tyr Glu Glu Ile Pro Met Asp Thr Phe Val Val Ser Thr
        195                 200                 205

Asp Thr Thr Asn Thr Phe Thr Ser Thr Pro Ile Pro Gly Pro Arg Ser
    210                 215                 220

Ser Ala Arg Leu Gly Leu Tyr Ser Arg Ala Thr Gln Gln Arg Pro Val
225                 230                 235                 240

Thr Thr Ser Ala Phe Leu Thr Ser Pro Ala Arg Leu Val Thr Tyr Asp
                245                 250                 255

Asn Pro Ala Tyr Glu Gly Leu Thr Glu Asp Thr Leu Val Phe Glu His
            260                 265                 270

Pro Ser Ile His Thr Ala Pro Asp Pro Asp Phe Met Asp Ile Val Ala
        275                 280                 285

Leu His Arg Pro Met Leu Ser Ser Lys Gln Gly Ser Val Arg Val Ser
    290                 295                 300

Arg Ile Gly Gln Arg Leu Ser Met Gln Thr Arg Arg Gly Thr Arg Phe
305                 310                 315                 320

Gly Ser Arg Val His Phe Phe His Asp Leu Ser Pro Ile Thr His Ser
                325                 330                 335

Ser Glu Thr Ile Glu Leu Gln Pro Leu Ser Ala Ser Ser Val Ser Ala
            340                 345                 350

Ala Ser Asn Ile Asn Asp Gly Leu Phe Asp Ile Tyr Val Asp Thr Ser
        355                 360                 365

Asp Val Asn Val Thr Asn Thr Thr Ser Ser Ile Pro Met His Gly Phe
    370                 375                 380

Ala Thr Pro Arg Leu Ser Thr Thr Ser Phe Pro Thr Leu Pro Ser Met
385                 390                 395                 400

Ser Thr His Ser Ala Asn Thr Thr Ile Pro Phe Ser Phe Pro Ala Thr
                405                 410                 415

Val His Val Gly Pro Asp Leu Ser Val Val Asp His Pro Trp Asp Ser
            420                 425                 430

Thr Pro Thr Ser Val Met Pro Gln Gly Asn Phe Val Met Val Ser Gly
        435                 440                 445

Trp Asp Phe Ile Leu His Pro Ser Tyr Phe Trp Arg Arg Arg Arg Lys
    450                 455                 460

Pro Val Pro Tyr Phe Phe Ala Asp Val Arg Val Ala Ala
465                 470                 475

<210> SEQ ID NO 94
<211> LENGTH: 463
<212> TYPE: PRT
<213> ORGANISM: Human papillomavirus type 43

<400> SEQUENCE: 94

Met Val Ser His Thr His Lys Arg Arg Lys Arg Ala Ser Ala Thr Gln
1               5                   10                  15

Leu Tyr Gln Thr Cys Lys Ala Ala Gly Thr Cys Pro Ser Asp Val Ile
            20                  25                  30

Asn Lys Val Glu His Thr Thr Ile Ala Asp Gln Ile Leu Lys Trp Ala
        35                  40                  45

Ser Met Gly Val Tyr Phe Gly Gly Leu Gly Ile Gly Thr Gly Ser Gly
    50                  55                  60

Thr Gly Gly Arg Thr Gly Tyr Val Pro Leu Thr Thr Gly Arg Thr Gly
65                  70                  75                  80

Ile Val Pro Lys Val Thr Ala Glu Pro Gly Val Val Ser Arg Pro Pro
            85                  90                  95

Ile Val Val Glu Ser Val Ala Pro Thr Asp Pro Ser Ile Val Ser Leu
            100                 105                 110

Ile Glu Glu Ser Ser Ile Ile Gln Ser Gly Ala Pro Ile Thr Asn Ile
            115                 120                 125

Pro Ser His Gly Gly Phe Glu Val Thr Ser Ser Gly Ser Glu Val Pro
        130                 135                 140

Ala Ile Leu Asp Val Ser Pro Ser Thr Ser Val His Ile Thr Thr Ser
145                 150                 155                 160

Thr His Leu Asn Pro Ala Phe Thr Asp Pro Thr Ile Val Gln Pro Thr
            165                 170                 175

Pro Pro Val Glu Ala Gly Gly Arg Ile Ile Ser His Ser Thr Val
        180                 185                 190

Thr Ala Asp Ser Ala Glu Gln Ile Pro Met Asp Thr Phe Val Ile His
            195                 200                 205

Ser Asp Pro Thr Thr Ser Thr Pro Ile Pro Gly Thr Ala Pro Arg Pro
        210                 215                 220

Arg Leu Gly Leu Tyr Ser Lys Ala Leu Gln Gln Val Glu Ile Val Asp
225                 230                 235                 240

Pro Thr Phe Leu Ser Ser Pro Gln Arg Leu Ile Thr Tyr Asp Asn Pro
            245                 250                 255

Val Phe Glu Asp Pro Asn Ala Thr Leu Thr Phe Glu Gln Pro Thr Val
            260                 265                 270

His Glu Ala Pro Asp Ser Arg Phe Met Asp Ile Val Thr Leu His Arg
            275                 280                 285

Pro Ala Leu Thr Ser Arg Arg Gly Ile Val Arg Phe Ser Arg Val Gly
        290                 295                 300

Ala Arg Gly Thr Met Tyr Thr Arg Ser Gly Ile Arg Ile Gly Gly Arg
305                 310                 315                 320

Val His Phe Phe Thr Asp Ile Ser Ser Ile Pro Thr Glu Glu Ser Ile
            325                 330                 335

Glu Leu Gln Pro Leu Gly Arg Ser Gln Ser Phe Pro Thr Val Ser Asp
            340                 345                 350

Thr Ser Asp Leu Tyr Asp Ile Tyr Ala Asp Glu Asn Leu Leu Asn Asn
        355                 360                 365

Asp Ile Ser Phe Thr Asp Thr His Val Ser Leu Gln Asn Ser Thr Lys
        370                 375                 380

Val Val Asn Thr Ala Val Pro Leu Ala Thr Val Pro Asp Ile Tyr Ala
385                 390                 395                 400

Gln Thr Gly Pro Asp Ile Ser Phe Pro Thr Ile Pro Ile His Ile Pro
            405                 410                 415

Tyr Ile Pro Val Ser Pro Ser Ile Ser Pro Gln Ser Val Ser Ile His
            420                 425                 430

Gly Thr Asp Phe Tyr Leu His Pro Ser Leu Trp His Leu Gly Lys Arg
        435                 440                 445

Arg Lys Arg Phe Ser Tyr Phe Phe Thr Asp Asn Tyr Val Ala Ala
450                 455                 460

<210> SEQ ID NO 95
<211> LENGTH: 460
<212> TYPE: PRT
<213> ORGANISM: Human papillomavirus type 44

```
<400> SEQUENCE: 95

Met Ala His Ser Arg Ala Arg Arg Lys Arg Ala Ser Ala Thr Gln
1               5                   10                  15

Leu Tyr Gln Thr Cys Lys Ala Ala Gly Thr Cys Pro Ser Asp Ile Ile
                20                  25                  30

Pro Lys Val Glu His Asn Thr Ile Ala Asp Gln Ile Leu Lys Trp Gly
            35                  40                  45

Ser Leu Gly Val Phe Phe Gly Leu Gly Ile Gly Thr Gly Ser Gly
    50                  55                  60

Thr Gly Gly Arg Thr Gly Tyr Ile Pro Leu Gln Ser Thr Pro Arg Pro
65                  70                  75                  80

Asp Ile Pro Ser Val Pro Thr Ala Arg Pro Pro Ile Leu Val Asp Thr
                85                  90                  95

Val Ala Pro Gly Asp Pro Ser Ile Val Ser Leu Val Glu Glu Ser Ala
                100                 105                 110

Ile Ile Asn Ser Gly Ala Pro Glu Leu Val Pro Pro Ser His Ala Gly
        115                 120                 125

Phe Glu Ile Thr Thr Ser Glu Ser Thr Thr Pro Ala Ile Leu Asp Val
    130                 135                 140

Ser Val Thr Thr His Thr Thr Ser Thr Ser Val Phe Lys Asn Pro Ser
145                 150                 155                 160

Phe Ala Asp Pro Ser Val Val Gln Ser Gln Pro Ala Val Glu Ala Gly
                165                 170                 175

Gly His Ile Leu Ile Ser Thr Ser Ser Ile Ser Ser His Pro Val Glu
            180                 185                 190

Glu Ile Pro Leu Asp Thr Phe Ile Val Ser Ser Ser Asp Ser Asn Pro
        195                 200                 205

Ala Ser Ser Thr Pro Ile Pro Ala Ser Gly Ala Arg Pro Arg Ile Gly
    210                 215                 220

Leu Tyr Ser Lys Ala Leu His Gln Val Gln Val Thr Asp Pro Ala Phe
225                 230                 235                 240

Leu Ser Ser Pro Gln Arg Leu Ile Thr Phe Asp Asn Pro Ala Tyr Glu
                245                 250                 255

Gly Glu Asp Val Thr Leu His Phe Ala His Asn Thr Ile His Glu Pro
                260                 265                 270

Pro Asp Asp Ala Phe Met Asp Ile Ile Arg Leu His Arg Pro Ala Ile
        275                 280                 285

Gln Ser Arg Arg Gly Arg Val Arg Phe Ser Arg Ile Gly Gln Arg Gly
    290                 295                 300

Ser Met Tyr Thr Arg Ser Gly Lys His Ile Gly Gly Arg Ile His Phe
305                 310                 315                 320

Tyr Gln Asp Ile Ser Pro Ile Ser Ala Ala Ala Glu Glu Ile Glu Leu
                325                 330                 335

His Pro Leu Val Ala Thr Ala Gln Asp Ser Gly Leu Phe Asp Ile Tyr
            340                 345                 350

Ala Glu Pro Asp Pro Asp Val Thr Glu Glu Pro Val Ser Leu Ser Phe
        355                 360                 365

Ser Thr Ser Thr Pro Phe Gln Arg Ser Ser Val Ser Ala Thr Pro Trp
    370                 375                 380

Gly Asn Thr Thr Val Pro Leu Ser Leu Pro Ala Asp Met Phe Val Gln
385                 390                 395                 400

Pro Gly Pro Asp Ile Ile Phe Pro Thr Ala Ser Thr Thr Thr Pro Tyr
                405                 410                 415
```

```
Ser Pro Val Thr Pro Ala Leu Pro Thr Gly Pro Val Phe Ile Ser Gly
        420                 425                 430

Ala Ala Phe Tyr Leu Tyr Pro Thr Trp Tyr Phe Ala Arg Lys Arg Arg
        435                 440                 445

Lys Arg Val Ser Leu Phe Phe Ala Asp Val Ala Ala
        450                 455                 460

<210> SEQ ID NO 96
<211> LENGTH: 518
<212> TYPE: PRT
<213> ORGANISM: Human papillomavirus type 47

<400> SEQUENCE: 96

Met Ala Arg Ala Arg Val Lys Arg Asp Ser Val Thr His Ile Tyr
1               5                   10                  15

Gln Thr Cys Lys Gln Ala Gly Thr Cys Pro Ser Asp Val Val Asn Lys
            20                  25                  30

Val Glu Gln Thr Thr Val Ala Asp Asn Ile Leu Lys Tyr Gly Ser Ala
        35                  40                  45

Gly Val Phe Phe Gly Gly Leu Gly Ile Gly Thr Gly Arg Gly Thr Gly
        50                  55                  60

Gly Ala Thr Gly Tyr Val Pro Leu Gly Glu Gly Pro Gly Val Arg Val
65                  70                  75                  80

Gly Gly Thr Pro Thr Val Val Arg Pro Ser Leu Val Pro Glu Ala Ile
                85                  90                  95

Gly Pro Val Asp Ile Leu Pro Ile Asp Thr Ile Ala Pro Val Glu Pro
            100                 105                 110

Thr Ala Ser Ser Leu Val Pro Leu Thr Glu Ser Ser Gly Ala Asp Leu
        115                 120                 125

Leu Pro Gly Glu Val Glu Thr Ile Ala Glu Ile His Pro Ile Pro Glu
    130                 135                 140

Gly Pro Thr Ile Asp Ser Pro Val Val Thr Thr Thr Thr Gly Ser Ser
145                 150                 155                 160

Ala Val Leu Glu Val Ala Pro Glu Pro Val Pro Pro Thr Arg Val Arg
                165                 170                 175

Ile Ala Arg Thr Gln Tyr His Asn Pro Ser Phe Gln Ile Leu Thr Glu
            180                 185                 190

Ser Thr Pro Ala Gln Gly Glu Ser Ser Leu Ala Asp His Ile Leu Val
        195                 200                 205

Thr Ser Gly Ser Gly Gly Gln Arg Ile Gly Gly Asp Ile Thr Asp Glu
    210                 215                 220

Ile Glu Leu Thr Glu Phe Pro Ser Arg Tyr Thr Phe Glu Ile Glu Glu
225                 230                 235                 240

Pro Thr Pro Pro Arg Lys Ser Ser Thr Pro Leu Gln Thr Val Ala Ser
                245                 250                 255

Ala Val Arg Arg Arg Gly Phe Ser Leu Thr Asn Arg Arg Leu Val Gln
            260                 265                 270

Gln Val Ala Val Asp Asn Pro Leu Phe Leu Ser Gln Pro Ser Lys Met
        275                 280                 285

Val Arg Phe Ser Phe Asp Asn Pro Ala Phe Glu Glu Val Thr Asn
        290                 295                 300

Ile Phe Glu Gln Asp Val Asn Ser Phe Glu Glu Pro Pro Asp Arg Asp
305                 310                 315                 320

Phe Leu Asp Ile Lys Gln Leu Gly Arg Pro Gln Tyr Ser Thr Thr Pro
```

```
                    325                 330                 335
Ala Gly Tyr Ile Arg Val Ser Arg Leu Gly Thr Arg Gly Thr Ile Arg
                340                 345                 350
Thr Arg Ser Gly Ala Gln Ile Gly Ser Gln Val His Phe Tyr Arg Asp
                355                 360                 365
Leu Ser Ser Ile Asn Thr Glu Asp Pro Ile Glu Leu Gln Leu Leu Gly
                370                 375                 380
Gln His Ser Gly Asp Ala Thr Ile Val Gln Gly Pro Val Glu Ser Thr
385                 390                 395                 400
Phe Ile Asp Met Asp Ile Ala Glu Asn Pro Leu Ser Glu Thr Ile Asp
                405                 410                 415
Ala Ser Ser Asn Asp Leu Leu Leu Asp Glu Thr Val Glu Asp Phe Ser
                420                 425                 430
Gly Ser Gln Leu Val Ile Gly Asn Arg Arg Ser Thr Thr Ser Tyr Thr
                435                 440                 445
Val Pro Arg Phe Glu Thr Thr Arg Ser Ser Tyr Tyr Val Gln Asp
                450                 455                 460
Thr Asp Gly Tyr Tyr Val Ala Tyr Pro Glu Ser Arg Asp Thr Ile Asp
465                 470                 475                 480
Ile Ile Tyr Pro Thr Pro Glu Leu Pro Val Val Ile His Thr His
                485                 490                 495
Asp Asn Ser Gly Asp Phe Tyr Leu His Pro Ser Leu Arg Arg Lys
                500                 505                 510
Arg Lys Arg Lys Tyr Leu
                515

<210> SEQ ID NO 97
<211> LENGTH: 502
<212> TYPE: PRT
<213> ORGANISM: Human papillomavirus type 48

<400> SEQUENCE: 97

Met Ser Leu Arg Arg Arg Lys Arg Ala Ser Pro Thr Asp Leu Tyr Lys
1               5                   10                  15
Thr Cys Leu Gln Gly Gly Asp Cys Ile Pro Asp Val Lys Asn Lys Phe
                20                  25                  30
Glu Asn Ser Thr Ile Ala Asp Trp Leu Leu Lys Ile Phe Gly Ser Leu
            35                  40                  45
Val Tyr Phe Gly Asn Leu Gly Ile Gly Ser Gly Lys Gly Ser Gly Gly
        50                  55                  60
Ser Phe Gly Tyr Arg Pro Leu Gly Ser Ala Gly Ser Gly Arg Pro Ala
65                  70                  75                  80
Thr Asp Leu Pro Val Thr Arg Pro Asn Val Val Ile Glu Pro Ile Gly
                85                  90                  95
Pro Gln Ser Ile Val Pro Ile Asp Pro Gly Ala Ser Ser Ile Val Pro
                100                 105                 110
Leu Val Glu Gly Gly Pro Asp Ile Ser Phe Ile Ala Pro Asp Ala Gly
            115                 120                 125
Pro Gly Ile Gly Gly Glu Asp Ile Glu Leu Phe Thr Phe Arg Asp Pro
        130                 135                 140
Ala Thr Asp Val Gly Gly Val Ser Gly Gly Pro Thr Thr Ile Ser Thr
145                 150                 155                 160
Glu Glu Ser Glu Thr Ala Ile Ile Asp Ala Leu Pro Ser Ala Thr Thr
                165                 170                 175
```

```
Pro Lys Gln Leu Phe Tyr Asp Ser Tyr Thr Gln Thr Ile Leu Gln Thr
                180                 185                 190

Gln Val Asn Pro Phe Leu Asn Asn Ala Ile Ser Asp Thr Asn Val Phe
            195                 200                 205

Val Asp Pro Leu Phe Ala Gly Glu Thr Ile Gly Asp Asn Ile Phe Glu
        210                 215                 220

Glu Ile Pro Leu Gln Asn Leu Asn Phe Ser Phe Pro Arg Glu Ser Thr
225                 230                 235                 240

Pro Val Lys Pro Gly Arg Gly Leu Arg Thr Pro Ala Gln Arg Ser Tyr
                245                 250                 255

Ser Arg Phe Met Glu Gln Tyr Pro Ile Gln Ala Pro Glu Phe Leu Ser
            260                 265                 270

Gln Pro Ser Arg Leu Val Gln Phe Glu Phe Glu Asn Pro Ala Phe Asp
        275                 280                 285

Pro Asp Ile Ser Ile Gln Phe Gln Arg Asp Val Asn Ser Leu Glu Ala
        290                 295                 300

Ala Pro Asn Pro Ala Phe Ala Asp Ile Ala Tyr Leu Ser Arg Pro His
305                 310                 315                 320

Met Ser Ala Thr Ser Glu Gly Leu Val Arg Val Ser Arg Ile Gly Ser
                325                 330                 335

Arg Ala Val Leu Gln Thr Arg Ser Gly Leu Thr Ile Gly Pro Lys Val
            340                 345                 350

His Tyr Tyr Met Asp Leu Ser Ala Ile Ser Thr Glu Ala Ile Glu Leu
        355                 360                 365

Gln Thr Phe Ala Asp Ser Gly His Val His Thr Ile Val Asp Asp Phe
        370                 375                 380

Leu Ser Val Thr Ala Leu Asp Asp Pro Ala Asn Ile Ala Asp Ile Asn
385                 390                 395                 400

Tyr Thr Glu Asp Asp Leu Leu Asp Pro Leu Leu Glu Asn Phe Asn Asn
                405                 410                 415

Ser His Ile Thr Val Gln Gly Val Asp Glu Glu Gly Glu Thr Val Ala
            420                 425                 430

Leu Pro Ile Pro Ser Ile Thr Asn Ser Ser Lys Thr Phe Val Thr Asp
        435                 440                 445

Ile Ala Glu Asn Gly Leu Phe Ala Asn Asp Thr Asp Ser Leu Leu Thr
        450                 455                 460

Pro Ala Ser Thr Ile Val Pro Ala Ile Asn Trp Phe Pro Leu Phe Asp
465                 470                 475                 480

Ser Tyr Ser Asp Phe Ala Leu Asp Pro Phe Phe Ile Pro Arg Lys Lys
                485                 490                 495

Arg Arg Leu Asp Ile Leu
            500

<210> SEQ ID NO 98
<211> LENGTH: 521
<212> TYPE: PRT
<213> ORGANISM: Human papillomavirus type 49

<400> SEQUENCE: 98

Met Val Arg Ala Arg Arg Thr Lys Arg Asp Ser Val Thr Asn Ile Tyr
1               5                   10                  15

Arg Thr Cys Lys Gln Ala Gly Asn Cys Pro Pro Asp Val Val Asn Lys
            20                  25                  30

Val Glu Gln Thr Thr Ile Ala Asp Gln Ile Leu Lys Phe Gly Ser Thr
        35                  40                  45
```

```
Gly Val Phe Gly Gly Leu Gly Ile Gly Thr Gly Arg Gly Thr Gly
             50                  55                  60
Gly Ser Thr Gly Tyr Val Pro Ile Gly Glu Gly Pro Ala Ile Arg Val
 65                  70                  75                  80
Gly Gly Thr Pro Ser Val Arg Pro Gly Ile Leu Pro Glu Ala Ile
                 85                  90                  95
Gly Pro Ala Asp Ile Ile Pro Ile Asp Thr Val Asn Pro Ile Asp Pro
                100                 105                 110
Asn Ala Ser Ser Val Val Pro Leu Thr Asp Thr Gly Pro Asp Leu Leu
                115                 120                 125
Pro Gly Thr Ile Glu Thr Ile Ala Glu Val Asn Pro Ala Pro Asp Ile
130                 135                 140
Pro Arg Val Asp Thr Ser Val Val Thr Thr Ser Arg Gly Ser Ser Ala
145                 150                 155                 160
Val Leu Glu Val Ala Ser Glu Pro Thr Pro Thr Arg Thr Arg Ile
                165                 170                 175
Ser Arg Thr Gln Tyr His Asn Pro Ser Phe Gln Ile Leu Thr Glu Ser
                180                 185                 190
Thr Pro Ser Leu Gly Glu Ser Ala Leu Thr Asp His Val Val Val Thr
                195                 200                 205
Ser Gly Ser Gly Gly Gln Pro Ile Gly Val Thr Pro Val Glu Ile
210                 215                 220
Glu Leu Gln Glu Leu Pro Ser Arg Tyr Thr Phe Glu Ile Glu Glu Pro
225                 230                 235                 240
Thr Pro Pro Arg Arg Ser Ser Thr Pro Leu Arg Asn Ile Thr Gln Ala
                245                 250                 255
Val Gly Asn Leu Arg Arg Ser Leu Tyr Asn Arg Leu Thr Gln Gln
                260                 265                 270
Val Asn Val Gln Asp Pro Leu Phe Leu Gln Gln Pro Ser Arg Leu Val
                275                 280                 285
Arg Phe Ala Phe Asp Asn Pro Val Phe Glu Glu Val Thr Gln Ile
290                 295                 300
Phe Glu Arg Asp Val Ala Ala Val Glu Glu Pro Pro Asp Arg Asp Phe
305                 310                 315                 320
Leu Asp Ile Ala Lys Leu Ser Arg Pro Leu Tyr Ser Glu Thr Pro Gln
                325                 330                 335
Gly Tyr Val Arg Val Ser Arg Leu Gly Asn Arg Ala Ser Ile Arg Thr
                340                 345                 350
Arg Ser Gly Ala Thr Val Gly Ala Gln Val His Phe Tyr Thr Asp Leu
                355                 360                 365
Ser Thr Ile Asp Ala Glu Glu Ser Ile Glu Leu Ser Leu Leu Gly Glu
                370                 375                 380
His Ser Gly Asp Ala Thr Ile Val Gln Gly Pro Val Glu Ser Ser Phe
385                 390                 395                 400
Val Asp Leu Asn Val Gln Glu Leu Pro Gln Val Ile Glu Val Asp Pro
                405                 410                 415
Glu Pro Thr Phe His Ser Asp Asp Leu Leu Leu Asp Glu Gln Asn Glu
                420                 425                 430
Asp Phe Ser Gly Ser Gln Leu Val Tyr Gly Ser Gly Arg Arg Ser Thr
                435                 440                 445
Thr Phe Val Pro Arg Phe Ser Thr Pro Arg Ser Asp Thr Phe Tyr
                450                 455                 460
```

```
Val Gln Asp Leu Glu Gly Tyr Ala Val Ser Tyr Pro Glu Arg Arg Asn
465                 470                 475                 480

Tyr Pro Glu Ile Ile Tyr Pro Gln Pro Asp Leu Pro Thr Val Ile Ile
            485                 490                 495

His Thr Ala Asp Thr Ser Gly Asp Phe Tyr Leu His Pro Ser Leu Arg
            500                 505                 510

Arg Arg Lys Arg Lys Arg Thr Tyr Leu
            515                 520

<210> SEQ ID NO 99
<211> LENGTH: 506
<212> TYPE: PRT
<213> ORGANISM: Human papillomavirus type 50

<400> SEQUENCE: 99

Met Leu Arg Arg Arg Lys Arg Ala Ser Pro Thr Asp Leu Tyr Arg Ser
1               5                   10                  15

Cys Leu Gln Gly Gly Asp Cys Ile Pro Asp Val Gln Asn Lys Phe Glu
            20                  25                  30

Gly Asn Thr Ile Ala Asp Trp Leu Leu Lys Ile Phe Gly Gly Leu Val
            35                  40                  45

Tyr Phe Gly Asn Leu Gly Ile Gly Thr Gly Arg Gly Thr Gly Gly Thr
50                  55                  60

Phe Gly Tyr Arg Pro Phe Gly Ala Pro Gly Ser Gly Arg Pro Thr Gln
65                  70                  75                  80

Glu Leu Pro Ile Ala Arg Pro Asn Val Val Ile Asp Pro Leu Gly Pro
                85                  90                  95

Ala Pro Ile Val Pro Val Asp Pro Ser Ala Ala Ser Ile Val Pro Leu
            100                 105                 110

Val Glu Gly Ala Pro Asp Val Gly Phe Ala Ala Pro Asp Ala Gly Pro
            115                 120                 125

Ala Ala Gly Gly Thr Asp Ile Glu Leu Tyr Thr Ile Thr Asn Ser Thr
130                 135                 140

Thr Asp Val Gly Ala Val Gly Gly Gly Pro Thr Val Thr Ser Asn Glu
145                 150                 155                 160

Glu Phe Glu Val Ala Val Ile Asp Ala Gln Pro Ile Ala Pro Tyr Pro
                165                 170                 175

Lys Gln Leu Leu Tyr Asp Ser Thr Ile Ala Ala Thr Phe Glu Thr Gln
            180                 185                 190

Ile Asn Pro Phe Ile Asn Pro Asp Ile Asn Asn Val Asn Val Leu Val
            195                 200                 205

Asp Pro Ser Phe Ala Gly Asp Thr Val Gly Asp Tyr Phe Glu Glu
210                 215                 220

Ile Pro Leu Glu Arg Leu Asp Ile Gln Thr Phe Asp Ile Leu Glu Pro
225                 230                 235                 240

Pro Thr Glu Ser Thr Pro Thr Gln Leu Gly Asn Arg Phe Val Ser Arg
                245                 250                 255

Ala Arg Asp Leu Tyr Ser Arg Phe Val Ala Gln Gln Pro Ile Ser Glu
            260                 265                 270

Pro Asp Phe Leu Ser Gln Pro Ser Arg Leu Val Gln Phe Glu Tyr Arg
            275                 280                 285

Asn Pro Ala Phe Asp Pro Asp Val Ser Leu Tyr Phe Glu Arg Asp Leu
            290                 295                 300

Glu Gly Leu Arg Ala Ala Pro Leu Gln Glu Phe Ala Asp Val Val Tyr
305                 310                 315                 320
```

Leu Gly Arg Pro Arg Val Ser Thr Ser Glu Gly Thr Ile Arg Val
            325                 330                 335

Ser Arg Leu Gly Thr Arg Ala Ala Leu Thr Thr Arg Ser Gly Leu Ser
            340                 345                 350

Val Gly Pro Gln Val His Phe Tyr Met Asp Leu Ser Asp Ile Pro Pro
            355                 360                 365

Glu Asp Ser Ile Glu Leu His Thr Leu Asn Val Thr Pro Gln Thr Ser
        370                 375                 380

Thr Ile Val Asp Asp Ile Leu Ala Thr Thr Phe Asp Asp Pro Ala
385                 390                 395                 400

Asn Ser Leu Phe Thr Gln Phe Asn Glu Asp Val Leu Thr Asp Asp Val
            405                 410                 415

Glu His Asn Phe Thr Glu Ser His Leu Val Ile Pro Ala Thr Asp Glu
            420                 425                 430

Glu Asn Asp Thr Ala Ile Asn Ile Ile Asn Leu Arg Asn Ile Pro Leu
        435                 440                 445

Thr Val Gly Met Asn Ser Gly Asp Ile Ser Thr Thr Leu Ser Asp Tyr
            450                 455                 460

Asn Ile Leu Asp Ala Ser Leu Ile Val Lys Ser Asn Val Ser Glu Gln
465                 470                 475                 480

Pro Leu Phe Val Leu Asp Tyr Ser Asp Tyr Asp Leu His Pro Gly Leu
            485                 490                 495

Leu Pro Lys Arg Arg Arg Ile Asp Tyr Phe
            500                 505

<210> SEQ ID NO 100
<211> LENGTH: 468
<212> TYPE: PRT
<213> ORGANISM: Human papillomavirus type 51

<400> SEQUENCE: 100

Met Val Ala Thr Arg Ala Arg Arg Arg Lys Arg Ala Ser Val Thr Gln
1               5                   10                  15

Leu Tyr Ser Thr Cys Lys Ala Ala Gly Thr Cys Pro Pro Asp Val Val
            20                  25                  30

Asn Lys Val Glu Gly Thr Thr Leu Ala Asp Lys Ile Leu Gln Trp Ser
        35                  40                  45

Gly Leu Gly Ile Phe Leu Gly Gly Leu Gly Ile Gly Thr Gly Ser Gly
    50                  55                  60

Ser Gly Gly Arg Thr Gly Tyr Ile Pro Leu Gly Gly Gly Gly Arg Pro
65                  70                  75                  80

Gly Val Val Asp Ile Ala Pro Ala Arg Pro Pro Ile Ile Ile Asp Leu
                85                  90                  95

Trp His His Thr Glu Pro Ser Ile Val Asn Leu Val Glu Asp Ser Ser
            100                 105                 110

Ile Ile Gln Ser Gly Ser Pro Ile Pro Thr Phe Thr Gly Thr Asp Gly
        115                 120                 125

Phe Glu Ile Thr Ser Ser Ser Thr Thr Pro Ala Val Leu Asp Ile
        130                 135                 140

Thr Pro Ser Ala Gly Thr Val His Val Ser Ser Thr Asn Ile Glu Asn
145                 150                 155                 160

Pro Leu Tyr Ile Glu Pro Pro Ser Ile Glu Ala Pro Gln Ser Gly Glu
            165                 170                 175

Val Ser Asp Ile Tyr Leu Leu Val His Tyr Ser Gly Thr His Gly Tyr

```
                180                 185                 190
Glu Glu Ile Pro Met Glu Val Phe Ala Ser Asn Val Ser Thr Gly Thr
            195                 200                 205
Glu Pro Ile Ser Ser Thr Pro Thr Pro Gly Val Ser Arg Ile Ala Ala
        210                 215                 220
Pro Arg Leu Tyr Ser Lys Ser Tyr Thr Gln Val Lys Val Thr Asn Pro
225                 230                 235                 240
Asp Phe Ile Ser Lys Pro Ser Thr Phe Val Thr Phe Asn Asn Pro Ala
                245                 250                 255
Phe Glu Pro Ile Asp Thr Ser Ile Thr Phe Glu Glu Pro Asp Ala Val
            260                 265                 270
Ala Pro Asp Pro Asp Phe Leu Asp Ile Ile Thr Leu His Arg Pro Ala
        275                 280                 285
Leu Thr Ser Arg Arg Gly Thr Val Arg Phe Ser Arg Leu Gly Gln Lys
        290                 295                 300
Ala Thr Met Arg Thr Arg Ser Gly Lys Gln Ile Gly Ala Arg Val His
305                 310                 315                 320
Tyr Tyr His Asp Ile Ser Arg Ile Ala Pro Ala Asp Glu Leu Glu Met
                325                 330                 335
Gln Pro Leu Leu Ser Pro Ser Asn Asn Tyr Ser Tyr Asp Ile Tyr Ala
            340                 345                 350
Asp Leu Asp Glu Ala Glu Thr Gly Phe Ile Gln Pro Thr His Thr Thr
        355                 360                 365
Pro Met Ser His Ser Ser Leu Ser Arg Gln Leu Pro Ser Leu Ser Ser
    370                 375                 380
Ser Met Ser Ser Ser Tyr Ala Asn Val Thr Ile Pro Phe Ser Thr Thr
385                 390                 395                 400
Tyr Ser Val Pro Ile His Thr Gly Pro Asp Val Val Leu Pro Thr Ser
                405                 410                 415
Pro Thr Val Trp Pro Tyr Val Pro His Thr Ser Ile Asp Thr Lys His
            420                 425                 430
Ser Ile Val Ile Leu Gly Gly Asp Tyr Tyr Leu Trp Pro Tyr Thr His
        435                 440                 445
Leu Leu Arg Lys Arg Arg Lys Arg Ile Pro Tyr Phe Phe Thr Asp Gly
    450                 455                 460
Ile Val Ala His
465

<210> SEQ ID NO 101
<211> LENGTH: 466
<212> TYPE: PRT
<213> ORGANISM: Human papillomavirus type 52

<400> SEQUENCE: 101

Met Arg Tyr Arg Arg Ser Thr Arg His Lys Arg Ala Ser Ala Thr Gln
1               5                   10                  15
Leu Tyr Gln Thr Cys Lys Ala Ser Gly Thr Cys Pro Pro Asp Val Ile
                20                  25                  30
Pro Lys Val Glu Gly Thr Thr Ile Ala Asp Gln Leu Leu Lys Tyr Gly
            35                  40                  45
Ser Leu Gly Val Phe Phe Gly Gly Leu Gly Ile Gly Thr Gly Ala Gly
        50                  55                  60
Ser Gly Gly Arg Ala Gly Tyr Val Pro Leu Ser Thr Arg Pro Pro Thr
65                  70                  75                  80
```

-continued

```
Ser Ser Ile Thr Thr Ser Thr Ile Arg Pro Pro Val Thr Val Glu Pro
                 85                  90                  95
Ile Gly Pro Leu Glu Pro Ser Ile Val Ser Met Ile Glu Glu Thr Thr
            100                 105                 110
Phe Ile Glu Ser Gly Ala Pro Ala Pro Ser Ile Pro Ser Ala Thr Gly
        115                 120                 125
Phe Asp Val Thr Thr Ser Ala Asn Asn Thr Pro Ala Ile Ile Asn Val
    130                 135                 140
Thr Ser Ile Gly Glu Ser Ser Val Gln Ser Val Ser Thr His Leu Asn
145                 150                 155                 160
Pro Thr Phe Thr Glu Pro Ser Ile Ile Gln Pro Pro Ala Pro Ala Glu
                165                 170                 175
Ala Ser Gly His Val Leu Phe Ser Ser Pro Thr Ile Ser Thr His Thr
            180                 185                 190
Tyr Glu Glu Ile Pro Met Asp Thr Phe Val Thr Ser Thr Asp Ser Ser
        195                 200                 205
Ser Val Thr Ser Ser Thr Pro Ile Pro Gly Ser Arg Pro Thr Thr Arg
    210                 215                 220
Leu Gly Leu Tyr Ser Arg Ala Thr Gln Gln Val Lys Val Val Asp Pro
225                 230                 235                 240
Ala Phe Met Ser Ser Pro Gln Lys Leu Val Thr Tyr Asn Asn Pro Val
                245                 250                 255
Phe Glu Gly Val Asp Thr Asp Glu Thr Ile Ile Phe Asp Arg Ser Gln
            260                 265                 270
Leu Leu Pro Ala Pro Asp Pro Asp Phe Leu Asp Ile Ile Ala Leu His
        275                 280                 285
Arg Pro Ala Leu Thr Ser Arg Arg Gly Thr Val Arg Phe Ser Arg Leu
    290                 295                 300
Gly Asn Lys Ala Thr Leu Arg Thr Arg Ser Gly Lys Gln Ile Gly Ala
305                 310                 315                 320
Arg Val His Tyr Tyr His Asp Ile Ser Pro Ile Gln Pro Ala Glu Val
                325                 330                 335
Gln Glu Asp Ile Glu Leu Gln Pro Leu Leu Pro Gln Ser Val Ser Pro
            340                 345                 350
Tyr Thr Ile Asn Asp Gly Leu Tyr Asp Val Tyr Ala Asp Ser Leu Gln
        355                 360                 365
Gln Pro Thr Phe His Leu Pro Ser Thr Leu Ser Thr His Asn Asn Thr
    370                 375                 380
Phe Thr Val Pro Ile Asn Ser Gly Ile Asp Phe Val Tyr Gln Pro Thr
385                 390                 395                 400
Met Ser Ile Glu Ser Gly Pro Asp Ile Pro Leu Pro Ser Leu Pro Thr
                405                 410                 415
His Thr Pro Phe Val Pro Ile Ala Pro Thr Ala Pro Ser Thr Ser Ile
            420                 425                 430
Ile Val Asp Gly Thr Asp Phe Ile Leu His Pro Ser Tyr Phe Leu Leu
        435                 440                 445
Arg Arg Arg Arg Lys Arg Phe Pro Tyr Phe Phe Thr Asp Val Arg Val
    450                 455                 460
Ala Ala
465

<210> SEQ ID NO 102
<211> LENGTH: 463
<212> TYPE: PRT
```

<213> ORGANISM: Human papillomavirus type 53

<400> SEQUENCE: 102

```
Met Val Ala His Arg Ala Arg Arg Lys Arg Ala Ser Ala Thr Gln
1               5                   10                  15

Leu Tyr Gln Thr Cys Lys Gln Ser Gly Thr Cys Pro Glu Asp Val Ile
                20                  25                  30

Asn Lys Ile Glu Gln Lys Thr Trp Ala Asp Lys Ile Leu Gln Trp Gly
            35                  40                  45

Ser Leu Phe Thr Phe Phe Gly Gly Leu Gly Ile Gly Thr Gly Ser Gly
        50                  55                  60

Thr Gly Gly Arg Thr Gly Tyr Ile Pro Leu Gly Thr Arg Pro Ser Thr
65                  70                  75                  80

Val Val Asp Val Thr Pro Ala Arg Pro Pro Ile Val Val Glu Ser Val
                85                  90                  95

Gly Pro Thr Asp Pro Ser Ile Val Thr Leu Val Glu Glu Ser Ser Val
            100                 105                 110

Ile Glu Ser Gly Ala Ser Phe Pro Asn Phe Thr Gly Thr Ala Gly Phe
        115                 120                 125

Glu Val Thr Ser Ser Ser Thr Thr Thr Pro Ala Val Leu Asp Ile Thr
130                 135                 140

Pro Thr Ser Thr Ser Val His Val Ser Ser Thr Thr Tyr Ser Asn Pro
145                 150                 155                 160

Thr Phe Val Asp Pro Pro Val Ile Glu Val Pro Gln Thr Gly Glu Val
                165                 170                 175

Ser Gly Asn Ile Leu Ile Ser Thr Pro Thr Ser Gly Val His Ser Tyr
            180                 185                 190

Glu Glu Ile Pro Met Gln Thr Phe Ala Val Gln Gly Thr Gly Asn Glu
        195                 200                 205

Pro Ile Ser Ser Thr Pro Ile Pro Gly Leu Arg Arg Ile Ala Ala Pro
210                 215                 220

Arg Leu Tyr Lys Lys Ala Phe Gln Gln Val Lys Val Thr Asp Pro Ala
225                 230                 235                 240

Phe Leu His Lys Pro Glu Thr Leu Ile Asn Val Asp Asn Pro Ile Phe
                245                 250                 255

Glu Thr Ala Asp Thr Thr Leu Thr Phe Ser Pro Ser Gly Val Ala Pro
            260                 265                 270

Asp Pro Asp Phe Leu Asp Ile Val Ala Leu His Arg Pro Ala Phe Thr
        275                 280                 285

Thr Arg Arg Gly Gly Val Arg Phe Ser Arg Leu Gly Thr Lys Ala Thr
290                 295                 300

Met Arg Thr Arg Ser Gly Lys Gln Ile Gly Ala Arg Val His Tyr Tyr
305                 310                 315                 320

Tyr Asp Val Ser Pro Ile Thr Gln Thr Glu Glu Ile Glu Met Gln Pro
                325                 330                 335

Leu Leu Ser Thr Asp Asn Thr Phe Asp Gly Leu Tyr Asp Ile Tyr Ala
            340                 345                 350

Asn Ile Asp Asp Glu Ala Pro Val Ser Ser Arg Phe Ser Ile Ala Thr
        355                 360                 365

Pro Ser Arg Leu Pro Thr Asn Thr Val Pro Leu Ser Phe Ser Gly Ser
370                 375                 380

Thr Ser Asn Val Thr Ile Pro Phe Gly Thr Ser Trp Asp Val Pro Ile
385                 390                 395                 400
```

-continued

```
Tyr Ser Gly Pro Asp Val Val Leu Pro Thr Gly Pro Pro Thr Trp Pro
                405                 410                 415

Tyr Ala Pro Gln Ser Pro Phe Asp Thr Thr His Asp Val Val Ile Gln
            420                 425                 430

Gly Ser Thr Phe Ala Leu Trp Pro Val Tyr Phe Leu Lys Arg Arg Arg
        435                 440                 445

Arg Lys Arg Ile Pro Tyr Phe Leu Ala Asp Gly Gly Val Ala Ala
    450                 455                 460
```

<210> SEQ ID NO 103
<211> LENGTH: 470
<212> TYPE: PRT
<213> ORGANISM: Human papillomavirus type 54

<400> SEQUENCE: 103

```
Met Ala Lys Ala Arg Ala Pro Arg Arg Lys Arg Ala Ser Ala Thr Gln
1               5                   10                  15

Leu Tyr Gln Thr Cys Lys Ala Ser Gly Thr Cys Pro Ser Asp Val Ile
                20                  25                  30

Pro Lys Val Glu Gly Thr Thr Ile Ala Asp Gln Ile Leu Arg Trp Gly
            35                  40                  45

Ser Met Gly Val Phe Phe Gly Gly Leu Gly Ile Gly Thr Gly Ser Gly
    50                  55                  60

Thr Gly Gly Arg Thr Gly Tyr Ile Pro Leu Gly Arg Pro Ser Thr Thr
65                  70                  75                  80

Leu Glu Pro Gly Pro Val Val Arg Pro Ala Gly Ala Val Glu Thr Val
                85                  90                  95

Ala Pro Ser Asp Pro Ser Ile Val Ser Leu Val Glu Glu Ser Ser Val
                100                 105                 110

Val Asp Val Gly Ala Pro Thr Pro Thr Ile Pro Thr His Gly Gly Phe
            115                 120                 125

Glu Ile Thr Thr Ser Ser Asp Ala Thr Pro Ala Ile Leu Asp Val Thr
    130                 135                 140

Ser Thr Thr Thr Pro Ile Arg Val Ser Val Thr Ser His Thr Asn Pro
145                 150                 155                 160

Ile Tyr Thr Glu Pro Ser Leu Leu Asp Pro Pro Pro Val Gln Met
                165                 170                 175

Asp Gly Arg Val Leu Val Ser Ser Thr Leu Pro Ser Ser Thr Ala
            180                 185                 190

Glu His Ile Pro Met Asp Thr Phe Ile Ile Met Gln Asp His Ile Gly
    195                 200                 205

Thr Thr Thr Ser Thr Pro Val Pro Arg Pro Ala Arg Pro Arg Leu
210                 215                 220

Gly Leu Tyr Ser Arg Ala Leu Gln Gln Val Pro Val His Asp Pro Ala
225                 230                 235                 240

Phe Leu Gln Gln Pro Ser Ser Leu Ile Thr Tyr Asp Asn Pro Val Tyr
                245                 250                 255

Glu Gly Asn Pro Asp Val Thr Leu His Phe Glu Gln Pro Thr Ile His
            260                 265                 270

Asn Ala Pro Asp Pro Ala Phe Met Asp Ile Phe Ala Leu His Arg Pro
    275                 280                 285

Ala Leu Thr Thr Arg Arg Gly Val Val Arg Tyr Ser Arg Val Gly Glu
    290                 295                 300

Arg Ala Thr Val His Thr Arg Ser Gly Leu Gln Leu Lys Pro Arg Val
305                 310                 315                 320
```

```
His Tyr Phe Gln Asp Leu Ser Pro Ile Ala His Val Pro Glu Glu Ile
            325                 330                 335

Glu Leu His Pro Leu Ile Ser Ala Asn Asn Thr Ser Ile Asn Asn Gly
            340                 345                 350

Leu Tyr Ser Asp Ile Tyr Asp Val Tyr Ala Asp Thr Asp Phe Ala Asp
            355                 360                 365

Thr Gly Gly Val Ser Thr Ser Thr Val Ser Arg Ser Ser Val His Thr
370                 375                 380

Thr Leu Gln Thr Thr Ser Ile Pro Ser Gln Tyr Gly Asn Thr Thr Val
385                 390                 395                 400

Pro Leu Thr Ala Ser Ser Pro Tyr Thr Pro Ile Pro Thr Ser Phe Arg
            405                 410                 415

Pro Ser Ser Gly Gln Ala Pro Phe Ile Pro Ala Arg Pro Ile Phe Pro
            420                 425                 430

Gln Thr Pro Ile Ala Val Asn Gly Gly Asp Phe Tyr Leu His Pro Ser
            435                 440                 445

Tyr Thr Ser Leu Arg Lys Arg Arg Lys Arg Leu Pro Tyr Phe Leu Ala
            450                 455                 460

Asp Gly Tyr Val Ala Ala
465                 470

<210> SEQ ID NO 104
<211> LENGTH: 460
<212> TYPE: PRT
<213> ORGANISM: Human papillomavirus type 55

<400> SEQUENCE: 104

Met Ala His Ser Arg Ala Arg Arg Lys Arg Ala Ser Ala Thr Gln
1               5                   10                  15

Leu Tyr Gln Thr Cys Lys Ala Ala Gly Thr Cys Pro Ser Asp Ile Ile
            20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
50                  55                  60

Thr Gly Gly Arg Thr Gly Tyr Ile Pro Leu Gln Ser Thr Pro Arg Pro
65                  70                  75                  80

Glu Ile Pro Ser Gly Pro Thr Thr Arg Pro Pro Ile Leu Val Asp Thr
            85                  90                  95

Val Ala Pro Gly Asp Pro Ser Ile Val Ser Leu Val Glu Glu Ser Ala
            100                 105                 110

Ile Ile Asn Ser Gly Ala Pro Glu Leu Val Pro Pro Ser His Gly Gly
            115                 120                 125

Phe Glu Ile Thr Thr Ser Glu Ser Thr Thr Pro Ala Ile Leu Asp Val
            130                 135                 140

Ser Val Thr Thr His Thr Thr Ser Thr Val Phe Arg Asn Pro Ser
145                 150                 155                 160

Phe Ala Asp Pro Ser Val Val Gln Ser Gln Pro Ala Val Glu Ala Gly
            165                 170                 175

Gly His Ile Leu Ile Ser Thr Ser Thr Ile Ser Ser His Pro Val Glu
            180                 185                 190

Glu Ile Pro Leu Asp Thr Phe Ile Val Ser Ser Asp Ser Asn Pro
            195                 200                 205

Ala Ser Ser Thr Pro Ile Pro Ala Ser Gly Ala Arg Pro Arg Ile Gly
```

Leu Tyr Ser Lys Ala Leu His Gln Val Gln Val Thr Asp Pro Ala Phe
225                 230                 235                 240

Leu Ser Ser Pro Gln Arg Leu Ile Thr Phe Asp Asn Pro Ala Tyr Glu
                245                 250                 255

Gly Glu Asp Val Ser Leu Glu Phe Ala His Asn Thr Ile His Gln Pro
            260                 265                 270

Pro Asp Asp Ala Phe Met Asp Ile Ile Arg Leu His Arg Pro Ala Ile
        275                 280                 285

Gln Ser Arg Arg Gly Arg Val Arg Phe Ser Arg Ile Gly Gln Arg Gly
    290                 295                 300

Ser Met Tyr Thr Arg Ser Gly Lys His Ile Gly Gly Arg Ile His Phe
305                 310                 315                 320

Tyr Gln Asp Ile Ser Pro Ile Ser Ala Ala Ala Glu Glu Ile Glu Leu
                325                 330                 335

His Pro Leu Val Ala Thr Ala His Asp Thr Ser Leu Phe Asp Ile Tyr
            340                 345                 350

Ala Glu Pro Asp Pro Asp Phe Thr Glu Glu Pro Val Pro Leu Ser Phe
        355                 360                 365

Ser Thr Ser Thr Pro Phe Gln Arg Ser Ser Val Ser Ala Thr Pro Trp
    370                 375                 380

Gly Asn Thr Thr Val Pro Leu Ser Leu Pro Gly Asp Met Phe Val Gln
385                 390                 395                 400

Pro Gly Pro Asp Ile Ile Phe Pro Thr Ala Ser Thr Thr Thr Pro Tyr
                405                 410                 415

Ser Pro Val Thr Pro Ala Leu Pro Thr Gly Pro Val Phe Ile Ser Gly
            420                 425                 430

Ala Thr Phe Tyr Leu Tyr Pro Ala Trp Tyr Phe Ala Arg Lys Arg Arg
        435                 440                 445

Lys Arg Val Ser Leu Phe Phe Ala Asp Val Ala Ala
    450                 455                 460

<210> SEQ ID NO 105
<211> LENGTH: 464
<212> TYPE: PRT
<213> ORGANISM: Human papillomavirus type 56

<400> SEQUENCE: 105

Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Val
                20                  25                  30

Asn Lys Ile Glu Gln Lys Thr Trp Ala Asp Lys Ile Leu Gln Trp Gly
            35                  40                  45

Ser Leu Phe Thr Tyr Phe Gly Gly Leu Gly Ile Gly Thr Gly Thr Gly
        50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg Pro Pro Ile Val Val Glu Ser Val
                85                  90                  95

Gly Pro Thr Asp Pro Ser Ile Val Thr Leu Val Glu Glu Ser Ser Val
            100                 105                 110

Ile Glu Ser Gly Ala Gly Ile Pro Asn Phe Thr Gly Ser Gly Gly Phe
        115                 120                 125

Glu Ile Thr Ser Ser Thr Thr Pro Ala Val Leu Asp Ile Thr
         130                 135                 140

Pro Thr Ser Ser Thr Val His Val Ser Ser Thr His Ile Thr Asn Pro
145                 150                 155                 160

Leu Phe Ile Asp Pro Val Ile Glu Ala Pro Gln Thr Gly Glu Val
                165                 170                 175

Ser Gly Asn Ile Leu Ile Ser Thr Pro Thr Ser Gly Ile His Ser Tyr
            180                 185                 190

Glu Glu Ile Pro Met Gln Thr Phe Ala Val His Gly Ser Gly Thr Glu
        195                 200                 205

Pro Ile Ser Ser Thr Pro Ile Pro Gly Phe Arg Arg Ile Ala Ala Pro
210                 215                 220

Arg Leu Tyr Arg Lys Ala Phe Gln Gln Val Lys Val Thr Asp Pro Thr
225                 230                 235                 240

Phe Leu Asp Arg Pro Ala Thr Leu Val Ser Ala Asp Asn Pro Leu Phe
                245                 250                 255

Glu Gly Thr Asp Thr Ser Leu Ala Phe Ser Pro Ser Gly Val Ala Pro
            260                 265                 270

Asp Pro Asp Phe Met Asn Ile Val Ala Leu His Arg Pro Ala Phe Thr
        275                 280                 285

Thr Arg Arg Gly Gly Val Arg Phe Ser Arg Leu Gly Arg Lys Ala Thr
290                 295                 300

Ile Gln Thr Arg Arg Gly Thr Gln Ile Gly Ala Arg Val His Tyr Tyr
305                 310                 315                 320

Tyr Asp Ile Ser Pro Ile Ala Gln Ala Glu Glu Ile Glu Met Gln Pro
                325                 330                 335

Leu Leu Ser Ala Asn Asn Ser Phe Asp Gly Leu Tyr Asp Ile Tyr Ala
            340                 345                 350

Asn Ile Asp Asp Glu Ala Pro Gly Leu Ser Ser Gln Ser Val Ala Thr
        355                 360                 365

Pro Ser Ala His Leu Pro Ile Lys Pro Ser Thr Leu Ser Phe Ala Ser
370                 375                 380

Asn Thr Thr Asn Val Thr Ala Pro Leu Gly Asn Val Trp Glu Thr Pro
385                 390                 395                 400

Phe Tyr Ser Gly Pro Asp Met Val Leu Pro Thr Gly Pro Ser Thr Trp
                405                 410                 415

Pro Phe Val Pro Gln Ser Pro Tyr Asp Val Thr His Asp Val Tyr Ile
            420                 425                 430

Gln Gly Ser Ser Phe Ala Leu Trp Pro Val Tyr Phe Phe Arg Arg Arg
        435                 440                 445

Arg Arg Lys Arg Ile Pro Tyr Phe Phe Ala Asp Gly Asp Val Ala Ala
450                 455                 460

<210> SEQ ID NO 106
<211> LENGTH: 465
<212> TYPE: PRT
<213> ORGANISM: Human papillomavirus type 57

<400> SEQUENCE: 106

Met Ser Pro Arg Ala Lys Arg Arg Lys Arg Ala Ser Pro Thr Asp Leu
1               5                   10                  15

Tyr Arg Thr Cys Lys Gln Ala Gly Thr Cys Pro Pro Asp Ile Ile Pro
                20                  25                  30

Arg Val Glu Gln Asp Thr Leu Ala Asp Arg Ile Leu Lys Trp Gly Ser
            35                  40                  45

```
Leu Gly Val Phe Phe Gly Leu Gly Ile Gly Thr Gly Ser Gly Thr
 50                  55                  60
Gly Gly Arg Thr Gly Tyr Ile Pro Val Gly Thr Arg Pro Thr Thr Val
 65                  70                  75                  80
Val Asp Val Gly Leu Ala Pro Arg Pro Val Val Ile Glu Pro Val
                 85                  90                  95
Gly Ala Ser Glu Pro Ser Ile Val Asn Leu Val Glu Asp Ser Ser Ile
                100                 105                 110
Ile Asn Ala Gly Ser Ser His Pro Thr Phe Thr Gly Thr Gly Gly Phe
                115                 120                 125
Glu Val Thr Thr Ser Thr Val Thr Asp Pro Ala Val Leu Asp Ile Thr
                130                 135                 140
Pro Ser Gly Asn Gly Val Gln Val Ser Ser Ser Phe Val Asn Pro
145                 150                 155                 160
Leu Phe Thr Asp Pro Ala Ile Ile Glu Ala Pro Gln Ala Gly Glu Val
                165                 170                 175
Thr Gly His Val Leu Val Ser Thr Ala Thr Ser Gly Ser His Gly Phe
                180                 185                 190
Glu Glu Ile Pro Met Gln Thr Phe Ala Thr Ser Gly Gly Asp Gly Gly
                195                 200                 205
Glu Pro Ile Ser Ser Thr Pro Val Pro Gly Val Arg Arg Val Ala Gly
                210                 215                 220
Pro Arg Leu Tyr Ser Arg Ala Asn Gln Gln Val Arg Val Arg Asp Pro
225                 230                 235                 240
Ala Phe Ile Asp Arg Pro Ala Asp Leu Val Thr Phe Asp Asn Pro Val
                245                 250                 255
Tyr Asp Pro Glu Glu Thr Ile Ile Phe Gln His Pro Gly Leu His Glu
                260                 265                 270
Pro Pro Asp Pro Asp Phe Leu Asp Ile Val Ser Leu His Arg Pro Ala
                275                 280                 285
Leu Thr Ser Thr Arg Gln Gly Thr Val Arg Phe Ser Arg Leu Gly Arg
                290                 295                 300
Arg Ala Thr Leu Arg Thr Arg Ser Gly Lys Gln Ile Gly Ala Arg Val
305                 310                 315                 320
His Phe Tyr His Asp Ile Ser Pro Val Ala Pro Glu Glu Leu Glu Met
                325                 330                 335
Glu Pro Leu Leu Pro Pro Thr Ser Glu Pro Leu Tyr Asp Ile Tyr Ala
                340                 345                 350
Glu Ser Asp Phe Leu Gln Pro Leu Asp Ser Asp Val Pro Ala Ala Pro
                355                 360                 365
Arg Gly Thr Leu Ser Leu Ala Asp Thr Ala Val Ser Ala Ser Thr Ala
                370                 375                 380
Ser Thr Leu Arg Gly Ala Thr Thr Val Pro Leu Ser Gly Gly Val Asp
385                 390                 395                 400
Val Pro Val Tyr Thr Gly Pro Asp Ile Asp Pro Ser Val Gly Pro Gly
                405                 410                 415
Met Gly Pro Leu Val Pro Val Ile Pro Ala Ile Pro Ser Ser Val Tyr
                420                 425                 430
Ile Val Gly Gly Asp Tyr Tyr Leu Leu Pro Ser Tyr Val Leu Trp Pro
                435                 440                 445
Lys Arg Arg Lys Arg Val His Tyr Phe Phe Ala Asp Gly Tyr Val Ala
450                 455                 460
```

Ala
465

<210> SEQ ID NO 107
<211> LENGTH: 472
<212> TYPE: PRT
<213> ORGANISM: Human papillomavirus type 58

<400> SEQUENCE: 107

Met Arg His Lys Arg Ser Thr Arg Arg Lys Arg Ala Ser Ala Thr Gln
1               5                   10                  15

Leu Tyr Gln Thr Cys Lys Ala Ser Gly Thr Cys Pro Pro Asp Val Ile
            20                  25                  30

Pro Lys Val Glu Gly Thr Thr Ile Ala Asp Gln Ile Leu Arg Tyr Gly
        35                  40                  45

Ser Leu Gly Val Phe Phe Gly Gly Leu Gly Ile Gly Thr Gly Ser Gly
    50                  55                  60

Thr Gly Gly Arg Thr Gly Tyr Val Pro Leu Gly Ser Thr Pro Pro Ser
65                  70                  75                  80

Glu Ala Ile Pro Leu Gln Pro Ile Arg Pro Pro Val Thr Val Asp Thr
                85                  90                  95

Val Gly Pro Leu Asp Ser Ser Ile Val Ser Leu Ile Glu Glu Ser Ser
            100                 105                 110

Phe Ile Asp Ala Gly Ala Pro Ala Pro Ser Ile Pro Thr Pro Ser Gly
        115                 120                 125

Phe Asp Ile Thr Thr Ser Ala Asp Thr Thr Pro Ala Ile Leu Asn Val
    130                 135                 140

Ser Ser Ile Gly Glu Ser Ser Ile Gln Thr Val Ser Thr His Leu Asn
145                 150                 155                 160

Pro Ser Phe Thr Glu Pro Ser Val Leu Arg Pro Pro Ala Pro Ala Glu
                165                 170                 175

Ala Ser Gly His Leu Ile Phe Ser Ser Pro Thr Val Ser Thr His Ser
            180                 185                 190

Tyr Glu Asn Ile Pro Met Asp Thr Phe Val Ile Ser Thr Asp Ser Gly
        195                 200                 205

Asn Val Thr Ser Ser Thr Pro Ile Pro Gly Ser Arg Pro Val Ala Arg
    210                 215                 220

Leu Gly Leu Tyr Ser Arg Asn Thr Gln Gln Val Lys Val Val Asp Pro
225                 230                 235                 240

Ala Phe Leu Thr Ser Pro His Arg Leu Val Thr Tyr Asp Asn Pro Ala
                245                 250                 255

Phe Glu Gly Phe Asn Pro Glu Asp Thr Leu Gln Phe Gln His Ser Asp
            260                 265                 270

Ile Ser Pro Ala Pro Asp Pro Asp Phe Leu Asp Ile Val Ala Leu His
        275                 280                 285

Arg Pro Ala Leu Thr Ser Arg Arg Gly Thr Val Arg Tyr Ser Arg Val
    290                 295                 300

Gly Gln Lys Ala Thr Leu Arg Thr Arg Ser Gly Lys Gln Ile Gly Ala
305                 310                 315                 320

Lys Val His Tyr Tyr Gln Asp Leu Ser Pro Ile Gln Pro Val Gln Glu
                325                 330                 335

Gln Val Gln Gln Gln Gln Gln Phe Glu Leu Gln Ser Leu Asn Thr Ser
            340                 345                 350

Val Ser Pro Tyr Ser Ile Asn Asp Gly Leu Tyr Asp Ile Tyr Ala Asp
        355                 360                 365

```
Asp Ala Asp Thr Ile His Asp Phe Gln Ser Pro Leu His Ser His Thr
            370                 375                 380

Ser Phe Ala Thr Thr Arg Thr Ser Asn Val Ser Ile Pro Leu Asn Thr
385                 390                 395                 400

Gly Phe Asp Thr Pro Leu Val Ser Leu Glu Pro Gly Pro Asp Ile Ala
                405                 410                 415

Ser Ser Val Thr Ser Met Ser Ser Pro Phe Ile Pro Ile Ser Pro Leu
                420                 425                 430

Thr Pro Phe Asn Thr Ile Ile Val Asp Gly Ala Asp Phe Met Leu His
            435                 440                 445

Pro Ser Tyr Phe Ile Leu Arg Arg Arg Lys Arg Phe Pro Tyr Phe
    450                 455                 460

Phe Ala Asp Val Arg Val Ala Ala
465                 470

<210> SEQ ID NO 108
<211> LENGTH: 464
<212> TYPE: PRT
<213> ORGANISM: Human papillomavirus type 59

<400> SEQUENCE: 108

Met Val Ser His Arg Ala Ala Arg Arg Lys Arg Ala Ser Ala Thr Asp
1               5                   10                  15

Leu Tyr Lys Thr Cys Lys Gln Ala Gly Thr Cys Pro Ser Asp Val Ile
                20                  25                  30

Asn Lys Val Glu Gly Thr Thr Leu Ala Asp Lys Ile Leu Gln Trp Thr
            35                  40                  45

Ser Leu Gly Ile Phe Leu Gly Gly Leu Gly Ile Gly Thr Gly Ser Gly
        50                  55                  60

Thr Gly Gly Arg Thr Gly Tyr Ile Pro Leu Gly Gly Arg Thr Asn Thr
65                  70                  75                  80

Ile Val Asp Val Ser Pro Ala Lys Pro Pro Val Val Ile Glu Pro Val
                85                  90                  95

Gly Pro Thr Asp Pro Ser Ile Val Thr Leu Val Glu Asp Ser Ser Val
                100                 105                 110

Ile Thr Ser Gly Ala Pro Ala Pro Thr Phe Thr Gly Thr Ser Gly Phe
            115                 120                 125

Glu Ile Ser Thr Ser Ser Thr Thr Thr Pro Ala Val Leu Asp Ile Thr
        130                 135                 140

Pro Thr Ser Ser Val Gln Ile Ser Ser Ser Ser Phe Ile Asn Pro Ala
145                 150                 155                 160

Phe Thr Asp Pro Ser Val Ile Glu Val Pro Gln Thr Gly Glu Ile Ser
                165                 170                 175

Gly Asn Ile Leu Ile Ser Thr Pro Thr Ser Gly Ala His Gly Tyr Glu
            180                 185                 190

Glu Ile Pro Met Gln Thr Phe Ala Thr Glu Gly Thr Gly Leu Glu Pro
        195                 200                 205

Ile Ser Ser Thr Pro Asn Pro Thr Val Arg Arg Val Ala Gly Pro Arg
    210                 215                 220

Leu Tyr Ser Arg Ala Asn Gln Gln Val Arg Val Ser Asn Ala Asp Phe
225                 230                 235                 240

Leu Thr Arg Pro Ser Thr Phe Val Thr Tyr Asp Asn Pro Ala Tyr Asp
                245                 250                 255

Pro Ile Asp Thr Thr Leu Thr Phe Asp Pro Ser Ser Glu Val Pro Asp
```

```
            260                 265                 270
Pro Asp Phe Met Asp Ile Val Arg Leu His Arg Pro Ala Leu Thr Ser
            275                 280                 285

Arg Arg Ser Thr Val Arg Phe Ser Arg Leu Gly Gln Arg Ala Thr Met
            290                 295                 300

Phe Thr Arg Ser Gly Lys Gln Ile Gly Ala Arg Val His Phe Tyr His
305                 310                 315                 320

Asp Ile Ser Pro Ile Pro His Ala Glu Asp Ile Glu Leu Gln Pro Leu
                325                 330                 335

Val Ser Ser Gln Ala Ala Thr Asp Asp Ile Tyr Asp Ile Tyr Ala Asp
            340                 345                 350

Ile Thr Asp Glu Ala Pro Thr Ser Thr Ala Asn Thr Ala Phe Thr Ile
            355                 360                 365

Pro Lys Ser Ser Phe Gln Ser Leu Ser Leu Thr Arg Ser Ala Ser Ser
            370                 375                 380

Thr Phe Ser Asn Val Thr Val Pro Leu Ala Thr Ala Trp Asp Val Pro
385                 390                 395                 400

Val Asn Thr Gly Pro Asp Ile Val Leu Pro Asn Thr Asn Ile Val Glu
                405                 410                 415

Pro Thr Tyr Ser Thr Thr Pro Phe Thr Thr Ile Gln Ser Ile Asn Ile
                420                 425                 430

Glu Gly Thr Asn Tyr Phe Leu Trp Pro Ile Tyr Phe Leu Pro Arg
            435                 440                 445

Lys Arg Lys Arg Val Pro Tyr Phe Phe Thr Asp Gly Ser Met Ala Phe
            450                 455                 460

<210> SEQ ID NO 109
<211> LENGTH: 525
<212> TYPE: PRT
<213> ORGANISM: Human papillomavirus type 60

<400> SEQUENCE: 109

Met Tyr Ala Arg Val Lys Arg Val Lys Arg Asp Ser Val Glu Asn Leu
1               5                   10                  15

Tyr Lys Gln Cys Gln Leu Gly Ala Asp Cys Pro Pro Asp Val Arg Asn
            20                  25                  30

Lys Val Glu Gly Thr Thr Leu Ala Asp Arg Leu Leu Gln Ile Phe Gly
        35                  40                  45

Ser Ile Leu Tyr Leu Gly Asn Leu Gly Ile Gly Thr Gly Lys Gly Ser
    50                  55                  60

Gly Gly Ala Thr Gly Tyr Thr Pro Leu Gly Thr Ala Arg Val Pro Ala
65                  70                  75                  80

Ser Thr Pro Gly Thr Val Ile Lys Pro Thr Arg Pro Phe Ser Val Pro
                85                  90                  95

Leu Asp Pro Ile Gly Ser Gly Ile Pro Ser Gln Pro Val Gly Gly Arg
            100                 105                 110

Leu Pro Val Asp Ile Ile Asp Ala Ser Ala Ser Ser Ile Pro Leu
            115                 120                 125

Gln Glu Val Leu Pro Glu Thr Thr Ile Ile Val Gly Gly Asp Ser Gly
        130                 135                 140

Pro Gly Leu Gly Ala Ser Glu Ile Asp Ile Val Ser Glu Pro Arg Pro
145                 150                 155                 160

Asp Val Val Gly Val Asp Thr Gln Pro Thr Val Tyr Thr Ser Ile Asp
                165                 170                 175
```

```
Asn Thr Val Ala Thr Leu Asp Ile Thr Pro Ala Thr Pro Pro Val Lys
            180                 185                 190
Lys Ile Ile Leu Asp Pro Ile Ser Ser Gly Ser Glu Gly Ala Ala Ala
        195                 200                 205
Ile Thr Phe Ser Asp Ile Ser Ala Ala Asp Leu Asn Val Phe Val Asp
    210                 215                 220
Pro Gln Gly Ala Gly Asp Arg Ile Ser Phe Gly Glu Glu Ile Glu Leu
225                 230                 235                 240
Gly Pro Ile Asn Gln Pro Ala Gln Phe Glu Ile Glu Pro Pro Arg
            245                 250                 255
Thr Ser Thr Pro Gly Glu Gly Phe Gln Arg Val Thr Thr Arg Ala Arg
            260                 265                 270
Glu Leu Tyr Asn Arg Phe Val Gln Gln Pro Thr Gln Asn Ile Asp
            275                 280                 285
Phe Leu Gly Arg Pro Ser Arg Ala Val Gln Phe Glu Phe Glu Asn Pro
            290                 295                 300
Ala Phe Phe Asn Asp Glu Val Thr Met Gln Phe Glu Gln Asp Leu Gln
305                 310                 315                 320
Glu Val Ala Ala Ala Pro Asp Gln Asp Phe Ala Asp Val Arg Glu Leu
            325                 330                 335
Gly Arg Ala Arg Phe Ser Glu Thr Ser Ala Gly Thr Ile Arg Val Ser
            340                 345                 350
Arg Leu Gly Thr Lys Gly Thr Met Lys Thr Arg Ser Gly Leu Thr Ile
            355                 360                 365
Gly Gln Lys Val His Phe Tyr Phe Asp Ile Ser Asp Ile Pro Ala Ala
            370                 375                 380
Glu Thr Ile Gln Leu Arg Thr Leu Gly Glu Ser Ser His Asp Phe Ser
385                 390                 395                 400
Ala Val Asp Asn Ile Thr Glu Ser Thr Tyr Ile Asn Leu Thr Glu Thr
                405                 410                 415
Thr Asn Glu Gly Leu Ile Pro Asp Asn Ile Leu Glu Asp Glu Phe Thr
            420                 425                 430
Glu Asn Phe Asn Asn Ala Gln Leu Ile Phe Ala Thr Ile Asp Glu Gly
            435                 440                 445
Glu Ser Met Ile Met Pro Thr Ile Pro Pro Gly Val Ala Leu Lys Leu
            450                 455                 460
Phe Ile Pro Glu Ile Ala Ala Ser Val Leu Asn Val Val His Pro Ser
465                 470                 475                 480
Ser Glu Trp Thr Ile Leu Ile Pro Asn Val Pro Asp Glu Ile Ile Gln
            485                 490                 495
Pro Ala Met Ala Val Asp Val Tyr Asp Asp Phe Tyr Leu His Pro His
            500                 505                 510
Leu Leu Arg Arg Arg Lys Arg Lys Arg Leu Asp Phe Phe
            515                 520                 525

<210> SEQ ID NO 110
<211> LENGTH: 459
<212> TYPE: PRT
<213> ORGANISM: Human papillomavirus type 61

<400> SEQUENCE: 110

Met Ala Leu Lys Arg Arg Lys Arg Ala Ser Ala Thr Asp Leu Tyr Arg
1               5                   10                  15
Thr Cys Lys Gln Ser Gly Thr Cys Pro Pro Asp Val Val Pro Lys Val
            20                  25                  30
```

-continued

```
Glu Gly Asp Thr Leu Ala Asp Arg Ile Leu Lys Trp Ala Ser Leu Gly
     35                  40                  45

Val Phe Phe Gly Gly Leu Gly Ile Gly Thr Gly Ser Gly Thr Gly Gly
 50                  55                  60

Arg Thr Gly Tyr Val Pro Ile Gly Thr Arg Pro Pro Thr Val Val Asp
 65                  70                  75                  80

Ile Gly Pro Val Ser Arg Pro Pro Val Ile Asp Pro Val Gly Ala
                 85                  90                  95

Ala Asp Pro Ser Ile Val Thr Leu Val Glu Glu Ser Ser Val Ile Glu
                100                 105                 110

Ala Gly Ala Thr Val Pro Thr Phe Ser Gly Ser Gly Gly Phe Asn Val
                115                 120                 125

Thr Ser Ser Ser Thr Thr Thr Pro Ala Val Leu Asp Ile Thr Pro Ser
                130                 135                 140

Gly Gly Ser Val Gln Val Ser Ser Thr Ser Phe Ile Asn Pro Leu Phe
145                 150                 155                 160

Thr Glu Pro Ser Ile Ile Glu Pro Pro Gln Ala Gly Asp Leu Ala Gly
                165                 170                 175

His Val Ile Ser Ser Thr Pro Thr Ala Gly Ser His Ser Phe Glu Glu
                180                 185                 190

Ile Pro Met His Thr Phe Ala Thr Ser Glu Gly Pro Gly Ser Ser Thr
                195                 200                 205

Pro Leu Pro Gly Ile Arg Arg Leu Ala Arg Pro Arg Leu Asn Leu Tyr
                210                 215                 220

Ser Lys Ala Asn Gln Gln Ile Lys Val Ala Asn Pro Thr Phe Met Ser
225                 230                 235                 240

Asp Pro Ala Ser Leu Ile Thr Tyr Asp Asn Pro Ile Phe Asp Pro Glu
                245                 250                 255

Glu Thr Ile Ile Phe Glu His Pro Ser Ile Tyr Thr Pro Pro Asp Pro
                260                 265                 270

Asp Phe Leu Asp Ile Val Ser Leu His Arg Pro Ala Leu Thr Ser Arg
                275                 280                 285

Gln Gly Thr Val Arg Phe Ser Arg Leu Gly Gln Arg Ala Thr Leu Arg
                290                 295                 300

Thr Arg Ser Gly Arg Arg Ile Gly Ala Arg Val His Phe Tyr His Asp
305                 310                 315                 320

Ile Ser Pro Ile Pro Ser Asp Ala Val Glu Leu Gln Pro Leu Val Pro
                325                 330                 335

Ser Ser Ser Pro Ser Ile Thr Tyr Asp Ile Tyr Ala Asp Pro Glu Val
                340                 345                 350

Leu Asp Leu Pro Ala Gln His Thr Gln Pro Thr Leu Thr Val Gln Gly
                355                 360                 365

Pro Ser Leu Ser Ala Ala Ser Ala Ser Thr Lys Val His Asn Val Thr
370                 375                 380

Val Pro Leu Ala Thr Gly Leu Asp Thr Pro Val Thr Ser Gly Pro Asp
385                 390                 395                 400

Val Asp Phe Ala His Ala Pro Ala Pro Val Pro Ala Val Pro Tyr Val
                405                 410                 415

Pro Ala Thr His Pro His Ser Ile Tyr Ile Gln Gly Ser Asp Phe Tyr
                420                 425                 430

Leu Leu Pro Ala Tyr Val Phe Phe Pro Lys Arg Arg Lys Arg Val Pro
                435                 440                 445
```

```
Tyr Ser Phe Ser Asp Gly Phe Val Ala Ala Trp
    450                 455

<210> SEQ ID NO 111
<211> LENGTH: 475
<212> TYPE: PRT
<213> ORGANISM: Human papillomavirus type 62

<400> SEQUENCE: 111

Met Pro Lys Val Leu His Arg Arg Lys Arg Ala Ser Ala Thr Asp Leu
1               5                   10                  15

Tyr Arg Thr Cys Lys Val Ser Gly Thr Cys Pro Ser Asp Val Ile Pro
            20                  25                  30

Lys Val Glu Gly Asn Thr Leu Ala Asp Lys Ile Leu Lys Trp Ala Ser
        35                  40                  45

Leu Gly Val Phe Phe Gly Gly Leu Gly Ile Gly Thr Ala Ser Gly Thr
    50                  55                  60

Gly Gly Arg Thr Gly Tyr Ile Pro Ile Gly Gly Arg Pro Pro Ser Val
65                  70                  75                  80

Val Asp Ile Gly Pro Val Ser Arg Pro Pro Val Val Ile Glu Pro Val
                85                  90                  95

Gly Ala Thr Asp Pro Ser Ile Val Thr Leu Val Glu Asp Ser Ser Ile
            100                 105                 110

Ile Glu Ala Gly Ala Val His Pro Asn Phe Thr Gly Ser Ser Gly Phe
        115                 120                 125

Glu Val Thr Thr Ser Ser Thr Ala Thr Pro Ala Val Leu Asp Ile Ser
    130                 135                 140

Pro Thr Gly Thr Thr Val Gln Val Ser Ser Thr Asn Phe Leu Asn Pro
145                 150                 155                 160

Ala Tyr Thr Glu Pro Ser Ile Ile Asp Pro Pro Gln Thr Gly Glu Leu
                165                 170                 175

Ser Gly His Val Leu Thr Ser Thr Pro Thr Ala Gly Ser His Ser Tyr
            180                 185                 190

Glu Glu Ile Pro Met Val Thr Phe Ala Ser Asn Ala Gly Thr Gly Ser
        195                 200                 205

Glu Pro Ile Ser Ser Thr Pro Leu Pro Gly Val Arg Arg Val Ala Gly
    210                 215                 220

Pro Arg Leu Gly Leu Tyr Thr Lys Ala Thr Gln Gln Val Pro Val Ala
225                 230                 235                 240

Asp Pro Ala Phe Val Ser Arg Pro Ala Ser Phe Ala Thr Phe Asp Asn
                245                 250                 255

Pro Ile Tyr Asp Pro Glu Glu Thr Ile Ile Phe Glu His Pro Ser Ile
            260                 265                 270

Tyr Thr Pro Pro Asp Pro Asp Phe Leu Asp Ile Val Thr Leu His Arg
        275                 280                 285

Pro Ala Leu Thr Ser Arg Gln Gly Thr Val Arg Leu Ser Arg Val Gly
    290                 295                 300

Gln Arg Ala Ser Leu Arg Thr Arg Ser Gly Lys Arg Ile Gly Ala Arg
305                 310                 315                 320

Val His Phe Tyr His Asp Ile Ser Pro Ile Pro Ser Thr Thr Thr Gly
                325                 330                 335

Asp Ile Glu Leu Gln Pro Leu Leu Pro Ser Gly Ser Ser Ser Ala Asp
            340                 345                 350

Thr Leu Tyr Asp Val Tyr Ala Asp Asp Gln His Leu Asp Ala Val Leu
        355                 360                 365
```

-continued

```
Gln Ser Val Pro Ser Met Ser Ser Arg Pro Leu Val Pro Ser Asn Ala
        370                 375                 380

Thr Ile Ser Ala Thr Ser Val Ala Ser Ser His Thr Asn Val Thr Val
385                 390                 395                 400

Pro Leu Ser Thr Gly Leu Ser Val Pro Ala Ser Thr Gly Pro Asp Val
                405                 410                 415

Glu Leu Pro Gln Phe Ser Val Pro Val Ser Val Leu Thr Pro Ser Phe
            420                 425                 430

Pro Ala Thr Thr Pro Tyr Ser Ile Tyr Ile Val Gly Ser Asp Tyr Tyr
        435                 440                 445

Leu Phe Pro Ser Tyr Ile Phe Phe Pro Lys Lys His Lys Arg Leu His
    450                 455                 460

Tyr Phe Phe Thr Asp Gly Tyr Val Ala Ala Trp
465                 470                 475

<210> SEQ ID NO 112
<211> LENGTH: 504
<212> TYPE: PRT
<213> ORGANISM: Human papillomavirus type 63

<400> SEQUENCE: 112

Met Leu Arg Val Arg Lys Arg Arg Ala Ala Pro Gln Asp Ile Tyr Pro
1               5                   10                  15

Ala Cys Lys Val Ala Asn Asn Cys Pro Pro Asp Ile Gln Asn Lys Ile
            20                  25                  30

Glu Gln Thr Thr Val Ala Asp Lys Ile Leu Gln Tyr Gly Ser Leu Gly
        35                  40                  45

Ile Phe Leu Gly Gly Leu Gly Ile Gly Thr Gly Lys Gly Gly Gly Gly
    50                  55                  60

Arg Tyr Gly Tyr Thr Pro Leu Gly Asp Ser Gly Ala Val Arg Val Gly
65                  70                  75                  80

Gly Arg Ser Thr Pro Val Arg Pro Thr Val Pro Val Glu Thr Val Gly
                85                  90                  95

Pro Arg Asp Ile Leu Pro Ile Asp Ser Leu Asp Pro Leu Gly Pro Ser
            100                 105                 110

Val Ile Glu Leu Glu Asp Ile Pro Ala Thr Thr Val Glu Val Val Ala
        115                 120                 125

Glu Val His Pro Ile Ser Asp Thr Pro Gln Ile Pro Ala Pro Thr Thr
    130                 135                 140

Asp Glu Ser Ser Ser Ala Val Leu His Ile Pro Gln Glu Ser Pro Ala
145                 150                 155                 160

Ala Arg Thr Ile Thr Arg Ser Gln Tyr Asn Asn Pro Leu Phe Arg Ile
                165                 170                 175

Thr Ala Ser Ala Asp Ile Ala Ser Gly Glu Ala Ser Ala Ser Asp Asn
            180                 185                 190

Ile Phe Ile Asp Val Asp Thr Pro Gly Gln Ile Val Gly Gln Glu Ile
        195                 200                 205

Pro Leu Val Asn Phe Asp Met Gly Pro Ile Ser Thr Glu Gly Glu Leu
    210                 215                 220

Glu Thr Glu Phe Thr Thr Ser Thr Pro Arg Thr Thr Gln Val Gln Glu
225                 230                 235                 240

Arg Pro Thr Arg Phe Tyr Asn Arg Arg Tyr Glu Gln Val Pro Val
                245                 250                 255

Thr Ala Pro Glu Phe Ile Thr Arg Pro Ala Ser Leu Val Thr Phe Glu
```

```
            260                 265                 270
Asn Pro Ala Phe Glu Arg Ser Val Ser Leu Ile Phe Glu Gln Asp Leu
        275                 280                 285
Glu Asp Ile Leu Asn Ala Pro Asp Gln Asp Phe Arg Asp Ile Val Tyr
        290                 295                 300
Leu Ser Arg Pro Thr Tyr Ser Arg Ala Pro Asp Gly Arg Met Arg Leu
305                 310                 315                 320
Ser Arg Leu Gly Arg Arg Ala Thr Ile Ser Thr Arg Ser Gly Val Thr
                325                 330                 335
Ile Gly Ala Gln Ser His Phe Tyr Met Asp Ile Ser Ser Ile Ser Ser
                340                 345                 350
Asn Asp Gly Ile Glu Leu Gln Thr Leu Gly Glu Ala Ser Gly Glu Thr
                355                 360                 365
Val Val Gln Ser Ser Leu Ala Ala Ser Asp Pro Ile Glu Ala Glu His
        370                 375                 380
Ser Phe Ile Glu Pro Ala Pro Ser Ile Asp Ser Tyr Asp Ile Val Ser
385                 390                 395                 400
Leu Gln Ser Glu Thr Tyr Ser Asp Glu His Leu Leu Asp Met Tyr Glu
                405                 410                 415
Pro Val Gly Ser Ser Leu Gln Leu Gln Ile Ser Asp Val Arg Gly Arg
                420                 425                 430
Pro Thr Val Ile Asp Ile Pro Phe Arg Pro Arg Pro Pro Leu Gly
                435                 440                 445
Pro Ile Asn Ala Gly Val Asp Ile Tyr Ser Pro Thr Ala Ser Val Gly
        450                 455                 460
Ser Pro Thr Ile Asn Pro Thr Asp Leu Asp Ile Pro Leu Ile Ile Ile
465                 470                 475                 480
His Leu Asp Asn Ser Thr Gly Asp Tyr Asp Leu His Pro Ser Leu Arg
                485                 490                 495
Lys Arg Arg Lys Leu Val His Ile
                500

<210> SEQ ID NO 113
<211> LENGTH: 518
<212> TYPE: PRT
<213> ORGANISM: Human papillomavirus type 65

<400> SEQUENCE: 113

Met Gln Ala Ser Arg Arg Thr Lys Arg Asp Ser Ile Pro Asn Leu Tyr
1               5                   10                  15
Ala Lys Cys Gln Leu Ser Gly Asn Cys Leu Pro Asp Val Lys Asn Lys
                20                  25                  30
Val Glu Ala Asp Thr Leu Ala Asp Arg Leu Leu Arg Trp Leu Gly Ser
            35                  40                  45
Val Ile Tyr Leu Gly Gly Leu Gly Ile Gly Thr Gly Arg Gly Ser Gly
        50                  55                  60
Gly Ser Ser Gly Tyr Asn Pro Leu Gly Ala Pro Ser Arg Val Thr Pro
65                  70                  75                  80
Ser Gly Thr Val Ile Arg Pro Thr Val Pro Val Glu Gly Leu Gly Pro
                85                  90                  95
Ser Glu Ile Ile Pro Val Asp Val Val Asn Pro Gly Ser Ser Ser Val
                100                 105                 110
Val Pro Leu Glu Asp Leu Thr Val Pro Glu Val Thr Ile Asp Ser Gly
        115                 120                 125
```

```
Glu Val Gly Gly Gly Leu His Pro Ser Glu Ile Asp Val Val Thr
130                 135                 140

Ser Ser Asp Pro Ile Ser Asp Val Thr Gly Thr Ser Ser His Pro Thr
145                 150                 155                 160

Ile Ile Ser Gly Glu Asp Asn Ala Ile Ala Val Leu Asp Val Ser Pro
                165                 170                 175

Thr Glu Pro Pro Thr Lys Arg Ile Ala Leu Gly Thr Arg Gly Ala Thr
            180                 185                 190

Ser Thr Pro His Ile Ser Val Ile Ser Gly Thr Thr Glu Phe Gly Gln
        195                 200                 205

Ser Ser Asp Leu Asn Val Phe Val Asn Ala Thr Phe Ser Gly Asp Ser
210                 215                 220

Ile Gly Tyr Thr Glu Glu Ile Pro Leu Glu Glu Leu Asn Thr Ile Gln
225                 230                 235                 240

Gln Phe Glu Ile Glu Thr Pro Pro Lys Thr Ser Thr Pro Arg Glu Thr
                245                 250                 255

Ile Gly Arg Ala Leu Glu Arg Ala Arg Asp Leu Tyr Asn Arg Arg Val
            260                 265                 270

Gln Gln Ile Ala Thr Arg Asn Pro Ala Met Leu Gly Gln Pro Ser Arg
        275                 280                 285

Ala Ile Val Phe Gly Phe Glu Asn Pro Ala Phe Asp Ala Asp Ile Thr
290                 295                 300

Gln Val Phe Glu Arg Asp Leu Glu Gln Val Ala Ala Pro Asp Ala
305                 310                 315                 320

Asp Phe Ala Asp Ile Val Arg Ile Gly Arg Pro Arg Phe Ser Gln Thr
                325                 330                 335

Asp Thr Gly Gln Ile Arg Ile Ser Arg Leu Gly Arg Arg Gly Thr Ile
            340                 345                 350

Lys Thr Arg Ser Gly Leu Gln Ile Gly Gln Ala Val His Phe Tyr Tyr
        355                 360                 365

Asp Leu Ser Thr Ile Asp Thr Ala Asp Ala Ile Glu Leu Ser Thr Leu
370                 375                 380

Gly Gln His Ser Gly Glu Gln Ser Ile Val Asp Ala Met Ile Glu Ser
385                 390                 395                 400

Ser Phe Val Asp Pro Phe Glu Thr Pro Asp Pro Thr Tyr Thr Glu Glu
                405                 410                 415

Gln Gln Leu Leu Asp Pro Leu Thr Glu Asp Phe Ser Asn Ser His Leu
            420                 425                 430

Val Leu Thr Ser Ser Arg Arg Gly Ser Ser Phe Ser Ile Pro Thr Ile
        435                 440                 445

Pro Pro Gly Leu Gly Leu Arg Ile Tyr Val Asp Asp Val Gly Ser Asp
450                 455                 460

Leu Phe Val Ser Tyr Pro Glu Thr Arg Val Ile Pro Ala Gly Gly Leu
465                 470                 475                 480

Pro Thr Glu Pro Phe Thr Pro Leu Glu Pro Pro Phe Phe Ser Glu Phe
                485                 490                 495

Tyr Ser Ser Asp Phe Val Tyr Arg Pro Ser Leu Tyr Arg Lys Lys Arg
            500                 505                 510

Lys Arg Ser Asp Ile Phe
        515

<210> SEQ ID NO 114
<211> LENGTH: 464
<212> TYPE: PRT
```

<213> ORGANISM: Human papillomavirus type 66

<400> SEQUENCE: 114

```
Met Val Ala His Arg Ala Thr Arg Arg Lys Arg Ala Ser Ala Thr Gln
1               5                   10                  15

Leu Tyr Lys Thr Cys Lys Leu Ser Gly Thr Cys Pro Glu Asp Val Ile
            20                  25                  30

Asn Lys Val Glu Gln Lys Thr Trp Ala Asp Arg Ile Leu Gln Trp Gly
                35                  40                  45

Ser Leu Phe Thr Tyr Phe Gly Gly Leu Gly Ile Gly Thr Gly Ser Gly
    50                  55                  60

Ser Gly Gly Arg Ala Gly Tyr Val Pro Leu Gly Ser Arg Pro Ser Thr
65                  70                  75                  80

Ile Val Asp Val Thr Pro Ala Arg Pro Ile Val Val Glu Ser Val
                85                  90                  95

Gly Pro Thr Asp Pro Ser Ile Val Thr Leu Val Glu Glu Ser Ser Val
                100                 105                 110

Ile Asn Ser Gly Ala Gly Val Pro Asn Phe Thr Gly Ser Gly Gly Phe
            115                 120                 125

Glu Val Thr Ser Ser Ser Thr Thr Thr Pro Ala Val Leu Asp Ile Thr
    130                 135                 140

Pro Thr Ser Ser Thr Val His Val Ser Ser Thr Thr Ile Thr Asn Pro
145                 150                 155                 160

Leu Tyr Ile Asp Pro Pro Val Ile Glu Ala Pro Gln Thr Gly Glu Val
                165                 170                 175

Ser Gly Asn Ile Leu Ile Ser Thr Pro Thr Ser Gly Ile His Ser Tyr
            180                 185                 190

Glu Glu Ile Pro Met Gln Thr Phe Ala Ile His Gly Thr Gly Asn Glu
        195                 200                 205

Pro Ile Ser Ser Thr Pro Ile Pro Gly Phe Arg Arg Leu Ala Ala Pro
    210                 215                 220

Arg Leu Tyr Ser Arg Ala Phe Gln Gln Val Arg Val Thr Asp Pro Ala
225                 230                 235                 240

Phe Leu Asp Asn Pro Thr Thr Leu Ile Thr Ala Asp Asn Pro Val Phe
                245                 250                 255

Glu Gly Ala Asp Thr Thr Leu Thr Phe Ser Pro Ser Gly Val Ala Pro
            260                 265                 270

Asp Pro Asp Phe Met Asp Ile Val Ala Leu His Arg Pro Ala Phe Thr
        275                 280                 285

Thr Arg Arg Thr Gly Val Arg Phe Ser Arg Leu Gly Lys Lys Ala Thr
    290                 295                 300

Met Gln Thr Arg Arg Gly Thr Gln Ile Gly Ala Arg Val His Tyr Tyr
305                 310                 315                 320

Tyr Asp Ile Ser Pro Ile Ala Gln Ala Asp Glu Ile Glu Met Gln Pro
                325                 330                 335

Leu Leu Ser Thr Asp Asn Ser Phe Asp Gly Leu Tyr Asp Ile Tyr Ala
            340                 345                 350

Asn Ile Asp Asp Glu Ala Pro Ile Ser Phe Arg Gln Ser Gly Ala Thr
        355                 360                 365

Pro Ser Ala Gln Leu Pro Ile Lys Pro Ser Thr Leu Ser Phe Ala Ser
    370                 375                 380

Asn Thr Thr Asn Val Thr Ala Pro Leu Gly Asn Val Trp Glu Thr Pro
385                 390                 395                 400
```

Leu Tyr Ser Gly Pro Asp Ile Val Leu Pro Thr Gly Pro Ser Thr Trp
                    405                 410                 415

Pro Phe Val Pro Gln Ser Pro Tyr Asp Val Thr His Asp Val Tyr Ile
            420                 425                 430

Gln Gly Ala Thr Phe Ala Leu Trp Pro Val Tyr Phe Phe Lys Arg Arg
            435                 440                 445

Arg Arg Lys Arg Ile Pro Tyr Phe Phe Ala Asp Gly Asp Val Ala Ala
450                 455                 460

<210> SEQ ID NO 115
<211> LENGTH: 465
<212> TYPE: PRT
<213> ORGANISM: Human papillomavirus type 67

<400> SEQUENCE: 115

Met Arg His Lys Arg Ser Thr Arg Arg Lys Arg Ala Ser Ala Thr Gln
1               5                   10                  15

Leu Tyr Gln Thr Cys Lys Ala Ala Gly Thr Cys Pro Pro Asp Val Ile
            20                  25                  30

Pro Lys Val Glu Arg Thr Thr Ile Ala Asp Gln Ile Leu Lys Phe Gly
            35                  40                  45

Ser Leu Gly Val Phe Phe Gly Gly Leu Gly Ile Gly Thr Gly Ser Gly
    50                  55                  60

Thr Gly Gly Arg Thr Gly Tyr Val Pro Leu Ser Thr Arg Pro Pro Thr
65                  70                  75                  80

Ala Ser Ala Pro Thr Ser Thr Ile Arg Pro Pro Val Ser Val Asp Thr
                85                  90                  95

Val Gly Pro Leu Asp Ser Ser Ile Val Ser Met Ile Glu Glu Thr Ser
            100                 105                 110

Phe Ile Glu Ser Gly Ala Pro Ala Pro Ser Ile Pro Thr Ala Ser Gly
            115                 120                 125

Phe Asp Val Ala Thr Ser Ala Asp Asn Thr Pro Ala Ile Ile Asn Val
    130                 135                 140

Ser Ser Ile Gly Glu Ser Ser Val Gln Ser Val Thr Thr His Leu Asn
145                 150                 155                 160

Pro Thr Phe Thr Glu Pro Ser Val Leu Arg Pro Phe Ser Ser Ser Glu
                165                 170                 175

Ala Ser Gly His Leu Ile Phe Ser Thr Pro Thr Ile Ser Thr His Ser
            180                 185                 190

Tyr Glu Asp Ile Pro Met Asp Thr Phe Ile Val Ser Thr Thr Ser Asp
            195                 200                 205

Asn Val Thr Ser Ser Thr Pro Ile Pro Arg Pro Arg Pro Thr Ala Arg
    210                 215                 220

Leu Gly Leu Tyr Ser Lys Gly Thr Gln Gln Val Lys Val Val Asp Pro
225                 230                 235                 240

Ala Phe Leu Thr Ser Pro Arg Arg Leu Ile Thr Phe Asp Asn Pro Ala
                245                 250                 255

Phe Gln Pro Thr Glu Pro Asp Glu Thr Leu Tyr Phe Gln His Gln Asp
            260                 265                 270

Ile Ser Pro Ala Pro Asp Pro Asp Phe Leu Asp Ile Val Ala Leu His
            275                 280                 285

Arg Pro Ala Leu Thr Ser Arg Lys Gly Thr Ile Arg Phe Ser Arg Leu
    290                 295                 300

Gly Ser Lys Ala Thr Met Lys Thr Arg Ser Gly Lys Gln Ile Gly Ala
305                 310                 315                 320

Arg Val His Tyr Tyr Gln Asp Leu Ser Pro Ile Val Pro Ala Asp Ser
              325                 330                 335

Ile Glu Leu Gln Pro Leu Ser Arg Pro Val Ser Ser Ala Ser His Ser
              340                 345                 350

Ile Asn Asp Gly Leu Tyr Asp Val Tyr Met Asp Pro Asp Thr Pro Phe
              355                 360                 365

Pro Gln Pro Ser Ile Ser Tyr Ser Leu His Ser Pro Gln Thr Thr Asn
              370                 375                 380

Val Thr Val Pro Leu Ser Ser Gly Phe Asp Phe Pro Phe Ser Ser Thr
385                 390                 395                 400

Val Pro Leu Gln Pro Gly Pro Asp Ile Val Ser Pro Val Ala Pro Thr
              405                 410                 415

Tyr Thr Pro Phe Val Pro Val Ile Pro Thr Ser Pro Phe Asn Asn Val
              420                 425                 430

Leu Val Tyr Gly Ser Asp Phe Ile Leu His Pro Ser Tyr Phe Leu Arg
              435                 440                 445

Arg Arg Arg Lys Arg Phe Pro Tyr Phe Phe Ala Asp Val Arg Val Ala
              450                 455                 460

Ala
465

<210> SEQ ID NO 116
<211> LENGTH: 469
<212> TYPE: PRT
<213> ORGANISM: Human papillomavirus type 68

<400> SEQUENCE: 116

Met Val Ser His Arg Ala Ala Arg Arg Lys Arg Ala Ser Ala Thr Asp
1               5                   10                  15

Leu Tyr Lys Thr Cys Lys Gln Ser Gly Thr Cys Pro Ser Asp Val Ile
              20                  25                  30

Asn Lys Val Glu Gly Thr Thr Leu Ala Asp Lys Ile Leu Gln Trp Thr
              35                  40                  45

Ser Leu Gly Ile Phe Leu Gly Gly Leu Gly Ile Gly Thr Gly Ser Gly
        50                  55                  60

Thr Gly Gly Arg Ala Gly Tyr Ile Pro Leu Gly Gly Lys Pro Asn Thr
65                  70                  75                  80

Val Val Asp Val Ser Pro Ala Arg Pro Pro Val Val Ile Glu Pro Val
              85                  90                  95

Gly Pro Thr Glu Pro Ser Ile Val Gln Leu Val Glu Asp Ser Ser Val
              100                 105                 110

Ile Thr Ser Gly Thr Pro Val Pro Thr Phe Thr Gly Thr Ser Gly Phe
              115                 120                 125

Glu Ile Thr Ser Ser Ser Thr Thr Thr Pro Ala Val Leu Asp Ile Thr
          130                 135                 140

Pro Ser Ser Gly Ser Val Gln Val Ser Ser Thr Ser Phe Thr Asn Pro
145                 150                 155                 160

Ala Phe Thr Asp Pro Thr Ile Ile Glu Val Pro Gln Thr Gly Glu Val
              165                 170                 175

Ser Gly Asn Val Phe Val Ser Thr Pro Thr Ser Gly Thr His Gly Tyr
              180                 185                 190

Glu Glu Ile Pro Met Gln Val Phe Ala Thr His Gly Thr Gly Thr Glu
              195                 200                 205

Pro Ile Ser Ser Thr Pro Ile Pro Gly Val Ser Arg Val Ala Gly Pro

```
Arg Leu Tyr Ser Arg Ala His Gln Gln Val Arg Val Ser Asn Phe Asp
225                 230                 235                 240

Phe Val Thr His Pro Ser Ser Phe Val Thr Phe Asp Asn Pro Ala Phe
            245                 250                 255

Glu Pro Val Asp Thr Thr Leu Thr Tyr Glu Pro Ala Asp Ile Ala Pro
            260                 265                 270

Asp Pro Asp Phe Leu Asp Ile Val Arg Leu His Arg Pro Ala Leu Thr
            275                 280                 285

Ser Arg Arg Gly Thr Val Arg Phe Ser Arg Val Gly Lys Lys Ala Thr
        290                 295                 300

Met Phe Thr Arg Arg Gly Thr Gln Ile Gly Ala Gln Val His Tyr Tyr
305                 310                 315                 320

His Asp Ile Ser Asn Ile Thr Pro Ala Asp Ser Ile Glu Leu Gln Pro
                325                 330                 335

Leu Val Ala Pro Glu Gln Ala Asp Pro Met Asp Asn Leu Tyr Asp Ile
            340                 345                 350

Tyr Ala Pro Asp Thr Asp Asn Thr Thr Val Leu Asp Thr Ala Phe His
            355                 360                 365

Asn Ala Thr Phe Thr Thr Arg Ser His Ile Ser Val Pro Ser Leu Ala
370                 375                 380

Ser Ala Ala Ser Thr Thr Tyr Thr Asn Thr Thr Ile Pro Leu Gly Thr
385                 390                 395                 400

Ala Trp Asn Thr Pro Val Asn Thr Gly Pro Asp Val Val Leu Pro Ser
                405                 410                 415

Thr Thr Pro Gln Leu Pro Leu Thr Pro Ser Thr Pro Ile Asp Thr Thr
            420                 425                 430

Phe Ala Ile Thr Ile Tyr Gly Ser Asn Tyr Tyr Leu Leu Pro Leu Leu
            435                 440                 445

Phe Phe Leu Leu Lys Lys Arg Lys His Leu Pro Tyr Phe Phe Thr Asp
            450                 455                 460

Gly Ile Val Ala Ser
465

<210> SEQ ID NO 117
<211> LENGTH: 467
<212> TYPE: PRT
<213> ORGANISM: Human papillomavirus type 69

<400> SEQUENCE: 117

Met Val Ala Val Arg Ala Ser Arg Arg Lys Arg Ala Ser Ala Thr Asp
1               5                   10                  15

Leu Tyr Lys Thr Cys Lys Ala Ala Gly Thr Cys Pro Pro Asp Val Ile
            20                  25                  30

Pro Lys Ile Glu Gly Ser Thr Leu Ala Asp Lys Ile Leu Gln Trp Ser
        35                  40                  45

Gly Leu Gly Ile Phe Leu Gly Gly Leu Gly Ile Gly Thr Gly Thr Gly
    50                  55                  60

Thr Gly Gly Arg Thr Gly Tyr Ile Pro Leu Gly Gly Gly Gly Arg Pro
65                  70                  75                  80

Ser Val Val Asp Ile Gly Pro Thr Arg Pro Pro Ile Ile Glu Pro
                85                  90                  95

Val Gly Pro Thr Glu Pro Ser Ile Val Thr Leu Val Glu Glu Ser Ser
            100                 105                 110
```

```
Ile Ile Gln Ser Gly Ser Pro Phe Pro Asn Phe Ser Gly Gly Asp Gly
            115                 120                 125

Phe Glu Val Thr Thr Ser Ser Thr Thr Thr Pro Ala Val Leu Asp Ile
130                 135                 140

Thr Pro Ser Pro Gly Thr Val His Val Thr Ser Thr Asn Ile Gln Asn
145                 150                 155                 160

Pro Leu Tyr Ile Glu Pro Val Asp Ile Pro Gln Ser Gly Glu Ala
                165                 170                 175

Leu Gly His Ile Phe Thr Ser Thr Ser Thr Ala Gly Thr His Ser Tyr
            180                 185                 190

Glu Glu Ile Pro Met Glu Val Phe Ala Ser Asn Thr Ser Ser Gly Ser
        195                 200                 205

Lys Pro Ile Ser Ser Thr Pro Ile Pro Gly Ile Arg Arg Val Ala Ala
    210                 215                 220

Pro Arg Leu Tyr Ser Lys Ala Tyr Gln Gln Val Lys Val Thr Asp Pro
225                 230                 235                 240

Asn Phe Ile Ser Lys Pro Ser Thr Phe Ile Thr Phe Asp Asn Pro Ala
                245                 250                 255

Tyr Glu Pro Met Asp Thr Thr Leu Thr Phe Ser Ala Asp Ser His Val
            260                 265                 270

Ala Pro Asp Pro Asp Phe Leu Asp Ile Ile Ala Leu His Arg Pro Ala
        275                 280                 285

Leu Thr Ser Arg Arg Gly Thr Val Arg Phe Ser Arg Leu Gly Gln Lys
    290                 295                 300

Ala Thr Leu Lys Thr Arg Ser Gly Lys Gln Ile Gly Ala Lys Val His
305                 310                 315                 320

Tyr Tyr His Asp Ile Ser Pro Ile His Ala Thr Glu Glu Ala Ile Glu
                325                 330                 335

Leu Gln Pro Leu Ile Thr Ser Glu Gln His Ser Thr Pro Leu Phe Asp
            340                 345                 350

Val Tyr Ala Asp Ala Asp Pro Ala Pro Thr Phe Thr Phe Pro Ser Thr
        355                 360                 365

Thr Pro Thr Thr Ile Pro Arg Phe Ser Ser Thr Ile Phe Ser Thr Thr
    370                 375                 380

Ser Ser Ala Pro Leu Asn Val Thr Ile Pro Leu Ser Thr Ser Phe Asp
385                 390                 395                 400

Ile Pro Ile Tyr Asn Gly Pro Asp Ile Tyr Ala Pro Val Pro Ser Ser
                405                 410                 415

Thr Trp Pro Tyr Ile Pro Pro Pro Thr Thr Met Ser His Ser Val
            420                 425                 430

Val Ala Gln Gly Gly Asn Tyr Tyr Leu Trp Pro Tyr Ile Tyr Leu Ile
        435                 440                 445

His Lys Arg Arg Arg Lys Arg Val Pro Cys Phe Phe Ser Asp Gly Leu
    450                 455                 460

Ala Ala Tyr
465

<210> SEQ ID NO 118
<211> LENGTH: 466
<212> TYPE: PRT
<213> ORGANISM: Human papillomavirus type 70

<400> SEQUENCE: 118

Met Val Ser Ser Arg Ala Ser Arg Arg Lys Arg Ala Ser Ala Thr Asp
1               5                   10                  15
```

-continued

```
Ile Tyr Lys Thr Cys Lys Gln Ser Gly Thr Cys Pro Pro Asp Val Val
         20                  25                  30

Asn Lys Val Glu Gly Thr Thr Leu Ala Asp Arg Phe Leu Gln Trp Ala
         35                  40                  45

Ser Leu Gly Ile Phe Leu Gly Leu Gly Ile Gly Thr Gly Thr Gly
     50                  55                  60

Thr Gly Gly Arg Thr Gly Tyr Ile Pro Leu Gly Gly Arg Pro Ser Thr
65                  70                  75                  80

Val Val Asp Val Thr Pro Ala Arg Pro Pro Val Val Ile Glu Pro Val
                 85                  90                  95

Gly Pro Thr Glu Pro Ser Ile Val Gln Leu Val Glu Glu Ser Ser Val
                100                 105                 110

Val Ser Ser Gly Thr Pro Ile Pro Thr Phe Thr Gly Thr Ser Gly Phe
             115                 120                 125

Glu Ile Thr Ser Ser Ala Thr Thr Thr Pro Ala Val Leu Asp Ile Thr
130                 135                 140

Pro Ala Ser Gly Ser Val Gln Ile Ser Thr Thr Ser Tyr Thr Asn Pro
145                 150                 155                 160

Ala Phe Ala Asp Pro Ser Leu Ile Glu Val Pro Gln Thr Gly Glu Val
                 165                 170                 175

Ser Gly Asn Ile Phe Val Thr Thr Pro Thr Ser Gly Thr His Gly Tyr
             180                 185                 190

Glu Glu Ile Pro Met Gln Val Phe Ala Ser His Gly Thr Gly Thr Glu
             195                 200                 205

Pro Ile Ser Ser Thr Pro Val Pro Gly Val Ser Arg Val Ala Gly Pro
210                 215                 220

Arg Leu Tyr Ser Arg Ala Tyr His Gln Val Arg Val Asn Asn Phe Asp
225                 230                 235                 240

Phe Val Thr Arg Pro Ser Ser Phe Val Thr Phe Asp Asn Pro Ala Phe
                 245                 250                 255

Glu Pro Gly Asp Thr Ser Leu Thr Phe Glu Pro Ala Asp Thr Ala Pro
             260                 265                 270

Asp Pro Asp Phe Leu Asp Ile Val Arg Leu His Arg Pro Ala Leu Thr
             275                 280                 285

Ser Arg Arg Gly Thr Val Arg Phe Ser Arg Leu Gly Lys Lys Ala Thr
290                 295                 300

Met Phe Thr Arg Arg Gly Thr Gln Ile Gly Ala Gln Val His Tyr Tyr
305                 310                 315                 320

His Asp Ile Ser Asn Ile Thr Ala Thr Glu Asp Ile Glu Met Gln Pro
                 325                 330                 335

Leu Leu Thr Ser Glu Ser Thr Asp Gly Leu Tyr Asp Ile Tyr Ala Asp
             340                 345                 350

Ala Asp Ile Asp Asn Ala Met Leu His Thr Thr Ser His Thr Gly Ser
             355                 360                 365

Thr Gly Pro Arg Ser His Leu Ser Phe Pro Ser Ile Pro Ser Thr Val
         370                 375                 380

Ser Thr Lys Tyr Ser Asn Thr Thr Ile Pro Phe Thr Thr Ser Trp Asp
385                 390                 395                 400

Ile Pro Val Thr Thr Gly Pro Asp Ile Val Leu Pro Thr Ala Ser Pro
             405                 410                 415

Asn Leu Pro Phe Val Pro Pro Ser Ile Asp Thr Thr Val Ala Ile
             420                 425                 430
```

```
Ala Ile Gln Gly Ser Asn Tyr Leu Leu Pro Leu Leu Tyr Tyr Phe
            435                 440                 445

Leu Lys Lys Arg Lys Arg Ile Pro Tyr Phe Thr Asp Gly Phe Val
    450                 455                 460

Ala Val
465

<210> SEQ ID NO 119
<211> LENGTH: 44
<212> TYPE: PRT
<213> ORGANISM: Human papillomavirus

<400> SEQUENCE: 119

Asp Gln His Leu Ile Tyr Lys Pro Arg Gln Ser Thr Ser Ala Cys Lys
1               5                   10                  15

Gln Ile Val Leu Ala Ala Ser Thr Gly Asn Thr Asn Cys Pro Pro Asp
            20                  25                  30

Ile Val Ile Val Gln Pro Asn Asp Lys Arg Val Ile
            35                  40

<210> SEQ ID NO 120
<211> LENGTH: 20
<212> TYPE: PRT
<213> ORGANISM: Human papillomavirus
<220> FEATURE:
<221> NAME/KEY: misc_feature
<222> LOCATION: (17)..(17)
<223> OTHER INFORMATION: Xaa can be any naturally occurring amino acid

<400> SEQUENCE: 120

Ala Asx Tyr Cys Asp Cys Lys Glu Phe Gly His Cys Pro Pro Asp Ile
1               5                   10                  15

Xaa Lys Leu Met
            20

<210> SEQ ID NO 121
<211> LENGTH: 35
<212> TYPE: PRT
<213> ORGANISM: Human papillomavirus

<400> SEQUENCE: 121

Ala Ser Ala Thr Gln Leu Tyr Lys Thr Cys Lys Gln Ala Gly Thr Cys
1               5                   10                  15

Pro Pro Asp Ile Ile Pro Lys Val Glu Gly Lys Thr Ile Ala Asp Gln
            20                  25                  30

Ile Leu Gln
        35
```